(12) United States Patent
Jewett et al.

(10) Patent No.: US 9,528,137 B2
(45) Date of Patent: Dec. 27, 2016

(54) METHODS FOR CELL-FREE PROTEIN SYNTHESIS

(71) Applicant: Northwestern University, Evanston, IL (US)

(72) Inventors: Michael C. Jewett, Evanston, IL (US); Charles E. Hodgman, Evanston, IL (US); Rui Gan, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/213,390

(22) Filed: Mar. 14, 2014

(65) Prior Publication Data

US 2014/0295492 A1    Oct. 2, 2014

Related U.S. Application Data

(60) Provisional application No. 61/792,290, filed on Mar. 15, 2013.

(51) Int. Cl.
| | |
|---|---|
| *C12P 21/00* | (2006.01) |
| *C12P 19/34* | (2006.01) |
| *C12P 21/02* | (2006.01) |
| *C40B 50/06* | (2006.01) |
| *C12N 9/12* | (2006.01) |

(52) U.S. Cl.
CPC ............... *C12P 21/00* (2013.01); *C12P 19/34* (2013.01); *C12P 21/02* (2013.01); *C40B 50/06* (2013.01); *C12N 9/1241* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 4,683,195 | A | 7/1987 | Mullis et al. |
| 4,683,202 | A | 7/1987 | Mullis |
| 5,478,730 | A | 12/1995 | Alakhov et al. |
| 5,556,769 | A | 9/1996 | Wu et al. |
| 5,665,563 | A | 9/1997 | Beckler |
| 6,168,931 | B1 | 1/2001 | Swartz et al. |
| 6,518,058 | B1 | 2/2003 | Biryukov et al. |
| 6,783,957 | B1 | 8/2004 | Biryukov et al. |
| 6,869,774 | B2 | 3/2005 | Endo |
| 6,994,986 | B2 | 2/2006 | Swartz et al. |
| 7,118,883 | B2 | 10/2006 | Inoue et al. |
| 7,189,528 | B2 | 3/2007 | Higashide et al. |
| 7,338,789 | B2 | 3/2008 | Swartz et al. |
| 7,387,884 | B2 | 6/2008 | Suzuki et al. |
| 7,399,610 | B2 | 7/2008 | Shikata et al. |
| 2006/0211083 | A1* | 9/2006 | Katzen et al. ............... 435/68.1 |

OTHER PUBLICATIONS

Tuite et al. "mRNA-Dependent Yeast Cell-free Translation Systems: Theory and Practice" Yeast vol. 2: 35-52 (1986).*
Gasior et al. "The Preparation and Characterization of a Cell-free System from *Saccharomyces cerevisiae* That Translates Natural Messenger Ribonucleic Acid" The Journal of Biological Chemistry vol. 254, No. 10, Issue of May 25, pp. 3965-3969, 1979.*
Saini, P. et al. "Hypusine-containing protein eIF5A promotes translation elongation," Nature 459, 118-121 (2009).
Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4), 227-259.
Sawasaki, T., et al., A cell-free protein synthesis system for high-throughput proteomics. Proceedings of the National Academy of Sciences 99, 14652-14657 (2002).
Shrestha P, et al., Streamlined extract preparation for *Escherichia coli*-based cell-free protein synthesis by sonication or bead vortex mixing. Biotechniques 53(3), 163-174 (2012).
Sissons, C. H. Yeast protein synthesis: Preparation and analysis of a highly active cell-free system. Biochem J 144, 131-140 (1974).
Stech, M. et al. "Production of functional antibody fragments in a vesicle-based eukaryotic cell-free translation system," J. Biotechnol. 164, 220-231 (2012).
Suzuki, T. et al. "N-terminal protein modifications in an insect cell-free protein synthesis system and their identification by mass spectrometry," Proteomics 6, 4486-4495 (2006).
Suzuki, T. et al. "Protein prenylation in an insect cell-free protein synthesis system and identification of products by mass spectrometry," Proteomics 7, 1942-1950 (2007).
Suzuki, T. et al. "Preparation of ubiquitin-conjugated proteins using an insect cell-free protein synthesis system," J. Biotechnol. 145, 73-78 (2010).
Swartz, J., Developing cell-free biology for industrial applications. J Ind Microbiol Biotechnol 33, 476-485 (2006).
Tabor, C. W. et al., Polyamines in microorganisms. Microbiol Rev 49, 81-99 (1985).

(Continued)

*Primary Examiner* — Thane Underdahl
(74) *Attorney, Agent, or Firm* — Andrus Intellectual Property Law, LLP

(57) ABSTRACT

Cell-free protein synthesis systems and methods of using the same for producing in vitro protein materials in high yield are disclosed. The cell-free protein synthesis platform includes (a) a *Saccharomyces cerevisiae* cellular extract prepared from mid-exponential to late-exponential batch cultures in the range from about 6 $OD_{600}$ to about 18 $OD_{600}$ or fed-batch cultures harvested in mid-exponential to late-exponential phase; (b) a reaction buffer; and (c) a translation template or (c') a transcription template from which a translation template can be prepared in situ with an RNA polymerase. A method of performing high-throughput protein synthesis in vitro is also provided that utilizes a combined transcription/translation reaction with the cell-free protein synthesis platform from *Saccharomyces cerevisiae*, an RNA polymerase and a transcription template prepared from a source DNA using an amplification procedure.

18 Claims, 32 Drawing Sheets

(56) References Cited

OTHER PUBLICATIONS

Takai, K et al. "Practical cell-free protein synthesis system using purified wheat embryos," Nat. Protoc. 5, 227-238 (2010).
Tarui, H. et al. "Establishment and characterization of cell-free translation/glycosylation in insect cell (*Spodoptera frugiperda* 21) extract prepared with high pressure treatment," Appl. Microbiol. Biotechnol. 55, 446-453 (2001).
Tarun, S. Z. et al., A common function for mRNA 5' and 3' ends in translation initiation in yeast. Genes Dev 9, 2997-3007 (1995).
Thompson, S. R. et al. "Internal initiation in *Saccharomyces cerevisiae* mediated by an initiator tRNA/eIF2-independent internal ribosome entry site element," Proc. Natl. Acad. Sci. U.S.A 98, 12972-12977 (2001).
Tuite, M. F., et al., Faithful and efficient translation of homologous and heterologous mRNAs in an mRNA-dependent cell-free system from *Saccharomyces cerevisiae*. J Biol Chem 255, 8761-8766 (1980).
Wang, X. et al. "An optimized yeast cell-free system: Sufficient for translation of human papillomavirus 58 L1 mRNA and assembly of virus-like particles," J. Biosci. Bioeng. 106, 8-15 (2008).
Wang, X. et al. "Translational comparison of HPV58 long and short L1 mRNAs in yeast (*Saccharomyces cerevisiae*) cell-free system," J. Biosci. Bioeng. 110, 58-65 (2010).
Wu, C., et al., in Methods Enzymol vol. vol. 429 (ed Jon R. Lorsch) 203-225 (Academic Press, 2007).
Venter, J. C. et al., Environmental genome shotgun sequencing of the *Sargasso* sea. Science 304, 66-74, (2004).
Verge, V. et al., "Localization of a promoter in the putative internal ribosome entry site of the *Saccharomyces cerevisiae* TIF4631 gene," RNA 10, 277-286 (2004).
Yang, J. et al. "Rapid expression of vaccine proteins for B-cell lymphoma in a cell-free system," Biotechnol. Bioeng. 89, 503-511 (2005).
Yin, G. et al. "Aglycosylated antibodies and antibody fragments produced in a scalable in vitro transcription-translation system," MAbs 4, 217-225 (2012).
Zawada, J. F. et al. "Microscale to manufacturing scale-up of cell-free cytokine production—a new approach for shortening protein production development timelines," Biotechnol. Bioeng. 108, 1570-1578 (2011)).
Zhou, W., et al., "Transcript leader regions of two *Saccharomyces cerevisiae* mRNAs contain internal ribosome entry sites that function in living cells," Proc. Natl. Acad. Sci. U.S.A. 98, 1531-1536 (2001).
Zinser, E. et al. "Isolation and Biochemical Characterization of Organelles from the Yeast, *Saccharomyces cerevisiae*". Yeast 11, 493-536 (1995).
He, M. et al. "Single step generation of protein arrays from DNA by cell-free expression and in situ immobilisation (PISA method)". Nucleic Acids Research, 2001,vol. 29, No. 15, e73, p. 1-6.
Hussain, I. et al. "Translation of homologous and heterologous messenger RN As in a yeast cell-free system". Gene 46, p. 13-23 (1986).
Qu, F. et al. "Cap-Independent Translational Enhancement of Turnip Crinkle Virus Genomic and Subgenomic RNAs". Journal of Virology 74, No. 3, pp. 1085-1093 (2000).
Algire, M. A. et al. Development and characterization of a reconstituted yeast translation initiation system. RNA 8, 382-397 (2002).
Beaucage et al., Tetrahedron Letters 22, 1859-1862 (1981).
Brown et al., Meth. Enzymol. 68, 109-151 (1979).
Calhoun, K. A. & Swartz, J. R. Energizing cell-free protein synthesis with glucose metabolism. Biotechnol Bioeng 90, 606-613 (2005).
Calhoun KA, Swartz JR. 2006. Total amino acid stabilization during cell-free protein synthesis reactions. J Biotechnol 123(2):193-203.
Carlson, E. D. et al. "Cell-free protein synthesis: Applications come of age," Biotechnol. Adv. 30, 1185-1194, (2012).
Catherine, C. et al., "Cell-free platforms for flexible expression and screening of enzymes," Biotechnol Adv 31, 797-803 (2013).

Chang, H.-C. et al. "De novo folding of GFP fusion proteins: High efficiency in eukaryotes but not in bacteria," J. Mol. Biol. 353, 397-409 (2005).
Dove, A. "Uncorking the biomanufacturing bottleneck". Nat Biotechnol 20, 777-779 (2002).
Deniz, N. et al., "Translation initiation factors are not required for Dicistroviridae IRES function in vivo," RNA 15, 932-946 (2009).
Edwards, S. R., et al., "Dicistronic regulation of fluorescent proteins in the budding yeast *Saccharomyces cerevisiae*," Yeast 27, 229-236 (2010).
Endo Y, et al., "Cell-free expression systems for eukaryotic protein production." Curr Opin Biotechnol 17(4), 373-380 (2006).
Ezure, T et al. "A cell-free protein synthesis system from insect cells," Methods Mol. Biol. 607, 31-42 (2010).
Ferrer-Miralles, N., et al. "Microbial factories for recombinant pharmaceuticals," Microb. Cell. Fact. 8, 17 (2009).
Gasior, E. et al. "The analysis of intermediary reactions involved in protein synthesis, in a cell-free extract of *Saccharomyces cerevisiae* that translates natural messenger ribonucleic acid," J. Biol. Chem. 254, 3970-3976 (1979).
Gasior, E. et al. "The preparation and characterization of a cell-free system from *Saccharomyces cerevisiae* that translates natural messenger ribonucleic acid," J. Biol. Chem. 254, 3965-3969 (1979).
Goerke, A. R. et al. "Development of cell-free protein synthesis platforms for disulfide bonded proteins," Biotechnol. Bioeng. 99, 351-367 (2008).
Goodchild, "Conjugates of Oligonucleotides and Modified Oligonucleotides: A Review of Their Synthesis and Properties" Bioconjugate Chemistry 1(3): 165-187 (1990).
Goshima, N. et al. "Human protein factory for converting the transcriptome into an in vitro-expressed proteome," Nat. Methods 5, 1011-1017 (2008).
Heins, J. N., et al., "Characterization of a nuclease produced by *Staphylococcus aureus*." J Biol Chem 242, 1016-1020 (1967).
Hinnebusch, A. G., et al. "Mechanism of translation initiation in the yeast *Saccharomyces cerevisiae*," pp. 225-268 in Translational Control in Biology and Medicine, (eds. M. B. Mathews, N. Sonenberg and J. W. B. Hershey) (Cold Spring Harbor Laboratory Press, Cold Spring Harbor, N.Y. (2007).
Hoffmann, M. et al. "Rapid translation system: A novel cell-free way from gene to protein" in Biotechnol Annu Rev vol. 10, 1-30 (Elsevier, 2004).
Iizuka, N. et al. "Cap-dependent and cap-independent translation by internal initiation of mRNAs in cell extracts prepared from *Saccharomyces cerevisiae*," Mol. Cell. Biol. 14, 7322-7330 (1994).
Iizuka, N. & Sarnow, P. "Translation-competent extracts from *Saccharomyces cerevisiae*: Effects of L-A RNA, 5' cap, and 3' poly(A) tail on translational efficiency of mRNAs," Methods 11, 353-360 (1997).
Iskakova MB, et al,. 2006. Troubleshooting coupled in vitro transcription-translation system derived from *Escherichia coli* cells: Synthesis of high-yield fully active proteins. Nucleic Acids Res 34(19), e135 (2006).
Jackson, R. J. et al. In Methods Enzymol vol. 96 (eds. Becca Fleischer, Sidney Fleischer) Ch. 4, 50-74 (Academic Press, 1983).
Jewett, M. C. et al., "Mimicking the *Escherichia coli* cytoplasmic environment activates long-lived and efficient cell-free protein synthesis." Biotechnol Bioeng 86, 19-26 (2004).
Jewett, M. C. et al., "An integrated cell-free metabolic platform for protein production and synthetic biology.," Mol Syst Biol 2008, 4 (2008).
Jewett, M. C. et al., "In vitro integration of ribosomal RNA synthesis, ribosome assembly, and translation," Mol. Syst. Biol. 9, 678 (2013).
Kanter, G. et al. "Cell-free production of scFv fusion proteins: An efficient approach for personalized lymphoma vaccines," Blood 109, 3393-3399, (2007).
Kim D-M, et al., "Prolonging cell-free protein synthesis by selective reagent additions." Biotechnol Prog 16(3), 85-390 (2000).
Kim, R. G. et al., "Expression-independent consumption of substrates in cell-free expression system from *Escherichia coli*." J Biotechnol 84, 27-32, (2000).

(56) References Cited

OTHER PUBLICATIONS

Kovtun, O. et al. "Towards the construction of expressed proteomes using a Leishmania tarentolae based cell-free expression system," PLoS One 5, e14388 (2010).

Kozak, M., "An analysis of 5'-noncoding sequences from 699 vertebrate messenger RNAs," Nucleic Acids Res. 15, 8125-8148 (1987).

Kubick, S et al. In Current Topics in Membranes, vol. 63 (ed. Larry DeLucas) 25-49 (Academic Press, 2009).

Kurata, S. et al. "Ribosome recycling step in yeast cytoplasmic protein synthesis is catalyzed by eEF3 and ATP," Proc. Natl. Acad. Sci. U.S.A. 107, 10854-10859 (2010).

Leader, B., et al., "Protein therapeutics: A summary and pharmacological classification." Nat Rev Drug Discov 7, 21-39 (2008).

Liu, D. V. et al. "Streamlining Escherichia coli S30 extract preparation for economical cell-free protein synthesis," Biotechnol Prog 21, 460-465 (2005).

Madin, K. et al. "A highly efficient and robust cell-free protein synthesis system prepared from wheat embryos: Plants apparently contain a suicide system directed at ribosomes," Proc. Natl. Acad. Sci. U.S.A. 97, 559-564 (2000).

Merk, H. et al. "Cell-free synthesis of functional and endotoxin-free antibody Fab fragments by translocation into microsomes," Biotechniques 53, 153-160 (2012).

Michel-Reydellet N, et al., "Increasing PCR fragment stability and protein yields in a cell-free system with genetically modified Escherichia coli extracts." J Mol Microbiol Biotechnol 9(1), 26-34 (2005).

Mikami, S. et al. In Cell-Free Protein Production vol. 607 Methods in Molecular Biology (eds. Yaeta Endo, Kazuyuki Takai, & Takuya Ueda) Ch. 5, 43-52 (Humana Press, 2010).

Mureev, S. et al. "Species-independent translational leaders facilitate cell-free expression," Nat. Biotechnol. 27, 747-752 (2009).

Narang et al., "Improved Phosphotriester Method forthe Synthesis of Gene Fragments" Meth. Enzymol. 68:90-99 (1979).

Nielsen, J. et al. "Impact of systems biology on metabolic engineering of Saccharomyces cerevisiae," FEMS Yeast Res. 8, 122-131 (2008).

Owczarzy et al., "Predicting Stability of DNA Duplexes in Solutions Containing Magnesium and Monovalent Cations" Biochemistry, 47, 5336-5353 (2008).

Pogany, J. et al. "Authentic replication and recombination of tomato bushy stunt virus RNA in a cell-free extract from yeast," J. Virol. 82, 5967-5980 (2008).

Record Jr, M. T., et al., "Biophysical compensation mechanisms buffering E. coli protein-nucleic acid interactions against changing environments." Trends Biochem Sci 23, 190-194, (1998).

Rothblatt, J. A. et al. "Secretion in yeast: Reconstitution of the translocation and glycosylation of alpha-factor and invertase in a homologous cell-free system," Cell 44, 619-628 (1986).

* cited by examiner

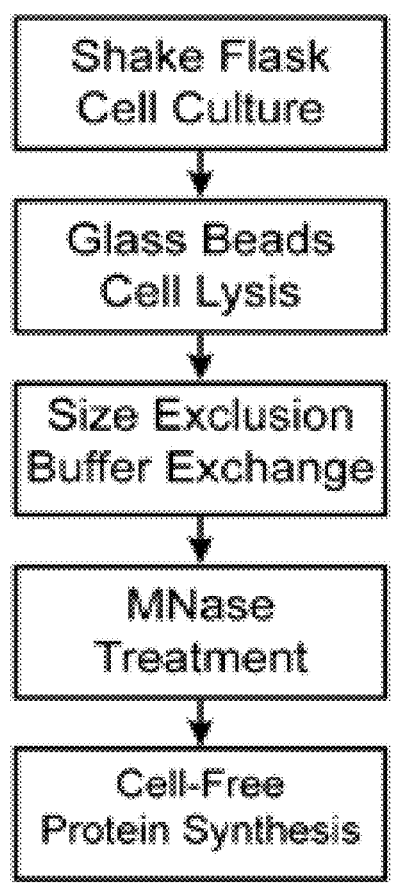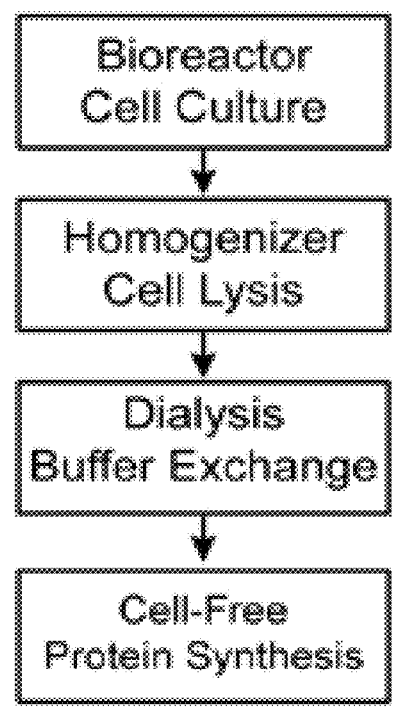
FIG. 1(A-B)

| Construct | ←5' UTR→ | ← ORF → | ← 3' UTR → | ← PolyA → | SEQ ID NO: |
|---|---|---|---|---|---|
| CappA90 | Cap analog | luciferase | None | 90 | 1 |
| HAPpA90 | HAP270 | luciferase | None | 90 | 2 |
| TFIIDpA90 | TFIID | luciferase | None | 90 | 3 |
| p150pA90 | p150 | luciferase | None | 90 | 4 |
| YAP1pA90 | YAP1 | luciferase | None | 90 | 5 |
| IGRpA90 | IGR | luciferase | None | 90 | 6 |
| A64pA90 | PolyA64 | luciferase | None | 90 | 7 |
| HedrinpA90 | Polyhedrin | luciferase | None | 90 | 8 |
| ΩpA90 | Ω | luciferase | None | 90 | 9 |
| TEVpA90 | TEV | luciferase | None | 90 | 10 |
| TbmpA90 | CfTbm | luciferase | None | 90 | 11 |
| ΩpA25 | Ω | luciferase | None | 25 | 12 |
| ΩpA50 | Ω | luciferase | None | 50 | 13 |
| ΩpA170 | Ω | luciferase | None | 170 | 14 |
| ΩFBAL | Ω | luciferase | FBA1 1465nt | 0 | 15 |
| ΩFBAS | Ω | luciferase | FBA1 659nt | 0 | 16 |
| ΩTMV13U200 | Ω | luciferase | TMV13U 200nt | 0 | 17 |
| ΩTMV13U400 | Ω | luciferase | TMV13U 400nt | 0 | 18 |
| ΩTMV13U700 | Ω | luciferase | TMV13U 700nt | 0 | 19 |
| ΩTMV23U | Ω | luciferase | TMV23U | 0 | 20 |
| ΩN3U | Ω | luciferase | None | 0 | 21 |
| N5UpA90 | None | luciferase | None | 90 | 22 |
| ΩpA | Ω | luciferase | None | 0 | 23 |
| Luc | None | luciferase | None | 0 | 24 |

FIG. 2

METHODS FOR CELL-FREE PROTEIN SYNTHESIS

CROSS-REFERENCE TO RELATED APPLICATIONS

This application claims benefit of priority to U.S. provisional application No. 61/792,290, filed on Mar. 15, 2013, which is incorporated by reference in its entirety.

SEQUENCE LISTING

The instant application contains a Sequence Listing, which has been submitted in ASCII format via EFS-Web and is hereby incorporated by reference in its entirety. Said ASCII copy, created on Mar. 14, 2014, is named NWN01-035-US_ST25.txt, and is 212,736 bytes in size.

FIELD OF THE INVENTION

This invention pertains to cell-free protein synthesis systems and methods of using the same for producing in vitro protein materials in high yield.

BACKGROUND OF THE INVENTION

Cell-free protein synthesis (CFPS) platforms have emerged as a powerful technology for protein expression. Prominent applications include the production of pharmaceutical proteins and vaccines (Goerke, A. R. et al. "Development of cell-free protein synthesis platforms for disulfide bonded proteins," *Biotechnol. Bioeng.* 99, 351-367 (2008); Kanter, G. et al. "Cell-free production of scFv fusion proteins: An efficient approach for personalized lymphoma vaccines," *Blood* 109, 3393-3399, (2007); Stech, M. et al. "Production of functional antibody fragments in a vesicle-based eukaryotic cell-free translation system," *J. Biotechnol.* 164, 220-231 (2012); Yang, J. et al. "Rapid expression of vaccine proteins for B-cell lymphoma in a cell-free system," *Biotechnol. Bioeng.* 89, 503-511 (2005); Yin, G. et al. "Aglycosylated antibodies and antibody fragments produced in a scalable in vitro transcription-translation system," *MAbs* 4, 217-225 (2012); Zawada, J. F. et al. "Microscale to manufacturing scale-up of cell-free cytokine production—a new approach for shortening protein production development timelines," *Biotechnol. Bioeng.* 108, 1570-1578 (2011)). Such systems enable expression in vitro of proteins that are difficult to produce in vivo, as well as high-throughput production of protein libraries for protein evolution, functional genomics, and structural studies (Madin, K. et al. "A highly efficient and robust cell-free protein synthesis system prepared from wheat embryos: Plants apparently contain a suicide system directed at ribosomes," *Proc. Natl. Acad. Sci. U.S.A.* 97, 559-564 (2000); Takai, K et al. "Practical cell-free protein synthesis system using purified wheat embryos," *Nat. Protoc.* 5, 227-238 (2010)). Prokaryotic *Escherichia coli* extract based cell-free systems have developed rapidly (for a review, see Carlson, E. D. et al. "Cell-free protein synthesis: Applications come of age," *Biotechnol. Adv.* 30, 1185-1194, (2012)). Yet an integrated eukaryotic platform with similar productivity, scalability, protein folding capability, and cost effectiveness has lagged behind.

The major eukaryotic CFPS platforms previously developed include systems made from wheat germ extract (WGE) (Goshima, N. et al. "Human protein factory for converting the transcriptome into an in vitro-expressed proteome," *Nat. Methods* 5, 1011-1017 (2008); Hoffmann, M. et al. in *Biotechnol Annu Rev* Vol. 10, 1-30 (Elsevier, 2004); Takai et al. (2010)), rabbit reticulocyte lysate (RRL) (Jackson, R. J. et al. in *Methods Enzymol* Vol. Vol. 96 (eds. Becca Fleischer, Sidney Fleischer) Ch. 4, 50-74 (Academic Press, 1983)); insect cell extract (ICE) (Ezure, T et al. "A cell-free protein synthesis system from insect cells," *Methods Mol. Biol.* 607, 31-42 (2010); Kubick, S et al. in *Current Topics in Membranes*, Vol. 63 (ed. Larry DeLucas) 25-49 (Academic Press, 2009); Tarui, H. et al. "Establishment and characterization of cell-free translation/glycosylation in insect cell (*Spodoptera frugiperda* 21) extract prepared with high pressure treatment," *Appl. Microbiol. Biotechnol.* 55, 446-453 (2001)); *Leishmania tarentolae* extract (Kovtun, O. et al. "Towards the construction of expressed proteomes using a *Leishmania tarentolae* based cell-free expression system," *PLoS One* 5, e14388 (2010); Mureev, S. et al. "Species-independent translational leaders facilitate cell-free expression," *Nat. Biotechnol.* 27, 747-752 (2009)); and HeLa and hybridoma cell extract (Mikami, S. et al. in *Cell-Free Protein Production* Vol. 607 *Methods in Molecular Biology* (eds. Yaeta Endo, Kazuyuki Takai, & Takuya Ueda) Ch. 5, 43-52 (Humana Press, 2010)).

Compared to the *E. coli* system, these methods have advantages for producing some types of complex proteins and can achieve post-translational modifications not found in bacteria (Chang, H.-C. et al. "De novo folding of GFP fusion proteins: High efficiency in eukaryotes but not in bacteria," *J. Mol. Biol.* 353, 397-409 (2005)). Insect cell-extract systems, for example, have demonstrated acetylation and N-myristoylation (Suzuki, T. et al. "N-terminal protein modifications in an insect cell-free protein synthesis system and their identification by mass spectrometry," *Proteomics* 6, 4486-4495 (2006)); isoprenylation (Suzuki, T. et al. "Protein prenylation in an insect cell-free protein synthesis system and identification of products by mass spectrometry," *Proteomics* 7, 1942-1950 (2007)); ubiquitination (Suzuki, T. et al. "Preparation of ubiquitin-conjugated proteins using an insect cell-free protein synthesis system," *J. Biotechnol.* 145, 73-78 (2010)), core glycosylation (Merk, H. et al. "Cell-free synthesis of functional and endotoxin-free antibody Fab fragments by translocation into microsomes," *Biotechniques* 53, 153-160 (2012); Tarui et al. (2001)); disulfide bond formation in single chain antibody fragments (Stech et al. (2012)); and significant advances in expression and modification of membrane bound proteins (Kubick et al. (2009)). However, eukaryotic cell-free platforms often have limited batch protein yields (Carlson et al. (2012)), or depend on costly and inefficient continuous exchange reactions that do not scale commercially (Zawada et al. (2011)). Furthermore, eukaryotic CFPS systems are generally limited by laborious and expensive extract preparation methods. For example, WGE, which is the most common eukaryotic system, requires lengthy preparation steps that include grinding, sieving, extensive washing, and eye selection of the embryo to ensure the embryo is in the proper stage of development (Takai et al. (2010)). An additional challenge of this approach is that approximately 5 mL of active extract is produced from 5 to 6 kg of starting material after 4 to 5 days of processing (Id.) In contrast, *E. coli* can be processed quickly and under precise growth conditions to develop a highly active and robust CFPS platform, where 60 g of cells (wet weight) can be converted to 120 mL of extract in only 4-6 hours of preparation (Liu, D. V. et al. "Streamlining *Escherichia coli* S30 extract preparation for economical cell-free protein synthesis," *Biotechnol Prog* 21, 460-465 (2005)). The above limitations motivate the need for a new eukaryotic CFPS platform that is robust, easy to prepare, highly active, and amenable to economical scale-up.

S. cerevisiae, like E. coli, is a microbe that can be grown quickly under precise conditions in either a bioreactor or shake flasks. Furthermore, S. cerevisiae as a eukaryotic organism is suited to fold eukaryotic proteins and has previously shown some ability for post-translational modifications in vitro, such as glycosylation (Rothblatt, J. A. et al. "Secretion in yeast: Reconstitution of the translocation and glycosylation of alpha-factor and invertase in a homologous cell-free system," Cell 44, 619-628 (1986)). Because it is a model organism for molecular study, S. cerevisiae is well understood at the biochemical level, has a wealth of documented "omics" that can prove useful when trying to characterize a cell-free system, and genetic tools are readily available for facile changes to the host strain (Nielsen, J. et al. "Impact of systems biology on metabolic engineering of Saccharomyces cerevisiae," FEMS Yeast Res. 8, 122-131 (2008)). S. cerevisiae is also an important bio-manufacturing production platform and accounted for 18.5% of all FDA and EMA licensed recombinant protein biopharmaceuticals as of January 2009 (Ferrer-Miralles, N., et al. "Microbial factories for recombinant pharmaceuticals," Microb. Cell. Fact. 8, 17 (2009)).

Despite these attractive features, yeast based CFPS systems have not been extensively developed as a protein synthesis platform since their origin in the 1970s and early 1980s (Gasior, E. et al. "The analysis of intermediary reactions involved in protein synthesis, in a cell-free extract of Saccharomyces cerevisiae that translates natural messenger ribonucleic acid," J. Biol. Chem. 254, 3970-3976 (1979); Gasior, E. et al. "The preparation and characterization of a cell-free system from Saccharomyces cerevisiae that translates natural messenger ribonucleic acid," J. Biol. Chem. 254, 3965-3969 (1979)). Instead, the majority of research involving yeast cell-free translation systems has focused on investigating translation from a fundamental perspective, such as elucidating cap-dependent translation (Iizuka, N. et al. "Cap-dependent and cap-independent translation by internal initiation of mRNAs in cell extracts prepared from Saccharomyces cerevisiae," Mol. Cell. Biol. 14, 7322-7330 (1994); Iizuka, N. & Sarnow, P. "Translation-competent extracts from Saccharomyces cerevisiae: Effects of L-A RNA, 5' cap, and 3' poly(A) tail on translational efficiency of mRNAs," Methods 11, 353-360 (1997)) and characterizing translation initiation factors (Algire, M. A. et al. "Development and characterization of a reconstituted yeast translation initiation system," RNA 8, 382-397 (2002); Hinnebusch, A. G., et al. "Mechanism of translation initiation in the yeast Saccharomyces cerevisiae," pp. 225-268 in Translational Control in Biology and Medicine, (eds. M. B. Mathews, N. Sonenberg and J. W. B. Hershey) (Cold Spring Harbor Laboratory Press, Cold Spring Harbor, N.Y. (2007); Kurata, S. et al. "Ribosome recycling step in yeast cytoplasmic protein synthesis is catalyzed by eEF3 and ATP," Proc. Natl. Acad. Sci. U.S.A. 107, 10854-10859 (2010); Saini, P. et al. "Hypusine-containing protein eIF5A promotes translation elongation," Nature 459, 118-121 (2009); Thompson, S. R. et al. "Internal initiation in Saccharomyces cerevisiae mediated by an initiator tRNA/eIF2-independent internal ribosome entry site element," Proc. Natl. Acad. Sci. U.S.A 98, 12972-12977 (2001)). Despite this focus, some recent work has shown the potential to use yeast CFPS for making proteins of interest, such as virus-like particles (Wang, X. et al. "An optimized yeast cell-free system: Sufficient for translation of human papillomavirus 58 L1 mRNA and assembly of virus-like particles," J. Biosci. Bioeng. 106, 8-15 (2008); Wang, X. et al. "Translational comparison of HPV58 long and short L1 mRNAs in yeast (Saccharomyces cerevisiae) cell-free system," J. Biosci. Bioeng. 110, 58-65 (2010)) and additional viral proteins (Pogany, J. et al. "Authentic replication and recombination of tomato bushy stunt virus RNA in a cell-free extract from yeast," J. Virol. 82, 5967-5980 (2008)).

BRIEF SUMMARY OF THE INVENTION

In first aspect, a cell-free protein synthesis platform for preparing protein from a translation template is disclosed. The cell-free protein synthesis platform includes (a) a Saccharomyces cerevisiae cellular extract, (b) a reaction buffer, and (c) the translation template. The Saccharomyces cerevisiae cellular extract is prepared from mid-exponential to late-exponential batch cultures in the range from about 6 $OD_{600}$ to about 18 $OD_{600}$ or fed-batch cultures harvested in mid-exponential to late-exponential phase.

In a second aspect, a cell-free protein synthesis platform for preparing protein from a transcription template is disclosed. The cell-free protein synthesis platform includes (a) a Saccharomyces cerevisiae cellular extract, (b) a reaction buffer, (c) an RNA polymerase, and (d) the transcription template. The Saccharomyces cerevisiae cellular extract is prepared from mid-exponential to late-exponential cultures in the range from about 6 $OD_{600}$ to about 18 $OD_{600}$. The RNA polymerase is capable of transcribing the transcription template to form a translation template and the Saccharomyces cerevisiae cellular extract can sustain protein synthesis through a combined transcription/translation reaction.

In a third aspect, a method of performing high-throughput protein synthesis in vitro is disclosed. The method includes several steps. The first step is providing a source nucleic acid. The second step is preparing a transcription template from the source nucleic acid. The third step is synthesizing protein in vitro using a cell-free protein synthesis platform utilizing the transcription template. The cell-free protein synthesis platform comprises (i) a Saccharomyces cerevisiae cellular extract, (ii) a reaction buffer, and (iii) an RNA polymerase. The Saccharomyces cerevisiae cellular extract is prepared from mid-exponential to late-exponential cultures in the range from about 6 $OD_{600}$ to about 18 $OD_{600}$. The RNA polymerase is capable of transcribing from the transcription template to form the translation template, and the Saccharomyces cerevisiae cellular extract can sustain protein synthesis through a combined transcription/translation reaction.

BRIEF DESCRIPTION OF THE FIGURES

FIG. 1A depicts a schematic of an exemplary prior art method for yeast extract preparation and CFPS system.

FIG. 1B depicts a schematic of the disclosed innovative method for yeast extract preparation and CFPS system.

FIG. 2 depicts exemplary expression constructs (SEQ ID NOS:1-24) to evaluate the effects of 5'-UTR and 3'-UTR elements in the DNA transcription template.

Values show means with error bars representing standard deviations (s.d.) of at least 3 independent experiments.

Figure 12A:
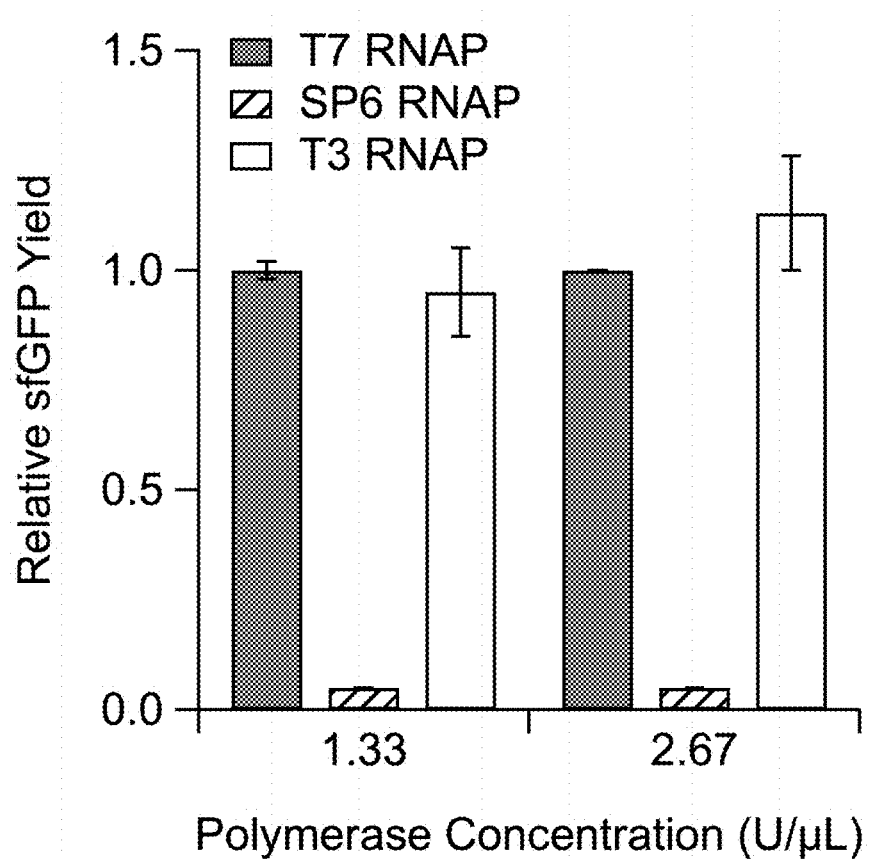

FIG. 12A depicts commercially available RNAP (New England Biolabs, Ipswitch, Mass.) from bacteriophage SP6 and T3 were compared to the established T7 RNAP for activity in yeast CFPS reactions. Values are displayed relative to T7 RNAP at the given concentration. Values represent means with error bars displaying high and low values of 2 independent experiments.

Figure 12B:
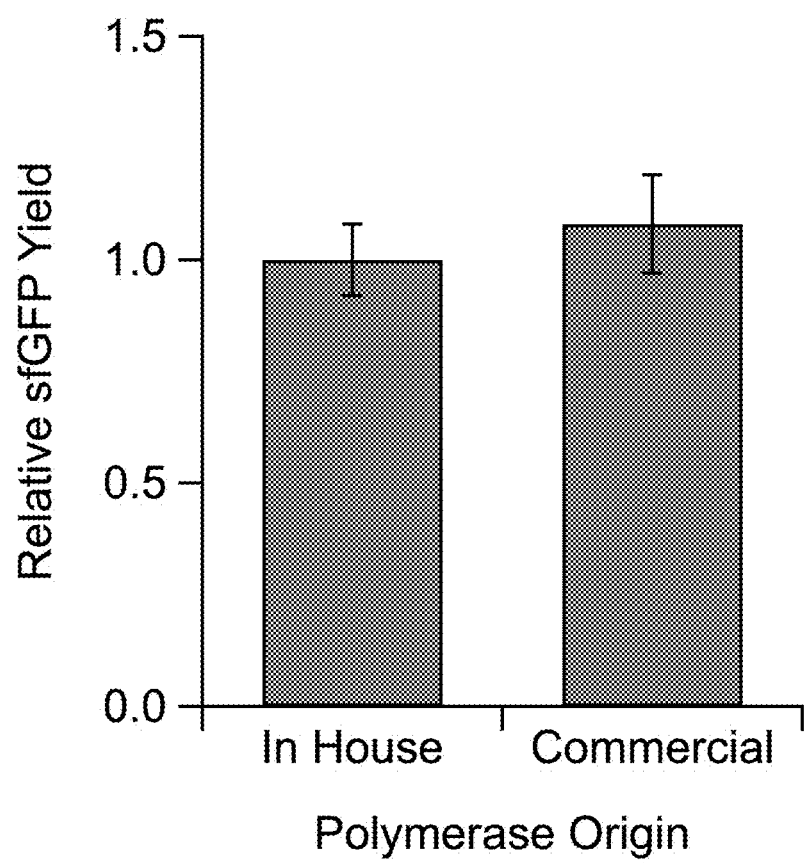

FIG. 12B depicts an exemplary comparison of T7 RNAP that is commercially available to T7 RNAP prepared in house. Values are displayed relative to T7 RNAP prepared in house. Values represent means with error bars displaying high and low values of 2 independent experiments.

Figure 13A:
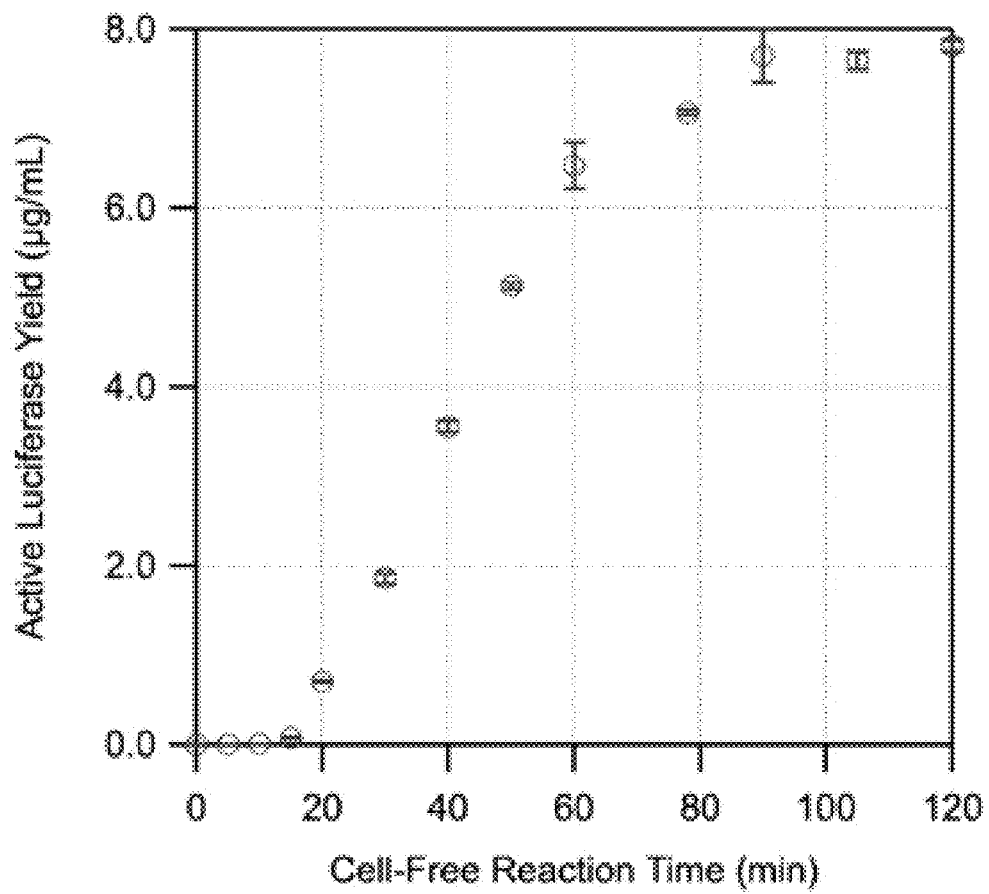

FIG. 13A depicts synthesis of active luciferase over the course of a batch reaction. Fifteen μL batch reactions were prepared in different tubes for each time point and sampled for active luciferase yield.

Figure 13B:
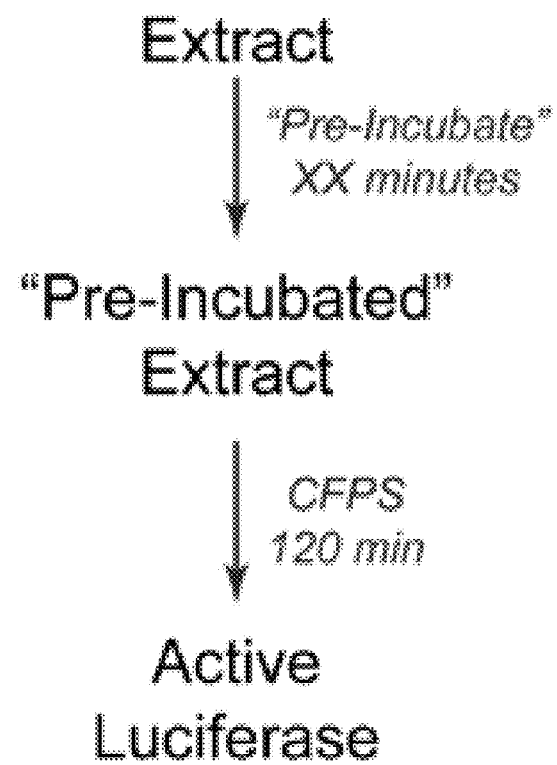

FIG. 13B illustrates an exemplary experimental design schematic of "pre-incubation" experiments.

Figure 13C:
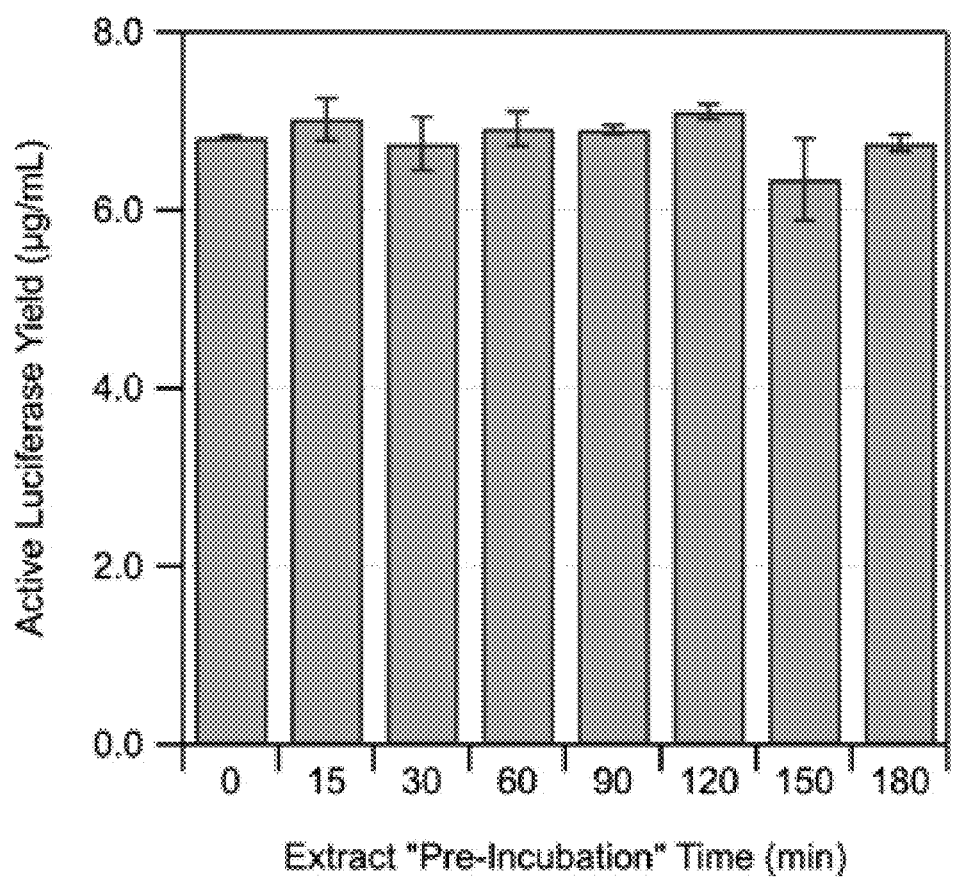

FIG. 13C depicts active luciferase yield from extracts pre-incubated for the specified time. Values show means with error bars representing standard deviations (s.d.) of at least 3 independent experiments.

DETAILED DESCRIPTION OF THE INVENTION

A novel cell-free protein synthesis (CFPS) platform from yeast extract is disclosed. The platform provides a 250-fold increase in protein synthesis yield and 2000-fold reduction in protein synthesis cost over extant prior art methods. The new platform displays robust protein synthesis from combined transcription-translation systems having the capability of efficiently utilizing linear transcription templates as input substrates. These improvements have direct implications for high-throughput protein expression, industrial synthesis of pharmaceutical or biotechnological relevant proteins, bench-top laboratory protein expression using an in vitro protein expression kit, protein expression for crystallography and proteomics.

DEFINITIONS

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where $n$ is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases.

Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, the term "cap" (or "5'-cap") refers to a chemical modification of the 5'-terminus of a translation template. A cap for eukaryotic translation templates can include a guanine nucleotide connected to the mRNA via a 5' to 5' triphosphate linkage ("5',5'-GpppG" or "G(5')ppp(5')G"). The N-7 position guanine cap can methylated ("m$^7$GpppG" or "m$^7$G(5)ppp(5')G"). Translation templates that include cap can be designated by 5',5'-GpppG-, G(5')ppp(5')G-, m$^7$G(5')ppp(5')G- or m$^7$GpppG-translation templates.

As used herein, "cap-dependent," as the term modifies "translation" or "translation template," refers to the requirement of the translation template to include a 5'-cap for efficient protein synthesis from that translation template.

As used herein, "cap-independent," as the term modifies "translation" or "translation template," refers to the lack of a requirement that the translation template include a 5'-cap for efficient protein synthesis from that translation template.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer. A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Preparation of Active Yeast Cellular Extract Using Scalable Techniques

Because CFPS exploits an ensemble of catalytic proteins prepared from the crude lysate of cells, the cell extract (whose composition is sensitive to growth media, lysis method, and processing conditions) is the most critical component of extract-based CFPS reactions.

Yeast extracts for CFPS platforms disclosed herein can be prepared in a variety of ways. FIG. 1A depicts a scheme for making yeast extracts using a prior art procedure based upon the method of Sarnow and coworkers (Iizuka et al. (1994); Iizuka & Sarnow (1997)). FIG. 1B depicts the innovative method disclosed herein for producing extracts. The disclosed method can include three steps: (1) expanding a yeast cell culture in a bioreactor; (2) performing mechanical lysis of the cells by high-pressure homogenization; (3) performing a buffer exchange to generate the resultant extracts for the CFPS platform. Tangential flow filtration can be used to generate the resultant extract, where CFPS platforms are prepared on a large-scale process in industry. In most cases, however, dialysis is preferred in part for ease of use where CFPS platforms are prepared on a smaller-scale process in the laboratory.

The composition of the cellular machinery at the time of harvest can directly affect the CFPS potential of the crude extract. Historically, yeast cells used for cell-free translation experiments have been harvested in early exponential phase (for examples, 1.5 OD$_{600}$ or 3-5 OD$_{600}$). Recovery of yeast cells during growth at mid-exponential to late-exponential phase (for example, a range from about 6 OD$_{600}$ to about 18 OD$_{600}$) can provide surprising benefits for translation using yeast extract-based CFPS platforms. For example, source cells for the yeast extracts disclosed herein can be obtained from mid-exponential to late-exponential batch cultures in the range from about 6 OD$_{600}$ to about 18 OD$_{600}$ or fed-batch cultures harvested in mid-exponential to late-exponential phase. Since the cells are rapidly dividing in this phase, they have a highly active translation machinery. Moreover, from a scaling standpoint, the ability to harvest at a later optical density can allow for larger cell mass recovery per fermentation, thereby leading to a larger volume of total crude extract prepared per fermentation for improved overall system economics. Typically, 1 L of cell culture yields about 6 g of wet cell mass when harvested at 12 OD$_{600}$ compared to ~1.5 g of wet cell mass when harvest at 3 OD$_{600}$. Subsequently, 1 g of wet cell mass leads to ~2 mL of crude extract.

Yeast culturing techniques and culture media are well known in the art. Exemplary yeast culture media include YPD media (yeast extract (10 g/l), bacto-peptone (20 g/l; Difco) and dextrose (20 g/l), adjusted to pH5.5) and YPAD media (yeast extract (10 g/l), bacto-peptone (20 g/l; Difco), dextrose (20 g/l) and adenine hemisulfate (30 mg/l), adjusted to pH5.5). For *Saccharomyces cerevisiae* cellular extracts prepared from the mid-exponential to late-exponential cultures having a range of about 6 OD$_{600}$ to about 18 OD$_{600}$, the yeast cells were cultured in YPAD media. Other yeast culture media, including variations of YPD and YPAD, as well as synthetic dextrose, which is composed of 6.7 g L$^{-1}$ Yeast Nitrogen Base (YNB) (Sigma-Aldrich, St. Louis, Mo.), 20 g L$^{-1}$ glucose and 50 mM potassium phosphate buffer, pH 5.5, and its variations, can be used to culture the source *Saccharomyces cerevisiae* cells for the preparation of the crude yeast extracts for the CFPS systems, platforms and reactions disclosed herein.

Furthermore, a step of adding inorganic phosphate to the growth media can increase protein synthesis capability for extracts generated. Typically, cells can be grown in media containing any source of inorganic phosphate, such as potassium phosphate, sodium phosphate, magnesium phosphate, calcium phosphate, among others, including mixed metal phosphates (for example, sodium potassium phosphate). Preferred concentrations of inorganic phosphate range from about 15 mM to about 250 mM, including about 50 mM, about 75 mM, about 100 mM, about 125 mM and about 150 mM, among other concentrations within this range. Without the claimed subject matter being bound to any particular theory, the addition of phosphate to the growth media can reduce phosphatase expression in the cells during growth that can stabilize nucleoside triphosphate (NTP) concentrations during the cell-free reaction using cellular extracts prepared from such cells.

CFPS Reaction Conditions for Translation-Only Reactions with Yeast S30 and S60 Extracts The ionic composition and temperature can have a profound effect on the efficiency and robustness of many protein-nucleic acid interactions and the proper function of protein biosynthesis. Altering the physicochemical environment of the CFPS reaction to better mimic the cytoplasm can improve protein synthesis activity. The following parameters can be considered alone or in combination with one or more other components to improve robust CFPS reaction platforms based upon crude yeast cellular extracts (for examples, yeast S30 and S60 extracts).

The temperature may be any temperature suitable for CFPS. Temperature may be in the general range from about 10° C. to about 40° C., including intermediate specific ranges within this general range, include from about 15° C.

to about 35° C., form about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C. Preferably, the reaction temperature can be about 21° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

The CFPS reaction preferably includes glutamate salts, NTPs, spermidine, putrescine, glycerol and magnesium.

Activating Combined Transcription and Translation Reactions in the CFPS Platform.

The present disclosure provides a novel transcription/translation system to circumvent the disadvantages associated with prior art eukaryotic CFPS platforms that rely exclusively upon exogenous RNA translation templates generated in separate costly and inefficient in vitro transcription reactions. According to one aspect, the present invention seeks to activate combined transcription and translation (Tx/Tl) in a one-pot reaction. The advantages of the combined transcription/translation (Tx/Tl) system in the CFPS platform include the following observations: (i) eliminates an extraneous processing step (in vitro transcription); (ii) removes the dependence of the reaction on the costly and potentially inhibitory $m^7G(5')ppp(5')G$ RNA cap structure analog; (iii) eliminates inconsistency issues with the capping reaction, a known problem for eukaryotic CFPS reactions (Takai et al. (2010)); and (iv) improves overall yields ~2-fold over cell-free translation only reactions when using a linear DNA template.

Consequently, a combined Tx/Tl system is preferred for the disclosed CFPS reactions. This leads to considerations of template requirements for carrying out combined transcription and translation.

(1) Translation Template Considerations (a) Optimization of 5'-UTR Elements

The CFPS strategy can leverage the use of certain translational elements in the untranslated region 5' (5'-UTR) of the open reading frame to be translated. In particular, a preferred translational element to include in the 5'-UTR include Internal Ribosome Entry Site (IRES) elements or cap-independent translation enhancer sequences to initiate translation. Such sequence elements can circumvent the need to utilize 5'-capped mRNA templates for efficient protein translation in the CFPS platforms.

To evaluate cap-independent translation initiation, 15 µL batch cell-free translation-only reactions were carried out at 24° C. for 1 h using different expression template constructs (see, for example, FIG. 2). These reactions were charged with 0.3 pmol purified in vitro transcribed luciferase mRNA having a 90-mer poly(A) tail. Initially, several yeast native internal ribosome entry site (IRES) sequences were evaluated, including the 5'-UTR of TFIID, HAP270, and YAP1 genes (Iizuka et al. (1994)), as well as the 5'-UTR of the gene TIF4631 that is the yeast homolog of the mammalian translation initiation factor eIF4G (the mRNA is called p150; see Verge, V. et al., "Localization of a promoter in the putative internal ribosome entry site of the *Saccharomyces cerevisiae* TIF4631 gene," *RNA* 10, 277-286 (2004); Edwards, S. R., and Wandless, T. J., "Dicistronic regulation of fluorescent proteins in the budding yeast *Saccharomyces cerevisiae,*" *Yeast* 27, 229-236 (2010)).

As a control, non-capped mRNAs harboring these different cap-independent translation leader sequences placed upstream of luciferase gene were compared to capped mRNA. Compared to capped luciferase mRNA, 5'-UTRs of HAP4 and TFIID showed low activities, while YAP1 and p150 did not direct translation (Table 1).

Certain non-native, viral cap-independent sequences were next considered. The Ω leader sequence (also referred to herein as "Ω leader," "Ω sequence," "Ω" or "Ω cap-independent translation enhancer") showed surprisingly high activity among all tested cap-independent translation sequences, outperforming the capped mRNA by almost 2-fold (Table 1). As the next best leader sequence, the polyhedrin 5'-UTR sequence was ~17% as efficient in initiating translation as capped mRNA (Table 1). The species-independent translational mRNA sequence A64pA90 showed a low efficiency of translation initiation. Finally, the intergenic region (IGR) IRES from cricket paralysis virus (CrPV), which initiates translation in yeast cells without initiation factors, was examined. Unfortunately, when compared to capped mRNA and mRNA harboring the Ω sequence, the CrPV IRES showed little activity in disclosed CFPS platform assay (Table 1). Thus, certain non-coding IRES elements function better than others in the disclosed CFPS platform for initiating combined Tx/Tl, wherein the Ω sequence proved superior to the other tested IRES elements or cap-independent translation enhancer sequences.

TABLE 1

The efficiency of cap-independent and IRES mediated yeast cell-free translation as compared to capped mRNA.

| Template[1] | Efficiency[2] |
|---|---|
| CappA90 (SEQ ID NO: 1) | 100 ± 20% |
| ΩpA90 (SEQ ID NO: 9) | 187 ± 13% |
| HedrinpA90 (SEQ ID NO: 8) | 17 ± 4% |
| A64pA90 (SEQ ID NO: 7) | 1.5 ± 0.2% |
| IGRpA90 (SEQ ID NO: 6) | <1 ± 0.02% |
| TFIIDpA90 (SEQ ID NO: 3) | <1 ± 0.07% |
| YAP1pA90 (SEQ ID NO: 5) | <1 ± 0.03% |
| p150pA90 (SEQ ID NO: 4) | <1 ± 0.08% |
| N5UpA90 (SEQ ID NO: 22) | 2 ± 0.3% |

[1]All templates include a luciferase coding sequence having a poly(A) tail of 90 nucleotides (pA90) (see FIG. 2). Cap—capped message. All other abbreviations described in the text.
[2]Efficiencies are normalized relative to the capped message (CappA90).

Figure 3A:
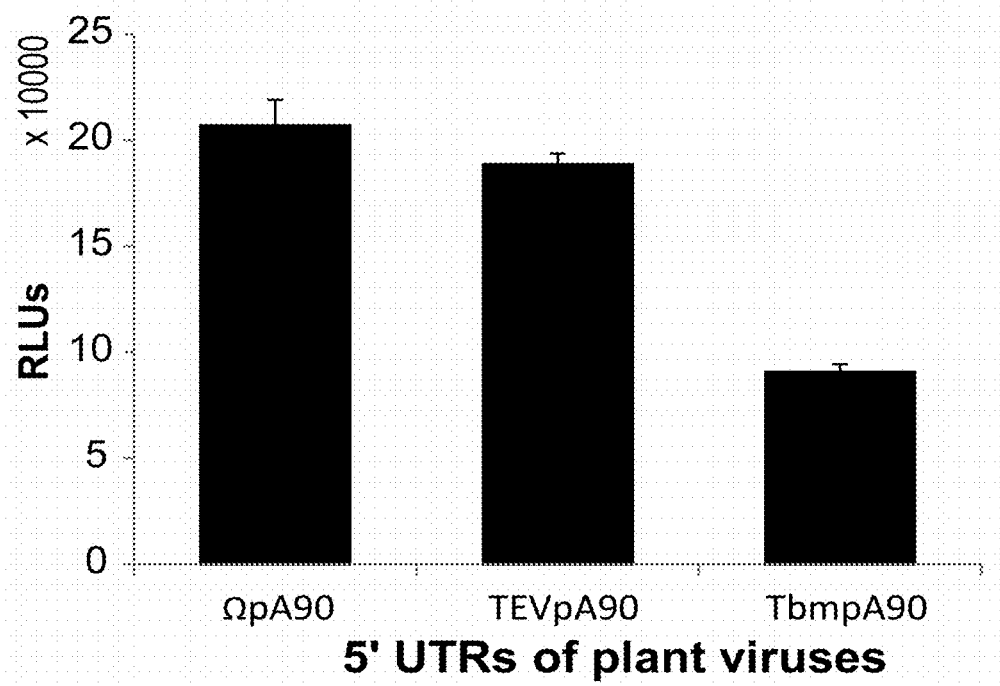
FIG. 3A depicts three 5'-UTRs from tobacco mosaic virus (Ω), tobacco etch virus (TEV), and tobamovirus (Tbm) were tested for the ability to enable translation initiation in combined yeast CFPS.

The 5'-UTRs from tobacco etch virus (TEV) and Crucifer-infecting tobamovirus (Tbm) were also evaluated. The TEV 5'-UTR showed ~5% lower activity than that of the Ω sequence; the activity of Tbm 5'-UTR is half of the Ω sequence (FIG. 3A).

Figure 3B:
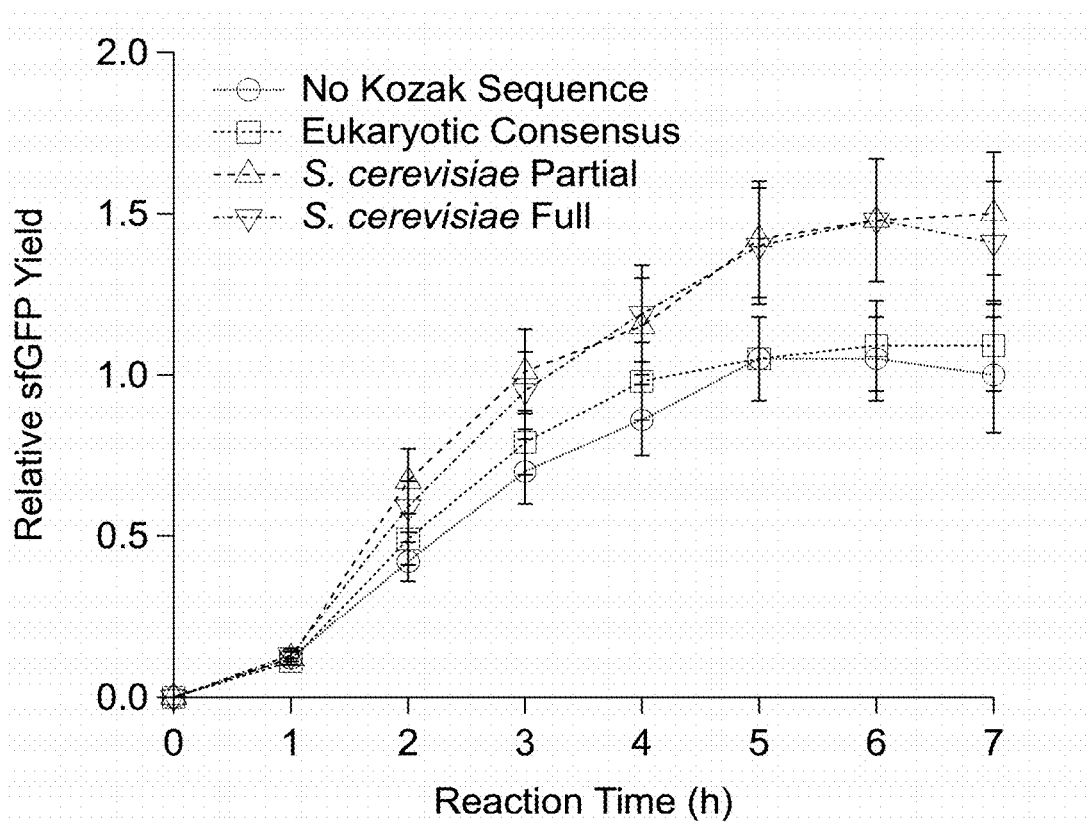
FIG. 3B depicts results of protein expression from templates that include Kozak sequences in yeast CFPS reactions. Yeast Tx/Tl CFPS reactions primed with PCR products containing the Ω sequence combined with variations of the Kozak sequence are compared over CFPS reaction lifetime. At the appropriate time point, 2 µL from each reaction were sampled and assayed for fluorescence intensity. Values show means with error bars representing high and low values of 2 independent experiments. Values are displayed relative to the final yield for a CFPS reaction without inclusion of any Kozak sequence.

Additionally, introduction of Kozak sequence elements in the 5'-UTR can lead to improved translation of expression templates. As shown in FIG. 3B, about a 40% improvement can be realized in sfGFP synthesis yields when different forms of the *S. cerevisiae* Kozak sequence are included in the 5'-UTR of expression templates.

(b) Optimization of 3'-UTR Elements

Figure 3C:
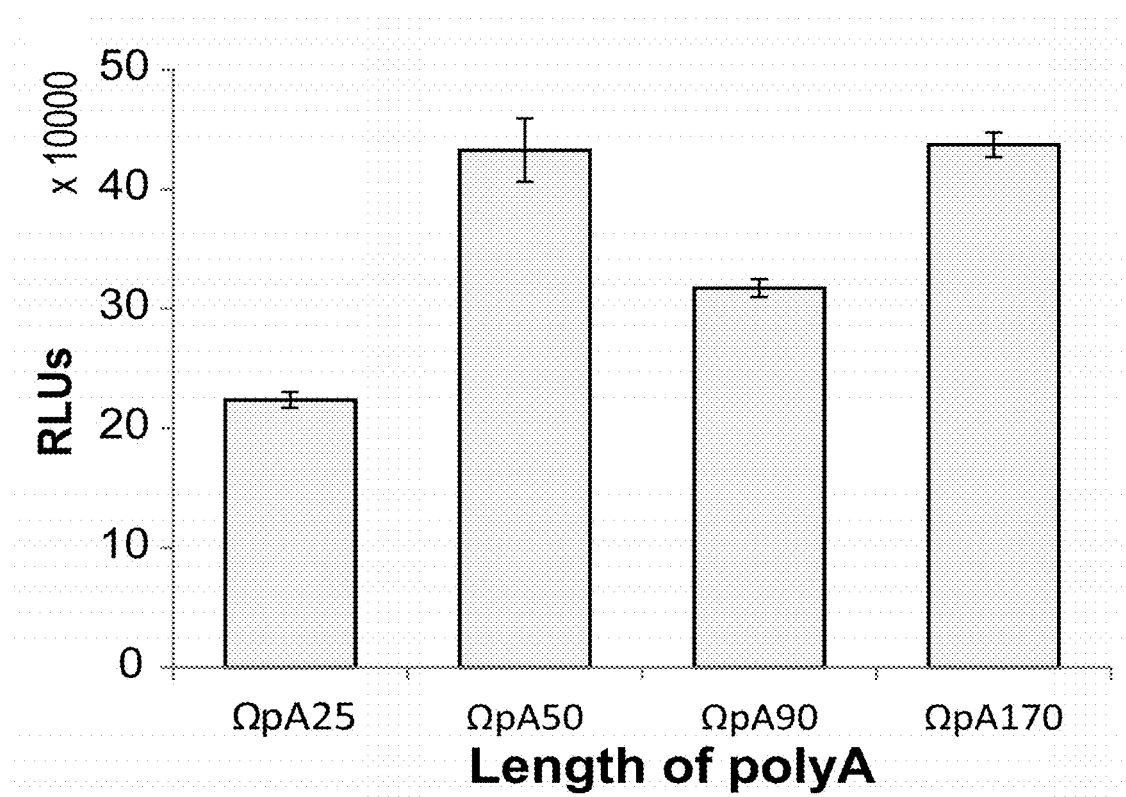
FIG. 3C depicts different lengths of Poly(A) tails, 25 nt, 50 nt, 90 nt, and 170 nt were tested for the ability to enable translation initiation in combined yeast CFPS.

Furthermore, the sequences found in the untranslated region 3' (3'-UTR) to the open reading frame to be translated can also affect translation. In particular, sequences that include poly(A)$_n$ tail can interact with Poly(A)-Binding Protein (PABP) to enhance protein synthesis and can promote enhance stability. The 3'-terminal poly(A)$_n$ sequence can include different lengths of adenosine residues, where $\underline{n}$ can range from about 20 to about 200. Different lengths of poly(A) tail were evaluated in the 3'-UTR of luciferase RNA transcripts for its ability to support efficient protein synthesis, wherein the 3'-terminal poly(A)$_n$ sequence had $\underline{n}$ of 25 nt, 50 nt, 90 nt and 170 nt. The length of poly(A) tail was optimized; 50 nt and 170 nt showed similar activities, while those of 90 nt and 25 nt showed 1.5~2-fold decrease in activity by comparison (FIG. 3C).

Figure 3D:
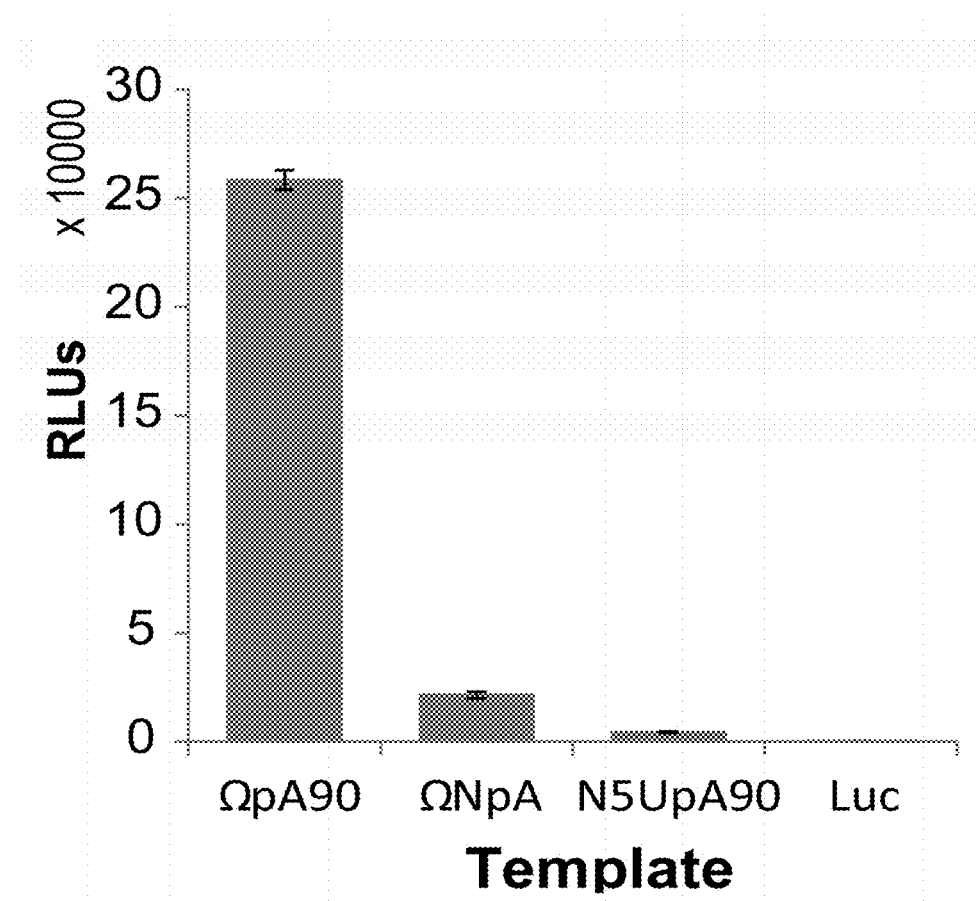
FIG. 3D depicts the effect of 5' Ω sequence and 3' poly(A) tail in cap-independent translation initiation of yeast CFPS demonstrates that both the leader sequence and poly(A) tail are required for efficient translation with Ω. The structures of the expression templates are shown in FIG. 2.

Notably, the poly(A) tail is essential for yeast CFPS. Without the poly(A) tail, luciferase synthesis is decreased to 8.3% of the complete template (FIG. 3D). After deletion of Ω, the protein yield decreased to 1.7%, with the protein yield decreased to 0.1% when missing both Ω and poly(A)90 tail (FIG. 3D).

Figure 3E:
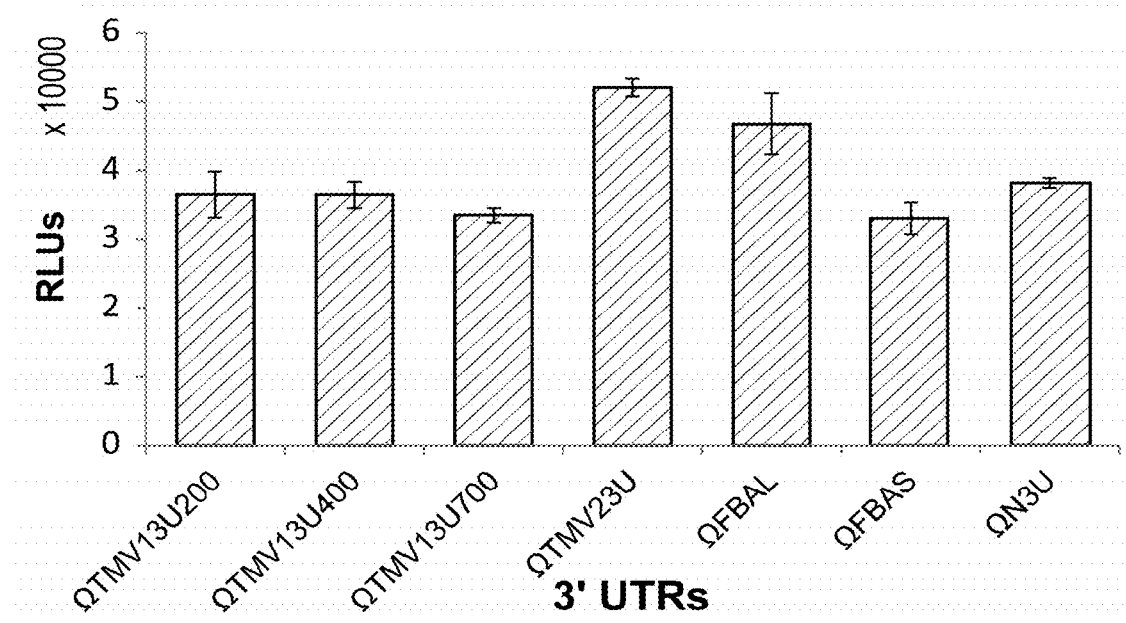
FIG. 3E The effect of various 3'-UTRs in combined yeast CFPS. Values show means with error bars representing standard deviations (s.d.) of at least 3 independent experiments. Luciferase data are presented in RLUs, or relative light units.

Finally, the contribution of various 3'-UTRs (for examples, SEQ ID NOs: 97, 98, 104, 106, 107 and 110) in combined Tx/Tl was investigated. As compared to the no 3'-UTR control, the protein yields of various 3'-UTRs changed slightly (86%-136%) (FIG. 3E). Notably, the overall system performance decreases in these experiments because the templates shown in FIG. 3E do not have poly(A) tails. These results suggest that 3'-UTRs in yeast CFPS have less functional importance than in other CFPS systems, such as the wheat germ CFPS.

(c) Optimization of Physiological Solutes in Combined Transcription-Translation Reactions with Yeast S60 Extract The combined Tx/Tl reactions from plasmid vectors equipped with the Ω leader sequence were specifically optimized using a yeast S60 extract as the CFPS platform. Specifically, a series of optimization experiments were conducted to explore the effect of temperature, DTT concentration, DNA template concentration, magnesium concentration, and nucleotide concentrations on batch Tx/Tl reactions. Excepting temperature, these variables were selected because they were newly required for the combined Tx/Tl system, as opposed to the translation only reactions described above. Notably, these variables are also interdependent, as has been observed before in the development of crude extract based CFPS systems. Here, trends for the aforementioned optimizations are disclosed with only a single variable deviating from the finalized solute concentrations as reported in Examples.

Figure 4A:
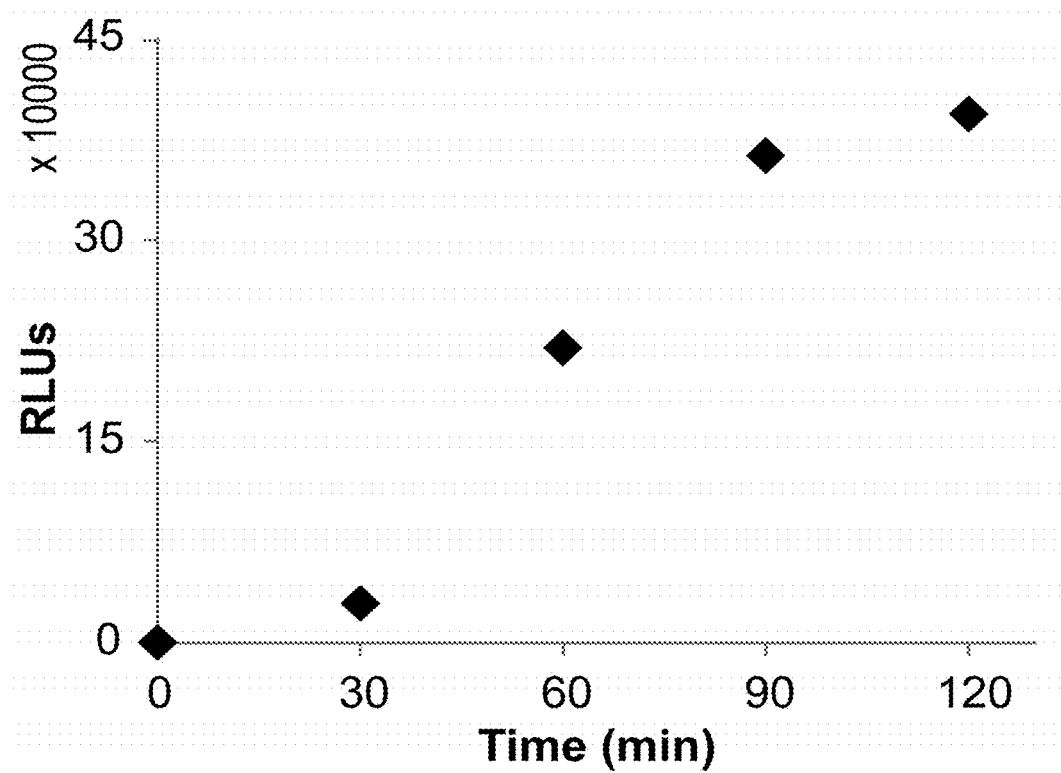
FIG. 4A depicts a time course for combined transcription and translation activated in yeast CFPS from the Ω leader sequence. Active luciferase synthesis is shown over the course of a standard batch reaction.
Figure 4B:
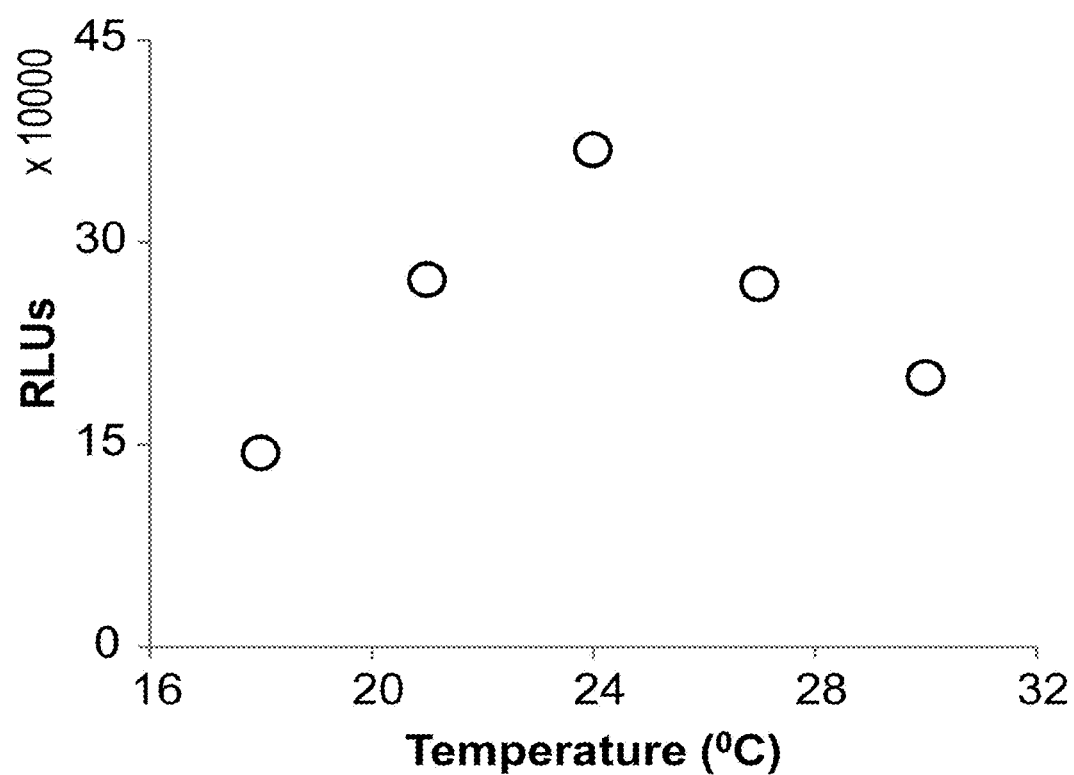
FIG. 4B depicts the physicochemical environment of the CFPS reaction was optimized by altering temperature. Values show means with error bars representing standard deviations (s.d.) of at least 3 independent experiments. Luciferase data are presented in RLUs, or relative light units.
Figure 4C:
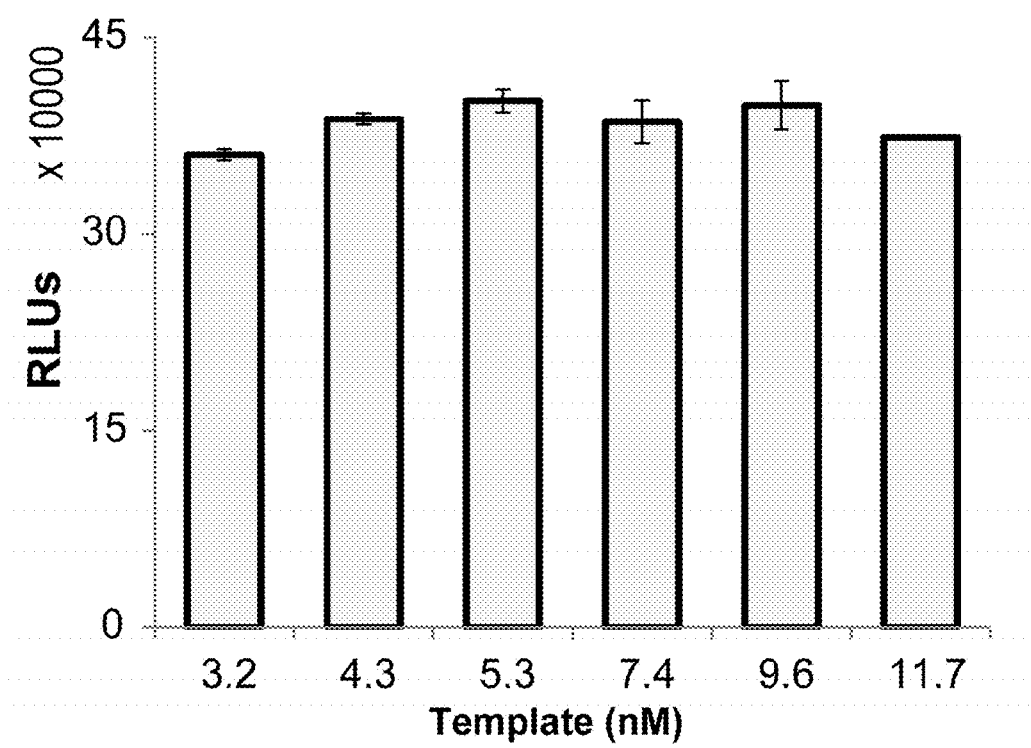
FIG. 4C depicts the physicochemical environment of the CFPS reaction was optimized by altering DNA template amount. Values show means with error bars representing standard deviations (s.d.) of at least 3 independent experiments. Luciferase data are presented in RLUs, or relative light units.
Figure 4D:
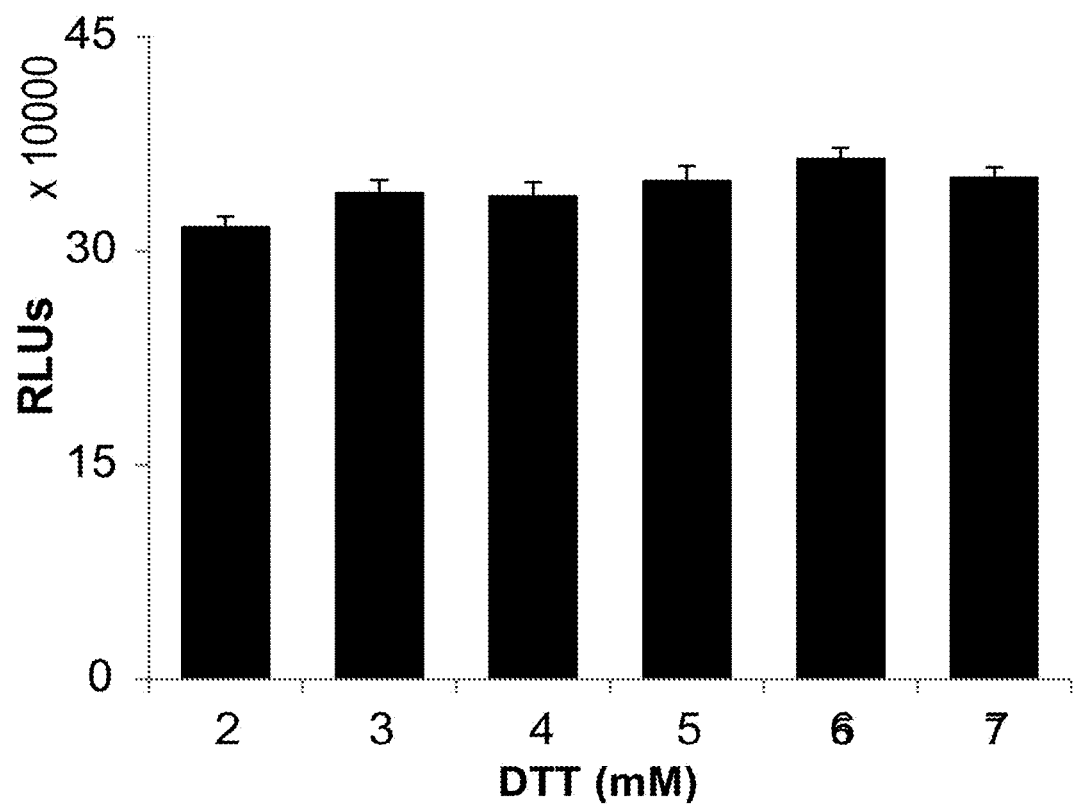
FIG. 4D depicts the physicochemical environment of the CFPS reaction was optimized by altering DTT concentration. Values show means with error bars representing standard deviations (s.d.) of at least 3 independent experiments. Luciferase data are presented in RLUs, or relative light units.

FIG. 4A shows active luciferase yield throughout the duration of a batch combined Tx/Tl reaction, monitored by samples taken at 0, 0.5, 1, 1.5, and 2 hours. The synthesis of luciferase shows slight lag during the first 0.5 h and then progresses linearly from 0.5-1.5 h, with reaction termination occurring by 2 hours. The lag in the first 30 minutes is possibly associated to a delay resulting from combining transcription and translation, and has been previously observed. The temperature optimum was observed to be approximately 24° C. (FIG. 4B). The combined Tx/Tl system was insensitive to template concentration above 3.2 nM, reaching saturation by ~5.3 nM (FIG. 4C). The system was also insensitive to DTT concentration over a range of 2-7 mM (FIG. 4D), suggesting that the S60 extract has a comparatively low potential of oxidation. This is important because the T7 RNA polymerase used to drive transcription in these particular examples requires a reducing environment for maximal activity.

Unique insights about the interdependence of the magnesium and nucleotide concentrations were obtained through the following optimization experiments. The four nucleotide triphosphates play a role in both transcription and translation, yet CTP and UTP were not present in initial, translation-only reactions. Since ATP is maintained through the creatine phosphate secondary energy system, the concentration of the other 3 types of nucleoside triphosphates, GTP, UTP, and CTP (abbreviated "GUC") were adjusted. Importantly, this required a change in magnesium concentration. It is well known that nucleotide concentration has a strong buffering/chelation effect on magnesium concentration and that optimal magnesium concentration is necessary for highly active CFPS. Thus, increasing the total nucleotide pool from 1.7 mM total (ATP, GTP only) to 7.5 mM total (ATP, GTP, CTP, UTP) when shifting from cell-free translation-only reactions (as described above) to combined Tx/Tl reactions, also required higher concentrations of magnesium (an increase of 1 mM to 6 mM). The optimal concentration of GUC with different magnesium concentrations was also investigated (Table 2). The maximum protein synthesis yield occurred when using 12 mM magnesium and 3.5 mM GUC.

TABLE 2

Optimization of [Mg]-[GUC]
Percent yield (%)[1]

| GUC (mM/each) | Mg (mM) | | | | |
|---|---|---|---|---|---|
| | 6 | 8 | 10 | 12 | 14 |
| 2 | *100 ±13.5* | 120 ± 0.5 | 105 ± 4.4 | 81 ± 10.3 | 55 ± 0.1 |
| 3 | 48 ± 5.8 | 121 ± 5.8 | 126 ± 8.2 | 100 ± 1.1 | 82 ± 4.4 |
| 3.5 | 3 ± 0.0 | 93 ± 2.1 | 119 ± 15.8 | 128 ± 3.1 | 102 ± 4.5 |
| 4 | 0 ± 0.0 | 49 ± 6.3 | 92 ± 31.2 | 115 ± 22.4 | 110 ± 4.5 |

[1]All reactions were performed using standard combined cell-free transcription-translation conditions except magnesium glutamate (Mg) and GTP/UTP/CTP (GUC) concentrations were varied. The luminescence value of standard reaction (6 mM Mg, 2 mM/each GUC) was counted as 100 (Bold and italic value). The luminescence values of all other samples were represented as the ratio to standard reaction. All values are the average of 3 individual reactions with standard deviations shown. The concentrations of Mg do not include Mg from S60 extract (see Examples). The values (Bold font) of highlighted the comparatively high-yield samples among different concentrations of Mg and GUC. The expression construct used in these experiments corresponds to SEQ ID NO: 9.

Notably, the highest yielding samples occurred along the diagonal of Table 2, indicating that unbalanced concentrations of magnesium and GUC significantly reduced the protein yield. With an eye towards ultimately developing a cost-effective CFPS system, the ~25% increase in yield with 150% additional nucleotide was insufficient motivation to keep the higher nucleotide concentrations, given the cost increase. As compared to cell-free translation alone, the newly designed combined Tx/Tl system improved overall protein synthesis yields more than 2-fold (up to 7 µg mL$^{-1}$). More importantly, it eliminated inconsistency issues with the capping reaction and further removed the dependence of the reaction on the costly and potentially inhibitory m$^7$GpppG RNA cap structure analog.

(2) Transcription Template Considerations

For high-level and high-throughput expression of protein libraries using CFPS platforms, the use of linear transcription templates as the source of DNA is preferred. This advantage allows CFPS reactions to be primed with DNA transcription templates that can prepared by an amplification reaction (for example, polymerase chain reaction (PCR)) without performing laborious cloning steps and without the need to use a circular DNA transcription template. A two-step overlap PCR method has been developed here that can be used to prime the yeast based CFPS reactions in a high-throughput fashion.

Figure 5:
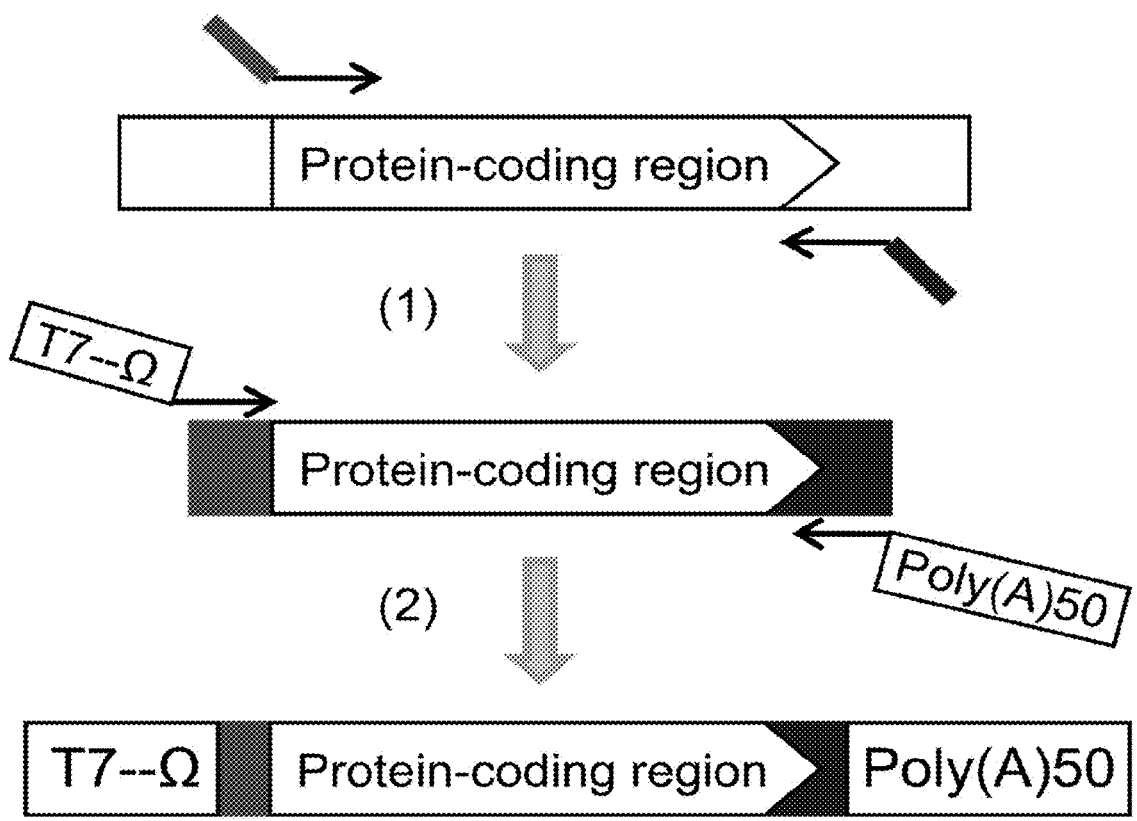
FIG. 5 depicts a schematic of a robust and rapid two-step method for assembly of linear DNA templates for high-throughput protein expression in yeast CFPS. In a first PCR assay (PCR 1; designated "(1)"), protein-coding sequences can be amplified directly from plasmid, genome, cDNA or other genetic material using gene-specific primers with universal tail sequence. In a second PCR assay (PCR 2; designated "(2)"), the T7 promoter, Ω sequence, and poly (A)50 are added to protein-coding region by overlapping PCR to the universal tail sequences. The assembled linear PCR product can be used directly as template in combined Tx/Tl yeast CFPS.

Referring to FIG. 5, in the first PCR reaction (PCR 1), the genes of interest are amplified using gene-specific primers complementary to the gene of interest with overhang regions for the second PCR reaction (PCR 2). The primers for PCR 1 can be comprised of short oligonucleotides (for example, about 30 nt to about 40 nt in length) that include a sequence having a length typically from about 15 nt to about 20 nt that can hybridize to the gene of interest and having about 15 nt to about 20 nt of non-gene-specific, unique sequences for secondary primer hybridization during PCR 2 (FIG. 5; for example, SEQ ID NOS: 25 and 26 for the luciferase gene (SEQ ID NO: 24)). PCR 2 can then be conducted with secondary primers that include a sequence complementary to the non-gene-specific, unique sequences found in the PCR 1 primers and also a sequence for a polymerase promoter element and Ω IRES element on the forward primer and a poly(A)$_{50}$ tail complement on the reverse primer (FIG. 5; for example, SEQ ID NOS: 27 and 28).

Preferred polymerases for use in the combined transcription/translation CFPS platform disclosed herein can be any polymerase that supports in vitro transcription in the yeast CFPS platform extract and reaction. Examples of suitable polymerases include *E. coli* RNA Polymerase, T3 RNA Polymerase, T7 RNA Polymerase and SP6 RNA Polymerase, among others. Phage RNA polymerases, such as T3, T7 and SP6 RNA Polymerases, are generally preferred for use in the yeast CFPS platform reaction disclosed herein, owing to the small size of the promoter element for these polymerases (for example, 17-20 nucleotides in length). Such polymerases are particular preferred when linear DNA transcription templates are generated by DNA amplification methods, because the polymerase promoter sequence must be included in the primer of PCR2 to generate the transcription unit having the promoter 5' to the gene encoding the open reading frame to be transcribed into RNA and subsequently translated as protein. In one aspect, T7 RNA Polymerase-directed synthesis of RNA in the combined transcription/translation system of the CFPS platform is preferred. Following construction according to this aspect, the entire linear template can be amplified using a universal T7 primer as one of the primers. Similar approaches can be used with linear templates that contain a promoter sequence specific for a different polymerase.

Figure 6A:
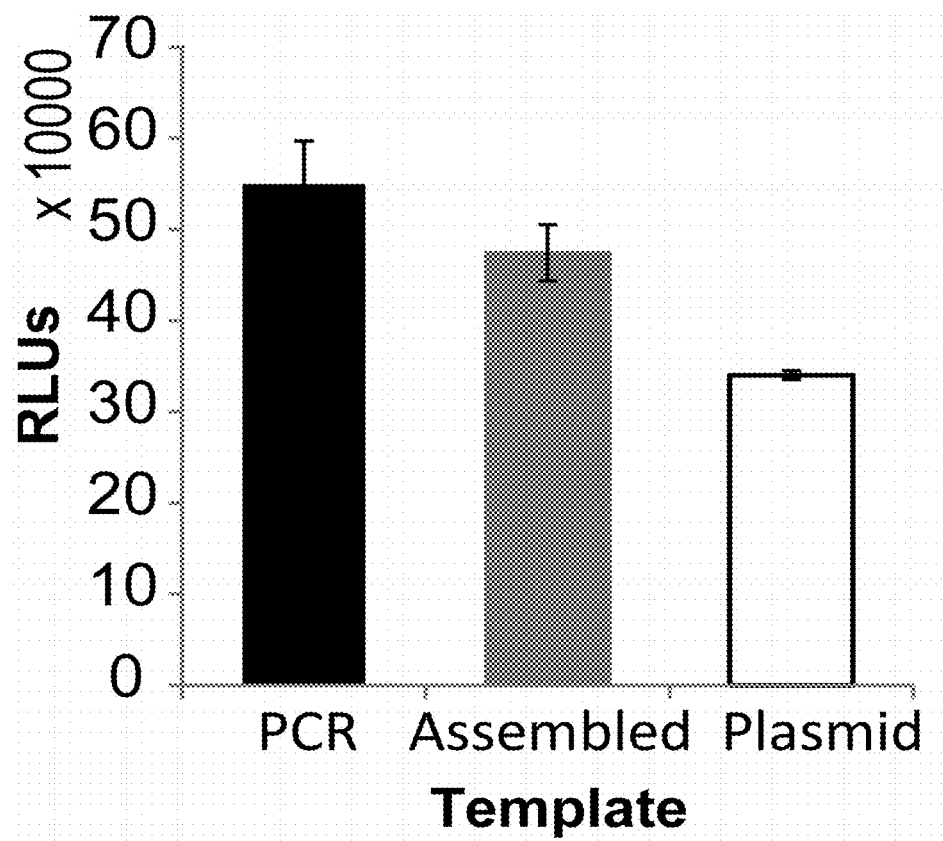
FIG. 6A illustrates a comparison of the efficiency in CFPS of PCR product amplified directly from plasmid, assembled linear DNA template, and plasmid. The concentration of template is 5.3 nM for each sample. These data show that linear templates outperform plasmid DNA. Values show means with error bars representing standard deviations (s.d.) of at least 4 independent experiments. Luciferase data are presented in RLUs, or relative light units.

After construction of linear templates, CFPS reactions were conducted using three different DNA templates: (i) PCR product amplified directly from plasmid; (ii) assembled linear DNA template produced by the two-step overlap PCR procedure described above; and (iii) circular plasmid. All three DNA templates can successfully synthesize luciferase, but surprisingly, the linear DNA templates performed ~40-60% better than the plasmid (FIG. 6A). To demonstrate utility of the approach, two other proteins, GFP and CAT, were also expressed using DNA templates assembled by the disclosed two-step PCR method. By comparison to commercial standard proteins, the yields of active protein are estimated as ~7 to 12.5 µg/ml (Table 3).

TABLE 3

Yield of active proteins from yeast CFPS programmed with linear DNA templates.[1]

| Protein | Yield (µg mL$^{-1}$ active protein) |
|---|---|
| Luciferase (SEQ ID NO: 30) | 7 ± 2 |
| GFP (SEQ ID NO: 33) | 12.5 ± 2.5 |
| CAT (SEQ ID NO: 36) | 10 ± 1 |

[1]Lucerferase (SEQ ID NO: 30) was prepared from coding sequence corresponding to SEQ ID NO: 24 and expression construct corresponding to SEQ ID NO: 29; green fluorescence protein (GFP; SEQ ID NO: 33) was prepared from coding sequence corresponding to SEQ ID NO: 31 and expression construct corresponding to SEQ ID NO: 32; and chloramphenicol acetyltransferase (CAT; SEQ ID NO: 36) was prepared from coding sequence corresponding to SEQ ID NO: 34 and expression construct corresponding to SEQ ID NO: 35.

Figure 6B:
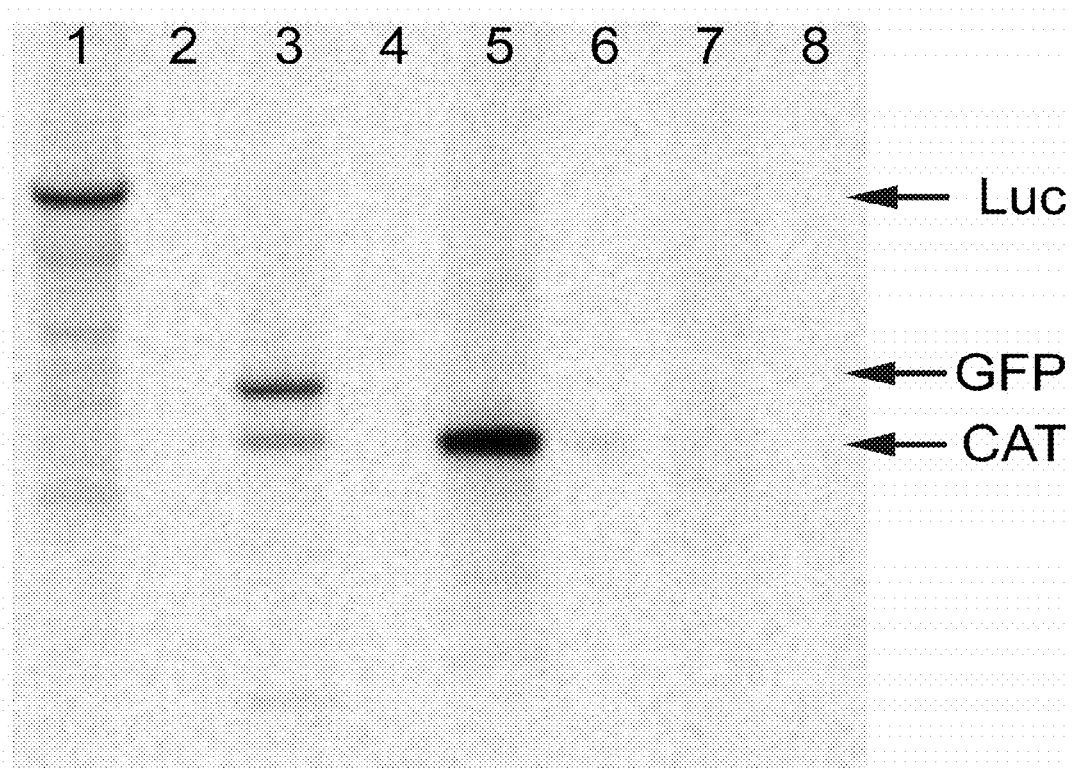
FIG. 6B illustrates expression of CFPS of luciferase (Luc), green fluorescence protein (GFP), and chloramphenicol acetyl transferase (CAT) using assembled, linear DNA templates. The [$^{35}$S]-methionine-labeled products were analyzed in SDS-PAGE and autoradiography. Lane 1 and 2: soluble and insoluble fraction of Luc; Lane 3 and 4: soluble and insoluble fraction of GFP; Lane 5 and 6: soluble and insoluble fraction of CAT; Lane 7 and 8: soluble and insoluble fraction of negative control reaction without template. Notably, nearly the entire product for each protein is soluble.

The solubility of each protein is also demonstrated in [$^{35}$S]-methionine autoradiography (FIG. 6B). Notably, more than 95% of the total protein produced was soluble in all cases. Overall, high-throughput combined Tx/Tl method enables one having ordinary skill in the art to proceed from DNA sequence to protein in less than six hours.

Due to the open architecture platform of both PCR and CFPS reactions, this process can be easily automated for high-throughput protein expression. For example, a reaction module containing programmed reagent additions and thermally-controlled reaction vessel incubation protocols can be used to generate linear transcription templates via amplification using PCR1 and PCR2 in a single-pot reaction. Once the linear transcription templates are prepared by amplification, the PCR mixtures can be processed to recover the linear transcription templates for use in the CFPS reaction in a separate module. Optionally, the PCR mixtures can be used directly in the CFPS reaction in a separate module without performing the processing step to recover the linear transcription templates. This latter option may be preferred in cases where the PCR mixture contribution to the CFPS reaction mixture is sufficiently small to not interfere with combined transcription/translation in the CFPS reaction.

Ability to Express a Variety of Proteins

Figure 7:
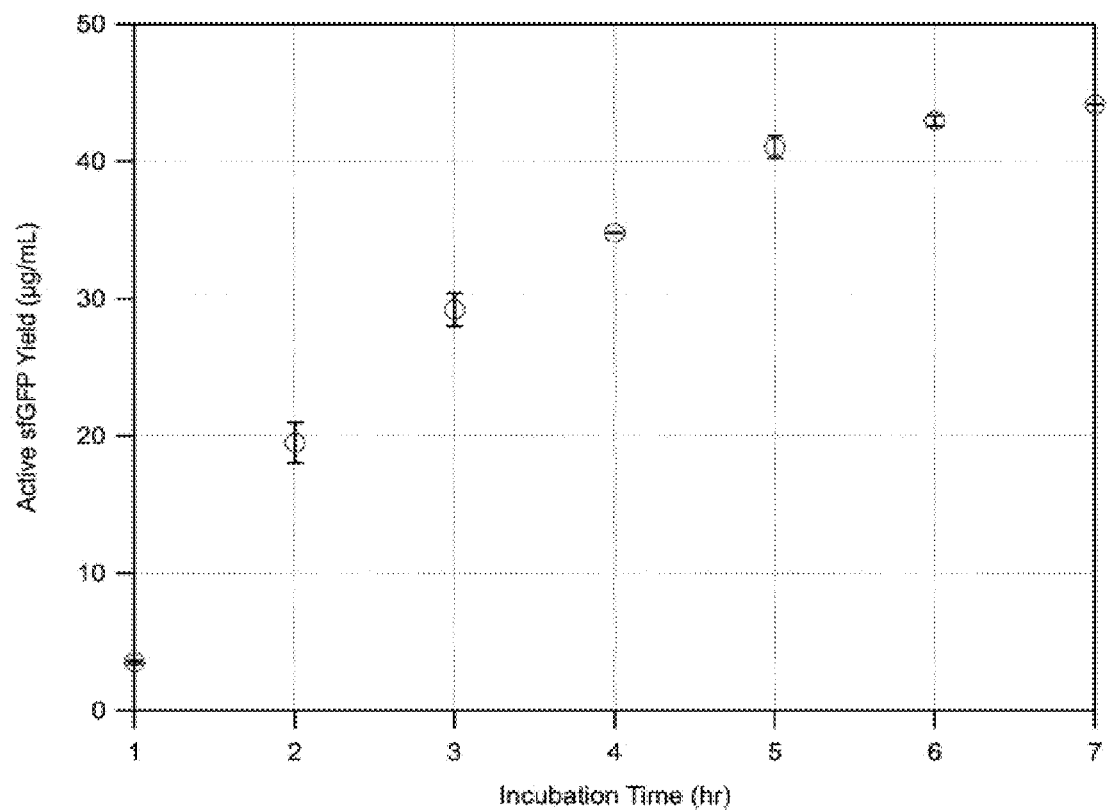
FIG. 7 depicts a time course assay of active SuperFolder GFP (sfGFP) in yeast CFPS batch reactions.

The developed cell-free protein synthesis platform has also demonstrated utility to express a variety of different proteins, including reporter proteins such as firefly luciferase, SuperFolder green fluorescent protein, and chloramphenicol acetyltransferase, as well as therapeutically relevant proteins such as single-chain antibody variable fragments (scFvs) and virus-like particles (VLPs) (Table 4). A major advantage of the disclosed yeast CFPS platform compared to prior art platforms is the expression of proteins in soluble and active form. Nearly 85-100% of complex proteins expressed (scFv and luciferase) are in their soluble form, compared to E. coli based CFPS where only ~15% of these same proteins synthesized are soluble. Additionally, the reaction is capable of synthesizing proteins for up to 6 h (FIG. 7), and this is the longest yeast CFPS batch synthesis disclosed.

TABLE 4

Exemplary protein synthesis yields with the yeast CFPS system

| Protein[1] | Molecular Weight (kDa) | Yield(s) (µg/mL) |
|---|---|---|
| Firefly Luciferase (SEQ ID NO: 30) | 61 | 12.4 ± 1.00 active protein |

TABLE 4-continued

Exemplary protein synthesis yields with the yeast CFPS system

| Protein[1] | Molecular Weight (kDa) | Yield(s) (µg/mL) |
|---|---|---|
| Chloramphenicol Acetyltransferase (SEQ ID NO: 36) | 25 | 10.00 ± 1.00 active protein |
| Superfolder Green Fluorescent Protein (SEQ ID NO: 39) | 27 | 42.99 ± 0.38 active protein |
| ANX scFv (SEQ ID NO: 42) | 27 | 4.97 ± 0.05 total protein<br>4.96 ± 0.13 soluble protein |
| BOT scFv (SEQ ID NO: 45) | 28 | 5.42 ± 0.03 total protein<br>4.83 ± 0.07 soluble protein |
| MS2 scFv (SEQ ID NO: 48) | 28 | 2.04 ± 0.04 total protein<br>1.94 ± 0.06 soluble protein |
| MS2-A scFv (SEQ ID NO: 51) | 28 | 1.41 ± 0.00 total protein<br>1.25 ± 0.01 soluble protein |
| 2E2 scFv (SEQ ID NO: 54) | 26 | 1.03 ± 0.01 total protein<br>0.91 ± 0.0. soluble protein |
| 2E2-3d scFv (SEQ ID NO: 57) | 26 | 1.60 ± 0.02 total protein<br>1.50 ± 0.02 soluble protein |
| Human Papillomavirus 16 L1 (SEQ ID NO: 60) | 51 | 3.26 ± 0.04 total protein<br>2.99 ± 0.03 soluble protein |

[1]Corresponding source nucleic acid sequences encoding the open reading frame (ORF) information (SEQ ID NOs: 24, 34, 37, 40, 43, 46, 49, 52, 55 and 58, respectively) were used for preparing linear templates for the expression constructs (SEQ ID NOs: 29, 35, 38, 41, 44, 47, 50, 53, 56 and 59, respectively) to express the identified proteins in the yeast CFPS system.

Figure 8:
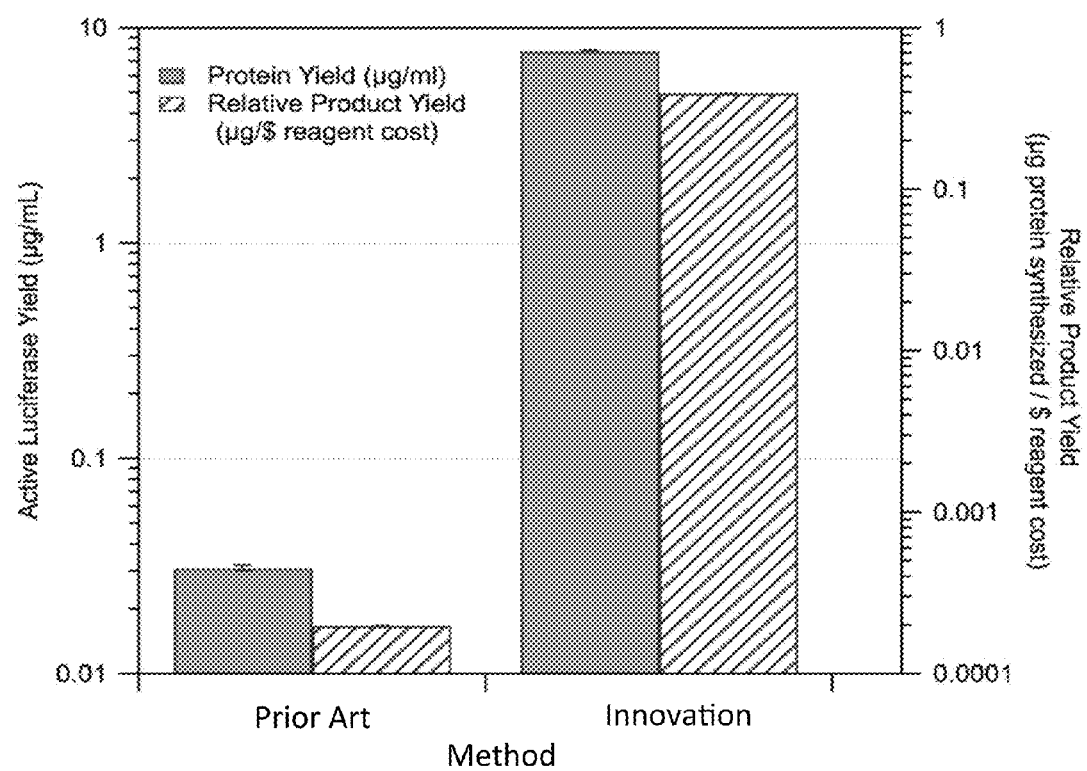
FIG. 8 illustrates a comparison of the disclosed yeast CFPS method to an exemplary prior art method, as measured by active protein synthesis yield (µg mL$^{-1}$; left axis) and relative product yield (µg protein synthesized per $ reagent cost; right axis). Substrate cost includes all substrates used to treat the crude extract, make the genetic template, and assemble the CFPS reaction.

The present yeast crude extract preparation method and the physicochemical environment of the in vitro system provide substantial advantages for protein synthesis. Overall, one can increase protein synthesis yield ~250-fold to 7.69±0.53 µg mL$^{-1}$ and increased relative product yield ~2000-fold to 0.39 µg protein synthesized per $ reagent cost using the disclosed yeast CFPS platform relative to the prior art yeast extract CFPS method (FIG. 8).

The improvements disclosed herein have implications for using yeast CFPS as a model to study translation. Referring to Table 5, both active protein synthesis of luciferase (SEQ ID NO: 30) from a linear luciferase expression template (SEQ ID NO: 29) using (i) extract derived from the prior art "benchtop" protocol (e.g., glass beads lysis) for combined Tx/Tl reactions and (ii) extract derived from optimized extract preparation protocol ("Innovation" in Table 5) for translation only reactions was improved.

TABLE 5

Relative comparison of CFPS methods

| Extract Preparation Method | MNase | Combined[1]/ Separated[2] Tx/Tl | CFPS Reaction Conditions | Active Luciferase Yield (µg/mL) | Fold Increase Relative to Prior Art MNase Treated Tx/Tl Reaction[3] |
|---|---|---|---|---|---|
| Prior Art | Yes | Separated | Prior Art | 0.03 +/− 0.00 | 1 |
| Prior Art | No | Combined | Innovation | 1.47 +/− 0.24 | 47 |
| Innovation | No | Separated | Innovation | 2.41 +/− 0.03 | 77 |
| Innovation | No | Combined | Innovation | 7.69 +/− 0.53 | 245 |

[1]Combined Tx/Tl means that transcription and translation occur together in a one-pot reaction.

[2]Separated Tx/Tl means that transcription of mRNA and capping was performed in a separate reaction prior to cell-free translation.

[3]Fold increase is normalized relative to the active luciferase yield obtained for extracts prepared by the prior art method using CFPS reactions conditions of the prior art (set at a value of 1).

For example, by altering the reaction conditions and taking advantage of the developed Tx/Tl method, a 47-fold increase in active protein synthesis over prior art methods was realized. Translation only reactions primed with extract generated with the optimized protocol developed in this disclosure show a similar increase with a 77-fold improvement over prior art methods. Furthermore, in both cases the yields crested the 1 μg mL$^{-1}$ threshold and demonstrate a significant improvement in utility of the cell-free system.

In first aspect, a cell-free protein synthesis platform for preparing protein from a translation template is disclosed. The cell-free protein synthesis platform includes the following components: (a) a *Saccharomyces cerevisiae* cellular extract prepared from mid-exponential to late-exponential batch cultures in the range from about 6 $OD_{600}$ to about 18 $OD_{600}$ or fed-batch cultures harvested in mid-exponential to late-exponential phase; (b) a reaction buffer; and (c) the translation template. The *Saccharomyces cerevisiae* cellular extract includes a crude extract, an S30 extract or an S60 extract. The reaction buffer includes NTPs, spermidine, putrescine, a glutamate salt, a magnesium salt and glycerol. The reaction buffer includes preferably glycerol. The reaction buffer includes at least one component selected from the group consisting of NTPs, a polyamine, an organic anion, a divalent cation, an alcohol and combinations thereof. In some embodiments, the polyamine is selected from spermidine and putrescine; the organic anion is selected from glutamate and acetate; the divalent cation is selected from magnesium, calcium and manganese; and the alcohol includes glycerol. The *Saccharomyces cerevisiae* cellular extract is not pre-treated with a micrococcal nuclease. The translation template includes at least one RNA. The at least one RNA includes an open reading frame, a 5'-UTR and a 3'-UTR. The 5'-UTR includes a cap-independent translation enhancing element. The cap-independent translation enhancing element is selected from a TMV Ω sequence, a TEV 5'-UTR element, and a Tbm 5'-UTR element. The 5'-UTR further includes a yeast Kozak sequence or variant thereof. The 3'-UTR includes a poly(A)$_n$ 3'-terminus, where n ranges from about 20 nucleotides to about 200 nucleotides in length. The value of n is selected preferably from 25 nucleotides, 50 nucleotides, 90 nucleotides, and 170 nucleotides.

In a second aspect, a cell-free protein synthesis platform for preparing protein from a transcription template is disclosed. The cell-free protein synthesis platform includes the following components: (a) a *Saccharomyces cerevisiae* cellular extract prepared from mid-exponential to late-exponential cultures in the range from about 6 $OD_{600}$ to about 18 $OD_{600}$; (b) a reaction buffer; (c) an RNA polymerase; and (d) the transcription template. The RNA polymerase is capable of transcribing the transcription template to form a translation template and the *Saccharomyces cerevisiae* cellular extract can sustain protein synthesis through a combined transcription/translation reaction. The *Saccharomyces cerevisiae* cellular extract includes an S30 extract or an S60 extract. The reaction buffer includes NTPs, spermidine, putrescine, a glutamate salt, a magnesium salt and glycerol. The reaction buffer includes preferably glycerol. The reaction buffer includes at least one component selected from the group consisting of NTPs, a polyamine, an organic anion, a divalent cation, an alcohol and combinations thereof. The polyamine is selected from spermidine and putrescine; the organic anion is selected from glutamate and acetate; the divalent cation is selected from magnesium, calcium and manganese; and the alcohol comprises glycerol. The *Saccharomyces cerevisiae* cellular extract is not pre-treated with a micrococcal nuclease. The RNA polymerase is selected from SP6 RNA Polymerase, T3 RNA Polymerase and T7 RNA polymerase. The RNA polymerase is selected from T3 RNA Polymerase and T7 RNA polymerase. The RNA polymerase includes preferably T7 RNA polymerase. The transcription template includes at least one DNA. The at least one DNA includes a linear DNA or a circular DNA. The at least one DNA encodes an open reading frame, a 5'-UTR and a 3'-UTR operably linked to a promoter specific for the RNA polymerase. The at least one DNA includes a linear DNA prepared from an amplification reaction. The amplification reaction includes a polymerase chain reaction. The 5'-UTR comprises a cap-independent translation enhancing element. The cap-independent translation enhancing element is selected from a TMV Ω sequence, a TEV 5'-UTR element, and a Tbm 5'-UTR element. The 5'-UTR further comprises a yeast Kozak sequence or variant thereof. The 3'-UTR includes a poly(A)$_n$ 3'-terminus, where n ranges from about 20 nucleotides to about 200 nucleotides in length. The value of n is selected preferably from 25 nucleotides, 50 nucleotides, 90 nucleotides, and 170 nucleotides.

In a third aspect, a method of performing high-throughput protein synthesis in vitro is disclosed. The method includes the following steps: (a) providing a source nucleic acid; (b) preparing a transcription template from the source nucleic acid; and (c) synthesizing protein in vitro using a cell-free protein synthesis platform utilizing the transcription template. The cell-free protein synthesis platform includes the following components: (i) a *Saccharomyces cerevisiae* cellular extract prepared from mid-exponential to late-exponential cultures in the range from about 6 $OD_{600}$ to about 18 $OD_{600}$; (ii) a reaction buffer; and (iii) an RNA polymerase. The RNA polymerase is capable of transcribing from the transcription template to form the translation template, and the *Saccharomyces cerevisiae* cellular extract can sustain protein synthesis through a combined transcription/translation reaction. The source nucleic acid includes genomic DNA, cDNA, RNA or a combination thereof. The step of preparing a transcription template from the source nucleic acid includes amplifying the source nucleic acid with a first primer and second primer in the presence of a DNA polymerase. The first and second primers include gene-specific sequences capable of hybridizing the gene encoding an open reading frame in the source nucleic acid. The transcription template includes a linear DNA encoding an open reading frame, a 5'-UTR and a 3'-UTR operably linked to a promoter specific for the RNA polymerase. The RNA polymerase is selected from SP6 RNA Polymerase, T3 RNA Polymerase and T7 RNA polymerase. The RNA polymerase is selected preferably from T3 RNA Polymerase and T7 RNA polymerase. The RNA polymerase includes preferably T7 RNA polymerase. The 5'-UTR includes a cap-independent translation enhancing element. The cap-independent translation enhancing element is selected from a TMV Ω sequence, a TEV 5'-UTR element, and a Tbm 5'-UTR element. The 5'-UTR further includes a yeast Kozak sequence or variant thereof. The 3'-UTR includes a poly(A)$_n$ 3'-terminus, where n ranges from about 20 nucleotides to about 200 nucleotides in length. The value of n is selected preferably from 25 nucleotides, 50 nucleotides, 90 nucleotides, and 170 nucleotides.

EXAMPLES

Example 1

Strains and Reagents

Yeast strains MBS and S288c were used. All chemicals were purchased from Sigma-Aldrich (St. Louis, Mo.) unless otherwise noted. DNA polymerase, T4 polynucleotide kinase, T4 DNA ligase, and restriction endonucleases were purchased from New England Biolabs (Ipswich, Mass.). T7 polymerase was prepared in lab (following the protocol developed by Swartz, J. R. et al., "Cell-free protein synthesis with prokaryotic combined transcription-translation," *Methods in molecular biology* (Clifton, N.J.) 267, 169-182 (2004)). Plasmids were extracted using Omega Kits (Omega Bio-Tek, Norcross, Ga.). All DNA oligonucleotides were purchased from Integrated DNA Technologies, Inc. (Coralville, Iowa).

Example 2

Nucleic Acid Manipulations

The schematic structures of exemplary expression templates described below are listed in part in FIG. 2. All nucleotide and amino acid sequences and their corresponding SEQ ID NOs are compiled in the SEQUENCE TABLE at the end of the Examples section. The luciferase-coding region was amplified from pK7LUC plasmid (SEQ ID NO: 61) (Jewett, M. C. et al., "In vitro integration of ribosomal RNA synthesis, ribosome assembly, and translation," *Mol. Syst. Biol.* 2013, 9, 678) using primers pET23LucA-f (SEQ ID NO: 62) and pET23LucA-r (SEQ ID NO: 63), and inserted into pET23c plasmid (SEQ ID NO: 64) with NdeI and XhoI sites to construct plasmid pET23LucA (SEQ ID NO: 65). Poly(A) tails with 25 nt and 50 nt were introduced into pET23LucA plasmid to replace 90 nt poly(A) using the primer pairs: PolyA-f (SEQ ID NO: 66)/PolyA25-r (SEQ ID NO: 67) and PolyA-f (SEQ ID NO: 66)/PolyA50-r (SEQ ID NO: 68). We were unable to produce a plasmid with a correctly identified 170 nt poly(A) due to the poor efficiency of PCR and sequencing for a 170 nt poly(A) region. However, we introduced a 170 nt poly(A) into linear DNA template by PCR using the primer PolyA-f (SEQ ID NO: 66) with the primer PolyA170-r (SEQ ID NO: 69) purchased from IDT with PAGE purification. Three yeast native internal ribosome entry site sequences, the 5'-UTR of TFIID, HAP270, and YAP1 genes (Iizuka et al. (1994)), were amplified from yeast genomic DNA using primer pairs TF5UTR-f (SEQ ID NO: 70)/TF5UTR-r (SEQ ID NO: 71), HAP270-f (SEQ ID NO: 72/HAP270-r (SEQ ID NO: 73), and YAP1-f (SEQ ID NO: 74)/YAP1-r (SEQ ID NO: 75), respectively, and inserted into plasmid pET23LucA (SEQ ID NO: 65) between the T7 promoter and luciferase with NdeI and XbaI. These three plasmids are identified as pET23TFIIDLucA (SEQ ID NO: 76), pET23HAP270LucA (SEQ ID NO: 77), and pET23YAP1LucA (SEQ ID NO: 78). The 5'-UTR of p150 gene (SEQ ID NO: 79; Zhou, W., Edelman, G. M., and Mauro, V. P., "Transcript leader regions of two *Saccharomyces cerevisiae* mRNAs contain internal ribosome entry sites that function in living cells," *Proc. Natl. Acad. Sci. U.S.A.* 98, 1531-1536 (2001)) was amplified from yeast genomic DNA using primers P150-f (SEQ ID NO: 80) and P150-r (SEQ ID NO: 81) flanking with XbaI and BamHI sites, and inserted into pET23LucA plasmid (SEQ ID NO: 65) where NdeI had been replaced with BamHI, since the insert fragment contains an NdeI site.

The Ω sequence (65 nt) from TMV (SEQ ID NO: 82) was introduced into pET23LucA upstream of luciferase with primers Sf-f (SEQ ID NO: 83) and Omega-r (SEQ ID NO: 84). The 5'-UTR of polyhedrin gene (44 nt) (SEQ ID NO: 85) was introduced into pET23LucA (SEQ ID NO: 65) with primers Sf-f (SEQ ID NO: 83) and Polyhedrin-r (SEQ ID NO: 86). A 5'-end poly(A)64 sequence (SEQ ID NO: 87) was introduced into pET23LucA (SEQ ID NO: 65) with primers Sf-f (SEQ ID NO: 83) and PolyA64-r (SEQ ID NO: 88). A 5'-UTR fragments (143 nt) (SEQ ID NO: 89) from tobacco etch virus (TEV) genome (Accession number: NC_001555) was cloned into pET23LucA (SEQ ID NO: 65) upstream of the luciferase gene by oligo TEV-r (SEQ ID NO: 90); another plant viral 5'-UTR fragment (65 nt) (SEQ ID NO: 91) from Crucifer tobamovirus (CfTbm) genome (Accession number: NC_003355.1) was inserted into pET23LucA (SEQ ID NO: 65) upstream of luciferase gene using oligo CfTbm-r (SEQ ID NO: 92). An IRES sequence of the cricket paralysis virus (CrPV) intergenic region (IGR) (SEQ ID NO: 93) was amplified from the plasmid pSaII-IGR (SEQ ID NO: 94) (Deniz, N. et al., "Translation initiation factors are not required for Dicistroviridae IRES function in vivo," *RNA* 15, 932-946 (2009)) using primers IGR-f (SEQ ID NO: 95) and IGR-r (SEQ ID NO: 96).

Two fragments (SEQ ID NOs: 97 and 98) were cloned from the 3'-UTR of yeast FBA1 gene (Accession number: NM_001179626) that encodes fructose 1,6-bisphosphate aldolase. The shorter fragment containing 662 nt from the first nucleotide after the stop codon (SEQ ID NO: 97) was amplified by primers FBA3UTR-f (SEQ ID NO: 99) and FBA3UTR1-r (SEQ ID NO: 100). The longer fragment containing 1465 nt from the first nucleotide after the stop codon (SEQ ID NO: 98) was amplified by primers FBA3UTR-f (SEQ ID NO: 99) and FBA3UTR2-r (SEQ ID NO: 101). The two 3'-UTR fragments were then placed after the stop codon of luciferase with XhoI and SacI sites. Two DNA fragments of TMV genome were synthesized (GenScript, Piscataway, N.J.). The first fragment, TMV1, ranges from 4920 to 5711 of genome (792 nt in length) (SEQ ID NO: 102) containing the sequence between two open-reading frame TMVgp1 and TMVgp6; the second fragment, TMV2 ranges from 6192 to 6395 genome (204 nt in length) (SEQ ID NO: 103). Three fragments, TMV13U200 (SEQ ID NO: 104), TMV13U400 (SEQ ID NO: 105), and TMV13U700 (SEQ ID NO: 106), were amplified from TMV1 with the length of 200 nt, 400 nt, and 700 nt respectively using primer pairs: TMV13U-f (SEQ ID NO: 107) and TMV13U200-r (SEQ ID NO: 108); TMV13U-f (SEQ ID NO: 107) and TMV13U400-r (SEQ ID NO: 109); and TMV13U-f (SEQ ID NO: 107) and TMV13U700-r (SEQ ID NO: 110), respectively. One fragment was amplified from TMV2 with the length of 204 nt (SEQ ID NO: 111) by using primer pairs TMV23U-f (SEQ ID NO: 112) and TMV23U-r (SEQ ID NO: 113). All four fragments amplified from TMV1 and TMV2 were placed after the stop codon of the luciferase-coding frame with XhoI and SacI sites as 3'-UTRs.

To assemble linear expression templates of luciferase, green fluorescence protein (GFP), and chloramphenicol acetyl transferase, the coding region of the 3 enzymes were amplified with primer pairs QEluc-f (SEQ ID NO: 114) and QEluc-r (SEQ ID NO: 115); QEGFP-f (SEQ ID NO: 116) and QEGFP-r (SEQ ID NO: 117); and QECAT-f (SEQ ID NO: 118) and QECAT-r (SEQ ID NO: 119), respectively. Therefore, T7 promoter (SEQ ID NO: 120), Ω sequence (SEQ ID NO: 121), and poly(A)50 tail (SEQ ID NO: 122) were overlapped to the coding region by primer pairs QET7Ome-f (SEQ ID NO: 123) and PolyA50-r (SEQ ID NO: 68), respectively.

Plasmid pET23c-GFP-cyc3 (SEQ ID NO: 124) was kindly provided by Dr. Markus Pech at the Max Planck Institute for Molecular Genetics (Iskakova M. B. et al., "Troubleshooting coupled in vitro transcription-translation system derived from *Escherichia coli* cells: Synthesis of high-yield fully active proteins," *Nucleic Acids Res.* 34(19): e135 (2006)). The gene encoding for firefly luciferase (60, 755 Da) (SEQ ID NO: 24) in place of GFP-cyc3 was inserted into the plasmid backbone as the reporter proteins. The luciferase gene was inserted between the T7 promoter (SEQ ID NO: 120) and T7 terminator (SEQ ID NO: 125) sequences using Nde1 and Xho1 restriction digest enzymes using the luciferase sense primer (SEQ ID NO: 126) and luciferase anti-sense primer (SEQ ID NO: 127). Encoded in the anti-sense primer was the addition of a 90-mer poly(A) tail to 3' end of the coding sequence. Plasmids were harbored in *E. coli* DH5α competent cells and purified using E.Z.N.A. Omega Plasmid DNA Maxi Kits (Omega Bio-Tek, Norcross, Ga.). For combined transcription/translation (Tx/Tl) reactions, the Ω cap-independent translation enhancer from tobacco mosaic virus was inserted in the 5'-UTR to remove the dependence of the 5'-cap for translation initiation to construct the pET23ΩLucA plasmid (SEQ ID NO: 128). For CFPS reactions, the coding sequence containing the Ω cap-independent translation enhancer, protein of interest, and polyA tail, was PCR amplified with backbone sense primer (SEQ ID NO: 129) and anti-sense primer (SEQ ID NO: 130) using Phusion High-Fidelity DNA Polymerase (New England Biolabs, Ipswich, Mass.). The PCR product was purified using the Qiagen PCR Purification Kit (Qiagen, Valencia, Calif.).

Example 3

In Vitro Transcription

In vitro transcription and mRNA capping was performed with the Ambion mMessage mMachine® Kit (Life Technologies, Grand Island, N.Y.) according to the manufacturer's instructions. The capped mRNA was purified following a phenol-chloroform extraction and desalted using a Micro Bio-Spin® 6 chromatography column (Biorad, Hercules, Calif.). Non-capped RNA was prepared according to Mureev et al. (2009). Poly(A)$_n$-containing mRNA was isolated using Dynabeads Oligo(dT)$_{25}$ magnetic beads (Life Technologies, Grand Island, N.Y.).

Example 4

Growth Conditions

Figure 9A:
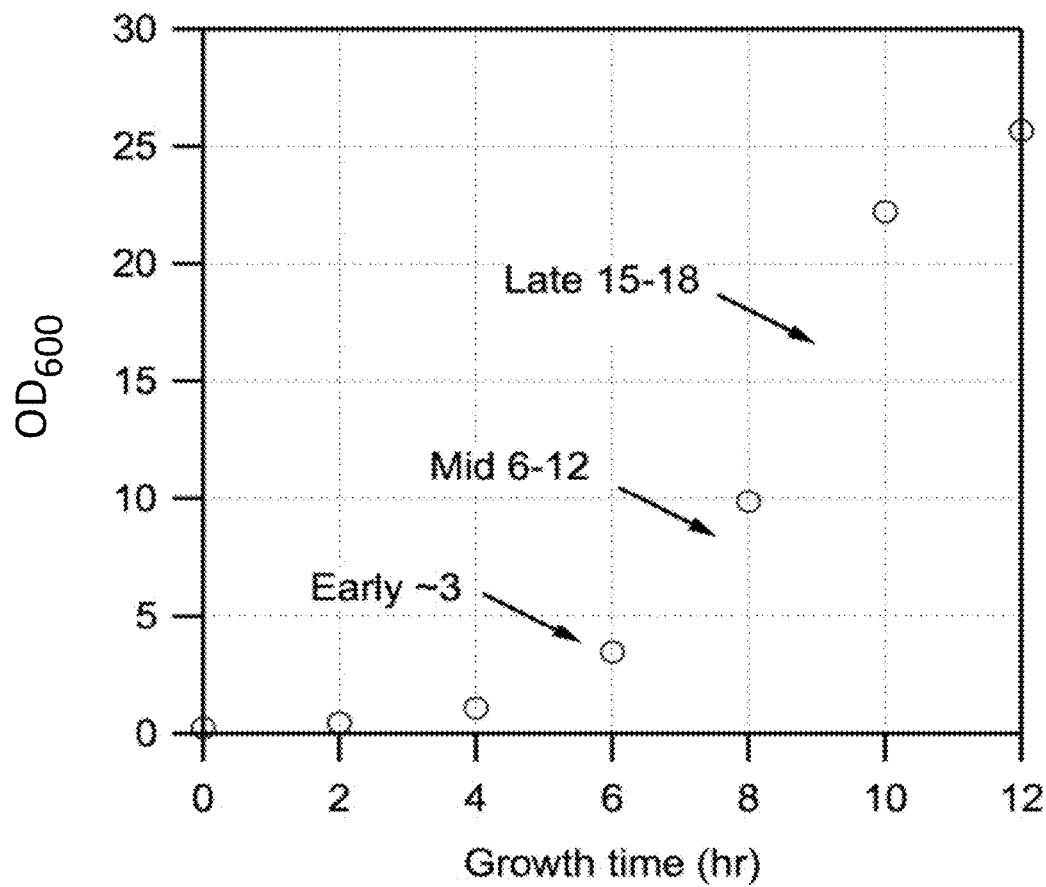
FIG. 9A depicts the effects of typical growth curve for yeast culture on YPAD media, pH 5.5 at 30° C.
Figure 9B:
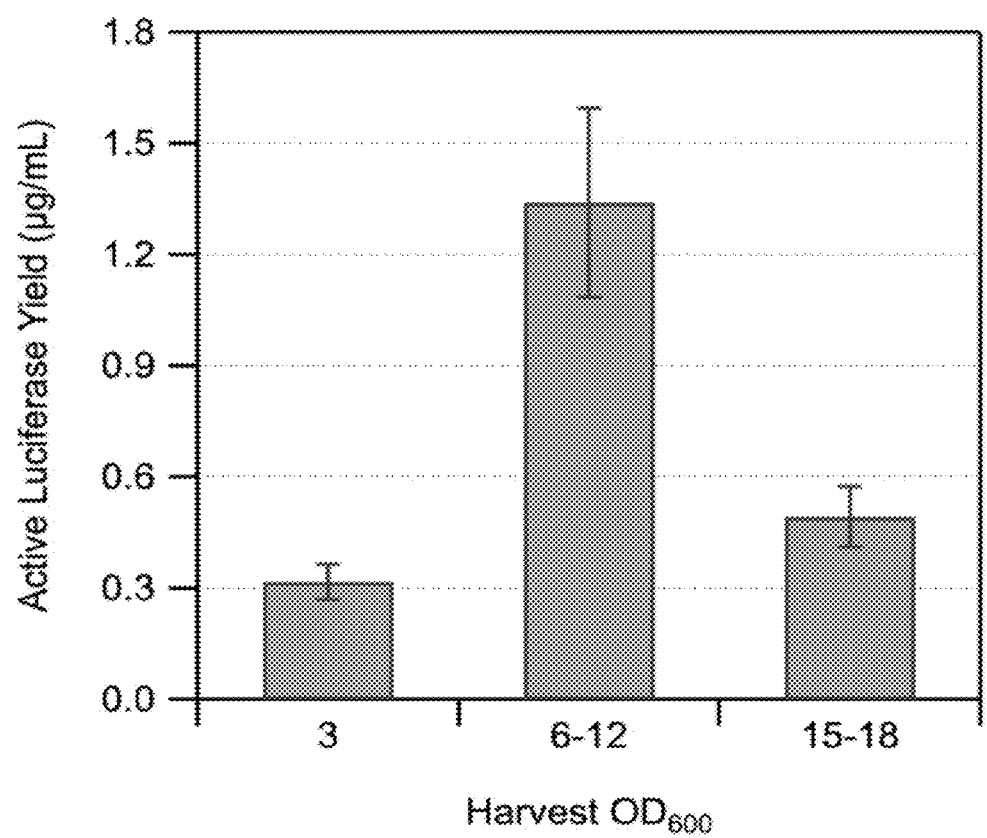
FIG. 9B depicts active luciferase yield in combined transcription and translation reactions from extracts made with cells harvested at 3, 6, 9, 12, 15, and 18 OD$_{600}$. Extracts were grouped together according to their protein synthesis activity. The groupings were 3, 6-12, and 15-18 OD$_{600}$ with most active extract at mid-exponential phase harvest. Values show means with error bars representing standard deviations (s.d.) of at least 3 independent experiments.
Figure 10:
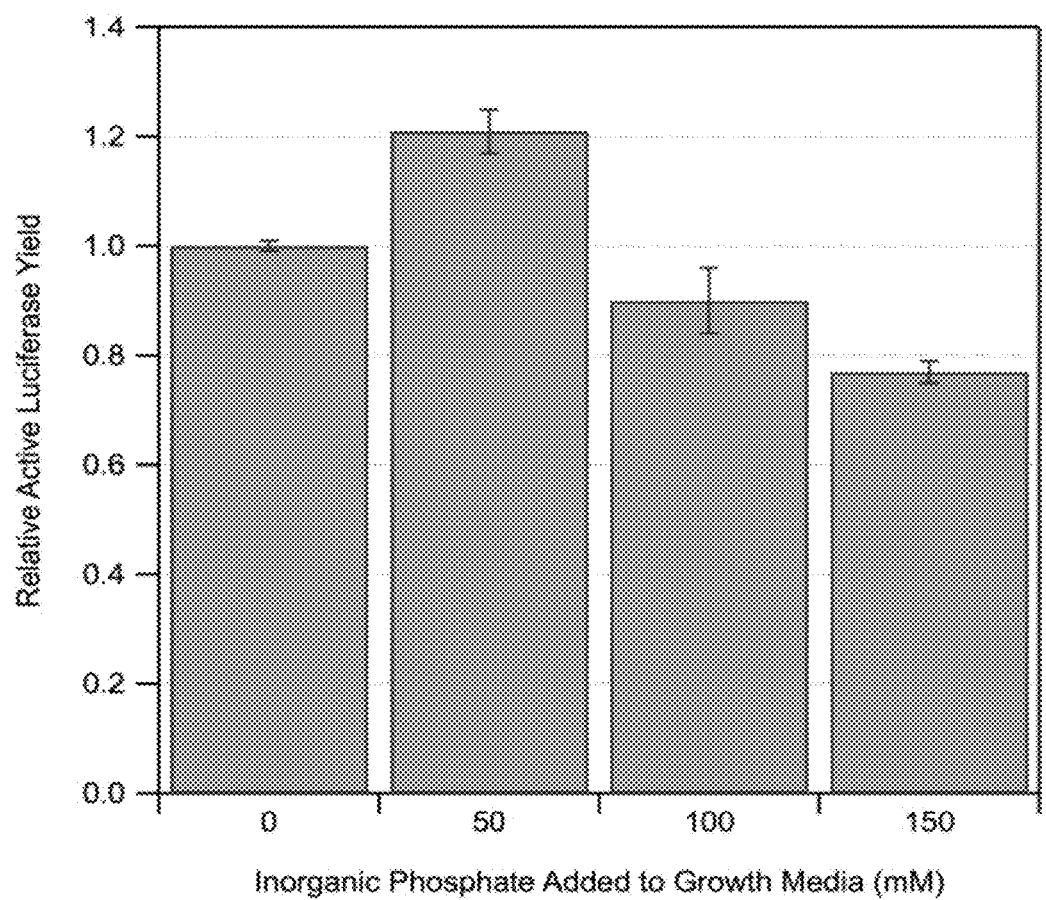
FIG. 10 depicts the effect of adding inorganic phosphate to the growth media affects CFPS activity. Cells were grown in shake flasks in YPAD media, pH 5.5 supplemented with 0, 50, 100, and 150 mM potassium phosphate (pH 5.5). Crude extract was subsequently made from the variable cell cultures and compared to each other for protein synthesis activity. Maximum protein synthesis occurred with media supplemented with 50 mM potassium phosphate.

The cultures of yeast cells were grown to 3, 6, 9, 12, 15 and 18 OD$_{600}$ and used to prepare individual batches of crude extract originating from each of these fermentations. Thereafter, combined transcription and translation in a 15 μL batch reaction with these different extracts were carried out for a period of 2 h. The most active extracts were obtained from yeast culture harvested at mid-exponential phase: 1.34±0.25 μg mL$^{-1}$ for OD$_{600}$ 6-12 compared to 0.32±0.05 μg mL$^{-1}$ for OD$_{600}$ of 3 and 0.49±0.08 μg mL$^{-1}$ for OD$_{600}$ 15-18 (FIG. 9A, B). Furthermore, the addition of inorganic phosphate to the growth media resulted in a 21% increase in protein synthesis capability for extracts generated from cells grown with 50 mM potassium phosphate (FIG. 10).

Example 5

Preparation of Yeast S30 Extract

For extract preparation, *S. cerevisiae* strain MBS (Thompson, S. R. et al., "Internal initiation in *Saccharomyces cerevisiae* mediated by an initiator tRNA/eIF2-independent internal ribosome entry site element," *Proc. Natl. Acad. Sci. U.S.A.* 98, 12972-12977 (2001)) was grown in either the BIOSTAT Cplus 10 L bioreactor (Sartorius Stedim Biotech S.A., Aubagne Cedex, France), or 1 L of culture in 2.5 L Tunair (Sigma-Aldrich, St. Louis, Mo.) shake flasks in YPAD media, pH 5.5 supplemented with 50 mM potassium phosphate to 12 OD$_{600}$. When the OD$_{600}$ reached 12, the yeast culture was cooled quickly to between 4-8° C. by either harvesting through a stainless steel coil immersed in an ice bath (when grown in the 10 L bioreactor) or by adding 1 L of ice per L of yeast culture (when grown in the shake flasks). To pellet the cells, the cell suspension was centrifuged for 10 min at 3,000×g and 4° C. The cell pellet was washed with 60 mL of Mannitol Buffer A (30 mM HEPES, pH 7.4 w/5M KOH, 100 mM potassium acetate, 2 mM magnesium acetate, 2 mM dithiothreitol, 8.5% (w/v) mannitol) per liter of starting culture followed by centrifugation for 5 min at 3,000×g and 4° C. This step was repeated 3 times with 20 mL of Mannitol Buffer A, with the final wash centrifuged at 4,000×g for 5 min. Potassium and magnesium glutamate were used in place of potassium and magnesium acetate as denoted in the text. Extra buffer was removed by placing the centrifugation bottle upside down and tapping against a paper towel. The cell pellet was weighed, flash-frozen on liquid N$_2$, and stored at −80° C. Alternatively, the extract preparation can be continued with cellular lysis.

Cell lysis was performed using one of two methods, either with 0.5 mm glass beads (Sigma-Aldrich, St. Louis, Mo.) or high-pressure homogenization. For glass beads lysis, a prior art method was used (Iizuka et al. (1994)). Briefly, 5-6 g of wet cell mass was combined with 1.5 mL of cold Lysis Buffer A (Mannitol Buffer A+0.5 mM PMSF) per 1 gram of wet cell mass in a 50 mL falcon tube and the suspension was thawed on ice. Note, PMSF was first dissolved in 100% ethanol and was added fresh before each use. In the cold room, the cells were lysed in capped 50 mL falcon tubes by five 1-min cycles of hand shaking (2 Hz) over a 50 cm hand path, with cooling on ice water for 1 min between cycles.

For high-pressure homogenization lysis, a minimum of 3 g of wet yeast cell pellet was lysed at one time. Again, 1.5 mL of cold Lysis Buffer A per 1 g of wet cell mass was added to the cell pellet and the suspension was thawed on ice. Immediately after cell thawing was completed, the cells were lysed by passing through an EmulsiFlex-05 Homogenizer (Avestin, Ottawa, ON, Canada) at 30,000 psi and a flow rate of approximately 1-3 mL per minute. The sample was collected through a cooling coil immediately upon exit that was submerged in ice water.

After cell disruption, the lysate was centrifuged at 4° C. and 25,000×g for 5 min. Immediately, the supernatant was transferred with a pipette into a clean Nalgene spherical bottom high-speed centrifuge bottle for the second centrifugation at 4° C. 25,000×g for 5 min. The aqueous fraction was carefully removed by avoiding crude cell debris at the bottom.

The lysate subsequently underwent buffer exchange through either dialysis or fast protein liquid chromatography (FPLC). For dialysis, the extract was dialyzed against four exchanges of 200-volumes of Buffer A/PMSF (Lysis Buffer A without the addition of mannitol) for 30 min each at 4° C. using Slide-A-Lyzer Dialysis Cassettes (2,000 Da MWCO; Thermo Fisher Scientific, Waltham, Mass.). The dialyzed extract was centrifuged at 12,000×g at 4° C. for 20 min to remove any degraded proteins.

For FPLC, the extract was loaded onto a Sephadex G-25 Superfine (GE Healthcare Biosciences, Pittsburgh, Pa.) column at 25% of the bed volume using the BioLogic DuoFlow FPLC (Bio-Rad, Hercules, Calif.). The extract was exchanged against Buffer A/PMSF with a flow rate of 0.65 mL per min at 4° C. Fractions were collected in 0.5 mL volumes. All fractions with an $A_{260}$ reading greater than 0.45 after 200-fold dilution were pooled together.

After buffer exchange, the extract was immediately aliquoted into 50, 100 and 200 μL samples as desired. The aliquots were rapidly frozen in liquid nitrogen and stored at −80° C. for long-term storage. No decrease in activity was seen after several months of storage at −80° C. or after up to 4 freeze-thaw cycles.

Example 6

Micrococcal Nuclease Pre-Treatment

For Micrococcal Nuclease (MNase) pre-treatment, 1 μL of 50 mM $CaCl_2$ and 0.72 μL of 25 $μL^{-1}$ Micrococcal Nuclease from *Staphylococcus aureus* (Sigma-Aldrich, St. Louis, Mo.; final concentration of 0.5 mM $CaCl_2$ and 0.18 U $μL^{-1}$ MNase) were added to 100 μL of crude extract on ice. The solution was mixed by pipetting up and down and the reaction was incubated at room temperature for 5 min. To quench the reaction, 1 μL of 250 mM EGTA was added to the reaction to a final concentration of 2 mM. The reaction was promptly mixed by pipetting up and down and the treated crude extract was placed back on ice and used for downstream CFPS reactions.

Example 7

Preparation of Yeast S60 Extract

Colonies of yeast strain were cultivated in rich media (2% peptone, 1% yeast extract, 2% glucose), shaking at 250 rpm at 30° C. overnight to saturation. The seeding culture was used to inoculate 1 L of fresh rich media with 1:1000 in 2.5 L Tunair (Sigma-Aldrich, St. Louis, Mo.), shaking at 250 rpm at 30° C. Cells were harvested at mid-logarithmic phase ($OD_{600}$ 10-12) by centrifugation at 3000 g for 10 min. Cell pellets were resuspended and washed three times in Buffer A (20 mM HEPES-KOH pH 7.4, 100 mM potassium acetate, 2 mM magnesium acetate). The wet pellet was weighed and suspended by vortex in lysis buffer (20 mM HEPES-KOH pH 7.4, 100 mM potassium acetate, 2 mM magnesium acetate, 2 mM DTT, 0.5 mM PMSF) with 1 mL buffer per gram of wet cell weight. Cells were lysed using an Avestin EmulsiFlex-C5 High Pressure Homogenizer (Avestin, Ottawa, ON, Canada) one time under 30,000 psig. The lysate was centrifuged at 4° C. and 30,000 g for 30 min, the supernatant was removed, placed in a clean spherical bottom high-speed centrifuge bottle and clarified again. Supernatant was desalted using dialysis tubing (Spectra/Por 3 MWCO 3500, Spectrum Labs, Rancho Dominguez, Calif.) against four exchanges of 50-volumes of lysis buffer (20 mM HEPES-KOH pH 7.4, 100 mM potassium acetate, 2 mM magnesium acetate, 2 mM DTT, 0.5 mM PMSF) for 30 min each at 4° C. After dialysis, extract was centrifuged at 60,000 g for 20 min at 4° C. Final extract was distributed into 100 μA aliquots in 1.5-mL Eppendorf tubes, frozen in liquid nitrogen and stored at −80° C. The protein concentration was determined using Quick Start™ Bradford Protein Assay (Bio-Rad Laboratories, Hercules, Calif.).

Example 8

Cell-Free Protein Synthesis Using Crude Yeast Extracts

CFPS reactions were carried out in 1.5 mL Eppendorf tubes at 21° C. in a temperature-controlled water bath in 15 μL reactions. The cell-free reaction mixture was assembled on ice from stock solutions to the following working concentrations for translation only reactions: 22 mM HEPES-KOH pH 7.4, 120 mM potassium glutamate, 2 mM magnesium glutamate, 0.75 mM adenosine triphosphate (ATP), 0.1 mM guanosine triphosphate (GTP), 0.04 mM of each of 20 amino acids, 25 mM creatine phosphate, 1.7 mM DTT, 1 mM putrescine, 0.5 mM spermidine, 0.27 mg $mL^{-1}$ creatine phosphokinase (from rabbit muscle; Sigma-Aldrich, St. Louis, Mo.), 26.7 U $mL^{-1}$ RNase Inhibitor (Qiagen, Valencia, Calif.), 600 ng in vitro transcribed mRNA, and 50% (v/v) yeast extract. For combined transcription and translation reactions the working concentrations varied slightly to: 22 mM HEPES-KOH pH 7.4, 120 mM potassium glutamate (unless otherwise noted), 5 mM magnesium glutamate (unless otherwise noted), 1.5 mM of each ATP, GTP, CTP and UTP, 0.08 mM of each of 20 amino acids, 25 mM creatine phosphate, 1.7 mM DTT, 1 mM putrescine, 0.5 mM spermidine, 0.27 mg $mL^{-1}$ creatine phosphokinase (from rabbit muscle, Sigma-Aldrich, St. Louis, Mo.), 26.7 U $mL^{-1}$ RNase Inhibitor (Qiagen, Valencia, Calif.), 250 ng ΩLucA PCR amplified DNA, 0.027 mg $mL^{-1}$ T7 RNA Polymerase (made in house following the protocol developed by Swartz et al. (2004) and 50% (v/v) yeast extract. The final concentration of yeast extract proteins was 25.7±1.0 mg $mL^{-1}$, as determined by Bradford Assay using commercially available assay reagents (Bio-Rad, Hercules, Calif.) compared to a bovine serum albumin protein standard. All other reagents were purchased from Sigma-Aldrich (St. Louis, Mo.) unless otherwise noted. The amount of active firefly luciferase produced was determined by adding 12 μL of CFPS sample to 30 μL of ONE-Glo Luciferase Assay System (Promega, Madison, Wis.) in a white 96-well plate. The total luminescence was read every two minutes over a 20-minute interval using a BioTek (Winooski, Vt.) Synergy 2 plate reader. The maximum amount of relative light units (RLUs) was recorded for each cell-free reaction. RLUs were then compared to a linear standard curve of recombinant luciferase (Promega, Madison, Wis.) added directly to the ONE-Glo reaction mixture.

For the pre-incubation experiments, all soluble components of the cell-free reaction were initially assembled on ice except the crude extract, T7 polymerase (T7 Pol), and creatine phosphokinase (CK). For each individual reaction, the T7 Pol and CK were added to the cell-free reaction immediately before the extract had finished "pre-incubating". After the pre-incubated extract was added to the reaction mixture, the CFPS reaction proceeded for an additional 2 h. In order to assay all of the samples simultaneously, the cell-free reactions were quenched by fast freezing in liquid nitrogen, stored at −20° C. and thawed simultaneously before being assayed for active luciferase yield.

Example 9

Yeast Cell-Free Translation Only Reactions Using mRNA Template Using the Yeast S60 Extract Yeast cell-free translation was prepared as described by Sarnow with some modifications (Iizuka & Sarnow (1997)).

CFPS reactions were primed with 20 nM mRNA in 15 μL reactions. The cell-free reaction mixture was assembled on ice from stock solutions to the following working concentrations: 25 mM HEPES-KOH pH 7.4, 120 mM potassium glutamate, 1 mM magnesium glutamate, 1.5 mM adenosine triphosphate (ATP), 0.2 mM guanosine triphosphate (GTP), 0.1 mM of each of 20 amino acids, 25 mM creatine phosphate, 1 mM DTT, 0.27 mg/mL creatine phosphokinase (C3755-1KU, Sigma), 200 U/mL RNase Inhibitor (Qiagen), and 50% (v/v) yeast S60 extract.

Example 10

Combined Transcription/Translation (Tx/Tl) Cell-Free Protein Synthesis Using the Yeast S60 Extract Combined cell-free transcription-translation reactions were carried out in 1.5-mL Eppendorf tubes in 15 μL reactions. The reaction was primed with 3.2 nM PCR product. The cell-free reaction mixture was prepared on ice from stock solutions to the following working concentrations for translation only reactions: 25 mM HEPES-KOH pH 7.4, 120 mM potassium glutamate, 6 mM magnesium glutamate, 1.5 mM ATP, 2 mM of each GTP, CTP and UTP, 0.1 mM of each of 20 amino acids, 25 mM creatine phosphate, 2 mM DTT, 0.27 mg/mL creatine phosphokinase (C3755-1KU, Sigma), 200 U/mL RNase Inhibitor (Qiagen), 27 μg/mL T7 RNA Polymerase, and 50% (v/v) yeast S60 extract. All combined cell-free transcription-translation reactions were performed using above conditions unless specified otherwise. For the analysis of [$^{35}$S]-methionine-labeled protein products, combined Tx/Tl cell-free protein synthesis was performed as described above except that [$^{35}$S]-methionine was supplemented with the final concentration of 0.58 μM. The protein products were resolved by NuPAGE® Novex® 4-12% Bis-Tris Gels (Invitrogen, Grand Island, N.Y.).

Example 11

Luciferase Activity Assay

The amount of active firefly luciferase was determined by ONE-GLO™ Luciferase Assay System (Promega), in a white 96-well plate. Five μL of CFPS sample was added to 30 μL of Luciferase Assay Buffer. Luminescence was read every 2 min over a 20 min period using a BioTek Synergy 2 plate reader (Winooski, Vt.).

Example 12

Chloramphenicol Acetyl Transferase Assay

Active chloramphenicol acetyl transferase (Catherine, C. et al., "Cell-free platforms for flexible expression and screening of enzymes," *Biotechnol Adv* 31, 797-803 (2013)) was measured as previously described (Jewett, M. C. et al., "An integrated cell-free metabolic platform for protein production and synthetic biology.," *Mol Syst Biol* 2008, 4 (2008)).

Example 13

Autoradiography

Autoradiography was used to determine the size of protein synthesized. 1.7 μL of $^{35}$S-Methionine (~18 μCu) (PerkinElmer, San Jose, Calif.) was added to each 15 μL CFPS reaction. Following 3 h incubation, the CFPS reaction was loaded onto a NuPAGE 4-12% Bis-Tris Gel (Life Technologies, Grand Island, N.Y.) following the manufacturer's instructions. The NuPAGE gels were stained with SimplyBlue SafeStain (Life Technologies, Grand Island, N.Y.) and all proteins present in the cell-free reaction were visualized using the Gel Doc XR+ (Bio-Rad, Hercules, Calif.). The gels were dried and exposed overnight on a Storage Phosphor Screen (GE Healthcare Biosciences, Pittsburgh, Pa.) and imaged with the Storm 860 Phosphoimager (GE Healthcare Biosciences, Pittsburgh, Pa.). This image was digitally compared to the SimplyBlue stained image that included a protein standard ladder to determine the length of synthesized proteins.

Example 14

Comparison of CFPS Platforms

Figure 1C:
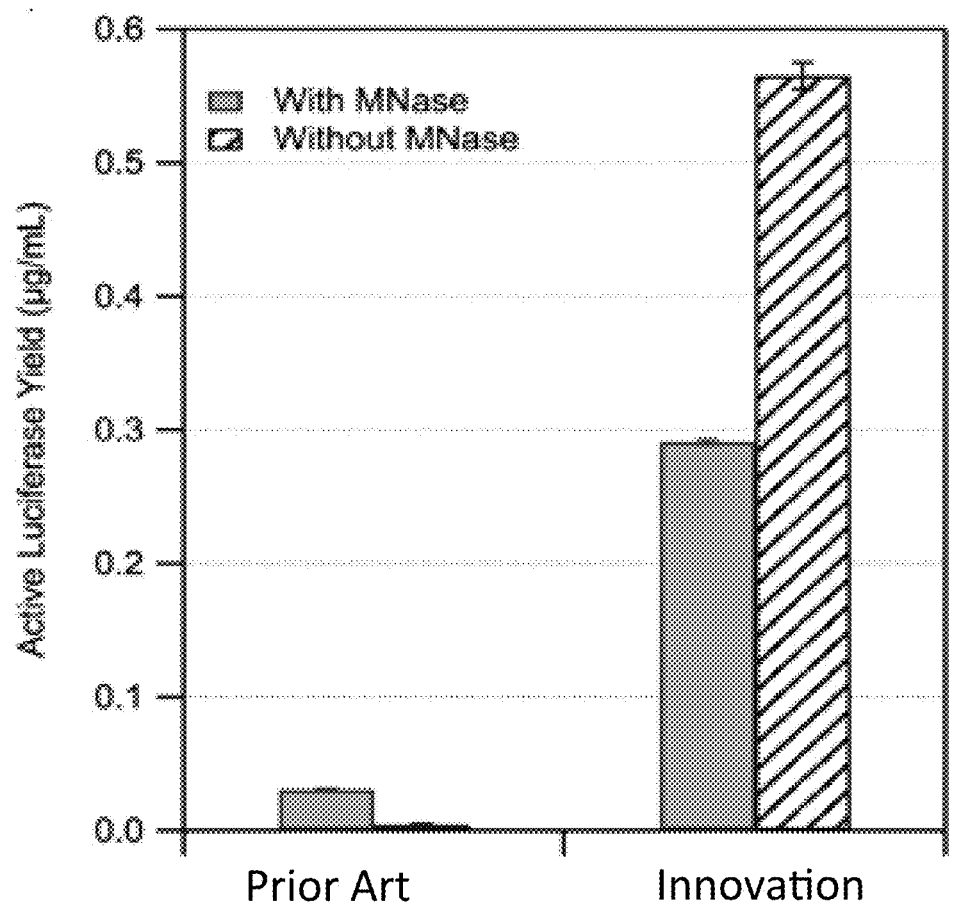
FIG. 1C illustrates active luciferase yield from cell-free translation only reactions, wherein the two extract preparation methods of FIGS. 1A and 1B are compared in the presence or absence of Micrococcal Nuclease (MNase) pre-treatment. Values show means with error bars representing standard deviations (s.d.) of at least 3 independent experiments.

FIG. 1A depicts a scheme for making yeast extracts using a prior art procedure based upon the method of Sarnow and coworkers (Iizuka et al. (1994); Iizuka, N. & Sarnow, P. (1997)). FIG. 1B depicts the method disclosed herein for preparing yeast extracts. The crude extracts prepared by these two methods were evaluated by assessing the total active luciferase yield from batch cell-free translation reactions with capped in vitro transcribed luciferase RNA prepared according to Example 3. Translation of luciferase was carried out in a 15 μL batch reaction for 2 hours at 21° C. Strikingly, extract from innovation method disclosed herein synthesized nearly an order or magnitude more active luciferase (380.9±2.2 ng mL$^{-1}$) relative to the prior art method (53.7±0.7 ng mL$^{-1}$) (FIG. 1C).

Example 15

Removal of Non-Essential Processing Steps

The merits of extraneous processing steps, specifically Micrococcal Nuclease (MNase) treatment and uncoupled in vitro transcription, were evaluated with the system. Both of these steps include costly reagents and were not obviously beneficial to the overall extract preparation design and CFPS reaction. MNase was originally introduced to the extract preparation protocol as a means of digesting endogenous mRNA and mitigating unwanted competition with the gene of interest, as it preferentially digests single stranded nucleic acids. When cell-free translation was performed using the disclosed extract preparation method with the removal of MNase pre-treatment disclosed CFPS reaction had an increase in active luciferase yield from 380.9±2.2 ng mL$^{-1}$ to 681.2±10.2 ng mL$^{-1}$ (FIG. 1C).

Figure 1D:
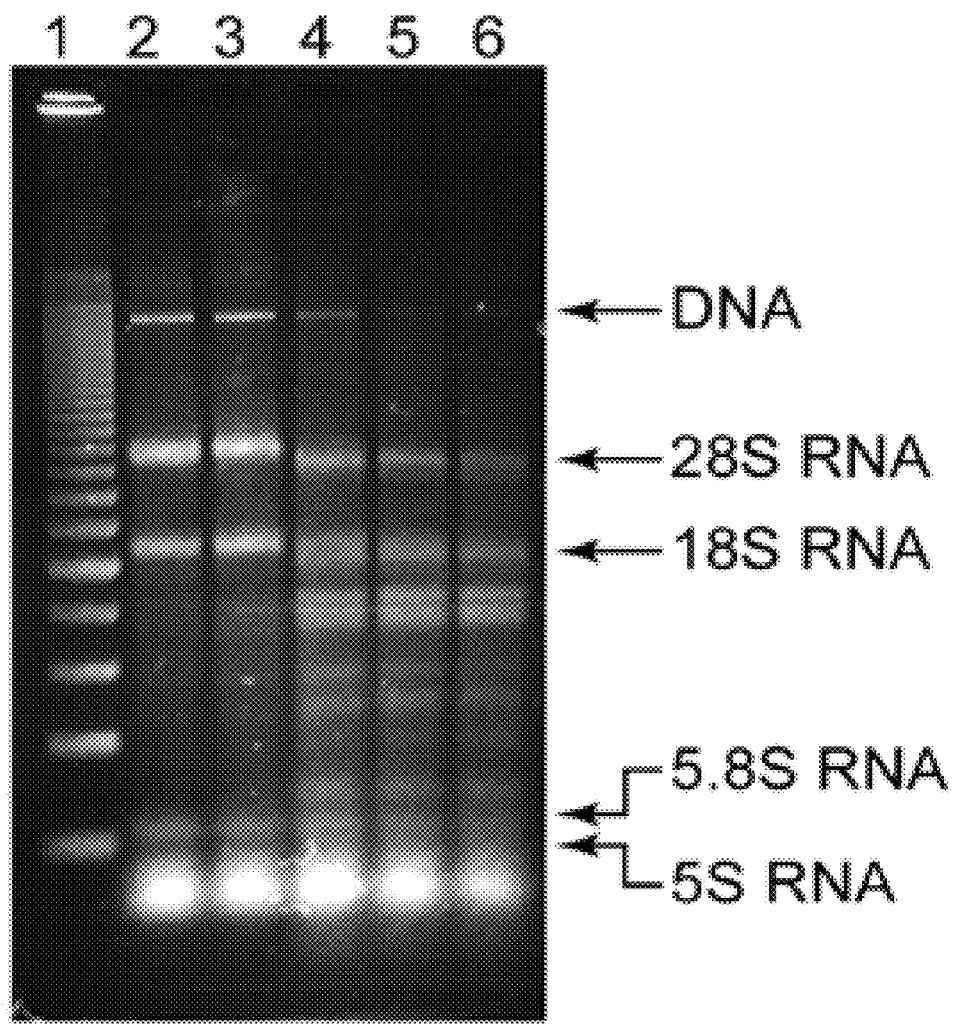
FIG. 1D illustrates that MNase pre-treatment degrades ribosomal RNA (rRNA), as shown by the disappearance of the original rRNA bands. Lane 1: 200 bp DNA step ladder (Promega, Madison, Wis.), lane 2: Crude extract with no MNase pre-treatment, lanes 3-6: Crude extract after MNase pre-treatment for 0, 10, 20, and 30 min, respectively.

Without the claimed subject matter being bound to any particular theory, the MNase decreased activity in the extract by non-productively degrading other RNA species that were beneficial for CFPS, specifically ribosomal RNA. To explore this hypothesis, RNA samples were prepared from extracts generated with and without MNase pre-treatment. The results suggest that in addition to digesting endogenous mRNA as expected, MNase also digests ribosomal RNA as an undesirable consequence (FIG. 1D). Consequently, MNase pre-treatment can be removed from for the CFPS reactions disclosed herein.

Example 16

CFPS Reaction Condition Variables

Figure 11A:
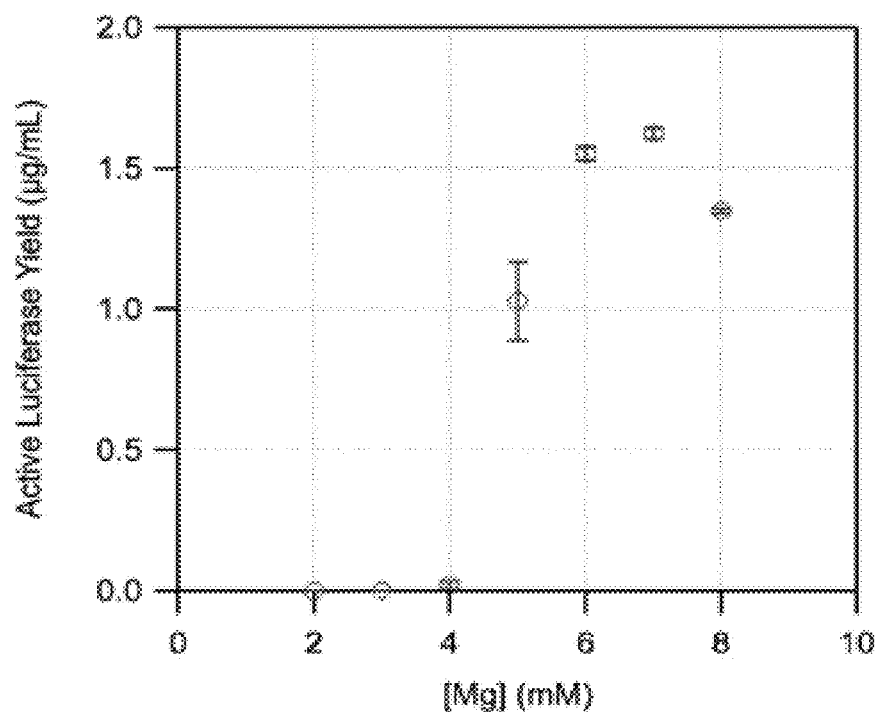
FIG. 11A depicts the physicochemical environment of the CFPS reaction as a function of magnesium concentration.
Figure 11B:
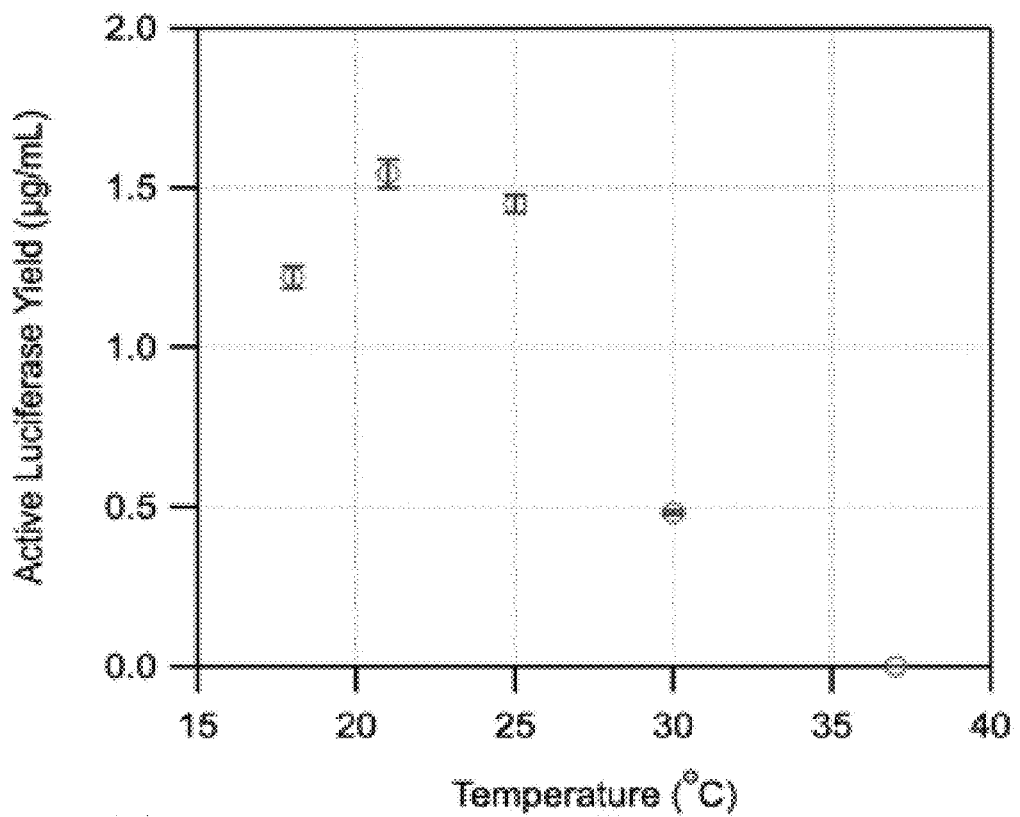
FIG. 11B depicts the physicochemical environment of the CFPS reaction as a function of temperature.

Because the combined transcription and translation reactions required an increase in NTP concentrations from 0.75 mM ATP, 0.1 mM GTP, 0 mM CTP, and 0 mM UTP to 1.5 mM of all NTPs, we initially sought to identify the magnesium concentration resulting in the largest luciferase yields (FIG. 11A). This is because preservation of the ionic composition, which includes free magnesium, is essential for many protein-nucleic acid interactions and the proper function of protein biosynthesis. We found the highest luciferase yields for 2-hour combined Tx/Tl reactions when magnesium concentration was increased from 2 mM, the concentration used for translation only (Iizuka et al. (1994)), to 7 mM. Next, the cell-free reaction temperature was optimized, thereby revealing that active luciferase yield was optimal at 21° C. (FIG. 11B).

Figure 11C:
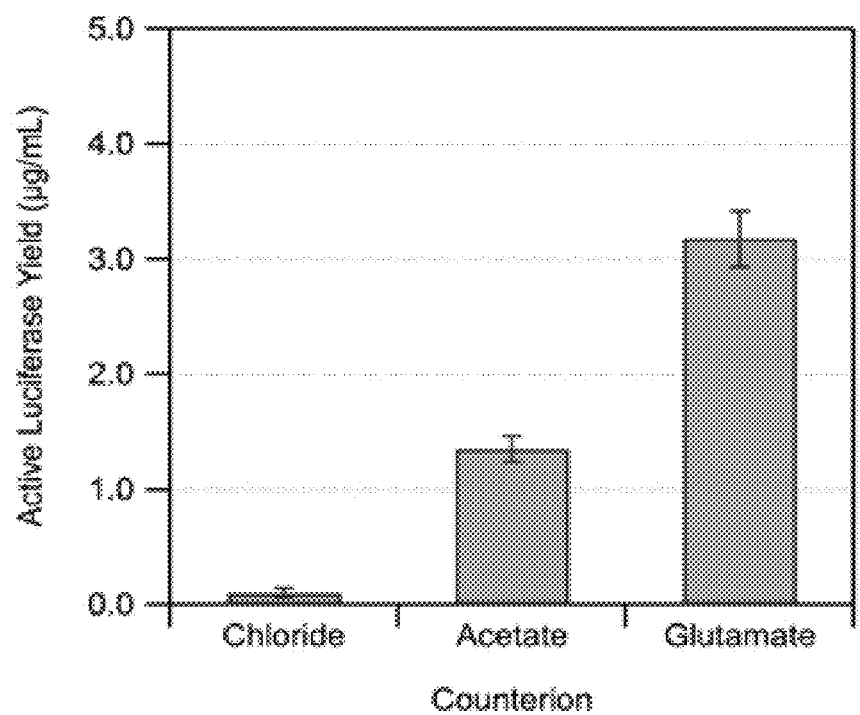
FIG. 11C depicts the physicochemical environment of the CFPS reaction as a function of anions used with potassium and magnesium salts (chloride, acetate, and glutamate as shown).
Figure 11D:
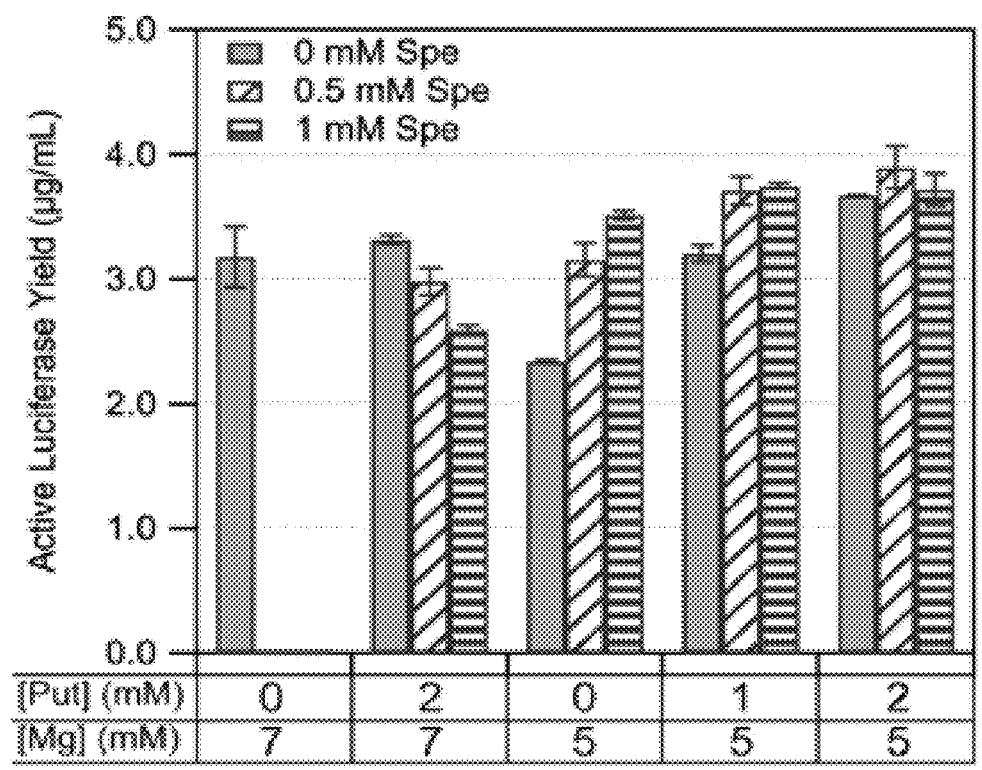
FIG. 11D depicts the physicochemical environment of the CFPS reaction as a function of polyamine concentration (putrescine and spermidine).
Figure 11E:
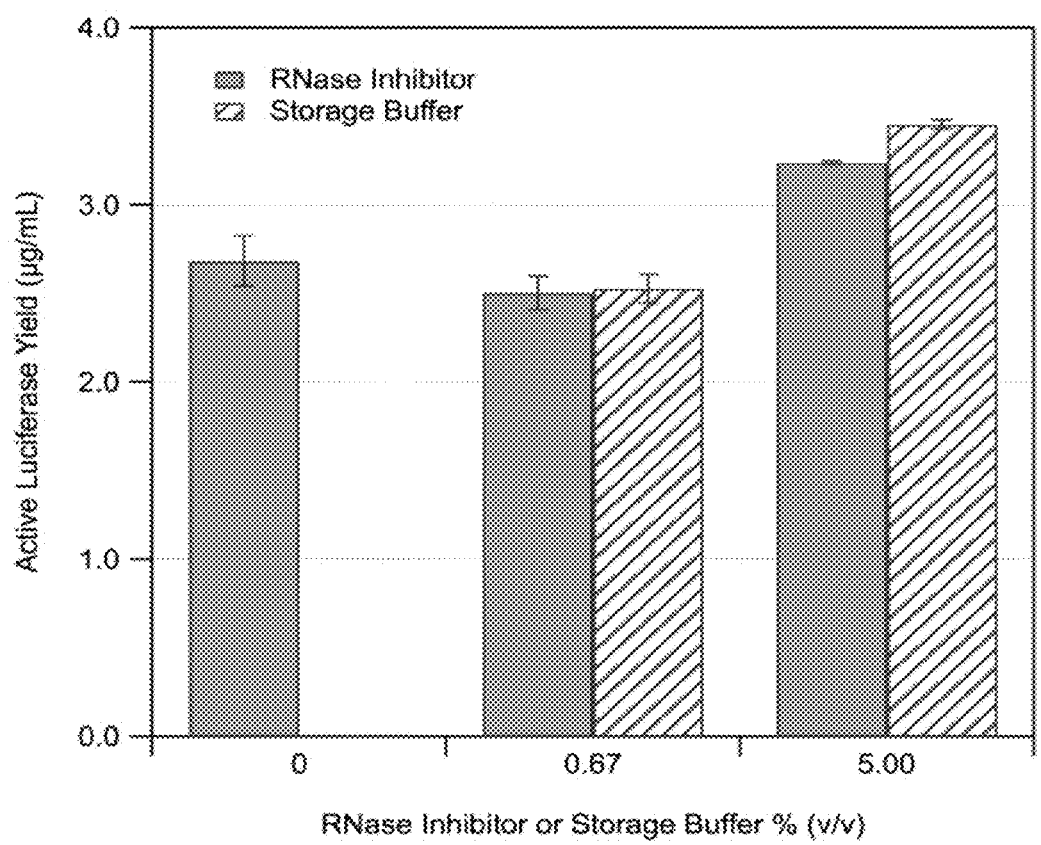
FIG. 11E depicts the effect of adding RNase Inhibitor to the CFPS reaction. RNase Inhibitor (Qiagen, Valencia, Calif.) and RNase Inhibitor "Storage Buffer" (2 mM KH$_2$PO$_4$, 8.0 mM Na$_2$HPO$_4$, 3.0 mM KCl, 150 mM NaCl, pH 7.4, and 50% glycerol) were each added to the cell-free reaction in equal volumes and compared for active luciferase yield.

The physicochemical environment of the CFPS reaction was optimized to better mimic the cytoplasm and improve protein synthesis activity. As an initial step, changes in the ionic composition were targeted, first seeking to use glutamate as the primary anion instead of acetate. Glutamate, which is the most predominant anion used in the cell, is also the preferred anionic species used in vitro because of its dispersed electron charge density compared to acetate or chloride. Substituting glutamate salts for acetate salts, improved active luciferase yield more than 2-fold from $1.35\pm0.11$ µg mL$^{-1}$ to $3.18\pm0.25$ µg mL$^{-1}$ (FIG. 11C). The inclusion of polyamines, specifically spermidine and putrescine, which act to modify the function of and stabilize DNA, RNA, and tRNA was investigated. Polyamines can improve bacterial CFPS. In the yeast CFPS system disclosed herein, the addition of polyamines to the CFPS reaction proved beneficial (FIG. 11D). The optimal concentrations of putrescine and spermidine for luciferase expression were 1 mM and 0.5 mM, respectively. In order to account for the increase in positively charged small molecules in the cell-free reaction, magnesium concentration was decreased from 7 to 5 mM (FIG. 11E). These combined changes improved active luciferase yield to $3.89\pm0.17$ µg mL$^{-1}$ (FIG. 11E).

Example 17

Effect of Added RNAse Inhibitor and Glycerol on CFPS Platform Performance

Figure 11F:
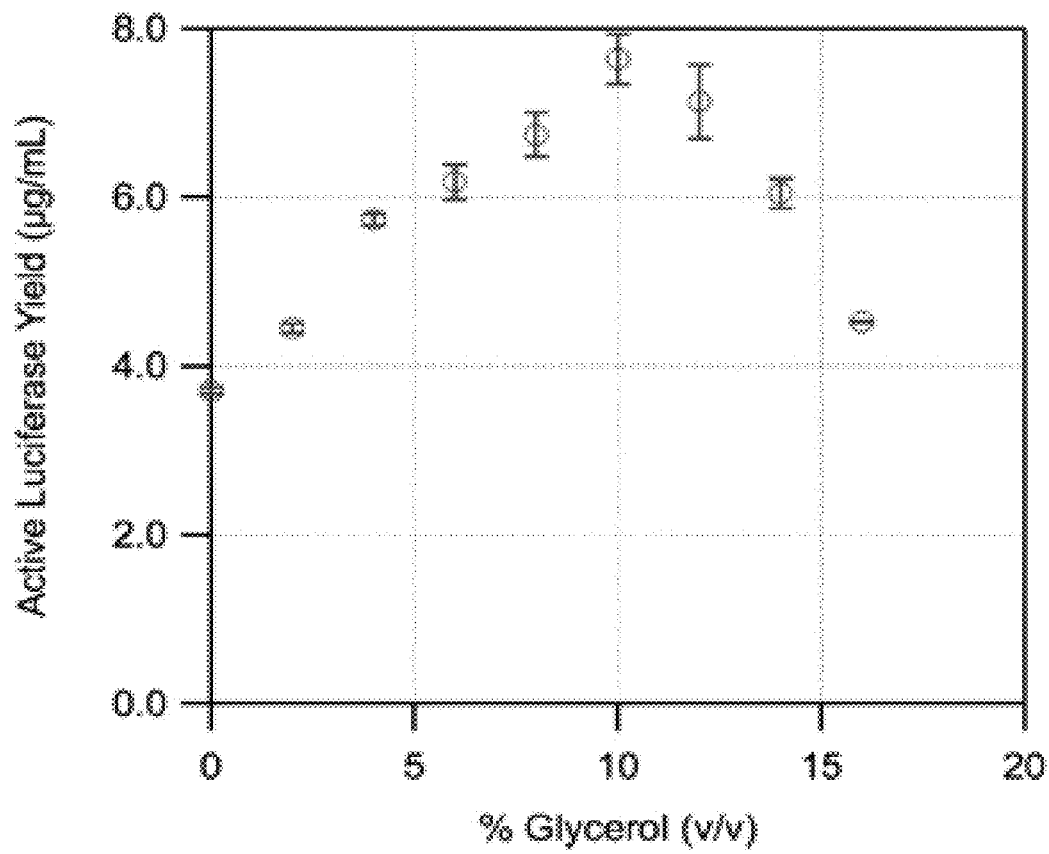
FIG. 11F depicts the physicochemical environment of the CFPS reaction as a function of glycerol concentration.

A technical design criteria for the disclosed system is that it maximizes protein synthesis yield, while minimizing reaction cost. Therefore, the necessity of adding RNase Inhibitor (Qiagen, Valencia, Calif.) to the cell-free reaction was investigated. RNase Inhibitor is expensive and may no longer be a productive component during combined Tx/Tl reactions (that is, mRNA could be continually synthesized with sufficient nucleotides present). Interestingly, the addition of the storage buffer of the RNase Inhibitor (2 mM KH$_2$PO$_4$, 8.0 mM Na$_2$HPO$_4$, 3.0 mM KCl, 150 mM NaCl, pH 7.4, and 50% glycerol) to the CFPS reaction had the same effect of adding the RNase Inhibitor itself in its storage buffer to the CFPS reaction (FIG. 11E). Furthermore, the removal of RNase Inhibitor had no obvious effect on overall yield. This result, unexpectedly, led to the discovery that the addition of glycerol (50% of the RNase Inhibitor storage buffer) improved active luciferase yields to $7.69\pm0.53$ µg mL$^{-1}$ (FIG. 11F). Overall, the disclosed CFPS system, which includes glutamate salts, NTPs, spermidine, putrescine, glycerol, and magnesium, resulted in a 6-fold improvement of CFPS yield systems lacking these components.

Example 18

Comparison of T3, T7 and SP6 RNA Polymerases in Combined Transcription/Translation Yeast CFPS Platform Systems The activity of three commonly used and commercially available phage RNA polymerases including T7, T3, and SP6 RNAP (New England Biolabs, Ipswich, Mass.) were compared in the combined Tx/Tl yeast CFPS platform. Motivation for this work stems from a desire to use the yeast CFPS platform with other polymerases. In addition, this example showcases the ease at which different templates can be investigated by simply varying the second round forward primer using our two-step PCR method. In this example, the three variable RNA Polymerase promoter regions were attached to the sfGFP gene used as the reporter protein (Table 6).

TABLE 6

Round 2 PCR Forward Primers with Variable RNAP Promoter Sequences.

| Primer Name | 5' → 3' Sequence[1] |
|---|---|
| T7-Ω-f (SEQ ID NO: 131) | ccgcgaaatTAATACGACTCACTATAGGGAGA tattttacaacaattaccaacaacaac |
| SP6-Ω-f (SEQ ID NO: 132) | ccgcgaaatATTTAGGTGACACTATAGAAGAG tattttacaacaattaccaacaacaac |
| T3-Ω-f (SEQ ID NO: 133) | ccgcgaaatAATTAACCCTCACTAAAGGGAA tattttacaacaattaccaacaacaac |

[1]Lowercase standard: 5' end GC clamp; Uppercase standard: RNAP Promoter sequence; lowercase italics standard: Ω sequence overlap.

As evident in FIG. 12A, both T7 and T3 RNA Polymerases are active in yeast CFPS reactions with comparable yield and SP6 RNA Polymerase is active, although with reduced productivity. In this experiment, each polymerase was normalized for the amount of Units added (1 U is defined as amount of enzyme that will incorporate 1 nmol ATP in a 50 µL reaction in 1 h at 37° C.). The storage buffer for each polymerase was identical (50 mM Tris-HCl, 100 mM NaCl, 20 mM β-mercaptoethanol, 1 mM EDTA, 50% Glycerol, and 0.1% Triton® X-100, pH 7.9) and differences in volume added were accounted for by supplying the reaction with additional storage buffer.

Because equal Units of each RNA Polymerase were supplied to each reaction, one would expect equivalent amounts of mRNA to be synthesized. To confirm activity of each polymerase on the generated PCR templates, separate in vitro transcription reactions confirmed amplification is possible under the appropriate conditions. Therefore, one possible explanation for the result in FIG. 12A is that only T7 and T3 RNA Polymerases are active in the given reaction conditions for yeast CFPS. Alternatively, the initial nucleotides transcribed by SP6 polymerase could negatively affect the Ω sequence function. Ultimately, this result confirms that T3 RNA Polymerase is an option for use in yeast CFPS reactions, but SP6 RNA Polymerase should be avoided in this particularly optimized platform. Furthermore, the commercially available T7 RNA Polymerase gives similar reaction yields to T7 RNA Polymerase prepared in house using the method Swartz et al. (2004) confirming that either source would be an appropriate option for general use (FIG. 12B).

Example 19

Effect of Kozak Sequence Elements on Yeast CFPS Platform

The inclusion of the Kozak sequence, which is a consensus sequence found in the 5'-UTR of mRNA, can assist in eukaryotic translation initiation (Kozak, M., "An analysis of 5'-noncoding sequences from 699 vertebrate messenger RNAs," *Nucleic Acids Res.* 15, 8125-8148 (1987)). The effects of including the Kozak sequence in the DNA template was investigated. Using the developed 2-step PCR method and only varying the initial forward primer, alternate forms of the Kozak sequence were inserted directly downstream of the Ω sequence. The specific primers are illustrated in Table 7, where the lower case font indicates gene-specific sequence hybridization, italics font indicates the *S. cerevisiae* consensus Kozak sequence; the bold font indicated the T7 RNA Polymerase promoter sequence; the underlined font indicates the Tobacco Mosaic Virus Ω Sequence (contains 5' overlap between PCR1- and PCR2-specific primers; and the double-underlined font indicates the 3' overlap between PCR1- and PCR2-specific primers for the superfolder GFP ("sfGFP") ORF (SEQ ID NO: 37) (Table 7).

TABLE 7

Primer Design for PCR Template Production

| Primer | Sequence (5' → 3') |
|---|---|
| P1.1-Ω-Kozak(*S. cer* partial)-sfGFP-f (SEQ ID NO.: 134) | ACAAACAACATTACAATTACTATTTACAATTAA *AAAAA*atgagcaaaggtgaagaactgt |
| P1.2-sfGFP-r (SEQ ID NO 135) | AGCAGCCGGATCTCAGTttattttcgaactggggatgg |
| P2.1-T7-Ω-f (SEQ ID NO.: 136) | CCGCGAAATTAATACGACTCACTATAGGGAGT ATTTTTACAACAATTACCAACAACAACAAACAA CAAACAACATTACAATTACTATTTACAATTA |
| P2.2-PolyA50-r (SEQ ID NO.: 137) | TTTTTTTTTTTTTTTTTTTTTTTTTTTTTTTT TTTTTTTTTTTTTGTTAGCAGCCGGATCTCAGT |

In the first PCR stage, sense and anti-sense primers were designed to anneal to the sfGFP sequence and add overlapping regions to each end of the PCR product. The 5'-end of the first stage PCR product contained a flanking sequence encoding the canonical yeast Kozak sequence (AAAAAA) and partially encoding the Ω sequence from tobacco mosaic virus. The 3'-end of the first stage PCR product contained an additional 17 nt flanking sequence. The second stage PCR sense and anti-sense primers were designed to anneal to the 5'- and 3'-flanking sequence, respectively. The 5'-region of the full-length PCR product encoded the full Ω sequence (65 nt) as well as the T7 Promoter sequence. The 3'-end encoded a 50 nt poly(T) sequence to extend the mRNA with a poly(A)$_{50}$ tail.

Three Kozak sequences were evaluated in sfGFP expression constructs including: (i) the consensus eukaryotic Kozak sequence, and the *S. cerevisiae* specific sequence (ii) with and (iii) without adjusting the second translated codon after the canonical AUG (Table 8).

TABLE 8

Kozak Sequences Investigated in Yeast CFPS Reactions

| Name[1] | 5' → 3' Sequence[2] |
|---|---|
| No Kozak (SEQ ID NO: 138) | cat ATG |
| Consensus Full (SEQ ID NO: 139) | cCC ACC ATG G |
| *S. cerevisiae* Partial (SEQ ID NO: 140) | aAa AaA ATG |
| *S. cerevisiae* Full (SEQ ID NO: 141) | aAa AaA ATG TCt |

[1]Expression constructs (5'-UTR containing an Ω sequence and the sfGFP open reading frame) containing these sequences are indicated in parentheses.
[2]Sequences shown coincide to sequence region candidate Kozak sequence. Lowercase italics font: Restriction digest scar (NdeI); lowercase standard font: most common base found at that position; uppercase standard font: highly conserved base found at that position; bold ATG: start codon.

FIG. 3B shows 40% improvement in sfGFP synthesis yields when either form of the *S. cerevisiae* Kozak sequence is included. Furthermore, the difference in synthesis yields is dominated by the rate of synthesis (as opposed to duration effects). This result would be representative of the fact that translation initiation is indeed catalytically limiting and enhancing the rate of initiation improves the overall protein synthesis yield in a finite reaction. Additionally, there was no significant difference between the *S. cerevisiae* partial and full Kozak sequences, suggesting the second translated codon present in sfGFP (AGC) is sufficient for enhanced expression. Furthermore, there was no significant difference between the consensus eukaryotic Kozak sequence and no Kozak sequence, thus supporting the notion that the yeast translation apparatus is evolutionarily distinct from higher eukaryotes.

Example 20

Extending the Reaction Lifetime

FIG. 13A shows active luciferase yield throughout the duration of the CFPS batch reaction. The final yield of luciferase after a 120-minute incubation was 7.69±0.53 μg mL$^{-1}$. This duration of synthesis is very robust, being the longest demonstrated for a yeast CFPS batch reaction. There are several potential reasons the cell-free reaction may stop synthesizing protein after 2 h. This list includes but is not limited to: DNA/mRNA degradation, substrate limitations, toxic molecule accumulation, and loss of crude extract activity. Activity loss of crude extract proteins would be particularly detrimental. To test the validity of this concern, a set of experiments were designed that were directed toward unveiling if degradation of factors in the extract alone could be responsible for reaction termination. The extract was pre-incubated at 21° C. for 0, 15, 30, 60, 90, 120, 150, and 180 minutes and then the pre-incubated extract was used for 2-hour batch CFPS assays (FIG. 13B, C). Strikingly, no change in final CFPS luciferase yield was found after up to three hours of pre-incubation. These data suggest that catalyst activity is not responsible for reaction cessation.

SEQUENCE TABLE

| Name (SEQ ID NO: ___) | Sequence (5' → 3' if nucleotides; N → C if amino acids) |
| --- | --- |
| CappA90 (SEQ ID NO: 1) | gagaccacaacggtttccctctagaaataattttgtttaactttaagaaggagatatacatatggaagacgccaaaa acataaagaaaggcccggcgccattctatccgctagaggatggaaccgctggagagcaactgcataaggctat gaagagatacgccctggttcctggaacaattgcttttacagatgcacatatcgaggtgaacatcacgtacgcgga atacttcgaaatgtccgttcggttggcagaagctatgaaacgatatgggctgaatacaaatcacagaatcgtcgta tgcagtgaaaactctcttcaatctttatgccggtgttgggcgcgttatttatcggagttgcagttgcgcccgcgaac gacatttataatgaacgtgaattgctcaacagtatgaacatttcgcagcctaccgtagtgtttgtttccaaaaaggg gttgcaaaaaattttgaacgtgcaaaaaaaattaccaataatccagaaaattattatcatggattctaaaacggatta ccagggattcagtcgatgtacacgttcgtcacatctcatctacctcccggttttaatgaatacgattttgtaccaga gtcctttgatcgtgacaaaacaattgcactgataatgaactcctctggatctactgggttacctaagggtgtggccc ttccgcatagaactgcctgcgtcagattctcgcatgccagagatcctattttttggcaatcaaatcattccggatactg cgattttaagtgttgttccattccatcacggttttggaatgtttactacactcggatatttgatatgtggatttcgagtcg tcttaatgtatagatttgaagaagagctgttttacgatccttcaggattacaaaattcaaagtgcgttgctagtacc aaccctattttcattcttcgccaaaagcactctgattgacaaatacgatttatctaatttacacgaaattgcttctgggg gcgcacctctttcgaaagaagtcggggaagcggttgcaaaacgcttccatcttccagggatacgacaaggatat gggctcactgagactacatcagctattctgattacacccgaggggatgataaaccgggcgcggtcggtaaagt tgttccattttttgaagcgaaggttgtggatctggataccgggaaaacgctgggcgttaatcagagaggcgaatta tgtgtcagaggacctatgattatgtccggttatgtaaacaatccggaagcgaccaacgccttgattgacaaggatg gatggctacattctggagacatagcttactgggacgaagacgaacacttcttcatagttgaccgcttgaagtcttta attaaatacaaaggataccaggtggccccgctgaattggagtcgatattgttacaacaccccaacatcttcgac gcgggcgtggcaggtcttcccgacgatgacgccgtgaacttcccgccgccgttgttgttttggagcacggaaa gacgatgacggaaaaagagatcgtggattacgtcgccagtcaagtaacaaccgccaaaaagttgcgcggagg agttgtgtttgtggacgaagtaccgaaaggtcttaccggaaaactcgacgcaagaaaaatcagagagatcctcat aaaggccaagaagggcggaaagtccaaattgtaaaaaaaaaaaaaaaaaaaaaaaaaaaaaaaaaaaaaaaa aaaaaaaaaaaaaaaaaaaaaaaaaaaaaaaaaaaaaaaaaaaaaaaaaaaaaaaa |
| HAPpA90 (SEQ ID NO: 2) | gagaccacaacggtttccctctagataaaccccagttttatatcgtatatgctatctacaggtccactttacacttaat aatataaaaatactactataaaggaaccagaaaaataaaaaagggtcattatttattttgagcagatcattatcaaac gcataggaagagaaaaaacacagtttatttttttttccacacatatttattggtctcctagtacatcaaagagcatttta atggggttgctgatttgttttacctacattttctagtacaaaaaaaaaacaaaaaaagacatatggaagacgccaaaa acataaagaaaggcccggtgccattctatccgctagaggatggaaccgctggagagcaactgcataaggctat gaagagatacgccctggttcctggaacaattgcttttacagatgcacatatcgaggtgaacatcacgtacgcgga atacttcgaaatgtccgttcggttggcagaagctatgaaacgatatgggctgaatacaaatcacagaatcgtcgta tgcagtgaaaactctcttcaatctttatgccggtgttgggcgcgttatttatcggagttgcagttgcgcccgcgaac gacatttataatgaacgtgaattgctcaacagtatgaacatttcgcagcctaccgtagtgtttgtttccaaaaaggg gttgcaaaaaattttgaacgtgcaaaaaaaattaccaataatccagaaaattattatcatggattctaaaacggatta ccagggattcagtcgatgtacacgttcgtcacatctcatctacctcccggttttaatgaatacgattttgtaccaga gtcctttgatcgtgacaaaacaattgcactgataatgaactcctctggatctactgggttacctaagggtgtggccc ttccgcatagaactgcctgcgtcagattctcgcatgccagagatcctattttttggcaatcaaatcattccggatactg cgattttaagtgttgttccattccatcacggttttggaatgtttactacactcggatatttgatatgtggatttcgagtcg tcttaatgtatagatttgaagaagagctgttttacgatccttcaggattacaaaattcaaagtgcgttgctagtacc aaccctattttcattcttcgccaaaagcactctgattgacaaatacgatttatctaatttacacgaaattgcttctgggg gcgcacctctttcgaaagaagtcggggaagcggttgcaaaacgcttccatcttccagggatacgacaaggatat gggctcactgagactacatcagctattctgattacacccgaggggatgataaaccgggcgcggtcggtaaagt tgttccattttttgaagcgaaggttgtggatctggataccgggaaaacgctgggcgttaatcagagaggcgaatta tgtgtcagaggacctatgattatgtccggttatgtaaacaatccggaagcgaccaacgccttgattgacaaggatg gatggctacattctggagacatagcttactgggacgaagacgaacacttcttcatagttgaccgcttgaagtcttta attaaatacaaaggataccaggtggccccgctgaattggagtcgatattgttacaacaccccaacatcttcgac gcgggcgtggcaggtcttcccgacgatgacgccgtgaacttcccgccgccgttgttgttttggagcacggaaa gacgatgacggaaaaagagatcgtggattacgtcgccagtcaagtaacaaccgccaaaaagttgcgcggagg agttgtgtttgtggacgaagtaccgaaaggtcttaccggaaaactcgacgcaagaaaaatcagagagatcctcat aaaggccaagaagggcggaaagtccaaattgtaaaaaaaaaaaaaaaaaaaaaaaaaaaaaaaaaaaaaaaa aaaaaaaaaaaaaaaaaaaaaaaaaaaaaaaaaaaaaaaaaaaaaaaaaaaaaaaa |
| TFIIDpA90 (SEQ ID NO: 3) | gagaccacaacggtttccctctagatcgatgcggccgcgaattcgggacgtgaaaattacagtagttactgtttttt ttggactataagatcggggaaagataacacataagaaataaaacgactactagttagactgctctgcggaaga agcaaggaagtaaaggctgcattttatttttctttctagtccaacataaacaggtgtatcaagagaaactttttaag agctcgtcgacggatccatatggaagacgccaaaaacataaagaaaggcccggcgccattctatccgctagag gatgaaccgctggagagcaactgcataaggctatgaagagatacgccctggttcctggaacaattgcttttaca gatgcacatatcgaggtgaacatcacgtacgcggaatacttcgaaatgtccgttcggttggcagaagctatgaaa cgatatgggctgaatacaaatcacagaatcgtcgtatgcagtgaaaactctcttcaatctttatgccggtgttggg cgcgttatttatcggagttgcagttgcgcccgcgaacgacatttataatgaacgtgaattgctcaacagtatgaaca tttcgcagcctaccgtagtgtttgtttccaaaaagggttgcaaaaaattttgaacgtgcaaaaaaaattaccaata atccagaaaattattatcatggattctaaaacggattaccagggatttcagtcgatgtacacgttcgtcacatctcat ctacctcccggttttaatgaatacgattttgtaccagagtccttttgatcgtgacaaaacaattgcactgataatgaact cctctggatctactgggttacctaagggtgtggcccttccgcatagaactgcctgcgtcagattacgcatgccag agatcctattttttggcaatcaaatcattccggatactgcgattttaagtgttgttccattccatcacggttttggaatgtt tactacactcggatatttgatatgtggatttcgagtcgtcttaatgtatagatttgaagaagagctgttttacgatccc |

-continued

```
                    ttcaggattacaaaattcaaagtgcgttgctagtaccaaccctattttcattcttcgccaaaagcactagattgacaa
                    atacgatttatctaatttacacgaaattgcttctggggcgcacctctttcgaaagaagtcggggaagcggttgca
                    aaacgcttccatcttccagggatacgacaaggatatgggctcactgagactacatcagctattctgattacacccg
                    agggggatgataaaccgggcgcggtcggtaaagttgttccattttttgaagcgaaggttgtggatctggataccg
                    ggaaaacgctgggcgttaatcagagaggcgaattatgtgtcagaggacctatgattatgtccggttatgtaaaca
                    atccggaagcgaccaacgccttgattgacaaggatggatggctacattctggagacatagcttactgggacgaa
                    gacgaacacttcttcatagttgaccgcttgaagtctttaattaaatacaaaggataccaggtggccccgctgaatt
                    ggagtcgatattgttacaacaccccaacatcttcgacgcgggcgtggcaggtcttcccgacgatgacgccggtg
                    aacttcccgccgccgttgttgttttggagcacggaaagacgatgacggaaaaagagatcgtggattacgtcgcc
                    agtcaagtaacaaccgccaaaaagttgcgcggaggagtgtgtttgtggacgaagtaccgaaaggtcttaccgg
                    aaaactcgacgcaagaaaaatcagagagatcctcataaaggccaagaagggcggaaagtccaaattgtaaaa
                    aaaaaaaaaaaaaaaaaaaaaaaaaaaaaaaaaaaaaaaaaaaaaaaaaaaaaaaaaaaaaaaaaaaaaaaaaa
                    aaaaaaaaaaaaaaaa P150pA90            gagaccacaacggtttccctctagacccagttcgatcctgggcgaaatcattttttgaaaattacattaataaggct
(SEQ ID NO: 4)      ttttttcaatatctctggaacaacgtttgtttctacttactaatagctttaaggaccctcttggacatcatgatggcagact
                    tccatcgtagtgggatgatcatatgatgggcgctatcctcatcgcgactcgataacgacgtgagaaacgattttttt
                    ttctcttttcaccgtatttttgtgcgtccttttcaattatagctttttttttattttttttttttctcgtactgtttcact
                    gacaaaagttttttttcaagaaaaattttcgatgccgcgttctctgtgtgcaacggatggatggtagatggaatttcaata
                    tgttgcttgaaattttaccaatcttgatattgtgataatttacttaattatgattcttcctcttcccttcaatttcttaaa
                    gcttcttacttactccttcttgctcataaataagcaaggtaagaggacaactgtaattacctattacaataggatccata
                    tggaagacgccaaaaacataaagaaaggcccggcgccattctatccgctagaggatggaaccgctggagagcaactgcata
                    aggctatgaagagatacgcccttggttcctggaacaattgcttttacagatgcacatatcgaggtgaacatcacgta
                    cgcggaatacttcgaaatgtccgttcggttggcagaagctatgaaacgatatgggctgaatacaaatcacagaat
                    cgtcgtatgcagtgaaaactctcttcaattctttatgccggtgttgggcgcgttatttatcggagttgcagttgcgcc
                    cgcgaacgacatttataatgaacgtgaattgctcaacagtatgaacattttcgcagcctaccgtagtgtttgtttccaa
                    aaagggggttgcaaaaaattttgaacgtgcaaaaaaaattaccaataatccagaaaattattatcatgggattctaaaa
                    cggattaccagggatttcagtcgatgtacacgttcgtcacatctcatctacctcccggttttaatgaatacgattttgt
                    accagagtcctttgatcgtgacaaaacaattgcactgataatgaactcctctggatctactgggttacctaagggtg
                    tggcccttccgcatagaactgcctgcgtcagattctcgcatgccagagatcctattttttggcaatcaaatcattccg
                    gatactgcgattttaagtgttgttccattccatcacggttttggaatgtttactacactcggatatttgatatgtggatttc
                    gagtcgtcttaatgtatagatttgaagaagagctgtttttacgatcccttcaggattacaaaattcaaagtgcgttgct
                    agtaccaaccctattttcattcttcgccaaaagcactctgattgacaaatacgatttatctaatttacacgaaattgcttct
                    ggggcgcaccctctttcgaaagaagtcggggaagcggttgcaaaacgcttccatcttccagggatacgaca
                    aggatatgggctcactgagactacatcagctattctgattacacccgagggggatgataaaccgggcgcggtcg
                    gtaaagttgttccattttttgaagcgaaggttgtggatctggataccgggaaaacgctgggcgttaatcagagagg
                    cgaattatgtgtcagaggacctatgattatgtccggttatgtaaacaatccggaagcgaccaacgccttgattgac
                    aaggatggatggctacattctggagacatagcttactgggacgaagacgaacacttcttcatagttgaccgcttga
                    agtctttaattaaatacaaaggataccaggtggccccgctgaattggagtcgatattgttacaacaccccaacat
                    cttcgacgcgggcgtggcaggtcttcccgacgatgacgccggtgaacttcccgccgccgttgttgttttggagca
                    cggaaagacgatgacggaaaaagagatcgtggattacgtcgccagtcaagtaacaaccgccaaaaagttgcg
                    cggaggagttgtgtttgtggacgaagtaccgaaaggtcttaccggaaaactcgacgcaagaaaaatcagagag
                    atcctcataaaggccaagaagggcggaaagtccaaattgtaaaaaaaaaaaaaaaaaaaaaaaaaaaaaaaaaa
                    aaaaaaaaaaaaaaaaaaaaaaaaaaaaaaaaaaaaaaaaaaaaaaaaaa YAP1pA90            gagaccacaacggtttccctctagatagtaaccagccctagctgtttggttgatttgacctaggttactcttttctttttt
(SEQ ID NO: 5)      ctgggtgcgggtaacaatttgggccccgcaaagcgcgtctttgtcatgggaaccggaaaccctccgatgaag
                    agtaggagggtggcaactgatggatgcgtaaggtcttaagagatacatttgcttaatagtcttccgttaccgatta
                    agcacagtacctttacgttatatataggattggtgtttagcttttttttcctgagccctggttgacttgtgcatgaacac
                    gagccatttttagtttgtttaagggaagttttttgccacccaaaacgtttaaagaaggaaaagttgtttcttaaacccat
                    atggaagacgccaaaaacataaagaaaggcccggcgccattctatccgctagaggatggaaccgctggagag
                    caactgcataaggctatgaagagatacgcccttggttcctggaacaattgcttttacagatgcacatatcgaggtga
                    acatcacgtacgcggaatacttcgaaatgtccgttcggttggcagaagctatgaaacgatatgggctgaatacaa
                    atcacagaatcgtcgtatgcagtgaaaactctcttcaattctttatgccggtgttgggcgcgttatttatcggagttgc
                    agttgcgcccgcgaacgacatttataatgaacgtgaattgctcaacagtatgaacattttcgcagcctaccgtagtg
                    tttgtttccaaaaagggggttgcaaaaaattttgaacgtgcaaaaaaaattaccaataatccagaaaattattatcatg
                    gattctaaaacggattaccagggatttcagtcgatgtacacgttcgtcacatctcatctacctcccggttttaatgaat
                    acgattttgtaccagagtcctttgatcgtgacaaaacaattgcactgataatgaactcctctggatctactgggttac
                    ctaagggtgtggcccttccgcatagaactgcctgcgtcagattctcgcatgccagagatcctattttttggcaatcaa
                    atcattccggatactgcgattttaagtgttgttccattccatcacggttttggaatgtttactacactcggatatttgata
                    tgtggatttcgagtcgtcttaatgtatagatttgaagaagagctgtttttacgatcccttcaggattacaaaattcaaa
                    gtgcgttgctagtaccaaccctattttcattcttcgccaaaagcactctgattgacaaatacgatttatctaatttacac
                    gaaattgcttctggggcgcaccctctttcgaaagaagtcggggaagcggttgcaaaacgcttccatcttccagg
                    gatacgacaaggatatgggctcactgagactacatcagctattctgattacacccgagggggatgataaaccgg
                    gcgcggtcggtaaagttgttccattttttgaagcgaaggttgtggatctggataccgggaaaacgctgggcgttaa
                    tcagagaggcgaattatgtgtcagaggacctatgattatgtccggttatgtaaacaatccggaagcgaccaacgc
                    cttgattgacaaggatggatggctacattctggagacatagcttactgggacgaagacgaacacttcttcatagtt
                    gaccgcttgaagtctttaattaaatacaaaggataccaggtggccccgctgaattggagtcgatattgttacaac
                    accccaacatcttcgacgcgggcgtggcaggtcttcccgacgatgacgccggtgaacttcccgccgccgttgtt
                    gttttggagcacggaaagacgatgacggaaaaagagatcgtggattacgtcgccagtcaagtaacaaccgcca
                    aaaagttgcgcggaggagttgtgtttgtggacgaagtaccgaaaggtcttaccggaaaactcgacgcaagaaa
                    aatcagagagatcctcataaaggccaagaagggcggaaagtccaaattgtaaaaaaaaaaaaaaaaaaaaaaa
                    aaaaaaaaaaaaaaaaaaaaaaaaaaaaaaaaaaaaaaaaaaaaaaaaaaaaaaaaaaaaaaaaaaaaaaaaa IGRpA90             agaccacaacggtttccctctagagcaaaaatgtgatcttgcttgtaaatacaattttgagaggttaataaattacaa
(SEQ ID NO: 6)      gtagtgctatttttgtatttaggttagctatttagctttacgttccaggatgcctagtggcagccccacaatatccagg
                    aagccctctctgcggttttcagattaggtagtcgaaaacctaagaaatttacctgctacatttcaagattcatatgg
                    aagacgccaaaaacataaagaaaggcccggcgccattctatccgctagaggatggaaccgctggagagcaac
                    tgcataaggctatgaagagatacgcccttggttcctggaacaattgcttttacagatgcacatatcgaggtgaacat
```

-continued

```
                    cacgtacgcggaatacttcgaaatgtccgttcggttggcagaagctatgaaacgatatgggctgaatacaaatca
                    cagaatcgtcgtatgcagtgaaaactctcttcaattctttatgccggtgttgggcgcgttatttatcggagttgcagtt
                    gcgcccgcgaacgacatttataatgaacgtgaattgctcaacagtatgaacatttcgcagcctaccgtagtgtttgt
                    ttccaaaaagggggttgcaaaaaattttgaacgtgcaaaaaaattaccaataatccagaaaattattatcatggatt
                    ctaaaacggattaccagggatttcagtcgatgtacacgttcgtcacatctcatctacctcccggttttaatgaatacg
                    attttgtaccagagtcctttgatcgtgacaaaacaattgcactgataatgaactcctctggatctactgggttacctaa
                    gggtgtggcccttccgcatagaactgcctgcgtcagattctcgcatgccagagatcctatttttggcaatcaaatca
                    ttccggatactgcgattttaagtgttgttccattccatcacggttttggaatgtttactacactcggatatttgatatgtg
                    gatttcgagtcgtcttaatgtatagatttgaagaagagctgttttttacgatcccttcaggattacaaaattcaaagtgc
                    gttgctagtaccaaccctatttttcattcttcgccaaaagcactctgattgacaaatacgatttatctaatttacacgaaa
                    ttgcttctgggggcgcacctctttcgaagaagtcggggaagcggttgcaaaacgcttccatcttccagggatac
                    gacaaggatatgggctcactgagactacatcagctattctgattacacccgaggggatgataaaccgggcgc
                    ggtcggtaaagttgttccattttttgaagcgaaggttgtggatctggataccgggaaaacgctgggcgttaatcag
                    agaggcgaattatgtgtcagaggacctatgattatgtccggttatgtaaacaatccggaagcgaccaacgccttg
                    attgacaaggatggatggctacattctggagacatagcttactgggacgaagacgaacacttcttcatagttgacc
                    gcttgaagtctttaattaaatacaaaggataccaggtggcccccgctgaattggagtcgatattgttacaacaccc
                    caacatcttcgacgcgggcgtggcaggtcttcccgacgatgacgccggtgaacttcccgccgccgttgttgtttt
                    ggagcacggaaagacgatgacggaaaaagagatcgtggattacgtcgccagtcaagtaacaaccgccaaa
                    agttgcgcggaggagttgtgtttgtggacgaagtaccgaaaggtcttaccggaaaactcgacgcaagaaaatc
                    agagagatcctcataaaggccaagaagggcggaaagtccaaattgtaaaaaaaaaaaaaaaaaaaaaaaaa
                    aaaaaaaaaaaaaaaaaaaaaaaaaaaaaaaaaaaaaaaaaaaaaaaaaaaaaaaaaaaaa A64pA90             gagaaaaaaaaaaaaaaaaaaaaaaaaaaaaaaaaaaaaaaaaaaaaaaaaaaaaaaaaaaaaacatat
(SEQ ID NO: 7)      ggaagacgccaaaaacataaagaaaggcccggcgccattctatccgctagaggatggaaccgctggagagc
                    aactgcataaggctatgaagagatacgccctggttcctggaacaattgcttttacagatgcacatatcgaggtgaa
                    catcacgtacgcggaatacttcgaaatgtccgttcggttggcagaagctatgaaacgatatgggctgaatacaaa
                    tcacagaatcgtcgtatgcagtgaaaactctcttcaattctttatgccggtgttgggcgcgttatttatcggagttgca
                    gttgcgcccgcgaacgacatttataatgaacgtgaattgctcaacagtatgaacatttcgcagcctaccgtagtgtt
                    tgtttccaaaaagggggttgcaaaaaattttgaacgtgcaaaaaaattaccaataatccagaaaattattatcatgg
                    attctaaaacggattaccagggatttcagtcgatgtacacgttcgtcacatctcatctacctcccggttttaatgaata
                    cgattttgtaccagagtcctttgatcgtgacaaaacaattgcactgataatgaactcctctggatctactgggttacc
                    taagggtgtggcccttccgcatagaactgcctgcgtcagattctcgcatgccagagatcctatttttggcaatcaaa
                    tcattccggatactgcgattttaagtgttgttccattccatcacggttttggaatgtttactacactcggatatttgatat
                    gtggatttcgagtcgtcttaatgtatagatttgaagaagagctgttttttacgatcccttcaggattacaaaattcaaag
                    tgcgttgctagtaccaaccctatttttcattcttcgccaaaagcactctgattgacaaatacgatttatctaatttacacg
                    aaattgcttctgggggcgcacctctttcgaagaagtcggggaagcggttgcaaaacgcttccatcttccaggga
                    tacgacaaggatatgggctcactgagactacatcagctattctgattacacccgaggggatgataaaccgggc
                    gcggtcggtaaagttgttccattttttgaagcgaaggttgtggatctggataccgggaaaacgctgggcgttaatc
                    agagaggcgaattatgtgtcagaggacctatgattatgtccggttatgtaaacaatccggaagcgaccaacgcct
                    tgattgacaaggatggatggctacattctggagacatagcttactgggacgaagacgaacacttcttcatagttga
                    ccgcttgaagtctttaattaaatacaaaggataccaggtggcccccgctgaattggagtcgatattgttacaacac
                    cccaacatcttcgacgcgggcgtggcaggtcttcccgacgatgacgccggtgaacttcccgccgccgttgttgtt
                    ttggagcacggaaagacgatgacggaaaaagagatcgtggattacgtcgccagtcaagtaacaaccgccaaa
                    aagttgcgcggaggagttgtgtttgtggacgaagtaccgaaaggtcttaccggaaaactcgacgcaagaaaat
                    cagagagatcctcataaaggccaagaagggcggaaagtccaaattgtaaaaaaaaaaaaaaaaaaaaaaaa
                    aaaaaaaaaaaaaaaaaaaaaaaaaaaaaaaaaaaaaaaaaaaaaaaaaaaaaaaaaaaaaa HedrinpA90          gagtattttattctttcgtaaaaaaattagaaaaataaaatataaacatatggaagacgccaaaaacataaagaaa
(SEQ ID NO: 8)      ggcccggcgccattctatccgctagaggatggaaccgctggagagcaactgcataaggctatgaagagatacg
                    ccctggttcctggaacaattgcttttacagatgcacatatcgaggtgaacatcacgtacgcggaatacttcgaaat
                    gtccgttcggttggcagaagctatgaaacgatatgggctgaatacaaatcacagaatcgtcgtatgcagtgaaaa
                    ctctcttcaattctttatgccggtgttgggcgcgttatttatcggagttgcagttgcgcccgcgaacgacatttataat
                    gaacgtgaattgctcaacagtatgaacatttcgcagcctaccgtagtgtttgtttccaaaaagggggttgcaaaaat
                    tttgaacgtgcaaaaaaattaccaataatccagaaaattattatcatggattctaaaacggattaccagggatttca
                    gtcgatgtacacgttcgtcacatctcatctacctcccggttttaatgaatacgattttgtaccagagtcctttgatcgtg
                    acaaaacaattgcactgataatgaactcctctggatctactgggttacctaagggtgtggcccttccgcatagaac
                    tgcctgcgtcagattctcgcatgccagagatcctatttttggcaatcaaatcattccggatactgcgattttaagtgtt
                    gttccattccatcacggttttggaatgtttactacactcggatatttgatatgtggatttcgagtcgtcttaatgtataga
                    tttgaagaagagctgttttttacgatcccttcaggattacaaaattcaaagtgcgttgctagtaccaaccctatttttcatt
                    cttcgccaaaagcactctgattgacaaatacgatttatctaatttacacgaaattgcttctgggggcgcacctctttc
                    gaagaagtcggggaagcggttgcaaaacgcttccatcttccagggatacgacaaggatatgggctcactgag
                    actacatcagctattctgattacacccgaggggatgataaaccgggcgcggtcggtaaagttgttccattttttga
                    agcgaaggttgtggatctggataccgggaaaacgctgggcgttaatcagagaggcgaattatgtgtcagagga
                    cctatgattatgtccggttatgtaaacaatccggaagcgaccaacgccttgattgacaaggatggatggctacatt
                    ctggagacatagcttactgggacgaagacgaacacttcttcatagttgaccgcttgaagtctttaattaaatacaaa
                    ggataccaggtggcccccgctgaattggagtcgatattgttacaacaccccaacatcttcgacgcgggcgtggc
                    aggtcttcccgacgatgacgccggtgaacttcccgccgccgttgttgttttggagcacggaaagacgatgacgg
                    aaaaagagatcgtggattacgtcgccagtcaagtaacaaccgccaaaaagttgcgcggaggagttgtgtttgtg
                    gacgaagtaccgaaaggtcttaccggaaaactcgacgcaagaaaatcagagagatcctcataaaggccaag
                    aagggcggaaagtccaaattgtaaaaaaaaaaaaaaaaaaaaaaaaaaaaaaaaaaaaaaaaaaaaaaa
                    aaaaaaaaaaaaaaaaaaaaaaaaaaaaaaaaaaaaaaa ΩpA90               gagtattttacaacaattaccaacaacaacaaacaacaaacaacattacaattactatttacaattacatatggaag
(SEQ ID NO: 9)      acgccaaaaacataaagaaaggcccggcgccattctatccgctagaggatggaaccgctggagagcaactgc
                    ataaggctatgaagagatacgccctggttcctggaacaattgcttttacagatgcacatatcgaggtgaacatcac
                    gtacgcggaatacttcgaaatgtccgttcggttggcagaagctatgaaacgatatgggctgaatacaaatcacag
                    aatcgtcgtatgcagtgaaaactctcttcaattctttatgccggtgttgggcgcgttatttatcggagttgcagttgcg
                    cccgcgaacgacatttataatgaacgtgaattgctcaacagtatgaacatttcgcagcctaccgtagtgtttgtttcc
                    aaaaagggggttgcaaaaaattttgaacgtgcaaaaaaattaccaataatccagaaaattattatcatggattctaa
```

-continued

```
                  aacggattaccagggatttcagtcgatgtacacgttcgtcacatctcatctacctcccggttttaatgaatacgatttt
                  gtaccagagtcctttgatcgtgacaaaacaattgcactgataatgaactcctctggatctactgggttacctaaggg
                  tgtggcccttccgcatagaactgcctgcgtcagattctcgcatgccagagatcctattttggcaatcaaatcattcc
                  ggatactgcgattttaagtgttgttccattccatcacggttttggaatgtttactacactcggatatttgatatgtggatt
                  tcgagtcgtcttaatgtatagatttgaagaagagctgtttttacgatcccttcaggattacaaaattcaaagtgcgttg
                  ctagtaccaaccctatttttcattcttcgccaaaagcactctgattgacaaatacgatttatctaatttacacgaaattgc
                  ttctgggggcgcacctctttcgaaagaagtcggggaagcggttgcaaaacgcttccatcttccagggatacgac
                  aaggatatgggctcactgagactacatcagctattctgattacacccgaggggatgataaaccgggcgcggtc
                  ggtaaagttgttccattttttgaagcgaaggttgtggatctggataccgggaaaacgctgggcgttaatcagagag
                  gcgaattatgtgtcagaggacctatgattatgtccggttatgtaaacaatccggaagcgaccaacgccttgattga
                  caaggatggatggctacattctggagacatagcttactgggacgaagacgaacacttcttcatagttgaccgcttg
                  aagtctttaattaaatacaaaggataccaggtggcccccgctgaattggagtcgatattgttacaacaccccaaca
                  tcttcgacgcgggcgtggcaggtcttcccgacgatgacgccggtgaacttcccgccgccgttgttgttttggagc
                  acggaaagacgatgacggaaaaagagatcgtgattacgtcgccagtcaagtaacaaccgccaaaaagttgc
                  gcggaggagttgtgtttgtggacgaagtaccgaaaggtcttaccggaaaactcgacgcaagaaaaatcagaga
                  gatcctcataaaggccaagaaggggcggaaagtccaaattgtaaaaaaaaaaaaaaaaaaaaaaaaaaaaa
                  aaaaaaaaaaaaaaaaaaaaaaaaaaaaaaaaaaaaaaaaaaaaaaaaaaa TEVpA90          gaaataacaaatctcaacacaacatatacaaacaaacgaatctcaagcaatcaagcattctacttctattgcagc
(SEQ ID NO: 10)  aatttaaatcatttctttttaaagcaaaagcaattttctgaaaattttcaccatttacgaacgatagcaatggaagacgc
                  caaaaacataaagaaaggcccggcgccattctatccgctagaggatggaaccgctggagagcaactgcataa
                  ggctatgaagagatacgccctggttcctggaacaattgcttttacagatgcacatatcgaggtgaacatcacgtac
                  gcggaatacttcgaaatgtccgttcggttggcagaagctatgaaacgatatgggctgaatacaaatcacagaatc
                  gtcgtatgcagtgaaaactctcttcaattctttatgccggtgttgggcgcgttatttatcggagttgcagttgcgcc
                  gcgaacgacatttataatgaacgtgaattgctcaacagtatgaacatttcgcagcctaccgtagtgtttgtttccaaa
                  aagggggttgcaaaaaattttgaacgtgcaaaaaaaatttaccaataatccagaaaattattatcatggattctaaaac
                  ggattaccagggatttcagtcgatgtacacgttcgtcacatctcatctacctcccggttttaatgaatacgattttgta
                  ccagagtcctttgatcgtgacaaaacaattgcactgataatgaactcctctggatctactgggttacctaagggtgt
                  ggcccttccgcatagaactgcctgcgtcagattctcgcatgccagagatcctattttggcaatcaaatcattccgg
                  atactgcgattttaagtgttgttccattccatcacggttttggaatgtttactacactcggatatttgatatgtggatttcg
                  agtcgtcttaatgtatagatttgaagaagagctgtttttacgatcccttcaggattacaaaattcaaagtgcgttgcta
                  gtaccaaccctatttttcattcttcgccaaaagcactctgattgacaaatacgatttatctaatttacacgaaattgcttc
                  tgggggcgcacctctttcgaaagaagtcggggaagcggttgcaaaacgcttccatcttccagggatacgacaa
                  ggatatgggctcactgagactacatcagctattctgattacacccgaggggatgataaaccgggcgcggtcgg
                  taaagttgttccattttttgaagcgaaggttgtggatctggataccgggaaaacgctgggcgttaatcagagaggc
                  gaattatgtgtcagaggacctatgattatgtccggttatgtaaacaatccggaagcgaccaacgccttgattgaca
                  aggatggatggctacattctggagacatagcttactgggacgaagacgaacacttcttcatagttgaccgcttgaa
                  gtctttaattaaatacaaaggataccaggtggcccccgctgaattggagtcgatattgttacaacaccccaacatct
                  tcgacgcgggcgtggcaggtcttcccgacgatgacgccggtgaacttcccgccgccgttgttgttttggagcac
                  ggaaagacgatgacggaaaaagagatcgtgattacgtcgccagtcaagtaacaaccgccaaaaagttgcgc
                  ggaggagttgtgtttgtggacgaagtaccgaaaggtcttaccggaaaactcgacgcaagaaaaatcagagaga
                  tcctcataaaggccaagaaggggcggaaagtccaaattgtaaaaaaaaaaaaaaaaaaaaaaaaaaaaaaa
                  aaaaaaaaaaaaaaaaaaaaaaaaaaaaaaaaaaaaaaaaaaaaaaaaaaa TbmpA90          gatttaaattattgcaacaacaacaacaattacaataataacaaacaaaatacaaacaacaacaacatggaagac
(SEQ ID NO: 11)  gccaaaaacataaagaaaggcccggcgccattctatccgctagaggatggaaccgctggagagcaactgcat
                  aaggctatgaagagatacgccctggttcctgaacaattgcttttacagatgcacatatcgaggtgaacatcacgt
                  acgcggaatacttcgaaatgtccgttcggttggcagaagctatgaaacgatatgggctgaatacaaatcacagaa
                  tcgtcgtatgcagtgaaaactctcttcaattctttatgccggtgttgggcgcgttatttatcggagttgcagttgcgcc
                  cgcgaacgacatttataatgaacgtgaattgctcaacagtatgaacatttcgcagcctaccgtagtgtttgtttccaa
                  aaagggggttgcaaaaaattttgaacgtgcaaaaaaaatttaccaataatccagaaaattattatcatggattctaaaa
                  cggattaccagggatttcagtcgatgtacacgttcgtcacatctcatctacctcccggttttaatgaatacgattttgt
                  accagagtcctttgatcgtgacaaaacaattgcactgataatgaactcctctggatctactgggttacctaagggtg
                  tggcccttccgcatagaactgcctgcgtcagattctcgcatgccagagatcctattttggcaatcaaatcattccg
                  gatactgcgattttaagtgttgttccattccatcacggttttggaatgtttactacactcggatatttgatatgtggatttc
                  gagtcgtcttaatgtatagatttgaagaagagctgtttttacgatcccttcaggattacaaaattcaaagtgcgttgct
                  agtaccaaccctatttttcattcttcgccaaaagcactctgattgacaaatacgatttatctaatttacacgaaattgctt
                  ctgggggcgcacctctttcgaaagaagtcggggaagcggttgcaaaacgcttccatcttccagggatacgaca
                  aggatatgggctcactgagactacatcagctattctgattacacccgaggggatgataaaccgggcgcggtcg
                  gtaaagttgttccattttttgaagcgaaggttgtggatctggataccgggaaaacgctgggcgttaatcagagagg
                  cgaattatgtgtcagaggacctatgattatgtccggttatgtaaacaatccggaagcgaccaacgccttgattgac
                  aaggatggatggctacattctggagacatagcttactgggacgaagacgaacacttcttcatagttgaccgcttga
                  agtctttaattaaatacaaaggataccaggtggcccccgctgaattggagtcgatattgttacaacaccccaacat
                  cttcgacgcgggcgtggcaggtcttcccgacgatgacgccggtgaacttcccgccgccgttgttgttttggagca
                  cggaaagacgatgacggaaaaagagatcgtggattacgtcgccagtcaagtaacaaccgccaaaaagttgcg
                  cggaggagttgtgtttgtggacgaagtaccgaaaggtcttaccggaaaactcgacgcaagaaaaatcagagag
                  atcctcataaaggccaagaaggggcggaaagtccaaattgtaaaaaaaaaaaaaaaaaaaaaaaaaaaaaaa
                  aaaaaaaaaaaaaaaaaaaaaaaaaaaaaaaaaaaaaaaaaaaaaaaaaaa ΩpA25            gagtatttttacaacaattaccaacaacaacaaacaacaaacaacattacaattactatttacaattacatatggaag
(SEQ ID NO: 12)  acgccaaaaacataaagaaaggcccggtgccattctatccgctagaggatggaaccgctggagagcaactgc
                  ataaggctatgaagagatacgccctggttcctgaacaattgcttttacagatgcacatatcgaggtgaacatcac
                  gtacgcggaatacttcgaaatgtccgttcggttggcagaagctatgaaacgatatgggctgaatacaaatcacag
                  aatcgtcgtatgcagtgaaaactctcttcaattctttatgccggtgttgggcgcgttatttatcggagttgcagttgcg
                  cccgcgaacgacatttataatgaacgtgaattgctcaacagtatgaacatttcgcagcctaccgtagtgtttgtttcc
                  aaaaagggggttgcaaaaaattttgaacgtgcaaaaaaaattaccaataatccagaaaattattatcatggattctaa
                  aacggattaccagggatttcagtcgatgtacacgttcgtcacatctcatctacctcccggttttaatgaatacgatttt
                  gtaccagagtcctttgatcgtgacaaaacaattgcactgataatgaactcctctggatctactgggttacctaaggg
                  tgtggcccttccgcatagaactgcctgcgtcagattctcgcatgccagagatcctattttggcaatcaaatcattcc
```

-continued

```
                    ggatactgcgatttttaagtgttgttccattccatcacggttttggaatgtttactacactcggatatttgatatgtggatt
                    tcgagtcgtcttaatgtatagatttgaagaagagctgttttttacgatcccttcaggattacaaaattcaaagtgcgttg
                    ctagtaccaaccctatttttcattcttcgccaaaagcactctgattgacaaatacgatttatctaatttacacgaaattgc
                    ttctgggggcgcacctctttcgaagaagtcggggaagcggttgcaaaacgcttccatcttccagggatacgac
                    aaggatatgggctcactgagactacatcagctattctgattacacccgaggggatgataaaccgggcgcggtc
                    ggtaaagttgttccatttttttgaagcgaaggttgtggatctggataccggggaaaacgctgggcgttaatcagagag
                    gcgaattatgtgtcagaggacctatgattatgtccggtatgtaaacaatccggaagcgaccaacgccttgattga
                    caaggatggatggctacattctggagacatagcttactgggacgaagacgaacacttcttcatagttgaccgcttg
                    aagtctttaattaaatacaaaggataccaggtggcccccgctgaattggagtcgatattgttacaacacccccaaca
                    tcttcgacgcgggcgtggcaggtcttcccgacgatgacgccggtgaacttcccgccgccgttgttgttttggagc
                    acggaaagacgatgacggaaaaagagatcgtggattacgtcgccagtcaagtaacaaccgcgaaaaagttgc
                    gcggaggagttgtgtttgtggacgaagtaccgaaaggtcttaccggaaaactcgacgcaagaaaaatcagaga
                    gatcctcataaaggccaagaagggcgaaagtccaaattgtaaggatccgtacgagctcatgcgaattcctcga
                    gcaccaccaccaccaccactgagatccggctgctaacaaaaaaaaaaaaaaaaaaaaaaaaaaaa
ΩpA50               gagtattttacaacaattaccaacaacaacaaacaacaaacaacattacaattactatttacaattacatatggaag
(SEQ ID NO: 13)     acgccaaaaacataaagaaaggcccggtgccattctatccgctagaggatggaaccgctggagagcaactgc
                    ataaggctatgaagagatacgccctggttcctgaacaattgcttttacagatgcacatatcgaggtgaacatcac
                    gtacgcggaatacttcgaaatgtccgttcggttggcagaagctatgaaacgatatgggctgaatacaaatcacag
                    aatcgtcgtatgcagtgaaaactctcttcaattctttatgccggtgttgggcgcgttatttatcggagttgcagttgcg
                    cccgcgaacgacatttataatgaacgtgaattgctcaacagtatgaacatttcgcagcctaccgtagtgtttgtttcc
                    aaaaaggggttgcaaaaaattttgaacgtgcaaaaaaaattaccaataatccagaaaattattatcatcgattctaa
                    aacggattaccagggatttcagtcgatgtacacgttcgtcacatctcatctacctcccggttttaatgaatacgattttt
                    gtaccagagtcctttgatcgtgacaaaacaattgcactgataatgaactcctctggatctactgggttacctaaggg
                    tgtggcccttccgcatagaactgcctgcgtcagattacgcatgccagagatcctatttttggcaatcaaatcattcc
                    ggatactgcgatttttaagtgttgttccattccatcacggttttggaatgtttactacactcggatatttgatatgtggatt
                    tcgagtcgtcttaatgtatagatttgaagaagagctgttttttacgatcccttcaggattacaaaattcaaagtgcgttg
                    ctagtaccaaccctatttttcattcttcgccaaaagcactctgattgacaaatacgatttatctaatttacacgaaattgc
                    ttctgggggcgcacctctttcgaagaagtcggggaagcggttgcaaaacgcttccatcttccagggatacgac
                    aaggatatgggctcactgagactacatcagctattctgattacacccgaggggatgataaaccgggcgcggtc
                    ggtaaagttgttccatttttttgaagcgaaggttgtggatctggataccggggaaaacgctgggcgttaatcagagag
                    gcgaattatgtgtcagaggacctatgattatgtccggtatgtaaacaatccggaagcgaccaacgccttgattga
                    caaggatggatggctacattctggagacatagcttactgggacgaagacgaacacttcttcatagttgaccgcttg
                    aagtctttaattaaatacaaaggataccaggtggcccccgctgaattggagtcgatattgttacaacacccccaaca
                    tcttcgacgcgggcgtggcaggtcttcccgacgatgacgccggtgaacttcccgccgccgttgttgttttggagc
                    acggaaagacgatgacggaaaaagagatcgtggattacgtcgccagtcaagtaacaaccgcgaaaaagttgc
                    gcggaggagttgtgtttgtggacgaagtaccgaaaggtcttaccggaaaactcgacgcaagaaaaatcagaga
                    gatcctcataaaggccaagaagggcgaaagtccaaattgtaaggatccgtacgagctcatgcgaattcctcga
                    gcaccaccaccaccaccactgagatccggctgctaacaaaaaaaaaaaaaaaaaaaaaaaaaaaaaaaaaa
                    aaaaaaaaaaaaa
ΩpA170              gagtattttacaacaattaccaacaacaacaaacaacaaacaacattacaattactatttacaattacatatggaag
(SEQ ID NO: 14)     acgccaaaaacataaagaaaggcccggtgccattctatccgctagaggatggaaccgctggagagcaactgc
                    ataaggctatgaagagatacgccctggttcctgaacaattgcttttacagatgcacatatcgaggtgaacatcac
                    gtacgcggaatacttcgaaatgtccgttcggttggcagaagctatgaaacgatatgggctgaatacaaatcacag
                    aatcgtcgtatgcagtgaaaactctcttcaattctttatgccggtgttgggcgcgttatttatcggagttgcagttgcg
                    cccgcgaacgacatttataatgaacgtgaattgctcaacagtatgaacatttcgcagcctaccgtagtgtttgtttcc
                    aaaaaggggttgcaaaaaattttgaacgtgcaaaaaaaattaccaataatccagaaaattattatcatcgattctaa
                    aacggattaccagggatttcagtcgatgtacacgttcgtcacatctcatctacctcccggttttaatgaatacgattttt
                    gtaccagagtcctttgatcgtgacaaaacaattgcactgataatgaactcctctggatctactgggttacctaaggg
                    tgtggcccttccgcatagaactgcctgcgtcagattctcgcatgccagagatcctatttttggcaatcaaatcattcc
                    ggatactgcgatttttaagtgttgttccattccatcacggttttggaatgtttactacactcggatatttgatatgtggatt
                    tcgagtcgtcttaatgtatagatttgaagaagagctgttttttacgatcccttcaggattacaaaattcaaagtgcgttg
                    ctagtaccaaccctatttttcattcttcgccaaaagcactctgattgacaaatacgatttatctaatttacacgaaattgc
                    ttctgggggcgcacctctttcgaaagaagtcggggaagcggttgcaaaacgcttccatcttccagggatacgac
                    aaggatatgggctcactgagactacatcagctattctgattacacccgaggggatgataaaccgggcgcggtc
                    ggtaaagttgttccatttttttgaagcgaaggttgtggatctggataccggggaaaacgctgggcgttaatcagagag
                    gcgaattatgtgtcagaggacctatgattatgtccggtatgtaaacaatccggaagcgaccaacgccttgattga
                    caaggatggatggctacattctggagacatagcttactgggacgaagacgaacacttcttcatagttgaccgcttg
                    aagtctttaattaaatacaaaggataccaggtggcccccgctgaattggagtcgatattgttacaacacccccaaca
                    tcttcgacgcgggcgtggcaggtcttcccgacgatgacgccggtgaacttcccgccgccgttgttgttttggagc
                    acggaaagacgatgacggaaaaagagatcgtggattacgtcgccagtcaagtaacaaccgcgaaaaagttgc
                    gcggaggagttgtgtttgtggacgaagtaccgaaaggtcttaccggaaaactcgacgcaagaaaaatcagaga
                    gatcctcataaaggccaagaagggcgaaagtccaaattgtaaggatccgtacgagctcatgcgaattcctcga
                    gcaccaccaccaccaccactgagatccggctgctaacaaaaaaaaaaaaaaaaaaaaaaaaaaaaaaaaaa
                    aaaaaaaaaaaaaaaaaaaaaaaaaaaaaaaaaaaaaaaaaaaaaaaaaaaaaaaaaaaaaaaaaaaaa
                    aaaaaaaaaaaaaaaaaaaaaaaaaaaaaaaaaaaaaaaaaaaaaaaaaaaaaa
ΩFBAL               gagtattttacaacaattaccaacaacaacaaacaacaaacaacattacaattactatttacaattacatatggaag
(SEQ ID NO: 15)     acgccaaaaacataaagaaaggcccggtgccattctatccgctagaggatggaaccgctggagagcaactgc
                    ataaggctatgaagagatacgccctggttcctgaacaattgcttttacagatgcacatatcgaggtgaacatcac
                    gtacgcggaatacttcgaaatgtccgttcggttggcagaagctatgaaacgatatgggctgaatacaaatcacag
                    aatcgtcgtatgcagtgaaaactctcttcaattctttatgccggtgttgggcgcgttatttatcggagttgcagttgcg
                    cccgcgaacgacatttataatgaacgtgaattgctcaacagtatgaacatttcgcagcctaccgtagtgtttgtttcc
                    aaaaaggggttgcaaaaaattttgaacgtgcaaaaaaaattaccaataatccagaaaattattatcatcgattctaa
                    aacggattaccagggatttcagtcgatgtacacgttcgtcacatctcatctacctcccggttttaatgaatacgattttt
                    gtaccagagtcctttgatcgtgacaaaacaattgcactgataatgaactcctctggatctactgggttacctaaggg
                    tgtggcccttccgcatagaactgcctgcgtcagattctcgcatgccagagatcctatttttggcaatcaaatcattcc
                    ggatactgcgatttttaagtgttgttccattccatcacggttttggaatgtttactacactcggatatttgatatgtggatt
```

-continued

```
                              tcgagtcgtcttaatgtatagatttgaagaagagctgttttttacgatcccttcaggattacaaaattcaaagtgcgttg
                              ctagtaccaacccatattttcattcttcgccaaaagcactctgattgacaaatacgatttatctaatttacacgaaattgc
                              ttctgggggcgcacctctttcgaaagaagtcggggaagcggttgcaaaacgcttccatcttccagggatacgac
                              aaggatatgggctcactgagactacatcagctattctgattacacccgaggggatgataaaccgggcgcggtc
                              ggtaaagttgttccattttttgaagcgaaggttgtggatctggataccgggaaaacgctgggcgttaatcagagag
                              gcgaattatgtgtcagaggacctatgattatgtccggttatgtaaacaatccggaagcgaccaacgccttgattga
                              caaggatggatggctacattctggagacatagcttactgggacgaagacgaacacttcttcatagttgaccgcttg
                              aagtctttaattaaatacaaaggataccaggtggccccgctgaattggagtcgatattgttacaacacccccaaca
                              tcttcgacgcgggcgtggcaggtcttcccgacgatgacgccggtgaacttcccgccgccgttgttgttttggagc
                              acggaaagacgatgacggaaaaagagatcgtggattacgtcgccagtcaagtaacaaccgcgaaaaagttgc
                              gcggaggagttgtgtttgtggacgaagtaccgaaaggtcttaccggaaaactcgacgcaagaaaaatcagaga
                              gatcctcataaaggccaagaagggcgaaagtccaaattgtaaggatccgtacgagctcgagtattgaatctgtt
                              tagaaataatggaatattattttttatttatttatttatattattggtcggctcttttcttctgaaggtcaatgacaaaatgata
                              tgaaggaaataatgatttctaaaattttacaacgtaagtatattttacaaaagcctagctcatcttttgtcatgcactatt
                              ttactcacgcttgaaattaacggccagtccactgcggagtcatttcaaagtcatcctaatcgatctatcgtttttgata
                              gctcattttggagttcgcgattgtcttctgttattcacaactgttttaattttattcattctggaactcttcgagttcttgt
                              aaagtctttcatagtagcttactttatcctccaacatatttaacttcatgtcaatttcggctcttaaattttccacatcatca
                              agttcaacatcatcttttaacttgaatttattctctagctcttccaaccaagcctcattgctccttgatttactggtgaaa
                              agtgatacactttgcgcgcaatccaggtcaaaacttcctgcaaagaattcaccaatttctcgacatcatagtacaa
                              tttgttttgttctcccatcacaatttaatatacctgatggattcttatgaagcgctgggtaatggacgtgtcactctactt
                              cgccttttttccctactccttttagtacggaagacaatgctaataaataagagggtaataataatattattaatcggcaa
                              aaaagattaaaacgccaagcgtttaattatcagaaagcaaacgtcgtaccaatccttgaatgcttcccaattgtatatt
                              aagagtcatcacagcaacatattcttgttattaaattaattattattgattttttgatattgtataaaaaaaccaaatatgta
                              taaaaaaagtgaataaaaaataccaagtatggagaaatatattagaagtctatacgttaaaaccagaacgtgcac
                              aattttttttaatctgccaaatggaaaaaacgaaatatacgaaaagaagttgaagtaatagttagaaaggcaaaa
                              aaggaaagaaacaattttaaaatatcttaagattatatttacattccttagaatatat
                              ccgaatgaaatgaccaacctacttgttttgtaaactgaggaagaaaagaatattatttctccgaaaacttgtcataccg
                              tagcttgtcttgcttttatttgcttttgaccttattttttttcaaaaatcaccgtgcttttttgtgagttttttagatgttgtgataaa
                              ttgtcacttctactgaattttttctcacagaacataaagcaaagggcgttccgttgaatgaacggatcttatatgcc
                              ttttcaagtgctcactgcgtctgaatgccttctcacagtcttttacacttgaaaggtttattttttatcgtagttgttggggtc
                              aatg
ΩFBAS                         gagtattttttacaacaattaccaacaacaacaaacaacaaacaacattacaattactatttacaattacatatggaag
(SEQ ID NO: 16)               acgccaaaaacataaagaaaggcccggtgccattctatccgctagaggatggaaccgctggagagcaactgc
                              ataaggctatgaagagatacgccctggttcctggaacaattgcttttacagatgcacatatcgaggtgaacatcac
                              gtacgcggaatacttcgaaatgtccgttcggttggcagaagctatgaaacgatatgggctgaatacaaatcacag
                              aatcgtcgtatgcagtgaaaactctcttcaattcttatgccggtgttgggcgcgttatttatcggagttgcagttgcg
                              cccgcgaacgacatttataatgaacgtgaattgctcaacagtatgaacatttcgcagcctaccgtagtgtttgtttcc
                              aaaaaggggttgcaaaaaattttgaacgtgcaaaaaaaattaccaataatccagaaaattattatcatggattctaa
                              aacggattaccagggatttcagtcgatgtacacgttcgtcacatctcatctacctcccggttttaatgaatacgatttt
                              gtaccagagtcctttgatcgtgacaaaacaattgcactgataatgaactcctaggatctactgggttacctaaggg
                              tgtggcccttccgcatagaactgcctgcgtcagattacgcatgccagagatcctattttttggcaatcaaatcattcc
                              ggatactgcgattttaagtgttgttccattccatcacgttttggaatgtttactacactcggatatttgatatgtggatt
                              tcgagtcgtcttaatgtatagatttgaagaagagctgttttttacgatcccttcaggattacaaaattcaaagtgcgttg
                              ctagtaccaacccatattttcattcttcgccaaaagcactctgattgacaaatacgatttatctaatttacacgaaattgc
                              ttctgggggcgcacctctttcgaaagaagtcggggaagcggttgcaaaacgcttccatcttccagggatacgac
                              aaggatatgggctcactgagactacatcagctattctgattacacccgaggggatgataaaccgggcgcggtc
                              ggtaaagttgttccattttttgaagcgaaggttgtggatctggataccgggaaaacgctgggcgttaatcagagag
                              gcgaattatgtgtcagaggacctatgattatgtccggttatgtaaacaatccggaagcgaccaacgccttgattga
                              caaggatggatggctacattctggagacatagcttactgggacgaagacgaacacttcttcatagttgaccgcttg
                              aagtctttaattaaatacaaaggataccaggtggccccgctgaattggagtcgatattgttacaacacccccaaca
                              tcttcgacgcgggcgtggcaggtcttcccgacgatgacgccggtgaacttcccgccgccgttgttgttttggagc
                              acggaaagacgatgacggaaaaagagatcgtggattacgtcgccagtcaagtaacaaccgcgaaaaagttgc
                              gcggaggagttgtgtttgtggacgaagtaccgaaaggtcttaccggaaaactcgacgcaagaaaaatcagaga
                              gatcctcataaaggccaagaagggcgaaagtccaaattgtaaggatccgtacgagctcgagtattgaatctgtt
                              tagaaataatggaatattattttttatttatttatttatattattggtcggctcttttcttctgaaggtcaatgacaaaatgata
                              tgaaggaaataatgatttctaaaattttacaacgtaagtatattttacaaaagcctagctcatcttttgtcatgcactatt
                              ttactcacgcttgaaattaacggccagtccactgcggagtcatttcaaagtcatcctaatcgatctatcgtttttgata
                              gctcattttggagttcgcgattgtcttctgttattcacaactgttttaattttattcattctggaactcttcgagttcttgt
                              aaagtctttcatagtagcttactttatcctccaacatatttaacttcatgtcaatttcggctcttaaattttccacatcatca
                              agttcaacatcatcttttaacttgaatttattctctagctcttccaaccaagcctcattgctccttgatttactggtgaaa
                              agtgatacactttgcgcgcaatccaggtcaaaacttcctgcaaagaattcaccaatttctcgacatcatagtacaa
                              tttgttttgttctcccatcacaatttaatatacctgatggattcttatgaagcgctgggtaatggacgtgtca
ΩTMV13U200                    gagtattttttacaacaattaccaacaacaacaaacaacaaacaacattacaattactatttacaattacatatggaag
(SEQ ID NO: 17)               acgccaaaaacataaagaaaggcccggtgccattctatccgctagaggatggaaccgctggagagcaactgc
                              ataaggctatgaagagatacgccctggttcctggaacaattgcttttacagatgcacatatcgaggtgaacatcac
                              gtacgcggaatacttcgaaatgtccgttcggttggcagaagctatgaaacgatatgggctgaatacaaatcacag
                              aatcgtcgtatgcagtgaaaactctcttcaattcttatgccggtgttgggcgcgttatttatcggagttgcagttgcg
                              cccgcgaacgacatttataatgaacgtgaattgctcaacagtatgaacatttcgcagcctaccgtagtgtttgtttcc
                              aaaaaggggttgcaaaaaattttgaacgtgcaaaaaaaattaccaataatccagaaaattattatcatggattctaa
                              aacggattaccagggatttcagtcgatgtacacgttcgtcacatctcatctacctcccggttttaatgaatacgatttt
                              gtaccagagtcctttgatcgtgacaaaacaattgcactgataatgaactcctaggatctactgggttacctaaggg
                              tgtggcccttccgcatagaactgcctgcgtcagattacgcatgccagagatcctattttttggcaatcaaatcattcc
                              ggatactgcgattttaagtgttgttccattccatcacgttttggaatgtttactacactcggatatttgatatgtggatt
                              tcgagtcgtcttaatgtatagatttgaagaagagctgttttttacgatcccttcaggattacaaaattcaaagtgcgttg
                              ctagtaccaacccatattttcattcttcgccaaaagcactctgattgacaaatacgatttatctaatttacacgaaattgc
                              ttctgggggcgcacctctttcgaaagaagtcggggaagcggttgcaaaacgcttccatcttccagggatacgac
                              aaggatatgggctcactgagactacatcagctattctgattacacccgaggggatgataaaccgggcgcggtc
```

-continued

```
ggtaaagttgttccatttttttgaagcgaaggttgtggatctggataccgggaaaacgctgggcgttaatcagagag
gcgaattatgtgtcagaggacctatgattatgtccggttatgtaaacaatccggaagcgaccaacgccttgattga
caaggatggatggctacattctggagacatagcttactgggacgaagacgaacacttcttcatagttgaccgcttg
aagtctttaattaaatacaaaggataccaggtggcccccgctgaattggagtcgatattgttacaacaccccaaca
tcttcgacgcgggcgtggcaggtcttcccgacgatgacgccggtgaacttcccgccgccgttgttgttttggagc
acggaaagacgatgacggaaaaagagatcgtggattacgtcgccagtcaagtaacaaccgcgaaaaagttgc
gcggaggagttgtgtttgtggacgaagtaccgaaaggtcttaccggaaaactcgacgcaagaaaaatcagaga
gatcctcataaaggccaagaagggcggaaagtccaaattgtaaggatccgtacgagctcaggaaaagtgaata
tcaatgagtttatcgacctgacaaaaatggagaagatcttaccgtcgatgtttacccctgtaaagagtgttatgtgtt
ccaaagttgataaaataatggttcatgagaatgagtcattgtcagaggtgaaccttcttaaaggagttaagcttattg
atagtggatacgtctgtttagccggtttgg
```

ΩTMV13U400
(SEQ ID NO: 18)

```
gagtatttttacaacaattaccaacaacaacaaacaacaaacaacattacaattactatttacaattacatatggaag
acgccaaaaacataaagaaaggcccggtgccattctatccgctagaggatggaaccgctggagagcaactgc
ataaggctatgaagagatacgccctggttcctggaacaattgcttttacagatgcacatatcgaggtgaacatcac
gtacgcggaatacttcgaaatgtccgttcggttggcagaagctatgaaacgatatgggctgaatacaaatcacag
aatcgtcgtatgcagtgaaaactctcttcaattctttatgccggtgttgggcgcgttatttatcggagttgcagttgcg
cccgcgaacgacatttataatgaacgtgaattgctcaacagtatgaacatttcgcagcctaccgtagtgtttgtttcc
aaaaaggggttgcaaaaaattttgaacgtgcaaaaaaaattaccaataatccagaaaattattatcatggattctaa
aacggattaccagggatttcagtcgatgtacacgttcgtcacatctcatctacctcccggttttaatgaatacgatttt
gtaccagagtcctttgatcgtgacaaaacaattgcactgataatgaactcctctggatctactgggttacctaaggg
tgtggcccttccgcatagaactgcctgcgtcagattctcgcatgccagagatcctatttttggcaatcaaatcattcc
ggatactgcgattttaagtgttgttccattccatcacggttttggaatgtttactacactcggatatttgatatgtggatt
tcgagtcgtcttaatgtatagatttgaagaagagctgtttttacgatcccttcaggattacaaaattcaaagtgcgttg
ctagtaccaaccctattttcattcttcgccaaaagcactctgattgacaaatacgatttatctaatttacacgaaattgc
ttctgggggcgcacctctttcgaaagaagtcggggaagcggttgcaaaacgcttccatcttccagggatacgac
aaggatatgggctcactgagactacatcagctattctgattacacccgagggggatgataaaccgggcgcggtc
ggtaaagttgttccatttttttgaagcgaaggttgtggatctggataccgggaaaacgctgggcgttaatcagagag
gcgaattatgtgtcagaggacctatgattatgtccggttatgtaaacaatccggaagcgaccaacgccttgattga
caaggatggatggctacattctggagacatagcttactgggacgaagacgaacacttcttcatagttgaccgcttg
aagtctttaattaaatacaaaggataccaggtggcccccgctgaattggagtcgatattgttacaacaccccaaca
tcttcgacgcgggcgtggcaggtcttcccgacgatgacgccggtgaacttcccgccgccgttgttgttttggagc
acggaaagacgatgacggaaaaagagatcgtggattacgtcgccagtcaagtaacaaccgcgaaaaagttgc
gcggaggagttgtgtttgtggacgaagtaccgaaaggtcttaccggaaaactcgacgcaagaaaaatcagaga
gatcctcataaaggccaagaagggcggaaagtccaaattgtaaggatccgtacgagctcaggaaaagtgaata
tcaatgagtttatcgacctgacaaaaatggagaagatcttaccgtcgatgtttacccctgtaaagagtgttatgtgtt
ccaaagttgataaaataatggttcatgagaatgagtcattgtcagaggtgaaccttcttaaaggagttaagcttattg
atagtggatacgtctgtttagccggtttggtcgtcacgggcgaatggaacttgcctgacaattgcagaggaggtgt
gagcgtgtgtctggtggacaaaaggatggaaagagccgacgaggccactctcggatcttactacacagcagct
gcaaagaaaagatttcagttcaaggtcgttcccaattatgctataaccacccaggacgcgatgaaaaacgtctgg
caagtt
```

ΩTMV13U700
(SEQ ID NO: 19)

```
gagtatttttacaacaattaccaacaacaacaaacaacaaacaacattacaattactatttacaattacatatggaag
acgccaaaaacataaagaaaggcccggtgccattctatccgctagaggatggaaccgctggagagcaactgc
ataaggctatgaagagatacgccctggttcctggaacaattgcttttacagatgcacatatcgaggtgaacatcac
gtacgcggaatacttcgaaatgtccgttcggttggcagaagctatgaaacgatatgggctgaatacaaatcacag
aatcgtcgtatgcagtgaaaactctcttcaattctttatgccggtgttgggcgcgttatttatcggagttgcagttgcg
cccgcgaacgacatttataatgaacgtgaattgctcaacagtatgaacatttcgcagcctaccgtagtgtttgtttcc
aaaaaggggttgcaaaaaattttgaacgtgcaaaaaaaattaccaataatccagaaaattattatcatggattctaa
aacggattaccagggatttcagtcgatgtacacgttcgtcacatctcatctacctcccggttttaatgaatacgatttt
gtaccagagtcctttgatcgtgacaaaacaattgcactgataatgaactcctctggatctactgggttacctaaggg
tgtggcccttccgcatagaactgcctgcgtcagattctcgcatgccagagatcctatttttggcaatcaaatcattcc
ggatactgcgattttaagtgttgttccattccatcacggttttggaatgtttactacactcggatatttgatatgtggatt
tcgagtcgtcttaatgtatagatttgaagaagagctgtttttacgatcccttcaggattacaaaattcaaagtgcgttg
ctagtaccaaccctattttcattcttcgccaaaagcactctgattgacaaatacgatttatctaatttacacgaaattgc
ttctgggggcgcacctctttcgaaagaagtcggggaagcggttgcaaaacgcttccatcttccagggatacgac
aaggatatgggctcactgagactacatcagctattctgattacacccgagggggatgataaaccgggcgcggtc
ggtaaagttgttccatttttttgaagcgaaggttgtggatctggataccgggaaaacgctgggcgttaatcagagag
gcgaattatgtgtcagaggacctatgattatgtccggttatgtaaacaatccggaagcgaccaacgccttgattga
caaggatggatggctacattctggagacatagcttactgggacgaagacgaacacttcttcatagttgaccgcttg
aagtctttaattaaatacaaaggataccaggtggcccccgctgaattggagtcgatattgttacaacaccccaaca
tcttcgacgcgggcgtggcaggtcttcccgacgatgacgccggtgaacttcccgccgccgttgttgttttggagc
acggaaagacgatgacggaaaaagagatcgtggattacgtcgccagtcaagtaacaaccgcgaaaaagttgc
gcggaggagttgtgtttgtggacgaagtaccgaaaggtcttaccggaaaactcgacgcaagaaaaatcagaga
gatcctcataaaggccaagaagggcggaaagtccaaattgtaaggatccgtacgagctcaggaaaagtgaata
tcaatgagtttatcgacctgacaaaaatggagaagatcttaccgtcgatgtttacccctgtaaagagtgttatgtgtt
ccaaagttgataaaataatggttcatgagaatgagtcattgtcagaggtgaaccttcttaaaggagttaagcttattg
atagtggatacgtctgtttagccggtttggtcgtcacgggcgaatggaacttgcctgacaattgcagaggaggtgt
gagcgtgtgtctggtggacaaaaggatggaaagagccgacgaggccactctcggatcttactacacagcagct
gcaaagaaaagatttcagttcaaggtcgttcccaattatgctataaccacccaggacgcgatgaaaaacgtctgg
caagttttagttaatattagaaatgtaaagatgtcagcgggtttctgtccgctttctctggagtttgtgtcggtgtgtatt
gtttatagaaataatataaaattaggtttgagagagaagattacaaacgtgagagacggagggcccatggaactt
acagaagaagtcgttgatgagttcatggaagatgtccctatgtcaatcaggcttgcaaagtttcgatctcggaccg
gaaaaaagagtgatgtccgtaaagggaaaaatagtagtagtgaccggtcagtgccgaacaagaactatagaaa
t
```

-continued

ΩTMV23U
(SEQ ID NO: 20)

gagtattttt acaacaattaccaacaacaacaaacaacaaacaacattacaattactatttacaattacatatggaag
acgccaaaaacataaagaaaggcccggtgccattctatccgctagaggatggaaccgctggagagcaactgc
ataaggctatgaagagatacgccctggttcctggaacaattgcttttacagatgcacatatcgaggtgaacatcac
gtacgcggaatacttcgaaatgtccgttcggttggcagaagctatgaaacgatatgggctgaatacaaatcacag
aatcgtcgtatgcagtgaaaactctcttcaattctttatgccggtgtttgggcgcgttatttatcggagttgcagttgcg
cccgcgaacgacatttataatgaacgtgaattgctcaacagtatgaacatttcgcagcctaccgtagtgtttgtttcc
aaaaagggggttgcaaaaaattttgaacgtgcaaaaaaaattaccaataatccagaaaattattatcatggattctaa
aacggattaccagggatttcagtcgatgtacacgttcgtcacatctcatctacctcccggttttaatgaatacgattttt
gtaccagagtcctttgatcgtgacaaaacaattgcactgataatgaactcctctggatctactgggttacctaaggg
tgtggcccttccgcatagaactgcctgcgtcagattctcgcatgccagagatcctatttttggcaatcaaatcattcc
ggatactgcgattttaagtgttgttccattccatcacggttttggaatgtttactacactcggatatttgatatgtggatt
tcgagtcgtcttaatgtatagatttgaagaagagctgttttacgatcccttcaggattacaaaattcaaagtgcgttg
ctagtaccaaccctatttttcattcttcgccaaaagcactctgattgacaaatacgatttatctaatttacacgaaattgc
ttctgggggcgcacctctttcgaaagaagtcggggaagcggttgcaaaacgcttccatcttccagggatacgac
aaggatatgggctcactgagactacatcagctattctgattacacccgaggggatgataaaccgggcgcggtc
ggtaaagtgttccatttttgaagcgaaggttgtggatctggataccgggaaaacgctgggcgttaatcagagag
gcgaattatgtgtcagaggacctatgattatgtccggtatgtaaacaatccggaagcgaccaacgccttgattga
caaggatggatggctacattctggagacatagcttactgggacgaagacgaacacttcttcatagttgaccgcttg
aagtctttaattaaatacaaaggataccaggtggccccgctgaattggagtcgatattgttacaacaccccaaca
tcttcgacgcgggcgtggcaggtcttcccgacgatgacgccggtgaacttcccgccgcgttgttgttttggagc
acggaaagacgatgacggaaaaagagatcgtggattacgtcgccagtcaagtaacaaccgcgaaaaagttgc
gcggaggagttgtgtttgtggacgaagtaccgaaaggtcttaccggaaaactcgacgcaagaaaaatcagaga
gatcctcataaaggccaagaagggcggaaagtccaaattgtaaggatccgtacgagctcggtagtcaagatgc
ataataaataacggattgtgtccgtaatcacacgtggtgcgtacgataacgcatagtgttttccctccacttagatc
gaagggttgtgtcttggatcgcgcgggtcaaatgtatatggttcatatacatccgcaggcacgtaataaagcgag
gggttcgaatccccccgttacccccggtaggggccca

ΩN3U
(SEQ ID NO: 21)

gagtattttt acaacaattaccaacaacaacaaacaacaaacaacattacaattactatttacaattacatatggaag
acgccaaaaacataaagaaaggcccggcgccattctatccgctagaggatggaaccgctggagagcaactgc
ataaggctatgaagagatacgccctggttcctggaacaattgcttttacagatgcacatatcgaggtgaacatcac
gtacgcggaatacttcgaaatgtccgttcggttggcagaagctatgaaacgatatgggctgaatacaaatcacag
aatcgtcgtatgcagtgaaaactctcttcaattctttatgccggtgtttgggcgcgttatttatcggagttgcagttgcg
cccgcgaacgacatttataatgaacgtgaattgctcaacagtatgaacatttcgcagcctaccgtagtgtttgtttcc
aaaaagggggttgcaaaaaattttgaacgtgcaaaaaaaattaccaataatccagaaaattattatcatggattctaa
aacggattaccagggatttcagtcgatgtacacgttcgtcacatctcatctacctcccggttttaatgaatacgattttt
gtaccagagtcctttgatcgtgacaaaacaattgcactgataatgaactcctctggatctactgggttacctaaggg
tgtggcccttccgcatagaactgcctgcgtcagattctcgcatgccagagatcctatttttggcaatcaaatcattcc
ggatactgcgattttaagtgttgttccattccatcacggttttggaatgtttactacactcggatatttgatatgtggatt
tcgagtcgtcttaatgtatagatttgaagaagagctgttttacgatcccttcaggattacaaaattcaaagtgcgttg
ctagtaccaaccctatttttcattcttcgccaaaagcactctgattgacaaatacgatttatctaatttacacgaaattgc
ttctgggggcgcacctctttcgaaagaagtcggggaagcggttgcaaaacgcttccatcttccagggatacgac
aaggatatgggctcactgagactacatcagctattctgattacacccgaggggatgataaaccgggcgcggtc
ggtaaagtgttccatttttgaagcgaaggttgtggatctggataccgggaaaacgctgggcgttaatcagagag
gcgaattatgtgtcagaggacctatgattatgtccggtatgtaaacaatccggaagcgaccaacgccttgattga
caaggatggatggctacattctggagacatagcttactgggacgaagacgaacacttcttcatagttgaccgcttg
aagtctttaattaaatacaaaggataccaggtggccccgctgaattggagtcgatattgttacaacaccccaaca
tcttcgacgcgggcgtggcaggtcttcccgacgatgacgccggtgaacttcccgccgcgttgttgttttggagc
acggaaagacgatgacggaaaaagagatcgtggattacgtcgccagtcaagtaacaaccgcgaaaaagttgc
gcggaggagttgtgtttgtggacgaagtaccgaaaggtcttaccggaaaactcgacgcaagaaaaatcagaga
gatcctcataaaggccaagaagggcggaaagtccaaattgtaa N5UpA90
(SEQ ID NO: 22)

gagaccacaacggtttccctctagaaataattttgtttaactttaagaaggagatatacatatggaagacgccaaaa
acataaagaaaggcccggcgccattctatccgctagaggatggaaccgctggagagcaactgcataaggctat
gaagagatacgccctggttcctggaacaattgcttttacagatgcacatatcgaggtgaacatcacgtacgcgga
atacttcgaaatgtccgttcggttggcagaagctatgaaacgatatgggctgaatacaaatcacagaatcgtcgta
tgcagtgaaaactctcttcaattctttatgccggtgtttgggcgcgttatttatcggagttgcagttgcgcccgcgaac
gacatttataatgaacgtgaattgctcaacagtatgaacatttcgcagcctaccgtagtgtttgttccaaaaaggg
gttgcaaaaaattttgaacgtgcaaaaaaaattaccaataatccagaaaattattatcatggattctaaaacggatta
ccagggatttcagtcgatgtacacgttcgtcacatctcatctacctcccggttttaatgaatacgattttgtaccaga
gtcctttgatcgtgacaaaacaattgcactgataatgaactcctctggatctactgggttacctaagggtggccc
ttccgcatagaactgcctgcgtcagattctcgcatgccagagatcctatttttggcaatcaaatcattccggatactg
cgattttaagtgttgttccattccatcacggttttggaatgtttactacactcggatatttgatatgtggatttcgagtcg
tcttaatgtatagatttgaagaagagctgttttacgatcccttcaggattacaaaattcaaagtgcgttgctagtacc
aaccctatttttcattcttcgccaaaagcactctgattgacaaatacgatttatctaatttacacgaaattgcttctgggg
gcgcacctctttcgaaagaagtcggggaagcggttgcaaaacgcttccatcttccagggatacgacaaggatat
gggctcactgagactacatcagctattctgattacacccgaggggatgataaaccgggcgcggtcggtaaagt
gttccatttttgaagcgaaggttgtggatctggataccgggaaaacgctgggcgttaatcagagaggcgaatta
tgtgtcagaggacctatgattatgtccggtatgtaaacaatccggaagcgaccaacgccttgattgacaaggatg
gatggctacattctggagacatagcttactgggacgaagacgaacacttcttcatagttgaccgcttgaagtcttta
attaaatacaaaggataccaggtggccccgctgaattggagtcgatattgttacaacaccccaacatcttcgac
gcgggcgtggcaggtcttcccgacgatgacgccggtgaacttcccgccgcgttgttgttttggagcacggaaa
gacgatgacggaaaaagagatcgtggattacgtcgccagtcaagtaacaaccgcaaaaagttgcgcggagg
agttgtgtttgtggacgaagtaccgaaaggtcttaccggaaaactcgacgcaagaaaaatcagagagatcctcat
aaaggccaagaagggcggaaagtccaaattgtaaaaaaaaaaaaaaaaaaaaaaaaaaaaaaaaaaaaaaa
aaaaaaaaaaaaaaaaaaaaaaaaaaaaaaaaaaaaaaaaaaaa -continued

| | |
|---|---|
| ΩNpA (SEQ ID NO: 23) | gagtattttttacaacaattaccaacaacaacaaacaacaaacaacattacaattactatttacaattacatatggaag<br>acgccaaaaacataaagaaaggcccggcgccattctatccgctagaggatggaaccgctggagagcaactgc<br>ataaggctatgaagagatacgccctggttcctggaacaattgcttttacagatgcacatatcgaggtgaacatcac<br>gtacgcggaatacttcgaaatgtccgttcggttggcagaagctatgaaacgatatgggctgaatacaaatcacag<br>aatcgtcgtatgcagtgaaaactctcttcaattctttatgccggtgttgggcgcgttatttatcggagttgcagttgcg<br>cccgcgaacgacatttataatgaacgtgaattgctcaacagtatgaacatttcgcagcctaccgtagtgtttgtttcc<br>aaaaaggggttgcaaaaattttgaacgtgcaaaaaaaattaccaataatccagaaaattattatcatggattctaa<br>aacggattaccagggatttcagtcgatgtacacgttcgtcacatctcatctacctcccggttttaatgaatacgattttt<br>gtaccagagtcctttgatcgtgacaaaacaattgcactgataatgaactcctctggatctactgggttacctaaggg<br>tgtggcccttccgcatagaactgcctgcgtcagattctcgcatgccagagatcctatttttggcaatcaaatcattcc<br>ggatactgcgattttaagtgttgttccattccatcacggttttggaatgtttactacactcggatatttgatatgtggatt<br>tcgagtcgtcttaatgtatagatttgaagaagagctgttttttacgatcccttcaggattacaaaattcaaagtgcgttg<br>ctagtaccaaccctatttttcattcttcgccaaaagcactctgattgacaaatacgatttatctaatttacacgaaattgc<br>ttctggggcgcaccctctttcgaaagaagtcggggaagcggttgcaaaacgcttccatcttccaggggatacgac<br>aaggatatgggctcactgagactacatcagctattctgattacacccgaggggatataaaccgggcgcggtc<br>ggtaaagttgttccatttttttgaagcgaaggttgtggatctggataccgggaaaacgctgggcgttaatcagagag<br>gcgaattatgtgtcagaggacctatgattatgtccggttatgtaaacaatccggaagcgaccaacgccttgattga<br>caaggatggatggctacattctggagacatagcttactgggacgaagacgaacacttcttcatagttgaccgcttg<br>aagtctttaattaaatacaaaggataccaggtggcccccgctgaattggagtcgatattgttacaacaccccaaca<br>tcttcgacgcgggcgtggcaggtcttcccgacgatgacgccggtgaacttcccgccgccgttgttgtttttggagc<br>acggaaagacgatgacggaaaagagatcgtggattacgtcgccagtcaagtaacaaccgccaaaaagttgc<br>gcggaggagttgtgtttgtggacgaagtaccgaaaggtcttaccggaaaactcgacgcaagaaaaatcagaga<br>gatcctcataaaggccaagaagggcggaaagtccaaattgtaa |
| Luciferase ORF (SEQ ID NO: 24) | atggaagacgccaaaaacataaagaaaggcccggaaccgctggagagcaactgcataaggctatgaagaga<br>tacgccctggttcctggaacaattgcttttacagatgcacatatcgaggtgaacatcacgtacgcggaatacttcg<br>aaatgtccgttcggttggcagaagctatgaaacgatatgggctgaatacaaatcacagaatcgtcgtatgcagtg<br>aaaactctcttcaattctttatgccggtgttgggcgcgttatttatcggagttgcagttgcgcccgcgaacgacattt<br>ataatgaacgtgaattgctcaacagtatgaacatttcgcagcctaccgtagtgtttgtttccaaaaaggggttgcaa<br>aaattttgaacgtgcaaaaaaaattaccaataatccagaaaattattatcatggattctaaaacggattaccaggg<br>atttcagtcgatgtacacgttcgtcacatctcatctacctcccggttttaatgaatacgattttgtaccagagtcctttg<br>atcgtgacaaaacaattgcactgataatgaactcctctggatctactgggttacctaagggtgtggcccatccgcat<br>agaactgcctgcgtcagattctcgcatgccagagatcctatttttggcaatcaaatcattccggatactgcgatttta<br>agtgttgttccattccatcacggttttggaatgtttactacactcggatatttgatatggattcgagtcgtcttaatg<br>tatagatttgaagaagagctgttttttacgatcccttcaggattacaaaattcaaagtgcgttgctagtaccaaccctat<br>tttcattatcgccaaaagcactctgattgacaaatacgatttatctaatttacacgaaattgatctggggcgcacc<br>tctttcgaagaagtcggggaagcggttgcaaaacgcttccatcttccaggatacgacaaggatatgggctca<br>ctgagactacatcagctattctgattacacccgagggatgataaaccgggcgcggtcggtaaagttgttccat<br>tttttgaagcgaaggttgtggatctggataccgggaaaacgctgcgttaatcagaggaccgaattatgtgtca<br>gaggacctatgattatgtccggttatgtaaacaatccggaagcgaccaacgccttgattgacaaggatggatggc<br>tacattctggagacatagcttactgggacgaagacgaacacttcttcatagttgaccgcttgaagtctttaattaaat<br>acaaaggataccaggtggccccccgctgaattggagtcgatattgttacaacaccccaacatcttcgacgcgggc<br>gtggcaggtcttcccgacgatgacgccggtgaacttcccgccgccgttgttgtttttggagcacggaaagacgat<br>gacggaaaagagatcgtggattacgtcgccagtcaagtaacaaccgccaaaaagttgcgcggaggagttgtg<br>tttgtggacgaagtaccgaaaggtcttaccggaaaactcgacgcaagaaaaatcagagagatcctcataaaggc<br>caagaagggcggaaagtccaaattgtgatcaccaaattgtaa |
| Forward Primer 1 (SEQ ID NO: 25) | ttactatttacaattacat*a*tggaagacgccaaaaac |
| Reverse Primer 1 (SEQ ID NO: 26) | agcagccggatctcagt*t*tacaatttggactttccgc |
| Forward Primer 2 (SEQ ID NO: 27) | acgctgcccgagatctcgatcccgcgaaattaatacgactcactatagggagtattttttacaacaattaccaacaa<br>caacaaacaacaaacaacattacaattactatttacaattacat |
| Reverse Primer 2 (SEQ ID NO: 28) | ttttttttttttttttttttttttttttttttttttttttttttttgttagcagccggatctcagt |
| Luciferase Expression Construct (Table 3) (SEQ ID NO: 29) | acgctgcccgagatctcgatcccgcgaaattaatacgactcactatagggagtattttttacaacaattaccaacaa<br>caacaaacaacaaacaacattacaattactatttacaattacatatggaagacgccaaaaacataaagaaaggcc<br>cggcgccattctatccgctagaggatggaaccgctggagagcaactgcataaggctatgaagagatacgccct<br>ggttcctggaacaattgcttttacagatgcacatatcgaggtgaacatcacgtacgcggaatacttcgaaatgtcc<br>gttcggttggcagaagctatgaaacgatatgggctgaatacaaatcacagaatcgtcgtatgcagtgaaaactct<br>cttcaattctttatgccggtgttgggcgcgttatttatcggagttgcagttgcgcccgcgaacgacatttataatgaa<br>cgtgaattgctcaacagtatgaacatttcgcagcctaccgtagtgtttgtttccaaaaaggggttgcaaaaattttg<br>aacgtgcaaaaaaaattaccaataatccagaaaattattatcatggattctaaaacggattaccagggatttcagtc<br>gatgtacacgttcgtcacatctcatctacctcccggttttaatgaatacgattttgtaccagagtcctttgatcgtgac<br>aaaacaattgcactgataatgaactcctctggatctactgggttacctaagggtgtggcccttccgcatagaactg<br>cctgcgtcagattctcgcatgccagagatcctatttttggcaatcaaatcattccggatactgcgattttaagtgttgt<br>tccattccatcacggttttggaatgtttactacactcggatatttgatatgtggatttcgagtcgtcttaatgtatagattt<br>gaagaagagctgttttttacgatcccttcaggattacaaaattcaaagtgcgttgctagtaccaaccctatttttcattct<br>tcgccaaaagcactctgattgacaaatacgatttatctaatttacacgaaattgcttctggggcgcacctctttcga<br>agaagtcggggaagcggttgcaaaacgcttccatcttccaggatacgacaaggatatgggctcactgagac<br>tacatcagctattctgattacacccgagggatgataaaccgggcgcggtcggtaaagttgttccatttttttgaag |

-continued

|   |   |
|---|---|
| | cgaaggttgtggatctggataccgggaaaacgctgggcgttaatcagagaggcgaattatgtgtcagaggacct<br>atgattatgtccggttatgtaaacaatccggaagcgaccaacgccttgattgacaaggatggatggctacattctg<br>gagacatagccttactgggacgaagacgaacacttcttcatagttgaccgcttgaagtctttaattaaatacaaagg<br>ataccaggtggccccgctgaattggagtcgatattgttacaacaccccaacatcttcgacgcgggcgtggcag<br>gtcttcccgacgatgacgccggtgaacttcccgccgccgttgttgttttggagcacggaaagacgatgacggaa<br>aaagagatcgtgattacgtcgccagtcaagtaacaacgccaaaaagttgcgcggaggagttgtgtttgtgga<br>cgaagtaccgaaaggtcttaccggaaaactcgacgcaagaaaaatcagagagatcctcataaaggccaagaa<br>gggcggaaagtccaaattgtaaactgagatccggctgctaacaaaaaaaaaaaaaaaaaaaaaaaaaaaaaa<br>aaaaaaaaaaaaaaaaaaa |
| Luciferase<br>(Protein)<br>(SEQ ID NO: 30) | MEDAKNIKKGPAPFYPLEDGTAGEQLHKAMKRYALVPGTIAFTDAHIE<br>VNITYAEYFEMSVRLAEAMKRYGLNTNHRIVVCSENSLQFFMPVLGA<br>LFIGVAVAPANDIYNERELLNSMNISQPTVVFVSKKGLQKILNVQKKLP<br>IIQKIIIMDSKTDYQGFQSMYTFVTSHLPPGFNEYDFVPESFDRDKTIALI<br>MNSSGSTGLPKGVALPHRTACVRFSHARDPIFGNQIIPDTAILSVVPFHH<br>GFGMFTTLGYLICGFRVVLMYRFEEELFLRSLQDYKIQSALLVPTLFSF<br>FAKSTLIDKYDLSNLHEIASGGAPLSKEVGEAVAKRFHLPGIRQGYGLT<br>ETTSAILITPEGDDKPGAVGKVVPFFEAKVVDLDTGKTLGVNQRGELC<br>VRGPMIMSGYVNNPEATNALIDKDGWLHSGDIAYWDEDEHFFIVDRL<br>KSLIKYKGYQVAPAELESILLQHPNIFDAGVAGLPDDDAGELPAAVVV<br>LEHGKTMTEKEIVDYVASQVTTAKKLRGGVVFVDEVPKGLTGKLDAR<br>KIREILIKAKKGGKSKL |
| GFP (ORF)<br>(SEQ ID NO: 31) | atggagaaaaaaatcactactccttccacccaccaccgccgtattccagagggactagatatcttgcgcagcct<br>agtggcaatactagttctagtgccctaatgcaaggtcaaaaggccccccaaaagcccttcacagaacctagtccct<br>gtcactccctcaacaactaagtccttttaaaaatgcgcagccgccaggatccatggtggtgagcaagggcgaggagct<br>gttcaccggggtggtgcccatcctggtcgagaggacggcgacgtaaacggccacaagttcagcgtgcgcgg<br>cgagggcgagggcgatgccaccaacggcaagagaccctgaagttcatctgcaccaccggcaagagcccgt<br>gccctggcccaccctcgtgaccaccctgacctacggcgtgcagtgcttcagccgctaccccgaccacatgaag<br>cagcacgacttcttcaagtccgccatgcccgaaggctacgtccaggagcgcaccatccacttcaaggacgacg<br>gcacctacaagacccgcgccgaggtgaagttcgagggcgacacccttggtgaaccgcatcgagctgaaggcc<br>atcgacttcaaggaggacggcaacatcctggggcacaagaggagtacaacttcaacagccacaacgtctatat<br>caccgccgacaagcagaagaacggcatcaaggccaacttcaagatccgccacaacgtggaggacggcagc<br>gtgcagctcgccgaccactaccagcagaacacccccatcggcgacggccccgtgctgctgcccgacaacca<br>ctacctgagcacccagtccaagagagcaaagacccgaacgagaagcgcgatcacatggtcctgctggagttc<br>gtgaccgccgcgggatcactcacggcatggacgagagtacaaggagctcggcatgggtcaccaccatcat<br>catcattaa |
| GFP Expression<br>Construct<br>(Table 3)<br>(SEQ ID NO: 32) | acgctgccccgagatctcgatcccgcgaaattaatacgactcactatagggagtattttacaacaattaccaacaa<br>caacaaacaacaaacaacattacaattactatttacaattacatatgagcaaaggtgaagaactgtttaccggcgtt<br>gtgccgattctggtggaactggatggcgatgtgaacggtcacaaattcagcgtgcgtggtgaaggtgaaggcg<br>atgccacgattggcaaactgacgctgaaatttatctgcaccaccggcaaactgccggtgccgtggccgacgctg<br>gtgaccaccctgacctatggcgtgcagtgtttagtgcgatccggatccacgataaacgctcacgatttattaaatct<br>gcaatgccggaaggctatgtgcaggaactgtacgattagctttaaagatgatggcaaatataaacgcgccgt<br>tgtgaaatttgaaggcgataccctggtgaaccgcattgaactgaaaggcacggattttaaagaagatggcaatat<br>cctgggccataaactggaatacaactttaatagccataatgtttatattacggcggataaacagaaaaatggcatc<br>aaagcgaattttaccgttcgccataacgttgaagatggcagtgtgcagctggcagatcattatcagcagaatacc<br>ccgattggtgatggtccggtgctgctgccggataatcattatctgagcacgcagaccgttctgtctaaagatccga<br>acgaaaaaggcacgcgggaccacatggttctgcacgaatatgtgaatgcggcaggtattacgtggagccatcc<br>gcagttcgaaaaataaactgagatccggctgctaacaaaaaaaaaaaaaaaaaaaaaaaaaaaaaaaaaaa<br>aaaaaaaaaaaa |
| GFP (Protein)<br>(SEQ ID NO: 33) | MEKKITTPSTPPPPYSRGTRYLAQPSGNTSSSALMQGQKAPQKPSQNLV<br>PVTPSTTKSFKNAPAPGSMVSKGEELFTGVVPILVELDGDVNGHKFSV<br>RGEGEGDATNGKLTLKFICTTGKLPVPWPTLVTTLTYGVQCFSRYPDH<br>MKQHDFFKSAMPEGYVQERTITFKDDGTYKTRAEVKFEGDTLVNRIEL<br>KGIDFKEDGNILGHKLEYNFNSHNVYITADKQKNGIKANFKIRHNVED<br>GSVQLADHYQQNTPIGDGPVLLPDNHYLSTQSKLSKDPNEKRDHMVL<br>LEFVTAAGITHGMDELYKELGMGHHHHHH |
| CAT (ORF)<br>(SEQ ID NO: 34) | atggaaaaaaaatcaccggctacaccaccgttgacatctctcagtggcaccgtaaagaacactttgaagcgttc<br>cagtctgtcgcgcagtgtacctacaaccagaccgttcagctagacatcaccgcgttcctgaaaaccgttaaaaaa<br>aacaaacaacaaattctacccggcgttcattcacatcctggcgcgtctgatgaacgcgcaccggaatttcgtatg<br>gcgatgaaagacggtgaactggttatctgggacttcgttcacccgtgctacaccgttttcgaacagacagaa<br>accttctcttctctgtggtctgaataccacgacgacttccgtcagttcctgcacatctactctcaggacgttgcgtgc<br>tacggtgaaaacctggcgtacttcccgaaaggttttcatcgaaaacatgttcttcgtttctgcgaacccgtgggtttct<br>ttcacctctttcgacctgaacgtggcgaacatggacaacttcttcgcgccggttttcactatgggtaaatactacac<br>ccagggtgacaaagttctgatgccgctggcgatccaggttcaccacgcggtttgcgacggttttccacgttggtcg<br>tatgctgaacgaactccagcagtattgcgacgaatggcagggtggtgcgtaa |
| CAT Expression<br>Construct<br>(Table 3)<br>(SEQ ID NO: 35) | acgctgccccgagatctcgatcccgcgaaattaatacgactcactatagggagtattttacaacaattaccaacaa<br>caacaaacaacaaacaacattacaattactatttacaattacatatggaaaaaaaatcaccggctacaccaccgt<br>tgacatctctcagtggcaccgtaaagaacactttgaagcgttccagtctgtcgcgcagtgtacctacaaccagac<br>cgttcagctagacatcaccgcgttcctgaaaaccgttaaaaaaaacaaacaacaaattctacccggcgttcattcac<br>atcctggcgcgtctgatgaacgcgcaccggaatttcgtatggcgatgaaagacggtgaactggttatctggga<br>ctctgttcacccgtgctacaccgttttccacgaacagaccgaaaccttctcttctctgtggtctgaataccacgacg<br>acttccgtcagttcctgcacatctactctcaggacgttgcgtgctacggtgaaaacctggcgtacttcccgaaagg<br>ttttcatcgaaaacatgttcttcgtttctgcgaacccgtgggtttctttcacctctttcgacctgaacgtggcgaacatg<br>gacaacttcttcgcgccggttttcactatgggtaaatactacacccagggtgacaaagttctgatgccgctggcga |

| | |
|---|---|
| | tccaggttcaccacgcggtttgcgacggtttccacgttggtcgtatgctgaacgaactccagcagtattgcgacg<br>aatggcagggtggtgcgtaaactgagatccggctgctaacaaaaaaaaaaaaaaaaaaaaaaaaaaaaaaaa<br>aaaaaaaaaaaaaaaaaa |
| CAT (Protein)<br>(SEQ ID NO: 36) | MEKKITGYTTVDISQWHRKEHFEAFQSVAQCTYNQTVQLDITAFLKTV<br>KKNKHKFYPAFIHILARLMNAHPEFRMAMKDGELVIWDSVHPCYTVF<br>HEQTETFSSLWSEYHDDFRQFLHIYSQDVACYGENLAYFPKGFIENMF<br>FVSANPWVSFTSFDLNVANMDNFFAPVFTMGKYYTQGDKVLMPLAIQ<br>VHHAVCDGFHVGRMLNELQQYCDEWQGGA |
| Superfolder GFP<br>(ORF)<br>(SEQ ID NO: 37) | atgagcaaaggtgaagaactgtttaccggcgttgtgccgattctggtggaactggatggcgatgtgaacggtca<br>caaattcagcgtgcgtggtgaaggtgaaggcgatgccacgattggcaaactgacgctgaaatttatctgcacca<br>ccggcaaactgccggtgccgtggccgacgctggtgaccaccctgacctatggcgttcagtgttttagtcgctatc<br>cggatcacatgaaacgtcacgatttctttaaatctgcaatgccggaaggctatgtgcaggaacgtacgattagcttt<br>aaagatgatggcaaatataaaacgcgcgccgttgtgaaatttgaaggcgatacctggtgaaccgcattgaact<br>gaaaggcacggattttaaagaagatggcaatatcctgggccataaactggaatacaactttaatagccataatgtt<br>tatattacggcggataaacagaaaaatggcatcaaagcgaattttaccgttcgccataacgttgaagatggcagt<br>gtgcagctggcagatcattatcagcagaataccccgattggtgatggtccggtgctgctgccggataatcattatc<br>tgagcacgcagaccgttctgtctaaagatccgaacgaaaaaggcacgcgggaccacatggttctgcacgaata<br>tgtgaatgcggcaggtattacgtggagccatccgcagttcgaaaaataa |
| Superfolder GFP<br>Expression<br>Construct<br>(Table 4)<br>(SEQ ID NO: 38) | acgctgccccgagatctcgatcccgcgaaattaatacgactcactataggagtattttacaacaattaccaacaa<br>caaacaacaaacaacattacaattactatttacaattaaaaaaaatgagcaaaggtgaagaactgtttaccgg<br>cgttgtgccgattctggtggaactggatggcgatgtgaacggtcacaaattcagcgtgcgtggtgaaggtgaag<br>gcgatgccacgattggcaaactgacgctgaaatttatctgcaccaccggcaaactgccggtgccgtggccgac<br>gctggtgaccaccctgacctatggcgttcagtgttttagtcgctatccggatcacatgaaacgtcacgatttctttaa<br>atctgcaatgccggaaggctatgtgcaggaacgtacgattagctttaaagatgatggcaaatataaaacgcgcg<br>ccgttgtgaaatttgaaggcgatacctggtgaaccgcattgaactgaaaggcacggattttaaagaagatggca<br>atatcctgggccataaactggaatacaactttaatagccataatgtttatattacggcggataaacagaaaaatggc<br>atcaaagcgaattttaccgttcgccataacgttgaagatggcagtgtgcagctggcagatcattatcagcagaata<br>ccccgattggtgatggtccggtgctgctgccggataatcattatctgagcacgcagaccgttctgtctaaagatcc<br>gaacgaaaaaggcacgcgggaccacatggttctgcacgaatatgtgaatgcggcaggtattacgtggagccat<br>ccgcagttcgaaaaataaactgagatccggctgctaacaaaaaaaaaaaaaaaaaaaaaaaaaaaaaaaa<br>aaaaaaaaaaaaaa |
| Superfolder GFP<br>(protein)<br>(SEQ ID NO: 39) | MSKGEELFTGVVPILVELDGDVNGHKFSVRGEGEGDATIGKLTLKFICT<br>TGKLPVPWPTLVTTLTYGVQCFSRYPDHMKRHDFFKSAMPEGYVQER<br>TISFKDDGKYKTRAVVKFEGDTLVNRIELKGTDFKEDGNILGHKLEYN<br>FNSHNVYITADKQKNGIKANFTVRHNVEDGSVQLADHYQQNTPIGDG<br>PVLLPDNHYLSTQTVLSKDPNEKGTRDHMVLHEYVNAAGITWSHPQF<br>EK |
| ANX scFv (ORF)<br>(SEQ ID NO: 40) | atggctcaggtacagttacaacaatcaggattagaactcgtaaaaccaggtgctagtgttaaaatctcctgcaaaa<br>caagtggttatacttttacagaatatacgatgcattgggtaaaacaatctcatggtaaaagtttagaatggatcgga<br>ggcatcaacccaaacaatggcggcacttcttataatcaaaaatttaaaggcaaagcaatcctacagtcgacaaat<br>cttcatccaccgcctatctcgaattacgtagtttaacatcagaagattcagccgtttattattgcgcacgtgacgatc<br>gttatccagattggtttgcttattgggggcaaggtaccacagttacagtatcctctggcggcggcggatctggcgg<br>cggcggctccggtggaggtggttctactgacatccaactgactcaatctcccctcatccctttctgcatcacttggcg<br>aacgcgtctcgatcacctgtcgcgcatacaagacatcggatcaaatttaaattggcttcaacaaaaacctgatgg<br>cacgatcaaacgccttatttatgccacctcctctcgatagcggcgtcccgaaacgttttctggttctcgtagcgg<br>ttcagactattcattgacaatcagctcactgaaagcgaagacttgtagattactattgccttcagtatgccagcag<br>cccacctacattggcggaggtacaaaattggaaattaaacgcgcggccgcatggagccatccgcagttcgag<br>aaataa |
| ANX scFv<br>Expression<br>Construct<br>(Table 4)<br>(SEQ ID NO: 41) | acgctgccccgagatctcgatcccgcgaaattaatacgactcactataggagtattttacaacaattaccaacaa<br>caaacaacaaacaacattacaattactatttacaattacatatggctcaggtacagttacaacaatcaggatta<br>gaactcgtaaaaccaggtgctagtgttaaaatctcctgcaaaacaagtggttatacttttacagaatatacgatgca<br>ttgggtaaaacaatctcatggtaaaagtttagaatggatcggaggcatcaacccaaacaatggcggcacttcttat<br>aatcaaaaatttaaaggcaaagcaatcctacagtcgacaaatcttcatccaccgcctatctcgaattacgtagttta<br>acatcagaagattcagccgtttattattgcgcacgtgacgatcgttatccagattggtttgcttattgggggcaaggt<br>accacagttacagtatcctctggcggcggcggatctggcggcggcggctccggtggaggtggttctactgacat<br>ccaactgactcaatctcccctcatccctttctgcatcacttggcgaacgcgtctcgatcacctgtcgcgcatctcaag<br>acatcggatcaaatttaaattggcttcaacaaaaacctgatggcacgatcaaacgccttatttatgccacctcctctc<br>gatagcggcgtcccgaaacgttttctggttctcgtagcggttcagactattcattgacaatcagctcactcgaa<br>agcgaagactttgtagattactattgccttcagtatgccagcagcccacctacattggcggaggtacaaaattgg<br>aaattaaacgcgcggccgcatggagccatccgcagttcgagaaataaactgagatccggctgctaacaaaaaa<br>aaaaaaaaaaaaaaaaaaaaaaaaaaaaaaaaaaaaaa |
| ANX scFv<br>(Protein)<br>(SEQ ID NO: 42) | MAQVQLQQSGLELVKPGASVKISCKTSGYTFTEYTMHWVKQSHGKSL<br>EWIGGINPNNGGTSYNQKFKGKAILTVDKSSTAYLELRSLTSEDSAVY<br>YCARDDRYPAWFAYWGQGTTVTVSSGGGGSGGGGSGGGGSTDIQLT<br>QSPSSLSASLGERVSITCRASQDIGSNLNWLQQKPDGTIKRLIYATSSLD<br>SGVPKRFSGSRSGSDYSLTISSLESEDFVDYYCLQYASSPPTFGGGTKLE<br>IKRAAAWSHPQFEK |
| BOT scFv (ORF)<br>(SEQ ID NO: 43) | atggctcaagttcagttacaagaatctggtggcggtttagttcaaccaggtggctctctccgtctctcatgtgccgc<br>atcgggcttcacctttctgaccattatatgtactgggtccgtcaagcgccggcaaaggacttgaatgggtagca<br>acaatctctgatggtggctcttataccattactctgactcagtcgaaggtcgttttacaacttctcgtgataactcaa<br>aaaatactctctatttacaaatgaacagcttacgtgccgaagatactgcaatttattattgttcccgttatcgttatgac |

|  |  |
|---|---|
|  | gacgctatggattattggggccaaggcacttttagtaacagtttcatccggtggtggcggctccggcggcggtgg<br>ctctggcggtggtggaagtacagaaattgttttaactcagagtccggcgacattatcactctccccggcgaacgt<br>gctacaatcctgtcgtgcctctgaaagcgtagattcatacggacactcctttatgcagtggtatcaacaaaaacc<br>gggacaagcaccacgtctcttaatttatcgtgcatcaaacttagaacctggggattccagcccgtttcagtggctctg<br>gatcaggtaccgattttacattaaccatctctagtttggaaccagaagacttcgcagtttattattgccagcaaggaa<br>atgaagtcccatttacattcggtcaaggtacaaaagtggaaattaaacgcgcggccgcatggagccatccgcag<br>ttcgagaaataa |
| BOT scFv<br>Expression<br>Construct<br>(Table 4)<br>(SEQ ID NO: 44) | acgctgcccgagatctcgatcccgcgaaattaat

| | |
|---|---|
| MS2-A scFv Expression Construct (Table 4) (SEQ ID NO: 50) | acgctgcccgagatctcgatcccgcgaaattaatacgactcactatagggagtattttacaacaattaccaacaa caacaaacaacaaacaacattacaattactatttacaattacatatggctgaagttaaattagtagaaagtggtggt ggtttggtaaaacctggtggatctcttaaactctcgtgcaaagcaagcggctttacttttcttatatgctatgtcatg ggtccgtcaaactcccgaaaaacgcttagaatgggtagcaacaatttcaacaggcggaggctatacatatttccc agattctgttaaagggcgcttacaatttcccgcgataatgcgaaaaatgctttatatttacaaatgaaatccttacgt tcagaagacacagctacgtattattgtgctcgtcaaggcgacttggtgattggtacttcgatgtatggggcgcag gcacgacagttacagtatcttcaggcggcggcggttctggtggcggtggctccggtggtggtggaagcacgga tgttgtactgacccaaactccccttatctttaccagtctcattaggcgatcaagcaaccatttcatgtcgctcttctcaat ctcttgttcactctaacggcaatacttacttacattggtatcttcaaaaaccaggccaatctcctaaactccttatttata aagttcaaatcgttttttcaggcgtcccagatcgttttccggctccggcagtgcaccgattttaccttaaaaatttct cgtgtagaagctgaagacttaggtgtatatttttgctttcaatcaacttacgttccctggacttttggtggtggtacga aattagaaattaaagcggccgcatggagccatccgcagttcgaaaaataaactgagatccggctgctaacaaaa aaaaaaaaaaaaaaaaaaaaaaaaaaaaaaaaaaaaaaaa |
| MS2-A scFv (Protein) (SEQ ID NO: 51) | MAEVKLVESGGGLVKPGGSLKLSCKASGFTFSSYAMSWVRQTPEKRL EWVATISTGGGYTYFPDSVKGRFTISRDNAKNALYLQMKSLRSEDTAT YYCARQGDFGDWYFDVWGAGTTVTVSSGGGGSGGGGSGGGGSTDV VLTQTPLSLPVSLGDQATISCRSSQSLVHSNGNTYLHWYLQKPGQSPK LLIYKVSNRFSGVPDRFSGSGSGTDFTLKISRVEAEDLGVYFCFQSTYV PWTFGGGTKLEIKAAAWSHPQFEK |
| 2E2 scFv (ORF) (SEQ ID NO: 52) | atggctgaagtgcagttggttgaatcaggtgggggttagtacagccgggtggtagtttacgtttgtcatgtgcgg catcaggtttttatttttagtagtgattggatgaattgggtacgtcaagcaccgggaaaaggattagaatgggtggc gaatattaatcaagatggttcagaaaaatattatgtggattcagttaaaggtcgttttacaatcagccgtgacaacgc acaaaatagcttatacttacaaatgaacagtttacgggcagaagacacagcagtatattattgtgcaaaggaatta gggccgtgggggcaagggacattagtgacggtgagtagcggggagggggcagcggccggtggtggttcgg gaggggggaggttcgacacaggcagtagttattcaggaaagcgcactcacgacatctccgggggggacggtta ttctcacttgccgcagcagtacaggaacgattacgacttctaactatgcaaattgggtccagaaaaaaccgaatca tgtgtttacgggtttaattggggcaacgagcattcgcgcgccgggagtgccggtacgttttagcgggtttcttattg gtggaaaggcagcattaactattacaggagcgcaaaccgaagatgatgctatgtattttttgcgcgttatggtataa cacacactatgttttttggaggtggcacgaaggttacagtattggggcaagcggccgcatggagccatccgcagt tcgagaaataa |
| 2E2 scFv Expression Construct (Table 4) (SEQ ID NO: 53) | acgctgcccgagatctcgatcccgcgaaattaatacgactcactatagggagtattttacaacaattaccaacaa caacaaacaacaaacaacattacaattactatttacaattacatatggctgaagtgcagttggttgaatcaggtggg ggtttagtacagccgggtggtagtttacgtttgtcatgtgcggcatcaggtttttatttttagtagtgattggatgaattg ggtacgtcaagcaccgggaaaaggattagaatgggtggcgaatattaatcaagatggttcagaaaaatattatgt ggattcagttaaaggtcgttttacaatcagccgtgacaacgcacaaaatagcttatacttacaaatgaacagtttac gggcagaagacacagcagtatattattgtgcaaaggaattagggccgtgggggcaagggacattagtgacggt gagtagcggggaggggggcagcggccggtggtggttcgggaggggggaggttcgacacaggcagtagttattc aggaaagcgcactcacgacatctccgggggggacggttattctcacttgccgcagcagtacaggaacgattac gacttctaactatgcaaattgggtccagaaaaaaccgaatcatgtgtttacgggtttaattggggcaacgagcattc gcgcgccgggagtgccggtacgttttagcgggtttcttattggtggaaaggcagcattaactattacaggagcgc aaaccgaagatgatgctatgtattttttgcgcgttatggtataacacacactatgttttttggaggtggcacgaaggtta cagtattggggcaagcggccgcatggagccatccgcagttcgagaaataaactgagatccggctgctaacaaa aaaaaaaaaaaaaaaaaaaaaaaaaaaaaaaaaaaaaaaa |
| 2E2 scFv (Protein) (SEQ ID NO: 54) | MAEVQLVESGGGLVQPGGSLRLSCAASGFIFSSDWMNWVRQAPGKGL EWVANINQDGSEKYYVDSVKGRFTISRDNAQNSLYLQMNSLRAEDTA VYYCAKELGPWGQGTLVTVSSGGGGSGGGGSGGGGSTQAVVIQESAL TTSPGGTVILTCRSSTGTITTSNYANWVQKKPNHVFTGLIGATSIRAPG VPVRFSGFLIGGKAALTITGAQTEDDAMYFCALWYNTHYVFGGGTKV TVLGQAAAWSHPQFEK |
| 2E2-3d scFv (ORF) (SEQ ID NO: 55) | atggctgaagtgcagttggttgaatcaggtgggggtttagtacagccgggtggtagtttacgtttgtcatgtaagg catcaggtttttatttttagtagtgattggatgaattggttccgtcaagcaccgggaaaaggattagaatgggtggcg aatattaatcaagatggttcagaaaaatattatgtggattcagttaaaggtcgttttacaatcagccgtgacaacgca caaaataccttatacttacaaatgaacagtttacgggcagaagacacaggagtatattattgtgcaaaggaattag ggccgtgggggcaagggacattagtgacggtgagtagcggggaggggggcagcggccggtggtggttcggg aggggggaggttcgacacaggcagtagttactcaggaaagcgcactcacgacatctccgggggggacggttac tctcacttgccgcagcagtacaggaacgattacgacttctaactatgcaaattgggtccagaaaaaaccgaatcat gtgtttacgggtttaattggggcaacgagcattcgcgcgccgggagtgccggtacgttttagcgggtctcttattg gtggaaaggcagcattaactattacaggagcgcaaaccgaagatgatgctatgtattttttgcgcgttatggtataa cacacactatgttttttggaggtggcacgaaggttacagtattggggcaagcggccgcatggagccatccgcagt tcgaaaaataa |
| 2E2-3d scFv Expression Construct (Table 4) (SEQ ID NO: 56) | acgctgcccgagatctcgatcccgcgaaattaatacgactcactatagggagtattttacaacaattaccaacaa caacaaacaacaaacaacattacaattactatttacaattacatatggctgaagtgcagttggttgaatcaggtggg ggtttagtacagccgggtggtagtttacgtttgtcatgtaaggcatcaggtttttatttttagtagtgattggatgaattg gttccgtcaagcaccgggaaaaggattagaatgggtggcgaatattaatcaagatggttcagaaaaatattatgt ggattcagttaaaggtcgttttacaatcagccgtgacaacgcacaaaataccttatacttacaaatgaacagtttac gggcagaagacacaggagtatattattgtgcaaaggaattagggccgtgggggcaagggacattagtgacggt gagtagcggggaggggggcagcggccggtggtggttcgggaggggggaggttcgacacaggcagtagttact caggaaagcgcactcacgacatctccgggggggacggttactctcacttgccgcagcagtacaggaacgatta cgacttctaactatgcaaattgggtccagaaaaaaccgaatcatgtgtttacgggtttaattggggcaacgagcatt cgcgcgccgggagtgccggtacgttttagcgggtctatattggtggaaaggcagcattaactattacaggagc gcaaaccgaagatgatgctatgtattttttgcgcgttatggtataacacacactatgttttttggaggtggcacgaagg ttacagtattggggcaagcggccgcatggagccatccgcagttcgaaaaataaactgagatccggctgctaaca aaaaaaaaaaaaaaaaaaaaaaaaaaaaaaaaaaaaaaaaaa |

| | |
|---|---|
| 2E2-3d scFv<br>(Protein)<br>(SEQ ID NO: 57) | MAEVQLVESGGGLVQPGGSLRLSCKASGFIFSSDWMNWFRQAPGKGL<br>EWVANINQDGSEDYYVDSVKGRFTISRDNAQNTLYLQMNSLRAEDTG<br>VYYCAKELGPWGQGTLVTVSSGGGGSGGGGSGGGGSTQAVVTQESA<br>LTTSPGGTVTLTCRSSTGTITTSNYANWVQKKPNHVFTGLIGATSIRAP<br>GVPVRFSGSLIGGKAALTITGAQTEDDAMYFCALWYNTHYVFGGGTK<br>VTVLGQAAAWSHPQFEK |
| HPV16L1 scFv<br>(ORF)<br>(SEQ ID NO: 58) | atgagcctgtggctgcccagcgaggccaccgtgtacctgcccccccgtgcccgtgagcaaggtggtgagcacc<br>gacgagtacgtggccaggaccaacatctactaccacgccggcaccagcaggctgctggccgtggccaccc<br>ctacttcccccatcaagaagcccaacaacaacaagatcctggtgcccaaggtgagcggcctgcagtacagggtg<br>ttcaggatccacctgcccgaccccaacaagttcggcttccccgacaccagcttctacaaccccgacacccagag<br>gctggtgtgggcctgcgtgggcgtggaggtgggcaggggccagcccctgggcgtgggcatcagcggccac<br>cccctgctgaacaagctggacgacaccgagaacgccagcgcctacgccgccaacgccggcgtggacaaca<br>gggagtgcatcagcatggactacaagcagacccagctgtgcctgatcggctgcaagccccccatcggcgagc<br>actggggcaagggcagcccctgcaccaacgtggccgtgaaccccggcgactgccccccctggagctgatc<br>aacaccgtgatccaggacggcgacatggtggacaccggcttcggcgccatggacttcaccaccctgcaggcc<br>aacaagagcgaggtgccctggacatctgcacatctgcaagtacccccgactacatcaagatggtgagcg<br>agccctacggcgacagcctgttcttctacctgaggagggagcagatgttcgtgaggcacctgttcaacagggcc<br>ggcgccgtgggcgagaacgtgcccgacgacctgtacatcaagggcagcggcagcaccgccaacctggca<br>gcagcaactactccccaccccagcggcagcatggtgaccagcgacgcccagatcttcaacaagccctactg<br>gctgcagaggcccagggccacaacaacggcatctgctgggcaaccagctgttcgtgaccgtggtggacac<br>caccaggagcaccaacatgagcctgtgcgccgccatcagcaccagcgagaccacctacaagaacaccaactt<br>caaggagtacctgaggcacggcgaggagtacgacctgcagttcatcttccagctgtgcaagatcacctgacc<br>gccgacgtgatgacctacatccacagcatgaacagcaccatcctggaggactggaacttcggcctgcagcccc<br>cccccggcaccctggaggacacctacaggttcgtgaccagccaggccatcgcctgccagaagcacacc<br>ccccccgcccaaggaggacccctgaagaagtacacctctgggaggtgaacctgaaggagaagttcagc<br>gccgacctggaccagttcccctgggcaggaagttcctgctgcaggccggcctgaaggccaagcccaagttc<br>accctgggcaagaggaaggccacccccaccaccagcagcaccagcaccaccgccaagaggaagaagagg<br>aagctgtga |
| HPV16L1 scFv<br>Expression<br>Construct<br>(Table 4)<br>(SEQ ID NO: 59) | acgctgcccgagatctcgatcccgcgaaattaatacgactcactataggagtattttacaacaattaccaacaa<br>caacaaacaacaaacaacattacaattactattcaattacatatgagcctgtggctgcccagcgaggccaccgt<br>gtacctgcccccccgtgcccgtgagcaaggtggtgagcaccgacgagtacgtggccaggaccaacatctacta<br>ccacgccggcaccagcaggctgctggccgtggccacccctacttcccccatcaagaagcccaacaacaacaa<br>gatcctggtgcccaaggtgagcggcctgcagtacagggtgttcaggatccacctgcccgaccccaacaagttc<br>ggcttccccgacaccagcttctacaaccccgacacccagaggctggtgtgggcctgcgtgggcgtggaggtg<br>ggcaggggccagcccctgggcgtgggcatcagcggccaccccctgctgaacaagctggacgacaccgaga<br>acgccagcgcctacgccgccaacgccggcgtggacaacagggagtgcatcagcatggactacaagcagacc<br>cagctgtgcctgatcggctgcaagccccccatcggcgagcactggggcaagggcagcccctgcaccaacgt<br>ggccgtgaaccccggcgactgccccccctggagctgatcaacaccgtgatccaggacggcgacatggtgg<br>acaccggcttcggcgccatggacttcaccaccctgcaggccaacaagagcgaggtgccctggacatctgca<br>ccagcatctgcaagtaccccgactacatcaagatggtgagcgagccctacggcgacagcctgttcttctacctg<br>aggagggagcagatgttcgtgaggcacctgttcaacagggccggcgccgtgggcgagaacgtgcccgacga<br>cctgtacatcaagggcagcggcagcaccgccaacctggcagcagcaactactcccccaccccagcggca<br>gcatggtgaccagcgacgcccagatcttcaacaagccctactggctgcagagggcccagggccacaacaac<br>ggcatctgctgggcaaccagctgttcgtgaccgtggtggacaccaccaggagcaccaacatgagcctgtgc<br>gccgccatcagcaccagcgagaccacctacaagaacaccaacttcaaggagtacctgaggcacggcgagga<br>gtacgacctgcagttcatcttccagctgtgcaagatcacctgaccgccgacgtgatgacctacatccacagcat<br>gaacagcaccatcctggaggactggaacttcggcctgcagcccccccggcggcaccctggaggacacct<br>acaggttcgtgaccagccaggccatcgcctgccagaagcacaccccccccaaggaggacccctgga<br>agaagtacacccttctgggaggtgaacctgaaggagaagttcagcgccgacctggaccagttcccctgggca<br>ggaagttcctgctgcaggccggcctgaaggccaagcccaagttcaccctgggcaagaggaaggccacccc<br>caccaccagcagcaccagcaccaccgccaagaggaagaagaggaagctgtgaactgagatccggctgctaac<br>aaaaaaaaaaaaaaaaaaaaaaaaaaaaaaaaaaaaaaaaaaaaa |
| HPV16L1 scFv<br>(Protein)<br>(SEQ ID NO: 60) | MSLWLPSEATVYLPPVPVSKVVSTDEYVARTNIYYHAGTSRLLAVGHP<br>YFPIKKPNNNKILVPKVSGLQYRVFRIHLPDPNKFGFPDTSFYNPDTQR<br>LVWACVGVEVGRGQPLGVGISGHPLLNKLDDTENASAYAANAGVDN<br>RECISMDYKQTQLCLIGCKPPIGEHWGKGSPCTNVAVNPGDCPPLELIN<br>TVIQDGDMVDTGFGAMDFTTLQANKSEVPLDICTSICKYPDYIKMVSE<br>PYGDSLFFYLRREQMFVRHLFNRAGAVGENVPDDLYIKGSGSTANLAS<br>SNYFPTPSGSMVTSDAQIFNKPYWLQRAQGHNNGICWGNQLFVTVVD<br>TTRSTNMSLCAAISTSETTYKNTNFKEYLRHGEEYDLQFIFQLCKITLTA<br>DVMTYIHSMNSTILEDWNFGLQPPPGGTLEDTYRFVTSQAIACQKHTP<br>PAPKEDPLKKYTFWEVNLKEKFSADLDQFPLGRKFLLQAGLKAKPKFT<br>LGKRKATPTTSSTSTTAKRKKRKL |
| pK7LUC<br>(SEQ ID NO: 61) | tcgacggatcgttccactgagcgtcagaccccgtagaaaagatcaaaggatcttcttgagatcctttttttctgcgc<br>gtaatctgctgcttgcaaacaaaaaaaccaccgctaccagcggtggtttgtttgccggatcaagagctaccaact<br>ctttttccgaaggtaactggcttcagcagagcgcagataccaaatactgtccttctagtgtagccgtagttaggcca<br>ccacttcaagaactctgtagcaccgcctacatacctcgctctgctaatcctgttaccagtggctgctgccagtggc<br>gataagtcgtgtcttaccgggttggactcaagacgatagttaccggataaggcgcagcggtcgggctgaacgg<br>ggggttcgtgcacacagcccagcttggagcgaacgacctacaccgaactgagatacctacagcgtgagcattg<br>agaaagcgccacgcttcccgaagggagaaaggcggacaggtatccggtaagcggcagggtcggaacagga<br>gagcgcacgagggagcttccagggggaaacgcctggtatctttatagtcctgtcgggtttcgccacctctgactt<br>gagcgtcgatttttgtgatgctcgtcaggggggcggagcctatggaaaaacgccagcaacgcggcctttttacg<br>gttcctggccttttgctggccttttgctcacatgttcttcctgcgttatcccctgattctgtggataaccgtattaccgc<br>ctttgagtgagagataccgctcgccgcagccgaacgaccgagcgcagcgagtcagtgagcgaggaagcgg |

```
                        aagaagctcgcacgccaatacgcaaaccgcctctccccgcgcgttggccgattcattaatgcagctggcacga
                        caggtttcccgactggaaagcgggcagtgagcgcaacgcaattaatgtgagttagctcactcattaggcacccc
                        aggctttacactttatgcttccggctcgtatgttgtgtggaattgtgagcggataacaatttcacacaggaaacagct
                        atgaccatgattacgaattcagatctcgatcccgcgaaattaatacgactcactatagggagaccacaacggtttc
                        cctctagaaataattttgtttaacttaagaaggagatatacatatggaagacgccaaaaacataaagaaaggccc
                        ggcgccattctatccgctagaggatggaaccgctggagagcaactgcataaggctatgaagagatacgccctg
                        gttcctggaacaattgcttttacagatgcacatatcgaggtgaacatcacgtacgcggaatacttcgaaatgtccgt
                        tcggttggcagaagctatgaaacgatatgggctgaatacaaatcacagaatcgtcgtatgcagtgaaaactactt
                        caattctttatgccggtgttgggcgcgttatttatcggagttgcagttgcgcccgcgaacgacatttataatgaacgt
                        gaattgctcaacagtatgaacatttcgcagcctaccgtagtgtttgtttccaaaaaggggttgcaaaaaattttgaac
                        gtgcaaaaaaaattaccaataatccagaaaattattatcatggattctaaaacggattaccagggatttcagtcgat
                        gtacacgttcgtcacatacatctacctcccggttttaatgaatacgattttgtaccagagtcctttgatcgtgacaaa
                        acaattgcactgataatgaactcctctggatctactgggttacctaagggtgtggcccttccgcatagaactgcctg
                        cgtcagattctcgcatgccagagatcctattttttggcaatcaaatcattccggatactgcgattttaagtgttgttccat
                        tccatcacggttttggaatgtttactacactcggatatttgatatgtggatttcgagtcgtcttaatgtatagatttgaag
                        aagagctgtttttacgatcccttcaggattacaaaattcaaagtgcgttgctagtaccaaccctattttcattcttcgcc
                        aaaagcactctgattgacaaatacgatttatctaatttacacgaaattgcttctggggcgcacctctttcgaaaga
                        agtcggggaagcggttgcaaaacgcttccatcttccaggtatacgacaaggatatgggctcactgagactacat
                        cagctattctgattacacccgaggggggatgataaaccgggcgcggtcggtaaagttgttccattttttgaagcgaa
                        ggttgtggatctggataccgggaaaacgctgggcgttaatcagagaggcgaattatgtgtcagaggacctatga
                        ttatgtccggttatgtaaacaatccggaagcgaccaacgccttgattgacaaggatggatggctacattctggaga
                        catagcttactgggacgaagacgaacacttcttcaatagttgaccgcttgaagtctttaattaaatacaaaggatacc
                        aggtggcccccgctgaattggagtcgatattgttacaacacccccaacatcttcgacgcgggcgtggcaggtcttc
                        ccgacgatgacgccggtgaacttcccgccgccgttgttgtttggagcacggaaagacgatgacggaaaaaga
                        gatcgtggattacgtcgccagtcaagtaacaaccgcgcaaaaagttgcgcggaggagttgtgttgtggacgaag
                        taccgaaaggtcttaccggaaaactcgacgcaagaaaaatcagagagatcctcataaaggccaagaaggcg
                        gaaagtccaaattgtaagcgaccggctgctaacaaagcccgaaaggaagctgagttggctgctgccaccgct
                        gagcaataactagcataaccccttggggcctctaaacgggtcttgaggggttttttgctgaaaggaggaactatat
                        ccggataacctcgagctgcagggcatgcaagcttggcactggccgtcgttttacaacgtcgtgactgggaaaac
                        cctggcgttacccaacttaatcgccttgcagcacatccccctttcgccagctggcgtaatagcgaagaggcccg
                        caccgatcgcccttcccaacagttgcgcagcctgaatggcgaatgcgatttattcaacaaagccgccgtcccgtc
                        aagtcagcgtaatgctctgccagtgttacaaccaattaaccaattctgattagaaaaactcatcgagcatcaaatga
                        aactgcaatttattcatatcaggattatcaataccatatttttgaaaaagccgtttctgtaatgaaggagaaaactcac
                        cgaggcagttccataggatggcaagatcctggtatcggtctgcgattccgactcgtccaacatcaataaccctat
                        taatttccctctcgtcaaaaataaggttatcaagtgagaaatcaccatgagtgacgactgaatccggtgagaatggc
                        aaaagcttatgcatttattccagacttgttcaacaggccagccattacgctcgtcatcaaaatcactcgcatcaacc
                        aaaccgttattcattcgtgattgcgcctgagcgagacgaaatacgcgatcgctgttaaaaggacaattacaaaca
                        ggaatcgaatgcaaccggcgcaggaacactgccagcgcatcaacaatattttcacctgaatcaggatattcttct
                        aatacctggaatgctgttttcccggggatcgcagtggtgagtaaccatgcatcatcaggagtacggataaaatgc
                        ttgatggtcggaagaggcataaattccgtcagccagtttagtctgaccatctcatctgtaacatcattggcaacgct
                        acctttgccatgtttcagaaacaactctggcgcatcgggcttcccatacaatcgatagattgtcgcacctgattgcc
                        cgacattatcgcgagcccatttatacccatataaatcagcatccatgttggaatttaatcgcggcttcgagcaagac
                        gtttcccgttgaatatggctcataacaccccttgtattactgtttatgtaagcagacagttttattgttcatgatgatat
                        ttttatcttgtgcaataatcatcagagattttgagacaacaacgtggctttgttgaataaatcgaacttttgctgagttg
                        aaggatcagatcacgcatcttcccgacaacgcagaccgttccgtggcaaagcaaaagttcaaaatcaccaactg
                        gcccacctacaacaaagctctcatcaaccgtggctccctcacttttctggctggatgatggggcgattcaggcctg
                        gtatgagtcagcaacaccttcttcacgaggcagacctc
pET23LucA-f              ggtggtcatatggaagacgccaaaaacat
(SEQ ID NO: 62)

pET23LucA-r              ggtggtctcgagttttttttttttttttttttttttttttttttttttttttttttttttttttttttttttttttttt
(SEQ ID NO: 63)          ttttttttttttttttttttttacaatttggactttccgc pET23c                   gaatgacttggttgagtactcaccagtcacagaaaagcatcttacggatggcatgacagtaagagaattatgcag
(SEQ ID NO: 64)          tgctgccataaccatgagtgataacactgcggccaacttacttctgacaacgatcggaggaccgaaggagctaa
                         ccgcttttttgcacaacatgggggatcatgtaactcgccttgatcgttgggaaccggagctgaatgaagccatacc
                         aaacgacgagcgtgacaccacgatgcctgcagcaatggcaacaacgttgcgcaaactattaactggcgaacta
                         cttactctagcttcccggcaacaattaatagactggatggaggcggataaagttgcaggaccacttctgcgctcg
                         gcccttccgctggctggttttattgctgataaatctggagccggtgagcgtgggtctcgcggtatcattgcagcac
                         tggggccagatggtaagccctcccgtatcgtagttatctacacgacggggagtcaggcaactatggatgaacga
                         aatagacagatcgctgagataggtgcctcactgattaagcattggtaactgtcagaccaagtttactcatatatactt
                         tagattgatttaaaacttcatttttaatttaaaaggatctaggtgaagatcctttttgataatctcatgaccaaaatccctt
                         aacgtgagttttcgttccactgagcgtcagaccccgtagaaaagatcaaaggatcttcttgagatcctttttttctgc
                         gcgtaatctgctgcttgcaaacaaaaaaaccaccgctaccagcggtggtttgtttgccggatcaagagctaccaa
                         ctctttttccgaaggtaactggcttcagcagagcgcagataccaaatactgtccttctagtgtagccgtagttaggc
                         caccacttcaagaactctgtagcaccgcctacatacctcgctctgctaatcctgttaccagtggctgctgccagtg
                         gcgataagtcgtgtcttaccgggttggactcaagacgatagttaccggataaggcgcagcggtcgggctgaac
                         ggggggttcgtgcacacagcccagcttggagcgaacgacctacaccgaactgagatacctacagcgtgagct
                         atgagaaagcgccacgcttcccgaagggagaaaggcggacaggtatccggtaagcggcagggtcggaaca
                         ggagagcgcacgagggagcttccagggggaaacgcctggtatctttatagtcctgtcgggtttcgccacctctg
                         acttgagcgtcgatttttgtgatgctcgtcaggggggcggagcctatgaaaaacgccagcaacgcggcctttt
                         acggttcctggccttttgctggccttttgctcacatgttctttcctgcgttatcccctgattctgtggataaccgtattac
                         cgcctttgagtgagctgataccgctcgccgcagccgaacgaccgagcgcagcgagtcagtgagcgaggaag
                         cggaagagcgcctgatgcggtattttctccttacgcatctgtgcggtatttcacaccgcatatatggtgcactctca
                         gtacaatctgctctgatgccgcatagttaagccagtatacactccgctatcgctacgtgactgggtcatggctgcg
                         ccccgacacccgccaacacccgctgacgcgccctgacgggcttgtctgctcccggcatccgcttacagacaag
                         ctgtgaccgtctccgggagctgcatgtgtcagaggttttcaccgtcatcaccgaaacgcgcgaggcagctgcgg
                         taaagctcatcagcgtggtcgtgaagcgattcacagatgtctgcctgttcatccgcgtccagctcgttgagtttctc
```

-continued

```
                 cagaagcgttaatgtctggcttctgataaagcgggccatgttaagggcggttttttcctgttttggtcactgatgcctc
                 cgtgtaagggggatttctgttcatggggtaatgataccgatgaaacgagagaggatgctcacgatacgggtta
                 ctgatgatgaacatgcccggttactggaacgttgtgagggtaaacaactggcggtatggatgcggcggacca
                 gagaaaaatcactcagggtcaatgccagcgcttcgttaatacagatgtaggtgttccacagggtagccagcagc
                 atcctgcgatgcagatccggaacataatggtgcagggcgctgacttccgcgttcccagactttacgaacacgg
                 aaaccgaagaccattcatgttgttgctcaggtcgcagacgttttgcagcagcagtcgcttcacgttcgctcgcgta
                 tcggtgattcattctgctaaccagtaaggcaaccccgccagcctagccgggtcctcaacgacaggagcacgatc
                 atgcgcaccgtggccaggacccaacgctgcccgagatctcgatcccgcgaaattaatacgactcactatagg
                 gagaccacaacggtttccctctagaaataattttgtttaactttaagaaggagatatacatatggctagcgactgg
                 tggacagcaaatgggtcgcggatccgaattcgagctccgtcgacaagcttgcggccgcactcgagcaccacc
                 accaccaccactgagatccggctgctaacaaagcccgaaaggaagctgagttggctgctgccaccgctgagc
                 aataactagcataaccccttggggcctctaaacgggtcttgaggggttttttgctgaaaggaggaactatatccgg
                 attggcgaatgggacgcgccctgtagcggcgcattaagcgcggcgggtgtggtggttacgcgcagcgtgacc
                 gctacacttgccagcgccctagcgcccgctcctttcgctttcttcccttcctttctcgccacgttcgccggctttccc
                 cgtcaagctctaaatcgggggctccctttagggttccgatttagtgctttacggcacctcgaccccaaaaaacttg
                 attagggtgatggttcacgtagtgggccatcgccctgatagacggtttttcgccctttgacgttggagtccacgttc
                 tttaatagtggactcttgttccaaactggaacaacactcaaccctatctcggtctattcttttgatttataagggattttg
                 ccgatttcggcctattggttaaaaaatgagctgatttaacaaaaatttaacgcgaattttaacaaaatattaacgttta
                 caatttcaggtggcacttttcggggaaatgtgcgcggaacccctatttgtttatttttctaaatacattcaaatatgtat
                 ccgctcatgagacaataaccctgataaatgcttcaataatattgaaaaaggaagagtatgagtattcaacatttccg
                 tgtcgcccttattccctttttgcggcattttgccttcctgtttttgctcacccagaaacgctggtgaaagtaaaagatg
                 ctgaagatcagttgggtgcacgagtgggttacatcgaactggatctcaacagcggtaagatccttgagagttttcg
                 ccccgaagaacgttttccaatgatgagcacttttaaagttctgctatgtggcgcggtattatcccgtattgacgccg
                 ggcaagagcaactcggtcgccgcatacactattctca pET23LucA        gccagcgccctagcgcccgctcctttcgctttcttcccttcctttctcgccacgttcgccggctttccccgtcaagct
(SEQ ID NO: 65)  ctaaatcgggggctccctttagggttccgatttagtgctttacggcacctcgaccccaaaaaacttgattagggtg
                 atggttcacgtagtgggccatcgccctgatagacggtttttcgccctttgacgttggagtccacgttctttaatagtg
                 gactcttgttccaaactggaacaacactcaaccctatctcggtctattcttttgatttataagggattttgccgatttcg
                 gcctattggttaaaaaatgagctgatttaacaaaaatttaacgcgaattttaacaaaatattacaatttcag
                 gtggcacttttcggggaaatgtgcgcggaacccctatttgtttatttttctaaatacattcaaatatgtatccgctcatg
                 agacaataaccctgataaatgcttcaataatattgaaaaaggaagagtatgagtattcaacatttccgtgtcgccctt
                 attccctttttgcggcattttgccttcctgtttttgctcacccagaaacgctggtgaaagtaaaagatgctgaagatc
                 agttgggtgcacgagtgggttacatcgaactggatacagcggtaagatccttgagagttttcgccccgaag
                 aacgttttccaatgatgagcacttttaaagttctgctatgtggcgcggtattatcccgtattgacgccgggcaagag
                 caactcggtcgccgcatacactattctcagaatgacttggttgagtactcaccagtcacagaaaagcatcttacgg
                 atggcatgacagtaagagaattatgcagtgctgccataaccatgagtgataacactgcggccaacttacttctgac
                 aacgatcggaggaccgaaggagctaaccgcttttttgcacaacatggggatcatgtaactcgccttgatcgttg
                 ggaaccggagctgaatgaagccataccaaacgacgagcgtgacaccacgatgcctgcagcaatggcaacaa
                 cgttgcgcaaactattaactggcgaactacttactctagcttcccggcaacaattaatagactggatggaggcgg
                 ataaagttgcaggaccacttctgcgctcggcccttccggctggctggtttattgctgataaatctggagccggtga
                 gcgtgggtctcgcggtatcattgcagcactggggccagatggtaagccctcccgtatcgtagttatctacacgac
                 ggggagtcaggcaactatggatgaacgaaatagacagatcgctgagataggtgcctcactgattaagcattggt
                 aactgtcagaccaagtttactcatatatactttagattgatttaaaacttcattttttaatttaaaaggatctaggtgaaga
                 tcctttttgataatctcatgaccaaaatcccttaacgtgagttttcgttccactgagcgtcagaccccgtagaaaaga
                 tcaaaggatcttcttgagatcctttttttctgcgcgtaatctgctgcttgcaaacaaaaaaaccaccgctaccagcg
                 gtggtttgtttgccggatcaagagctaccaactctttttccgaaggtaactggcttcagcagagcgcagataccaa
                 atactgtccttctagtgtagccgtagttaggccaccacttcaagaactctgtagcaccgcctacatacctcgctctg
                 ctaatcctgttaccagtggctgctgccagtggcgataagtcgtgtctaccgggttggactcaagacgatagttac
                 cggataaggcgcagcggtcgggctgaacggggggttcgtgcacacagcccagcttggagcgaacgacctac
                 accgaactgagatacctacagcgtgagctatgagaaagcgcttcccgaaggagaaaaggcggacag
                 gtatccggtaagcggcagggtcggaacaggagagcgcacgagggagcttccagggggaaacgcctggtatc
                 tttatagtcctgtcgggtttcgccacctctgacttgagcgtcgatttttgtgatgctcgtcaggggggcggagcctat
                 ggaaaaacgccagcaacgcggcctttttacggttcctggccttttgctggccttttgctcacatgttctttcctgcgtt
                 atcccctgattctgtggataaccgtattaccgcctttgagtgagctgataccgctcgccgcagccgaacgaccga
                 gcgcagcgagtcagtgagcgaggaagcggaagagcgcctgatgcggtattttctccttacgcatctgtgcggta
                 tttcacaccgcatatatggtgcactctcagtacaatctgctctgatgccgcatagttaagccagtatacactccgcta
                 tcgctacgtgactgggtcatggctgcgccccgacacccgccaacacccgctgacgcgccctgacgggcttgtc
                 tgctcccgcatccgcttacagacaagctgtgaccgtctccgggagctgcatgtgtcagaggttttcaccgtcatc
                 accgaaacgcgcgaggcagctgcggtaaagctcatcagcgtggtcgtgaagcgattcacagatgtctgcctgtt
                 catccgcgtccagctcgttgagtttctccagaagcgttaatgtctggcttctgataaagcgggccatgttaagggc
                 ggttttttcctgtttggtcactgatgcctccgtgtaaggggatttctgttcatggggtaatgataccgatgaaacg
                 agagaggatgctcacgatacgggttactgatgatgaacatgcccggttactggaacgttgtgagggtaaacaac
                 tggcggtatggatgcggcgggaccagagaaaaatcactcagggtcaatgccagcgcttcgttaatacagatgta
                 ggtgttccacagggtagccagcagcatcctgcgatgcagatccggaacataatggtgcagggcgctgacttcc
                 gcgtttccagactttacgaaacacggaaaccgaagaccattcatgttgttgctcaggtcgcagacgttttgcagca
                 gcagtcgcttcacgttcgctcgcgtatcggtgattcattctgctaaccagtaaggcaaccccgccagcctagccg
                 ggtcctcaacgacaggagcacgatcatgcgcaccgtggccaggacccaacgctgcccgagatctcgatccc
                 gcgaaattaatacgactcactatagggagaccacaacggtttccctctagaaataattttgtttaactttaagaagg
                 agatatacatatggaagacgccaaaaacataaagaaaggcccggcgccattctatccgctagaggatggaacc
                 gctggagagcaactgcataaggctatgaagagatacgccctggttcctggaacaattgcttttacagatgcacat
                 atcgaggtgaacatcacgtacgcggaatacttcgaaatgtccgttcggttggcagaagctatgaaacgatatggg
                 ctgaatacaaatcacagaatcgtcgtatgcagtgaaaactctcttcaatctttatgccggtgttgggcgcgttattta
                 tcggagttgcagttgcgcccgcgaacgacatttataatgaacgtgaattgctcaacagtatgaacatttcgcagcc
                 taccgtagtgtttgtttccaaaaaggggttgcaaaaaattttgaacgtgcaaaaaaaattaccaataatccagaaaa
                 ttattatcatggattctaaaacggattaccagggatttcagtcgatgtacacgttcgtcacatctcatctacctcccgg
                 ttttaatgaatacgattttgtaccagagtccttgatcgtgacaaaacaattgcactgataatgaactcctctggatct
                 actgggttacctaaggtgtggcccttccgcatagaactgcctgcgtcagattctcgcatgccagagatcctatttt
                 tggcaatcaaatcattccggatactgcgattttaagtgttgttccattccatcacggttttggaatgtttactacactcg
```

-continued

```
                    gatatttgatatgtggatttcgagtcgtcttaatgtatagatttgaagaagagctgttttttacgatcccttcaggattac
                    aaaattcaaagtgcgttgctagtaccaaccctattttcattcttcgccaaaagcactctgattgacaaatacgatttat
                    ctaatttacacgaaattgcttctgggggcgcacctcttttcgaaagaagtcggggaagcggttgcaaaacgcttcc
                    atcttccagggatacgacaaggatatgggctcactgagactacatcagctattctgattacacccgaggggatg
                    ataaaccggcgcggtcggtcaaagttgttccattttttgaagcgaaggttggatcggataccgggaaaacgc
                    tgggcgttaatcagagaggcgaattatgtgtcagaggacctatgattatgtccggttatgtaaacaatccggaagc
                    gaccaacgccttgattgacaaggatggatggctacattctggagacatagcttactgggacgaagacgaacact
                    tcttcatagttgaccgcttgaagtctttaattaaatacaaaggataccaggtggccccccgctgaattggagtcgata
                    ttgttacaacaccccaacatcttcgacgcgggcgtggcaggtcttcccgacgatgacgccggtgaactttcccgc
                    cgccgttgttgttttggagcacggaaagacgatgacggaaaaagagatcgtgattacgtcgccagtcaagtaa
                    caaccgccaaaaagttgcgcggaggagttgtgtttgtggacgaagtaccgaaaggtataccggaaaactcga
                    cgcaagaaaatcagagagatcctcataaaggccaagaagggcggaaagtccaaattgtaaaaaaaaaaaaa
                    aaaaaaaactcgagcaccaccaccaccaccactgagatccggctgctaacaaagcccgaaaggaagctgagt
                    tggctgctgccaccgctgagcaataactagcataacccttggggcctctaaacgggtcttgaggggttttttgct
                    gaaaggaggaactatatccggattggcgaatgggacgcgccctgtagcggcgcattaagcgcggcgggtgtg
                    gtggttacgcgcagcgtgaccgctacactt PolyA-f             gcccgaaaggaagctgagtt
(SEQ ID NO: 66)

PolyA25-r           ttttttttttttttttttttttttttgttagcagccggatctcagt
(SEQ ID NO: 67)

PolyA50-r           ttttttttttttttttttttttttttttttttttttttttttttttttttgttagcagccggatctcagt
(SEQ ID NO: 68)

PolyA170-r          tttttttttttttttttttttttttttttttttttttttttttttttttttttttttttttttttttttt
(SEQ ID NO: 69)     tttttttttttttttttttttttttttttttttttttttttttttttttttttttttttttttttttttt
                    ttttttttttttttttttttttttttttgttagcagccggatctcagt TF5UTR-f            ggtggttctagagggacgtgaaaattacagtagttactg
(SEQ ID NO: 70)

TF5UTR-r            ggtggtcatatgttaaaaaagtttctcttgatacacctgttt
(SEQ ID NO: 71)

HAP270-f            taaaccccagttttatatcgtatatg
(SEQ ID NO: 72)

HAP270-r            tctagagggaaaccgttgtggt
(SEQ ID NO: 73)

YAP1-f              ggtggttctagatagtaaccagccctagctgtt
(SEQ ID NO: 74)

YAP1-r              ggtggtcatatgggtttaagaaacaacttttccttc
(SEQ ID NO: 75)

pET23TFIIDLucA      ttccgatttagtgctttacggcacctcgaccccaaaaaacttgattagggtgatggttcacgtagtgggccatcgc
(SEQ ID NO: 76)     cctgatagacggttttttcgccctttgacgttggagtccacgttcttttaatagtggactcttgttccaaactggaacaac
                    actcaaccctatctcggtctattcttttgatttataagggattttgccgatttcggcctattggttaaaaaatgagctgat
                    ttaacaaaaatttaacgcgaattttaacaaaatattaacgtttacaatttcaggtggcacttttcggggaaatgtgcgc
                    ggaaccccatttgtttattttttctaaatacattcaaatatgtatccgctcatgagacaataaccctgataaatgcttca
                    ataatattgaaaaaggaagagtatgagtattcaacatttccgtgtcgcccttattcccttttttgcggcattttgccttc
                    ctgttttgctcacccagaaacgctggtgaaagtaaaagatgctgaagatcagttgggtgcacgagtgggttacat
                    cgaactggatctcaacagcggtaagatccttgagagttttcgccccgaagaacgttttccaatgatgagcacttttta
                    aagttctgctatgtggcgcggtattatcccgtattgacgccgggcaagagcaactcggtcgccgcatacactattc
                    tcagaatgacttggttgagtactcaccagtcacagaaaagcatcttacggatggcatgacagtaagagaattatg
                    cagtgctgccataaccatgagtgataacactgcggccaacttacttctgacaacgatcggaggaccgaaggag
                    ctaaccgcttttttgcacaacatgggggatcatgtaactcgccttgatcgttgggaaccggagagaatgaagcca
                    taccaaacgacgagcgtgacaccacgatgcctgcagcaatggcaacaacgttgcgcaaactattaactggcga
                    actacttactctagcttcccggcaacaattaatagactggatggaggcggataaagttgcaggaccacttctgcg
                    ctcggcccttccggctggctggtttattgctgataaatctggagccggtgagcgtgggtctcgcggtatcattgca
                    gcactggggccagatggtaagccctcccgtatcgtagttatctacacgacggggagtcaggcaactatgatga
                    acgaaatagacagatcgctgagataggtgcctcactgattaagcattggtaactgtcagaccaagtttactcatat
                    atactttagattgatttaaaacttcatttttaatttaaaaggatctaggtgaagatcctttttgataatctcatgaccaaaa
                    tcccttaacgtgagttttcgttccactgagcgtcagaccccgtagaaaagatcaaaggatcttcttgagatcctttttt
                    tctgcgcgtaatctgctgcttgcaaacaaaaaaaccaccgctaccagcggtggtttgtttgccggatcaagagct
                    accaactctttttccgaaggtaactggcttcagcagagcgcagataccaaatactgtccttctagtgtagccgtagt
                    taggccaccacttcaagaactctgtagcaccgcctacatacctcgctctgctaatcctgttaccagtggctgctgc
                    cagtggcgataagtcgtgtcttaccgggttggactcaagacgatagttaccggataaggcgcagcggtcgggct
                    gaacggggggttcgtgcacacagcccagcttggagcgaacgacctacaccgaactgagatacctacagcgtg
                    agctatgagaaagcgccacgcttcccgaagggagaaaggcggacaggtatccggtaagcggcagggtcgga
                    acaggagagcgcacgagggagcttccaggggaaacgcctggtatctttatagtcctgtcgggtttcgccacct
                    ctgacttgagcgtcgatttttgtgatgctcgtcaggggggcggagcctatggaaaaacgccagcaacgcggcct
                    ttttacggttcctggccttttgctggccttttgctcacatgttctttcctgcgttatccctgattctgtggataaccgtat
                    taccgcctttgagtgagctgataccgctcgccgcagccgaacgaccgagcgcagcgagtcagtgagcgagga
                    agcggaagagcgcctgatgcggtattttctccttacgcatctgtgcggtatttcacaccgcatatatggtgcactct
```

-continued

```
                        cagtacaatctgactgatgccgcatagttaagccagtatacactccgctatcgctacgtgactgggtcatggctg
                        cgccccgacacccgccaacacccgctgacgcgccctgacgggcttgtctgctcccggcatccgcttacagaca
                        agctgtgaccgtctccgggagctgcatgtgtcagaggttttcaccgtcatcaccgaaacgcgcgaggcagctgc
                        ggtaaagctcatcagcgtggtcgtgaagcgattcacagatgtctgcctgttcatccgcgtccagctcgttgagtttc
                        tccagaagcgttaatgtctggcttctgataaagcgggccatgttaagggcggttttttcctgtttggtcactgatgcc
                        tccgtgtaaggggggatttctgttcatggggtaatgataccgatgaaacgagagaggaggatgacacgatacgggtt
                        actgatgatgaacatgcccggttactggaacgttgtgagggtaaaacaactggcggtatggatgcggcgggacc
                        agagaaaaatcactcagggtcaatgccagcgcttcgttaatacagatgtaggtgttccacagggtagccagcag
                        catcctgcgatgcagatccggaacataatggtgcagggcgctgacttccgcgtttcagactttacgaaacacg
                        gaaaccgaagaccattcatgttgttgctcaggtcgcagacgttttgcagcagcagtcgcttcacgttcgctcgcgt
                        atcggtgattcattctgctaaccagtaaggcaacccgccagcctagccgggtcctcaacgacaggagcacgat
                        catgcgcacccgtggccaggaccaacgctgcccgagatctcgatcccgcgaaattaatacgactcactatag
                        ggagaccacaacggtttccctctagatcgatgcggccgcgaattcgggacgtgaaaattacagtagttactgttt
                        ttttggactataagatcggggaaagataacacataagaaataaaacgactactagttagactgctctgcggaag
                        aagcaaggaagtaaaggctgcatttttatttttcttttctagtccaacataaacaggtgtatcaagagaaactttttttaa
                        gagacgtcgacggatccatatggaagacgccaaaaacataaagaaaggcccggcgccattctatccgctaga
                        ggatggaaccgctggagagcaactgcataaggctatgaagagatacgccaggttcctggaacaattgcttttac
                        agatgcacatatcgaggtgaacatcacgtacgcggaatacttcgaaatgtccgttcggttggcagaagctatgaa
                        acgatatgggctgaatacaaatcacagaatcgtcgtatgcagtgaaaactctcttcaattcttatgccggtgttgg
                        gcgcgttatttatcggagttgcagttgcgcccgcgaacgacatttataatgaacgtgaattgctcaacagtatgaa
                        catttcgcagcctaccgtagtgtttgtttccaaaaagggggtgcaaaaaattttgaacgtgcaaaaaaaattaccaa
                        taatccagaaaattattatcatggattctaaaacggattcagtcgatgtacacgttcgtcacatctc
                        atctacctcccggttttaatgaatacgattttgtaccagagtccttgatcgtgacaaaacaattgcactgataatgaa
                        ctcctaggatctactgggttacctaagggtgtggcccttccgcatagaactgcctgcgtcagattacgcatgcc
                        agagatcctattttttggcaatcaaatcattccggatactgcgattttaagtgttgttccattccatcacggttttggaat
                        gtttactacactcggatatttgatatggtttcgagtcgtcttaatgtatagattttgaagaagagctgtttttttacgatc
                        ccttcaggattacaaaattcaaagtgcgttgctagtaccaaccctatttttcattcttcgccaaaagcactctgattgac
                        aaatacgatttatctaatttacacgaaattgcttctggggggcgcacctcttttcgaaagaagtcggggaagcggttg
                        caaaacgcttccatcttccagggatacgacaaggatatgggctcactgagactacatcagctattctgattacacc
                        cgaggggatgataaaccggggcggtcggtaaagttgttccattttttgaagcgaaggttgtggatctggatac
                        cgggaaaacgctgggcgttaatcagagaggcgaattatgtgtcagaggacctatgattatgtccggttatgtaaa
                        caatccggaagcgaccaacgccttgattgacaaggatgatggctacattctggagacatagcttactgggacg
                        aagacgaacacttcttcatagttgaccgcttgaagtctttaattaaatacaaaggataccaggtggcccccgctga
                        attggcgatattgttacaacaccccaatcttcgacgcgggcgtggcaggtcttccccgacgatgacgccg
                        gtgaacttcccgccgccgttgttgttttggagcacggaaagacgatgacggaaaaagagatcgtggattacgtc
                        gccagtcaagtaacaaccgccaaaaagttgcgcggaggagttgtgtttgtggacgaagtaccgaaaggtcttac
                        cggaaaactcgacgcaagaaaaatcagagagatcctcataaaggccaagaagggcggaaagtccaaattgta
                        aaaaaaaaaaaaaaaaaaaaaaaaaaaaaaaaaaaaaaaaaaaaaaaaaaaaaaaaa
                        aaaaaaaaaaaaaaaaaaactcgagcaccaccaccaccaccactgagatccggctgctaacaaagcccgaa
                        aggaagctgagttggctgctgccaccgctgagcaataactagcataaccccttggggcctctaaacgggtcttg
                        aggggttttttgctgaaaggaggaactatatccggattggcgaatgggacgcgccctgtagcggcgcattaagc
                        gcggcgggtgtggtggttacgcgcagcgtgaccgctacacttgccagcgccctagcgcccgctcctttcgcttt
                        cttcccttcctttctcgccacgttcgccggctttccccgtcaagctctaaatcgggggctcccctttaggg pET23HAP270LucA     tggcgaatgggacgcgccctgtagcggcgcattaagcgcggcgggtgtggtggttacgcgcagcgtgaccgc
(SEQ ID NO: 77)     tacacttgccagcgccctagcgcccgctcctttcgctttcttcccttcctttctcgccacgttcgccggctttccccgt
                    caagctctaaatcgggggctcccctttagggttccgatttagtgctttacggcacctcgaccccaaaaaacttgatta
                    gggtgatggttcacgtagtgggccatcgccctgatagacggtttttcgccctttgacgttggagtccacgttcttta
                    atagtggactcttgttccaaactggaacaacactcaaccctatccggtctattcttttgatttataagggattttgccg
                    atttcggcctattggttaaaaaatgagctgatttaacaaaaatttaacgcgaattttaacaaaatattaacgtttacaat
                    ttcaggtggcacttttcggggaaatgtgcgcggaacccctatttgtttatttttctaaatacattcaaatatgtatccgc
                    tcatgagacaataaccctgataaatgcttcaataatattgaaaaaggaagagtatgagtattcaacatttccgtgtc
                    gcccttattcccttttttgcggcattttgccttcctgtttttgctcacccagaaacgctggtgaaagtaaaagatgctg
                    aagatcagttgggtgcacgagtgggttacatcgaactggatctcaacagcggtaagatccttgagagttttcgcc
                    ccgaagaacgttttccaatgatgagcacttttaaagttctgctatgtggcgcggtattatcccgtattgacgccggg
                    caagagcaactcggtcgccgcatacactattctcagaatgacttggttgagtactcaccagtcacagaaaagcat
                    cttacggatggcatgacagtaagagaattatgcagtgctgccataaccatgagtgataacactgcggccaactta
                    cttctgacaacgatcggaggaccgaaggagctaaccgcttttttgcacaacatgggggatcatgtaactcgcctt
                    gatcgttgggaaccggagctgaatgaagccataccaaacgacgagcgtgacaccacgatgcctgcagcaatg
                    gcaacaacgttgcgcaaactattaactggcgaactacttactctagcttcccggcaacaattaatagactggatgg
                    aggcggataaagttgcaggaccacttctgcgctcggcccttccggctggctggtttattgctgataaatctggagc
                    cggtgagcgtgggtctcgcggtatcattgcagcactggggccagatggtaagccctcccgtatcgtagttatcta
                    cacgacggggagtcaggcaactatggatgaacgaaatagacagatcgctgagataggtgcctcactgattaag
                    cattggtaactgtcagaccaagtttactcatatatactttagattgatttaaaacttcatttttaatttaaaaggatctagg
                    tgaagatcctttttgataatctcatgaccaaaatcccttaacgtgagttttcgttccactgagcgtcagacccctag
                    aaaagatcaaaggatcttcttgagatccttttttttctgcgcgtaatctgctgcttgcaaacaaaaaaaccaccgctac
                    cagcggtggtttgtttgccggatcaagagctaccaactctttttccgaaggtaactggcttcagcagagcgcagat
                    accaaatactgtccttctagtgtagccgtagttaggccaccacttcaagaactctgtagcaccgcctacatacctc
                    gctctgctaatcctgttaccagtggctgctgccagtggcgataagtcgtgtcttaccgggttggactcaagacgat
                    agttaccggataaggcgcagcggtcgggctgaacggggggttcgtgcacacagcccagcttggagcgaacg
                    acctacaccgaactgagatacctacagcgtgagctatgagaaagcgccacgcttcccgaagggagaaaggcg
                    gacaggtatccggtaagcggcagggtcggaacaggagagcgcacgagggagcttccagggggaaacgcct
                    ggtatctttatagtcctgtcgggtttcgccacctctgacttgagcgtcgatttttgtgatgctcgtcaggggggcgga
                    gcctatgaaaaacgccagcaacgcggcctttttacggttcctggccttttgctggccttttgctcacatgttctttcc
                    tgcgttatcccctgattctgtggataaccgtattaccgcctttgagtgagctgataccgctcgccgcagccgaacg
                    accgagcgcagcgagtcagtgagcgaggaagcggaagagcgcctgatgcggtattttctccttacgcatctgt
                    gcggtatttcacaccgcatatatggtgcactctcagtacaatctgctctgatgccgcatagttaagccagtatacac
                    tccgctatcgctacgtgactgggtcatggctgcgccccgacacccgccaacacccgctgacgcgccctgacgg
                    gcttgtctgctcccggcatccgcttacagacaagctgtgaccgtctccgggagctgcatgtgtcagaggttttcac
```

-continued

```
                    cgtcatcaccgaaacgcgcgaggcagctgcggtaaagctcatcagcgtggtcgtgaagcgattcacagatgtc
                    tgcctgttcatccgcgtccagctcgttgagtttctccagaagcgttaatgtctggcttctgataaagcgggccatgtt
                    aagggcggttttttcctgtttggtcactgatgcctccgtgtaaggggatttctgttcatgggggtaatgataccgat
                    gaaacgagagaggatgctcacgatacgggttactgatgatgaacatgcccggttactggaacgttgtgagggta
                    aacaactggcggtatggatgcggcgggaccagagaaaaatcactcagggtcaatgccagcgcttcgttaatac
                    agatgtaggtgttccacagggtagccagcagcatcctgcgatgcagatccggaacataatggtgcagggcgct
                    gacttccgcgtttccagactttacgaaacacggaaaccgaagaccattcatgttgttgctcaggtcgcagacgtttt
                    gcagcagcagtcgcttcacgttcgctcgcgtatcggtgattcattctgctaaccagtaaggcaaccccgccagcc
                    tagccgggtcctcaacgacaggagcacgatcatgcgcacccgtggccaggacccaacgctgcccgagatctc
                    gatcccgcgaaattaatacgactcactatagggagaccacaacggtttccctctagataaacctccagttttatatc
                    gtatatgctatctacaggtccactttacacttaataatataaaaatactatataaaggaaccagaaaaataaaaaa
                    gggtcattatttatttgagcagatcattatcaaacgcataggaagagaaaaaacacagttttatttttttttccacacata
                    tttattggtctcctagtacatcaaagagcattttaatgggttgctgatttgttttacctacattttctagtacaaaaaaaa
                    aacaaaaaaagacatatggaagacgccaaaaacataaagaaaggcccggcgccattctatccgctagaggatg
                    gaaccgctggagagcaactgcataaggctatgaagagatacgccctggttcctggaacaattgcttttacagatg
                    cacatatcgaggtgaacatcacgtacgcggaatacttcgaaatgtccgttcggttggcagaagctatgaaacgat
                    atgggctgaatacaaatcacagaatcgtcgtatgcagtgaaaactctcttcaatctttatgccggtgttgggcgcg
                    ttatttatcggagttgcagttgcgcccgcgaacgacatttataatgaacgtgaattgctcaacagtatgaacatttcg
                    cagcctaccgtagtgtttgttccaaaaaggggttgcaaaaaattttgaacgtgcaaaaaaaattaccaataatcca
                    gaaaattattatcatggattctaaaacggattaccagggatttcagtcgatgtacacgttcgtcacatctcatctacct
                    cccggttttaatgaatacgattttgtaccagagtcctttgatcgtgacaaaacaattgcactgataatgaactcctctg
                    gatctactgggttacctaagggtgtggcccttccgcatagaactgcctgcgtcagattctcgcatgccagatctc
                    tatttttggcaatcaaatcattccggatactgcgattttaagtgttgttccattccatcacggttttggaatgtttactaca
                    ctcggatatttgatatgtggatttcgagtcgtcttaatgtatagatttgaagaagagctgtttttacgatcccttcagga
                    ttacaaaattcaaagtgcgttgctagtaccaaccctattttcattcttcgccaaaagcactctgattgacaaatacgat
                    ttatctaatttacacgaaattgcttctgggggcgcacctctttcgaaagaagtcggggaagcggttgcaaaacgct
                    tccatcttccagggatacgacaaggatatgggctcactgagactacatcagctattctgattacacccgagggg
                    atgataaaccgggcgcggtcggtaaagttgttccatttttttgaagcgaaggttgtggatctggataccgggaaaa
                    cgctgggcgttaatcagagaggcgaattatgtgtcagaggacctatgattatgtccggttatgtaaacaatccgga
                    agcgaccaacgccttgattgacaaggatggatgctacattcggagacatagcttactgggacgaagacgaac
                    acttcttcatagttgaccgcttgaagtctttaattaaatacaaaggataccaggtggccccgctgaattggagtcg
                    atattgttacaacaccccaacatcttcgacgcgggcgtggcaggtcttcccgacgatgacgccggtgaacttccc
                    gccgccgttgttgttttggagcacggaaagacgatgacggaaaagagatcgtggattacgtcgccagtcaagt
                    aacaacgcgaaaaagttgcgcggaggagttgtgtttgtggacgaagtaccgaaaggtcttaccggaaaactc
                    gacgcaagaaaaatcagagagatcctcataaaggccaagaagggcggaaagtccaaattgtaaaaataaaa
                    aaaaaaaaaaaaaaaaaaaaaaaaaaaaaaaaaaaaaaaaaaaaaaaaaaaaaaaaaaaaaaaaaaaa
                    aaaaaactcgagcaccaccaccaccaccactgagatccggctgctaacaaagcccgaaaggaagctgagttg
                    gctgctgccaccgctgagcaataactagcataaccccttggggcctctaaacgggtcttgaggggttttgctaaa
                    aggagaaactaacctat
pET23YAP1LucA      ttccgatttagtgctttacggcacctcgaccccaaaaaacttgattagggtgatggttcacgtagtgggccatcgc
(SEQ ID NO: 78)    cctgatagacggtttttcgccctttgacgttggagtccacgttctttaatagtggactcttgttccaaactggaacaac
                    actcaaccctatctcggtctattctttgatttataaggaattttgccgatttcggcctattggttaaaaaatgagctgat
                    ttaacaaaaatttaacgcgaattttaacaaaatattaacgtttacaatttcaggtggcacttttcggggaaatgtgcgc
                    ggaaccctatttgtttatttttctaaatacattcaaatatgtatccgctcatgagacaataaccctgataaatgcttca
                    ataatattgaaaaaggaagagtatgagtattcaactttccgtgtcgcccttattcccttttttgcggcattttgccttc
                    ctgtttttgctcaccagaaacgctggtgaaagtaaaagatgctgaagatcagttgggtgcacgagtgggttacat
                    cgaactggatctcaacagcggtaagatccttgagagttttcgccccgaagaacgttttccaatgatgagcactttta
                    aagttctgctatgtggcgcggtattatcccgtattgacgccgggcaagagcaactcggtcgccgcatacactattc
                    tcagaatgacttggttgagtactcaccagtcacagaaaagcatcttacggatggcatgacagtaagagaattatg
                    cagtgctgccataaccatgagtgataacactgcggccaacttacttctgacaacgatcggaggaccgaaggag
                    ctaaccgcttttttgcacaacatgggggatcatgtaactcgccttgatcgttgggaaccggagctgaatgaagcca
                    taccaaacgacgagcgtgacaccacgatgcctgcagcaatggcaacaacgttgcgcaaactattaactggcga
                    actacttactctagcttcccggcaacaattaatagactggatggaggcggataaagttgcaggaccacttctgcg
                    ctcggcccttccggctggctggtttattgctgataaatctggagccggtgagcgtgggtctcgcggtatcattgca
                    gcactggggccagatggtagccctcccgtatcgtagttatctacacgacggggagtcaggcaactatggatga
                    acgaaatagacagatcgctgagataggtgcctcactgattaagcattggtaactgtcagaccaagtttactcatat
                    atactttagattgatttaaaacttcatttttaatttaaaaggatctaggtgaagatcctttttgataatctcatgaccaaaa
                    tcccttaacgtgagttttcgttccactgagcgtcagaccccgtagaaaagatcaaaggatcttcttgagatccttttttt
                    tctgcgcgtaatctgctgcttgcaaacaaaaaaaccaccgctaccagcggtggtttgtttgccggatcaagagct
                    accaactctttttccgaaggtaactggcttcagcagagcgcagataccaaatactgtccttctagtgtagccgtagt
                    taggccaccacttcaagaactctgtagcaccgcctacatacctcgctctgctaatcctgttaccagtggctgctgc
                    cagtggcgataagtcgtgtcttaccgggttggactcaagacgatagttaccggataaggcgcagcggtcgggct
                    gaacggggggttcgtgcacacagcccagcttggagcgaacgacctacaccgaactgagatacctacagcgtg
                    agctatgagaaagcgccacgcttcccgaagggagaaaggcggacaggtatccggtaagcggcagggtcgga
                    acaggagagcgcacgagggagcttccagggggaaacgcctggtatctttatagtcctgtcgggtttcgccacct
                    ctgacttgagcgtcgatttttgtgatgctcgtcaggggggcggagcctatggaaaaacgccagcaacgcggcct
                    ttttacggttcctggccttttgctggccttttgctcacatgttctttcctgcgttatcccctgattctgtggataaccgtat
                    taccgcctttgagtgagctgataccgctcgccgcagccgaacgaccgagcgcagcgagtcagtgagcgagga
                    agcggaagagcgcctgatgcggtattttctccttacgcatctgtgcggtatttcacaccgcatatatggtgcactct
                    cagtacaatctgctctgatgccgcatagttaagccagtatacactccgctatcgctacgtgactgggtcatggctg
                    cgccccgacacccgccaacacccgctgacgcgccctgacgggcttgtctgctcccggcatccgcttacagaca
                    agctgtgaccgtctccgggagctgcatgtgtcagaggttttcaccgtcatcaccgaaacgcgcgaggcagctgc
                    ggtaaagctcatcagcgtggtcgtgaagcgattcacagatgtctgcctgttcatccgcgtccagctcgttgagtttc
                    tccagaagcgttaatgtctggcttctgataaagcgggccatgttaagggcggttttttcctgtttggtcactgatgcc
                    tccgtgtaaggggatttctgttcatgggggtaatgataccgatgaaacgagagaggatgctcacgatacgggtt
                    actgatgatgaacatgcccggttactggaacgttgtgagggtaaacaactggcggtatggatgcggcgggacc
                    agagaaaaatcactcagggtcaatgccagcgcttcgttaatacagatgtaggtgttccacagggtagccagcag
                    catcctgcgatgcagatccggaacataatggtgcagggcgctgacttccgcgtttccagactttacgaaacacg
```

-continued

```
                    gaaaccgaagaccattcatgttgttgctcaggtcgcagacgttttgcagcagcagtcgcttcacgttcgctcgcgt
                    atcggtgattcattctgctaaccagtaaggcaaccccgccagcctagccgggtcctcaacgacaggagcacgat
                    catgcgcaccgtggccaggacccaacgctgcccgagatctcgatcccgcgaaattaatacgactcactatag
                    ggagaccacaacggtttccctctagatagtaaccagccctagctgtttggttgatttgacctaggttactcttttcttt
                    tctgggtgcgggtaacaatttgggccccgcaaagcgccgtctttgtcatgggaaccggaaaccctccgatgaag
                    agtaggagggtggcaactgatggatgcgtaaggtcttaagagatacatttgcttaatagtcttccgtttaccgatta
                    agcacagtacctttacgttatatataggattggtgtttagcttttttcctgagcccctggttgacttgtgcatgaacac
                    gagccatttttagtttgtttaagggaagttttttgccacccaaaacgtttaaagaaggaaaagttgtttcttaaacccat
                    atggaagacgccaaaaacataaagaaaggcccggcgccattctatccgctagaggatggaaccgctggagag
                    caactgcataaggctatgaagagatacgccctggttcctggaacaattgcttttacagatgcacatatcgaggtga
                    acattcacgtacgcggaatacttcgaaatgtccgttcggttggcagaagctatgaaacgatatgggtgaatacaa
                    atcacagaatcgtcgtatgcagtgaaaactctcttcaattcttatgccggtgttgggcgcgttatttatcggagttgc
                    agttgcgcccgcgaacgacatttataatgaacgtgaattgctcaacagtatgaacatttcgcagcctaccgtagtg
                    tttgtttccaaaaagggggttgcaaaaaattttgaacgtgcaaaaaaaattaccaataatccagaaaattattatcatg
                    gattctaaaacggattaccagggatttcagtcgatgtacacgttcgtcacatctcatctacctcccggttttaatgaat
                    acgattttgtaccagagtcctttgatcgtgacaaaacaattgcactgataatgaactcctctgatctactgggttac
                    ctaagggtgtggcccttccgcatagaactgcctgcgtcagattctcgcatgccagagatcctatttttggcaatcaa
                    atcattccggatactgcgattttaagtgttgttccattccatcacggttttggaatgtttactacactcggatatttgata
                    tgtggatttcgagtcgtcttaatgtatagatttgaagaagagctgtttttacgatcccttcaggattacaaaattcaaa
                    gtgcgttgctagtaccaaccctatttttcattcttcgccaaaagcactctgattgacaaatacgatttatctaatttacac
                    gaaattgcttctggggcgcacctctttcgaaagaagtcggggaagcggttgcaaaacgcttccatcttccagg
                    gatacgacaaggatatgggctcactgagactacatcagctattctgattacacccgagggggatgataaaccgg
                    gcgcggtcggtaaagttgttccatttttttgaagcgaaggttgtggatctggataccgggaaaacgctgggcgttaa
                    tcagagaggcgaattatgtgtcagaggacctatgattatgtccggttatgtaaacaatccggaagcgaccaacgc
                    cttgattgacaaggatggatggctacattctggagacatagcttactgggacgaagacgaacacttcttcatagtt
                    gaccgcttgaagtctttaattaaatacaaaggataccaggtggccccgctgaattggagtcgatattgttacaac
                    accccaacatcttcgacgcgggcgtggcaggtcttcccgacgatgacgccggtgaacttcccgccgccgttgtt
                    gttttggagcacggaaagacgatgacggaaaagagatcgtggattacgtcgccagtcaagtaacaaccgcca
                    aaaagttgcgcggaggagttgtgtttgtggacgaagtaccgaaaggtcttaccggaaaactcgacgcaagaaa
                    aatcagagagatcctcataaaggccaagaagggcggaaagtccaaattgtaaaaaaaaaaaaaaaaaaaaa
                    aaaaaaaaaaaaaaaaaaaaaaaaaaaaaaaaaaaaaaaaaaaaaaaaaaaaaaaaaaaaaaaaaaaaac
                    tcgagcaccaccaccaccactgagatccggctgctaacaaagcccgaaaggaagctgagttggctgctg
                    ccaccgctgagcaataactagcataaccccctggggcctctaaacgggtcttgaggggttttttgctgaaaggag
                    gaactatatccggattggcgaatgggacgcgccctgtagcggcgcattaagcgcggcgggtgtggtggttacg
                    cgcagcgtgaccgctacacttgccagcgccctagcgcccgctcctttcgctttcttcccttcctttctcgccacgtt
                    cgccggctttccccgtcaagctctaaatcggggggctcccttaggg
```

| | |
|---|---|
| 5' UTR of p150 gene (SEQ ID NO: 79) | cccagttcgatcctgggcgaaatcatttttttgaaaattacattaataaggcttttttcaatatctctggaacaacgtttg tttctacttactaatagctttaaggaccctcttggacatcatgatggcagacttccatcgtagtgggatgatcatatga tgggcgtatcctcatcgcgactcgataacgacgtgagaaacgattttttttttttcttttcaccgtattttttgtgcgtcc tttttcaattatagatttttttattttttttttttttctcgtactgtttcactgacaaaagtttttttcaagaaaaattttc gatgccgcgttctctgtgtgcaacggatggatggtagatggaattcaatatgttgcttgaaattttaccaatcttgatat tgtgataatttacttaattatgattatcctcttcccttcaatttcttaaagcttcttacttactccttcttgctcataaa taagcaaggtaagaggacaactgtaattacctattacaata |
| P150-f (SEQ ID NO: 80) | ggtggttctagacccagttcgatcctgggcga |
| P150-r (SEQ ID NO: 81) | ggtggtggatcctattgtaataggtaattacagttgtcctct |
| Ω sequence (65 nt) from TMV (SEQ ID NO: 82) | tattttacaacaattaccaacaacaacaaacaacaaacaacattacaattactatttacaatta |
| Primer Sf-f (SEQ ID NO: 83) | catatggaagacgccaaaaacataa |
| Omega-r (SEQ ID NO: 84) | taattgtaaatagtaattgtaatgttgtttgttgttgttgttgttggtaattgttgtaaaatactccctatagtgagtcgt atta |
| 5'-UTR of polyhedrin gene (44 nt) (SEQ ID NO: 85) | tattttattctttcgtaaaaaaattagaaaaataaaatataaa |
| Polyhedrin-r (SEQ ID NO: 86) | tttatattttattttttctaatttttttacgaaagaataaaaatactccctatagtgagtcgtatta |
| 5'-end poly (A)64 (SEQ ID NO: 87) | aaaaaaaaaaaaaaaaaaaaaaaaaaaaaaaaaaaaaaaaaaaaaaaaaaaaaaaaaaaaaaaa |
| PolyA64-r (SEQ ID NO: 88) | ttttttttttttttttttttttttttttttttttttttttttttttttttttttttttttttttctccctatagtgagtc gtatta |

-continued

| | |
|---|---|
| 5'-UTR fragment (143 nt) from tobacco etch virus (TEV)(Accession number: NC_001555) genome (SEQ ID NO: 89) | aaataacaaatctcaacacaacatatacaaaacaaacgaatctcaagcaatcaagcattctacttctattgcagca<br>atttaaatcatttcttttaaagcaaaagcaattttctgaaaattttcaccatttacgaacgatagca |
| oligo TEV-r (SEQ ID NO: 90) | tgctatcgttcgtaaatggtgaaaattttcagaaaattgcttttgctttaaaagaaatgatttaaattgctgcaatagaa<br>gtagaatgatgattgcttgagattcgtttgttttgtatatgttgtgttgagatttgttatttccctatagtgagtcgtatta |
| 5'-UTR fragment (65 nt) from Crucifer tobamovirus (CfTbm) genome (Accession number: NC_003355.1) (SEQ ID NO: 91) | atttaaattattgcaacaacaacaacaattacaataataacaaacaaaatacaaacaacaacaac |
| CfTbm-r (SEQ ID NO: 92) | gttgttgttgtttgtattttgtttgttattattgtaattgttgttgttgttgcasataatttaaatccctatagtgagtcg<br>tatta |
| IRES sequence of the cricket paralysis virus (CrPV) intergenic region (IGR) (SEQ ID NO: 93) | aaagcaaaaatgtgatcttgcttgtaaatacaattttgagaggttaataaattacaagtagtgctatttttgtatttaggt<br>tagctatttagctttacgttccaggatgcctagtggcagccccacaatatccaggaagccctctctgcggtttttca<br>gattaggtagtcgaaaaacctaagaaatttacct |
| plasmid pSalI-IGR (SEQ ID NO: 94) | gccagcgccctagcgcccgctcctttcgctttcttcccttcctttctcgccacgttcgccggctttccccgtcaagct<br>ctaaatcgggggctccctttagggttccgatttagtgctttacggcacctcgaccccaaaaaacttgattagggtg<br>atggttcacgtagtgggccatcgccctgatagacggtttttcgccctttgacgttggagtccacgttctttaatagtg<br>gactcttgttccaaactggaacaacactcaaccctatctcggtctattcttttgatttataagggattttgccgatttcg<br>gcctattggttaaaaaatgagctgatttaacaaaaatttaacgcgaattttaacaaaatattaacgtttacaatttcag<br>gtggcacttttcggggaaatgtgcgcggaacccctatttgtttatttttctaaatacattcaaatatgtatccgctcatg<br>agacaataaccctgataaatgcttcaataatattgaaaaaggaagagtatgagtattcaacatttccgtgtcgccctt<br>attccctttttttgcggcattttgccttcctgtttttgctcacccagaaacgctggtgaaagtaaaagatgctgaagatc<br>agttgggtgcacgagtgggttacatcgaactggatctcaacagcggtaagatccttgagagttttcgccccgaag<br>aacgttttccaatgatgagcacttttaaagttctgctatgtggcgcggtattatcccgtattgacgccgggcaagag<br>caactcggtcgccgcatacactattctcagaatgacttggttgagtactcaccagtcacagaaaagcatcttacgg<br>atggcatgacagtaagagaattatgcagtgctgccataaccatgagtgataacactgcggccaacttacttctgac<br>aacgatcggaggaccgaaggagctaaccgcttttttgcacaacatgggggatcatgtaactcgccttgatcgttg<br>ggaaccggagctgaatgaagccataccaaacgacgagcgtgacaccacgatgcctgcagcaatggcaacaa<br>cgttgcgcaaactattaactggcgaactacttactctagcttcccggcaacaattaatagactggatggaggcgg<br>ataaagttgcaggaccacttctgcgctcggcccttccggctggctggtttattgctgataaatctggagccggtga<br>gcgtgggtctcgcggtatcattgcagcactggggccagatggtaagccctcccgtatcgtagttatctacacgac<br>ggggagtcaggcaactatggatgaacgaaatagacagatcgctgagataggtgcctcactgattaagcattggt<br>aactgtcagaccaagtttactcatatatactttagattgatttaaaacttcatttttaatttaaaaggatctaggtgaaga<br>tcctttttgataatctcatgaccaaaatcccttaacgtgagttttcgttccactgagcgtcagaccccgtagaaaaga<br>tcaaaggatcttcttgagatcctttttttctgcgcgtaatctgctgcttgcaaacaaaaaaaccaccgctaccagcg<br>gtggtttgtttgccggatcaagagctaccaactctttttccgaaggtaactggcttcagcagagcgcagataccaa<br>atactgtccttctagtgtagccgtagttaggccaccacttcaagaactctgtagcaccgcctacatacctcgctctg<br>ctaatcctgttaccagtggctgctgccagtggcgataagtcgtgtcttaccgggttggactcaagacgatagttac<br>cggataaggcgcagcggtcgggctgaacggggggttcgtgcacacagcccagcttggagcgaacgacctac<br>accgaactgagatacctacagcgtgagctatgagaaagcgccacgcttcccgaagggagaaaggcggacag<br>gtatccggtaagcggcagggtcggaacaggagagcgcacgagggagcttccagggggaaacgcctggtatc<br>tttatagtcctgtcgggtttcgccacctctgacttgagcgtcgatttttgtgatgctcgtcaggggggcggagcctat<br>ggaaaaacgccagcaacgcggcctttttacggttcctggccttttgctggccttttgctcacatgttctttcctgcgtt<br>atcccctgattctgtggataaccgtattaccgcctttgagtgagctgataccgctcgccgcagccgaacgaccga<br>gcgcagcgagtcagtgagcgaggaagcggaagagcgcctgatgcggtattttctccttacgcatctgtgcggta<br>tttcacaccgcatatatggtgcactctcagtacaatctgctctgatgccgcatagttaagccagtatacactccgcta<br>tcgctacgtgactgggtcatggctgcgccccgacacccgccaacacccgctgacgcgccctgacgggcttgtc<br>tgctcccggcatccgcttacagacaagctgtgaccgtctccgggagctgcatgtgtcagaggttttcaccgtcatc<br>accgaaacgcgcgaggcagctgcggtaaagctcatcagcgtggtcgtgaagcgattcacagatgtctgcctgtt<br>catccgcgtccagctcgttgagtttctccagaagcgttaatgtctggcttctgataaagcgggccatgttaagggc<br>ggtttttcctgtttggtcactgatgcctccgtgtaagggggatttctgttcatgggggtaatgataccgatgaaacg<br>agagaggatgctcacgatacgggttactgatgatgaacatgcccggttactggaacgttgtgagggtaaacaac<br>tggcggtatggatgcggcgggaccagagaaaaatcactcagggtcaatgccagcgcttcgttaatacagatgta<br>ggtgttccacagggtagccagcagcatcctgcgatgcagatccggaacataatggtgcagggcgctgacttcc<br>gcgtttccagactttacgaaacacggaaaccgaagaccattcatgttgttgctcaggtcgcagacgttttgcagca<br>gcagtcgcttcacgttcgctcgcgtatcggtgattcattctgctaaccagtaaggcaaccccgccagcctagccg<br>ggtcctcaacgacaggagcacgatcatgcgcacccgtggccaggacccaacgctgcccgagatctcgatccc<br>gcgaaattaatacgactcactatagggagaccacaacggtttccctctagagcaaaaatgtgatcttgcttgtaaat<br>acaattttgagaggttaataaattacaagtagtgctatttttgtatttaggttagctatttagctttacgttccaggatgc |

```
                            ctagtggcagccccacaatatccaggaagccctctctgcggttttttcagattaggtagtcgaaaaacctaagaaat
                            ttacctgctacatttcaagattcatatggaagacgccaaaaacataaagaaaggcccggcgccattctatccgcta
                            gaggatggaaccgctggagagcaactgcataaggctatgaagagatacgccctggttcctggaacaattgctttt
                            acagatgcacatatcgaggtgaacatcacgtacgcggaatacttcgaaatgtccgttcggttggcagaagctatg
                            aaacgatatgggctgaatacaaatcacagaatcgtcgtatgcagtgaaaactctcttcaatttctttatgccggtgttg
                            ggcgcgttatttatcggagttgcagttgcgcccgcgaacgacatttataatgaacgtgaattgctcaacagtatga
                            acatttcgcagcctaccgtagtgtttgtttccaaaaaggggttgcaaaaaattttgaacgtgcaaaaaaaaattacca
                            ataatccagaaaattattatcatggattctaaaacggattaccaggggatttcagtcgatgtacacgttcgtcacatct
                            catctacctcccggttttaatgaatacgattttgtaccagagtccttttgatcgtgacaaaacaattgcactgataatga
                            actcctctggatctactgggttacctaagggtgtggccctttccgcatagaactgcctgcgtcagattctcgcatgc
                            cagagatcctattttggcaatcaaatcattccggatactgcgattttaagtgttgttccattccatcacggttttggaa
                            tgtttactacactcggatatttgatatgtggatttcgagtcgtcttaatgtatagatttgaagaagagctgttttacgat
                            cccttcaggattacaaaattcaaagtgcgttgctagtaccaaccctattttcattcttcgccaaaagcactctgattga
                            caaatacgatttatctaattttacacgaaattgcttctgggggcgcacctctttcgaaagaagtcggggaagcggtt
                            gcaaaacgcttccatcttccagggatacgacaaggatatgggctcactgagactacatcagctattctgattacac
                            ccgagggggatgataaaacgggcgcggtcggtaaagttgttccattttttgaagcgaaggttgtggatctggata
                            ccggaaaacgctgggcgttaatcagagaggcgaattatgtgtcagaggacctatgattatgtccggttatgtaa
                            acaatccggaagcgaccaacgccttgattgacaaggatggatggctacattctggagacatagcttactgggac
                            gaagacgaacacttcttcatagttgaccgcttgaagtctttaattaaatacaaaggataccaggtggccccgctg
                            aattggagtcgatattgttacaacaccccaacatcttcgacgcgggcgtggcaggtcttcccgacgatgacgcc
                            ggtgaacttccgccgccgttgttgttttggagcacggaaagacgatgacggaaaaagagatcgtggattacgt
                            cgccagtcaagtaacaaccgccaaaaagttgcgcggaagtgctgtttgtggacgaagtaccgaaaggtctta
                            ccggaaaactcgacgcaagaaaaatcagagagatccctcataaaggccaagaagggcggaaagtccaaattgt
                            aaaaaaaaaaaaaaaaaaaaaaaaaaaaaaaaaaaaaaaaaaaaaaaaaaaaaaaaaaaaaaaaaaaaaaaaa
                            aaaaaaaaaaaaaaaaaaaactcgagcaccaccaccaccactgagatccggctgctaacaaagcccga
                            aaggaagctgagttggctgctgccaccgctgagcaataactagcataacccctggggcctctaaacgggtctt
                            gaggggttttttgctgaaaggaggaactatatccggattggcgaatgggacgcgccctgtagcggcgcattaag
                            cgcggcgggtgtggtggttacgcgcagcgtgaccgctacactt Primer IGR-f                ggtggttctagagcaaaaatgtgatcttgcttgta
(SEQ ID NO: 95)

Primer IGR-r                ggtggtcatatgaatcttgaaatgtagcaggtaaat
(SEQ ID NO: 96)

3'-UTR of yeast             gagtattgaatctgtttagaaataatggaatatattttttatttatttatttatattattggtcggctcttttcttctgaaggtc
FBA1 gene                   aatgacaaaatgatatgaaggaaataatgatttctaaaattttacaacgtaagatattttttacaaaagcctagctcatc
(Accession                  ttttgtcatgcactattttactcacgcttgaaattaacggccagtccactgcggagtcatttcaaagtcatcctaatcg
number:                     atctatcgtttttgatagctcattttggagttcgcgattgtcttctgttattcacaactgttttaattttttatttcattctggaa
NM_001179626)               ctcttcgagttctttgtaaagtctttcatagtagcttacttatcctccaacatatttaacttcatgtcaatttcggctctta
(short                      aattttccacatcatcaagttcaacatcatcttttaacttgaatttattctctagctcttccaaccaagcctcattgctcct
fragment)                   tgatttactggtgaaaagtgatacactttgcgcgcaatccaggtcaaaactttcctgcaaagaattcaccaatttctc
(SEQ ID NO: 97)             gacatcatagtacaatttgttttgttctcccatcacaatttaatatacctgatggattcttatgaagcgctgggtaatgg
                            acgtgtcactc 3'-UTR of yeast             gagtattgaatctgtttagaaataatggaatatattttttatttatttatttatattattggtcggctcttttcttctgaaggtc
FBA1 gene                   aatgacaaaatgatatgaaggaaataatgatttctaaaattttacaacgtaagatattttttacaaaagcctagctcatc
(Accession                  ttttgtcatgcactattttactcacgcttgaaattaacggccagtccactgcggagtcatttcaaagtcatcctaatcg
number:                     atctatcgtttttgatagctcattttggagttcgcgattgtcttctgttattcacaactgttttaattttttatttcattctggaa
NM_001179626)               ctcttcgagttctttgtaaagtctttcatagtagcttacttatcctccaacatatttaacttcatgtcaatttcggctctta
(long fragment)             aattttccacatcatcaagttcaacatcatcttttaacttgaatttattctctagctcttccaaccaagcctcattgctcct
(SEQ ID NO: 98)             tgatttactggtgaaaagtgatacactttgcgcgcaatccaggtcaaaactttcctgcaaagaattcaccaatttctc
                            gacatcatagtacaatttgttttgttctcccatcacaatttaatatacctgatggattcttatgaagcgctgggtaatgg
                            acgtgtcactctacttcgccttttccctactccttttagtacggaagacaatgctaataaataagagggtaataataa
                            tattattaatcggcaaaaaagattaaacgccaagcgtttaatttatcagaaagcaaacgtcgtaccaatccttgaatg
                            cttcccaattgtatattaagagtcatcacagcaacatattcttgttattaaattaattattattgattttttgatattgtataaa
                            aaaccaaatatgtataaaaaagtgaataaaaaataccaagtatggagaaatatattagaagtctatacgttaaa
                            accagaacgtgcacaattttttttaatctgccaaatggaaaaacggaaatatacggaaaagaagttgaagtaata
                            gttagaaaggcaaaaaggaaagaaacaatttaaaatatcttaagattaatattagaaacaaacaccaatgttcattt
                            cattccttagaatatatccgaatgaaatgaccaaccttacttgtttgtaaactgaggaagaaagaatattatttctccg
                            aaaacttgtcataccgtagctgtcttgcttttatttgcttttgaccttattttttcaaaaatcaccgtgcttttttgtgagttt
                            ttagatgttgtgataaattgtcacttctactgaatttttctcacagaacatacaagcaaagggcgttccgttgaatg
                            aacggatcttatatgccttttcaagtgctcactgcgtctgaatgccttctcacagtcttttacacttgaaaggtttatttt
                            atcgtagttgttggggtcaatg FBA3UTR-f                   ggtggtgagctcgagtattgaatctgtttagaaataatgg
(SEQ ID NO: 99)

FBA3UTR1-r                  ggtggtctcgagtgacacgtccattacccagc
(SEQ ID NO: 100)

FBA3UTR2-r                  ggtggtctcgagcattgaccccaacaactacg
(SEQ ID NO: 101)

TMV1,                       aggaaaagtgaatatcaatgagtttatcgacctgacaaaaatggagaagatcttaccgtcgatgtttacccctgta
ranges from                 aagagtgttatgtgttccaaagttgataaaataatggttcatgagaatgagtcattgtcagaggtgaaccttcttaaa
4920 to 5711 of             ggagttaagcttattgatagtggatacgtctgtttagccggtttggtcgtcacgggcgaatggaacttgcctgacaa
genome (792 nt              ttgcagaggaggtgtgagcgtgtgtctggtggacaaaaggatgaaagagccgacgaggccactctcggatct
in length)                  tactacacagcagctgcaaagaaaagatttcagttcaaggtcgttcccaattatgctataaccacccaggacgcg
```

| | |
|---|---|
| (SEQ ID NO: 102) | atgaaaaacgtctctggcaagttttagttaatattagaaatgtaaagatgtcagcgggtttctgtccgcctttctctggagt<br>ttgtgtcggtgtgtattgtttatagaaataatataaaattaggtttgagagagaagattacaaacgtgagagacgga<br>gggcccatggaacttacagaagaagtcgttgatgagttcatggaagatgtccctatgtcaatcaggcttgcaaag<br>tttcgatctcggaccggaaaaaagagtgatgtccgtaaaggaaaaatagtagtagtgaccggtcagtgccgaa<br>caagaactatagaaatgttaaggattttggaggaatgagtttaaaaaagaataatttaatcgatgatgattcggagg<br>ctactgtcgccgaatcggattcgttttaaat |
| TMV2 ranges from 6192 to 6395 genome (204 nt in length)<br>(SEQ ID NO: 103) | ggtagtcaagatgcataataaataacggattgtgtccgtaatcacacgtggtgcgtacgataacgcatagtgttttt<br>ccctccacttagatcgaagggttgtgtcttggatcgcgcgggtcaaatgtatatggttcatatacatccgcaggca<br>cgtaataaagcgaggggttcgaatccccccgttaccccggtaggggccca |
| TMV13U200<br>(SEQ ID NO: 104) | ggtggtctcgagccaaaccggctaaacaga |
| TMV13U400<br>(SEQ ID NO: 105) | ggtggtctcgagaacttgccagacgttttcat |
| TMV13U700<br>(SEQ ID NO: 106) | ggtggtctcgagatttctatagttcttgttcggca |
| TMV13U-f<br>(SEQ ID NO: 107) | ggtggtgagctcaggaaaagtgaatatcaatgagtttatc |
| TMV13U200-r<br>(SEQ ID NO: 108) | ggtggtctcgagccaaaccggctaaacaga |
| TMV13U400-r<br>(SEQ ID NO: 109) | ggtggtctcgagaacttgccagacgttttcat |
| TMV13U700-r<br>(SEQ ID NO: 110) | ggtggtctcgagatttctatagttcttgttcggca |
| TMV2 with the length of 204 nt<br>(SEQ ID NO: 111) | ggtagtcaagatgcataataaataacggattgtgtccgtaatcacacgtggtgcgtacgataacgcatagtgttttt<br>ccctccacttagatcgaagggttgtgtcttggatcgcgcgggtcaaatgtatatggttcatatacatccgcaggca<br>cgtaataaagcgaggggttcgaatccccccgttaccccggtaggggccca |
| TMV23U-f<br>(SEQ ID NO: 112) | ggtggtgagctcggtagtcaagatgcataata |
| TMV23U-r<br>(SEQ ID NO: 113) | ggtggtctcgagtgggcccctaccggggg |
| QEluc-f<br>(SEQ ID NO: 114) | ttactatttacaattacatatggaagacgccaaaaac |
| QEluc-r<br>(SEQ ID NO: 115) | agcagccggatctcagtttacaatttggactttccgc |
| QEGFP-f<br>(SEQ ID NO: 116) | ttactatttacaattacatatgagcaaaggtgaagaac |
| QEGFP-r<br>(SEQ ID NO: 117) | agcagccggatctcagtttattttttcgaactgcgga |
| QECAT-f<br>(SEQ ID NO: 118) | ttactatttacaattacatatggaaaaaaaaatcaccgg |
| QECAT-r<br>(SEQ ID NO: 119) | agcagccggatctcagtttacgcaccaccctgcc |
| T7 promoter<br>(SEQ ID NO: 120) | taatacgactcactataggggag |
| Ω sequence<br>(SEQ ID NO: 121) | tattttacaacaattaccaacaacaacaaacaacaaacaacattacaattactatttacaatta |
| poly(A)50 tail<br>(SEQ ID NO: 122) | aaaaaaaaaaaaaaaaaaaaaaaaaaaaaaaaaaaaaaaaaaaaaaaaaa |
| QET7Ome-f<br>(SEQ ID NO: 123) | acgctgcccgagatctcgatcccgcgaaattaatacgactcactatagggagtatttttacaacaattaccaacaa<br>caacaaacaacaaacaacattacaattactatttacaattacat |
| pET23c-GFP-cyc3<br>(SEQ ID NO: 124) | tggcgaatgggacgcgccctgtagcggcgcattaagcgcggcgggtgtggtggttacgcgcagcgtgaccgc<br>tacacttgccagcgccctagcgcccgctcctttcgctttcttcccttcctttctcgccacgttcgccggctttcccgt<br>caagctctaaatcgggggctccctttagggttccgatttagtgctttacggcacctcgaccccaaaaaacttgatta<br>gggtgatggttcacgtagtgggccatcgccctgatagacggtttttcgccctttgacgttggagtccacgttcttta<br>atagtggactcttgttccaaactggaacaacactcaaccctatctcggtctattcttttgatttataagggattttgccg |

|  | -continued |
|---|---|
|  | atttcggcctattggttaaaaaatgagctgatttaacaaaaatttaacgcgaattttaacaaaatattaacgtttacaat |
|  | ttcaggtggcacttttcggggaaatgtgcgcggaacccctatttgtttatttttctaaatacattcaaatatgtatccgc |
|  | tcatgagacaataaccctgataaatgcttcaataatattgaaaaaggaagagtatgagtattcaacatttccgtgtc |
|  | gcccttattccttttttgcggcattttgccttcctgtttttgctcacccagaaacgctggtgaaagtaaaagatgctg |
|  | aagatcagttgggtgcacgagtgggttacatcgaactggatctcaacagcggtaagatccttgagagttttcgcc |
|  | ccgaagaacgttttccaatgatgagcacttttaaagttctgctatgtggcgcggtattatcccgtattgacgccggg |
|  | caagagcaactcggtcgccgcatacactattctcagaatgacttggttgagtactcaccagtcacagaaaagcat |
|  | cttacggatggcatgacagtaagagaattatgcagtgctgccataaccatgagtgataacactgcggccaactta |
|  | cttctgacaacgatcggaggaccgaaggagctaaccgcttttttgcacaacatgggggatcatgtaactcgcctt |
|  | gatcgttgggaaccggagctgaatgaagccataccaaacgacgagcgtgacaccacgatgcctgcagcaatg |
|  | gcaacaacgttgcgcaaactattaactggcgaactacttactctagcttcccggcaacaattaatagactggatgg |
|  | aggcggataaagttgcaggaccacttctgcgctcggcccttccggctggctggtttattgctgataaatctggagc |
|  | cggtgagcgtgggtctcgcggtatcattgcagcactggggccagatggtaagccctcccgtatcgtagttatcta |
|  | cacgacggggagtcaggcaactatggatgaacgaaatagacagatcgctgagataggtgcctcactgattaag |
|  | cattggtaactgtcagaccaagtttactcatatatactttagattgatttaaaacttcattttttaatttaaaaggatctagg |
|  | tgaagatcctttttgataatctcatgaccaaaatcccttaacgtgagttttcgttccactgagcgtcagacccgtag |
|  | aaaagatcaaaggatcttcttgagatcctttttttctgcgcgtaatctgctgcttgcaaacaaaaaaaccaccgctac |
|  | cagcggtggtttgtttgccggatcaagagctaccaactctttttccgaaggtaactggcttcagcagagcgcagat |
|  | accaaatactgtccttctagtgtagccgtagttaggccaccacttcaagaactctgtagcaccgcctacatacctc |
|  | gctctgctaatcctgttaccagtggctgctgccagtggcgataagtcgtgtcttaccgggttggactcaagacgat |
|  | agttaccggataaggcgcagcggtcgggctgaacggggggttcgtgcacacagcccagcttggagcgaacg |
|  | acctacaccgaactgagatacctacagcgtgctgagaagcgccacgcttcccgaagggagaaaggcg |
|  | gacaggtatccggtaagcggcagggtcggaacaggagagcgcacgagggagcttccaggggggaaacgcct |
|  | ggtatctttatagtcctgtcgggtttcgccacctctgacttgagcgtcgatttttgtgatgctcgtcagggggcgga |
|  | gcctatggaaaaacgccagcaacgcggcctttttacggttcctggccttttgctggccttttgctcacatgttctttcc |
|  | tgcgttatcccctgattctgtggataaccgtattaccgcctttgagtgagctgataccgctcgccgcagccgaacg |
|  | accgagcgcagcgagtcagtgagcgaggaagcggaagagcgcctgatgcggtattttctccttacgcatctgt |
|  | gcggtatttcacaccgcatatatggtgcactctcagtacaatctgctctgatgccgcatagttaagccagtatacac |
|  | tccgctatcgctacgtgactgggtcatggctgcgccccgacacccgccaacacccgctgacgcgccctgacgg |
|  | gcttgtctgctcccggcatccgcttacagacaagctgtgaccgtctccgggagctgcatgtgtcagaggttttcac |
|  | cgtcatcaccgaaacgcgcgaggcagctgcggtaaagctcatcagcgtggtcgtgaagcgattcacagatgtc |
|  | tgcctgttcatccgcgtccagctcgttgagtttctccagaagcgttaatgtctggcttctgataaagcgggccatgtt |
|  | aagggcggttttttcctgtttggtcactgatgcctccgtgtaaggggggatttctgttcatgggggtaatgataccgat |
|  | gaaacgagagaggatgctcacgatacgggttactgatgatgaacatgcccggttactggaacgttgtgagggta |
|  | aacaactggcggtatggatgcggcgggaccagagaaaaatcactcagggtcaatgccagcgcttcgttaatac |
|  | agatgtaggtgttccacagggtagccagcagcatcctgcgatgcagatccggaacataatggtgcagggcgct |
|  | gacttccgcgtttccagactttacgaaacacggaaaccgaagaccattcatgttgttgctcaggtcgcagacgtttt |
|  | gcagcagcagtcgcttcacgttcgctcgcgtatcggtgattcattctgctaaccagtaaggcaaccccgccagcc |
|  | tagccgggtcctcaacgacaggagcacgatcatgctagtcatgctgcccggagatctc |
|  | gatcccgcgaaattaatacgactcactataggggagaccacaacggtttccctctagaaataattttgtttaactttaa |
|  | gaaggagatatacatatggctagcatgactagcaaaggagaagaacttttcactggagttgtcccaattcttgttg |
|  | aattagatggtgatgttaatgggcacaaattttctgtcagtggagagggtgaaggtgatgctacatacggaaagct |
|  | tacccttaaatttatttgcactactggaaaacttcctgttccatggccaacacttgtcactactttctcttatggtgttca |
|  | atgcttttcccgttatccggatcatatgaaacggcatgacttttttcaagagtgccatgcccgaaggttatgtacagg |
|  | aacgcactatatctttcaaagatgacgggaactacaagacgcgtgctgaagtcaagtttgaaggtgatacccttgt |
|  | taatcgtatcgagttaaaggtattgattttaaagaagatggaaacattctcggacacaaactcgagtacaactata |
|  | actcacacaatgtatacatcacggcagacaaacaaaagaatggaatcaaagctaacttcaaaattcgccacaac |
|  | attgaagatggatccgttcaactagcagaccattatcaacaaaatactccaattggcgatggccctgtccttttacc |
|  | agacaaccattacctgtcgacacaatctgccctttcgaaagatcccaacgaaaagagagaccacatggtcctc |
|  | ttgagtttgtaacagctgctgggattacacatggcatggatgaactatacaaacccgggatccggcgggcggcc |
|  | gcactcgagcaccaccaccaccaccactgagatccggctgctaacaaagcccgaaaggaagctgagttggct |
|  | gctgccaccgctgagcaataactagcataaccccttggggcctctaaacgggtcttgagggttttttgctgaaa |
|  | ggaggaactatatccggat |
| T7 terminator (SEQ ID NO: 125) | ctgagcaataactagcata |
| luciferase sense primer (SEQ ID NO: 126) | ggtggtcatatggaagacgccaaaaacat |
| luciferase antisense primer (SEQ ID NO: 127) | ggtggtctcgagttttttttttttttttttttttttttttttttttttttttttttttttttttttttttttttttttttttttttttttttttttttttttttttttttttttacaatttggactttccgc |
| pET2352LucA (SEQ ID NO: 128) | gccagcgccctagcgcccgctcctttcgctttcttcccttcctttctcgccacgttcgccggctttccccgtcaagct |
|  | ctaaatcggggctccctttagggttccgatttagtgctttacggcacctcgaccccaaaaaacttgattagggtg |
|  | atggttcacgtagtgggccatcgccctgatagacggtttttcgccctttgacgttggagtccacgttctttaatagtg |
|  | gactcttgttccaaactggaacaacactcaaccctatctcggtctattcttttgatttataagggattttgccgatttcg |
|  | gcctattggttaaaaaatgagctgatttaacaaaaatttaacgcgaattttaacaaaatattaacgtttacaatttcag |
|  | gtggcacttttcggggaaatgtgcgcggaacccctatttgtttatttttctaaatacattcaaatatgtatccgctcatg |
|  | agacaataaccctgataaatgcttcaataatattgaaaaaggaagagtatgagtattcaacatttccgtgtcgccctt |
|  | attccttttttgcggcattttgccttcctgtttttgctcacccagaaacgctggtgaaagtaaaagatgctgaagatc |
|  | agttgggtgcacgagtgggttacatcgaactggatctcaacagcggtaagatccttgagagttttcgccccgaag |
|  | aacgttttccaatgatgagcacttttaaagttctgctatgtggcgcggtattatcccgtattgacgccgggcaagag |
|  | caactcggtcgccgcatacactattctcagaatgacttggttgagtactcaccagtcacagaaaagcatcttacgg |
|  | atggcatgacagtaagagaattatgcagtgctgccataaccatgagtgataacactgcggccaacttacttctgac |
|  | aacgatcggaggaccgaaggagctaaccgcttttttgcacaacatgggggatcatgtaactcgccttgatcgttg |
|  | ggaaccggagctgaatgaagccataccaaacgacgagcgtgacaccacgatgcctgcagcaatggcaacaa |

```
                    cgttgcgcaaactattaactggcgaactacttactctagcttcccggcaacaattaatagactggatggaggcgg
                    ataaagttgcaggaccacttctgcgctcggcccttccggctggctggtttattgctgataaatctggagccggtga
                    gcgtgggtctcgcggtatcattgcagcactggggccagatggtaagccctcccgtatcgtagttatctacacgac
                    ggggagtcaggcaactatggatgaacgaaatagacagatcgctgagataggtgcctcactgattaagcattggt
                    aactgtcagaccaagtttactcatatatactttagattgatttaaaacttcattttaatttaaaaggatctaggtgaaga
                    tcctttttgataatctcatgaccaaaatcccttaacgtgagttttcgttccactgagcgtcagaccccgtagaaaaga
                    tcaaaggatcttcttgagatcctttttttctgcgcgtaatctgctgcttgcaaacaaaaaaaccaccgctaccagcg
                    gtggtttgtttgccggatcaagagctaccaactcttttccgaaggtaactggcttcagcagagcgcagataccaa
                    atactgtccttctagtgtagccgtagttaggccaccacttcaagaactctgtagcaccgcctacatacctcgctctg
                    ctaatcctgttaccagtggctgctgccagtggcgataagtcgtgtcttaccgggttggactcaagacgatagttac
                    cggataaggcgcagcggtcgggctgaacggggggttcgtgcacacagcccagcttggagcgaacgacctac
                    accgaactgagatacctacagcgtgagctatgagaaagcgccacgcttcccgaagggagaaaggcggacag
                    gtatccggtaagcggcagggtcggaacaggagagcgcacgagggagcttccaggggaaacgcctggtatc
                    tttatagtcctgtcgggtttcgccacctctgacttgagcgtcgatttttgtgatgctcgtcaggggggcggagccat
                    ggaaaaacgccagcaacgcggcctttttacggttcctggccttttgctggccttttgctcacatgttcttcctgcgtt
                    atcccctgattctgtggataaccgtattaccgcctttgagtgagctgataccgctcgccgcagccgaacgaccga
                    gcgcagcgagtcagtgagcgaggaagcggaagagcgcctgatgcggtattttctccttacgcatctgtgcggta
                    tttcacaccgcatatatggtgcactctcagtacaatctgctctgatgccgcatagttaagccagtatacactccgcta
                    tcgctacgtgactgggtcatggctgcgccccgacacccgccaacacccgctgacgcgccctgacgggcttgtc
                    tgctcccggcatccgcttacagacaagctgtgaccgtctccgggagctgcatgtgtcagaggttttcaccgtcatc
                    accgaaacgcgcgaggcagctgcggtaaagctcatcagcgtggtcgtgaagcgattcacagatgtctgcctgtt
                    catccgcgtccagctcgttgagtttctccagaagcgttaatgtctggcttctgataaagcgggccatgttaagggc
                    ggttttttcctgtttggtcactgatgcctccgtgtaagggggatttctgttcatgggggtaatgataccgatgaaacg
                    agagaggatgctcacgatacgggttactgatgatgaacatgcccggttactggaacgttgtgagggtaaacaac
                    tggcggtatggatgcggcgggaccagagaaaaatcactcagggtcaatgccagcgcttcgttaatacagatgta
                    ggtgttccacagggtagccagcagcatcctgcgatgcagatccggaacataatggtgcagggcgctgacttcc
                    gcgtttccagactttacgaaacacggaaaccgaagaccattcatgttgttgctcaggtcgcagacgttttgcagca
                    gcagtcgcttcacgttcgctcgcgtatcggtgattcattctgctaaccagtaaggcaacccccgccagcctagccg
                    ggtcctcaacgacaggagcacgatcatgcgcacccgtggccaggacccaacgctgcccgagatctcgatccc
                    gcgaaattaatacgactcactataggggagtattttacaacaattaccaacaacaacaaacaacaacattac
                    aattactatttacaattacatatggaagacgccaaaaacataaagaaaggcccggcgccattctatccgctagag
                    gatggaaccgctggagagcaactgcataaggctatgaagagatacgccctggttcctggaacaattgcttttaca
                    gatgcacatatcgaggtgaacatcacgtacgcggaatacttcgaaatgtccgttcggttggcagaagctatgaaa
                    cgatatgggctgaatacaaatcacagaatcgtcgtatgcagtgaaaactctcttcaattctttatgccggtgttggg
                    cgcgttatttatcggagttgcagttgcgcccgcgaacgacatttataatgaacgtgaattgctcaacagtatgaaca
                    tttcgcagcctaccgtagtgtttgtttccaaaaaggggttgcaaaaaattttgaacgtgcaaaaaaaattaccaata
                    atccagaaaattattatcatggattctaaaacggattaccagggatttcagtcgatgtacacgttcgtcacatctcat
                    ctacctcccggttttaatgaatacgattttgtaccagagtcctttgatcgtgacaaaacaattgcactgataatgaact
                    cctctggatctactgggttacctaagggtgtggcccttccgcatagaactgcctgcgtcagattctcgcatgccag
                    agatcctatttttggcaatcaaatcattccggatactgcgattttaagtgttgttccattccatcacggttttggaatgtt
                    tactacactcggatatttgatatgtggatttcgagtcgtcttaatgtatagatttgaagaagagctgtttttacgatccc
                    ttcaggattacaaaattcaaagtgcgttgctagtaccaaccctattttcattcttcgccaaaagcactctgattgacaa
                    atacgatttatctaatttacacgaaattgcttctgggggcgcacctctttcgaaagaagtcggggaagcggttgca
                    aaacgcttccatcttccagggatacgacaaggatatgggctcactgagactacatcagctattctgattacacccg
                    agggggatgataaaccgggcgcggtcggtaaagttgttccattttttgaagcgaaggttgtggatctggataccg
                    ggaaaacgctgggcgttaatcagagaggcgaattatgtgtcagaggacctatgattatgtccggttatgtaaaca
                    atccggaagcgaccaacgccttgattgacaaggatggatggctacattctggagacatagcttactgggacgaa
                    gacgaacacttcttcatagttgaccgcttgaagtctttaattaaatacaaaggataccaggtggccccgctgaatt
                    ggagtcgatattgttacaacaccccaacatcttcgacgcgggcgtggcaggtcttcccgacgatgacgccggtg
                    aacttcccgccgccgttgttgttttggagcacggaaagacgatgacggaaaaagagatcgtggattacgtcgcc
                    agtcaagtaacaaccgcgaaaaagttgcgcggaggagttgtgtttgtggacgaagtaccgaaaggtcttaccgg
                    aaaactcgacgcaagaaaaatcagagagatcctcataaaggccaagaagggcggaaagtccaaattgtaaaa
                    aaaaaaaaaaaaaaaaaaaaaaaaaaaaaaaaaaaaaaaaaaaaaaaaaaaaaaaaaaaaaaaaaaaaaaaa
                    aaaaaaaaaaaaaaaactcgagcaccaccaccaccaccactgagatccggctgctaacaaagcccgaaagg
                    aagctgagttggctgctgccaccgctgagcaataactagcataaccccttggggcctctaaacgggtcttgagg
                    ggttttttgctgaaaggaggaactatatccggattggcgaatgggacgcgccctgtagcggcgcattaagcgcg
                    gcgggtgtggtggttacgcgcagcgtgaccgctacactt backbone sense         gtgattcattctgctaaccag
primer
(SEQ ID NO: 129)

backbone anti-         ccccaagggggttatgctagt
sense primer
(SEQ ID NO: 130)

T7-Ω-f                 ccgcgaaattaatacgactcactatagggagatattttacaacaattaccaacaacaac
(SEQ ID NO: 131)

SP6-Ω-f                ccgcgaaatatttaggtgacactatagaagagtattttacaacaattaccaacaacaac
(SEQ ID NO: 132)

T3-Ω-f                 ccgcgaaataattaaccctcactaaagggaatattttacaacaattaccaacaacaac
(SEQ ID NO: 133)

P1.1-Ω-Kozak(No        acaaacaacattacaattactatttacaattacatatgagcaaaggtgaagaactgt
Kozak)-sfGFP-f
(SEQ ID NO: 134)
```

| | |
|---|---|
| P1.1-Ω-Kozak Consensus Full)-sfGFP-f (SEQ ID NO: 135) | acaaacaacattacaattactatttacaattacccaccatggagcaaaggtgaagaactgt |
| P1.1-Ω-Kozak (*S. cer* partial)-sfGFP-f (SEQ ID NO: 136) | acaaacaacattacaattactatttacaattaaaaaaaatgagcaaaggtgaagaactgt |
| P1.1-Ω-Kozak (*S. cer* full)-sfGFP-f (SEQ ID NO: 137) | acaaacaacattacaattactatttacaattaaaaaaaatgtctagcaaaggtgaagaactgt |
| Ω-(No Kozak)-sfGFP (SEQ ID NO: 138) | acgctgcccgagatctcgatcccgcgaaattaatacgactcactatagggagtattttacaacaattaccaacaa caacaaacaacaaacaacattacaattactatttacaattacatatgtctagcaaaggtgaagaactgtttaccggc gttgtgccgattctggtggaactggatggcgatgtgaacggtcacaaattcagcgtgcgtggtgaaggtgaagg cgatgccacgattggcaaactgacgctgaaatttatctgcaccaccggcaaactgccggtgccgtggccgacg ctggtgaccacccctgacctatggcgttcagtgttttagtcgctatccggatcacatgaaacgtcacgatttctttaaa tctgcaatgccggaaggctatgtgcaggaacgtacgattagattaaagatgatggcaaatataaaacgcgcgc cgttgtgaaatttgaaggcgatacccctggtgaaccgcattgaactgaaaggcacggatttttaaagaagatggcaa tatcctgggccataaactggaatacaactttaatagccataatgtatattacggcggataaacagaaaaatggca tcaaagcgaattttaccgttcgccataacgttgaagatggcagtgtgcagctggcagatcattatcagcagaatac cccgattggtgatggtccggtgctgctgccggataatcattatctgagcacgcagaccgttctgtctaaagatccg aacgaaaaggcacgcgggaccacatggttctgcacgaatatgtgaatgcggcaggtattacgtggagccatc cgcagttcgaaaaataaaactgagatccggctgctaacaaaaaaaaaaaaaaaaaaaaaaaaaaaaaaaaaa aaaaaaaaaaaaa |
| Ω-Kozak (Consensus)-sfGFP (SEQ ID NO: 139) | acgctgcccgagatctcgatcccgcgaaattaatacgactcactatagggagtattttacaacaattaccaacaa caacaaacaacaaacaacattacaattactatttacaattacccaccatggagcaaaggtgaagaactgtttaccg gcgttgtgccgattctggtggaactggatggcgatgtgaacggtcacaaattcagcgtgcgtggtgaaggtgaa ggcgatgccacgattggcaaactgacgctgaaatttatctgcaccaccggcaaactgccggtgccgtggccga cgctggtgaccacccctgacctatggcgttcagtgttttagtcgctatccggatcacatgaaacgtcacgatttcttta aatctgcaatgccggaaggctatgtgcaggaacgtacgattagctttaaagatgatggcaaatataaaacgcgc gccgttgtgaaatttgaaggcgatacccctggtgaaccgcattgaactgaaaggcacggatttttaaagaagatggc aatatcctgggccataaactggaatacaactttaatagccataatgtttatattacggcggataaacagaaaaatgg catcaaagcgaattttaccgttcgccataacgttgaagatggcagtgtgcagctggcagatcattatcagcagaat accccgattggtgatggtccggtgctgctgccggataatcattatctgagcacgcagaccgttctgtctaaagatc cgaacgaaaaggcacgcgggaccacatggttctgcacgaatatgtgaatgcggcaggtattacgtggagcca tccgcagttcgaaaaataaaactgagatccggctgctaacaaaaaaaaaaaaaaaaaaaaaaaaaaaaaaaaa aaaaaaaaaaaaaa |
| Ω-Kozak (*S. cer* partial)-sfGFP (SEQ ID NO: 140) | acgctgcccgagatctcgatcccgcgaaattaatacgactcactatagggagtattttacaacaattaccaacaa caacaaacaacaaacaacattacaattactatttacaattaaaaaaaatgagcaaaggtgaagaactgtttaccgg cgttgtgccgattctggtggaactggatggcgatgtgaacggtcacaaattcagcgtgcgtggtgaaggtgaag gcgatgccacgattggcaaactgacgctgaaatttatctgcaccaccggcaaactgccggtgccgtggccgac gctggtgaccacccctgacctatggcgttcagtgttttagtcgctatccggatcacatgaaacgtcacgatttctttaa atctgcaatgccggaaggctatgtgcaggaacgtacgattagctttaaagatgatggcaaatataaaacgcgcg ccgttgtgaaatttgaaggcgatacccctggtgaaccgcattgaactgaaaggcacggatttttaaagaagatggca atatcctgggccataaactggaatacaactttaatagccataatgtttatattacggcggataaacagaaaaatggc atcaaagcgaattttaccgttcgccataacgttgaagatggcagtgtgcagctggcagatcattatcagcagaata ccccgattggtgatggtccggtgctgctgccggataatcattatctgagcacgcagaccgttctgtctaaagatccg aacgaaaaggcacgcgggaccacatggttctgcacgaatatgtgaatgcggcaggtattacgtggagccat ccgcagttcgaaaaataaaactgagatccggctgctaacaaaaaaaaaaaaaaaaaaaaaaaaaaaaaaaaaa aaaaaaaaaaaaa |
| Ω-Kozak(*S. cer* full)-sfGFP (SEQ ID NO: 141) | acgctgcccgagatctcgatcccgcgaaattaatacgactcactatagggagtattttacaacaattaccaacaa caacaaacaacaaacaacattacaattactatttacaattaaaaaaaatgtctagcaaaggtgaagaactgtttacc ggcgttgtgccgattctggtggaactggatggcgatgtgaacggtcacaaattcagcgtgcgtggtgaaggtga aggcgatgccacgattggcaaactgacgctgaaatttatctgcaccaccggcaaactgccggtgccgtggccg acgctggtgaccacccctgacctatggcgttcagtgttttagtcgctatccggatcacatgaaacgtcacgatttctttt aaatctgcaatgccggaaggctatgtgcaggaacgtacgattagctttaaagatgatggcaaatataaaacgcgc gccgttgtgaaatttgaaggcgatacccctggtgaaccgcattgaactgaaaggcacggatttttaaagaagatggc aatatcctgggccataaactggaatacaactttaatagccataatgtttatattacggcggataaacagaaaaatgg catcaaagcgaattttaccgttcgccataacgttgaagatggcagtgtgcagctggcagatcattatcagcagaat accccgattggtgatggtccggtgctgctgccggataatcattatctgagcacgcagaccgttctgtctaaagatc cgaacgaaaaggcacgcgggaccacatggttctgcacgaatatgtgaatgcggcaggtattacgtggagcca tccgcagttcgaaaaataaaactgagatccggctgctaacaaaaaaaaaaaaaaaaaaaaaaaaaaaaaaaaa aaaaaaaaaaaaaa |

ADDITIONAL ACKNOWLEDGEMENTS

All references, including publications, patent applications, and patents, cited herein are hereby incorporated by reference to the same extent as if each reference were individually and specifically indicated to be incorporated by reference and were set forth in its entirety herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A cell-free protein synthesis platform for preparing protein from a transcription template, the cell-free protein synthesis platform comprising a reaction mixture formed by combining:
   (a) a *Saccharomyces cerevisiae* cellular extract prepared from mid-exponential to late-exponential cultures in the range from about 6 $OD_{600}$ to about 18 $OD_{600}$;
   (b) a reaction buffer;
   (c) a phage RNA polymerase; and
   (d) the transcription template,
   wherein the transcription template comprises: (i) at least one DNA encoding an open reading frame, (ii) a 5'-UTR comprising an internal ribosome entry site (IRES) or a cap-independent translation enhancer, and (iii) a 3'-UTR comprising a poly(A) 3'-terminus, and wherein the transcription template is operably linked to a promoter specific for the phage RNA polymerase; the phage RNA polymerase is capable of transcribing the transcription template to form a translation template; and the reaction mixture formed by combining (a), (b), (c), and (d) can sustain cell-free protein synthesis through a combined transcription/translation reaction.

2. The cell-free protein synthesis platform of claim 1, wherein the *Saccharomyces cerevisiae* cellular extract comprises an S30 extract.

3. The cell-free protein synthesis platform of claim 1, wherein the *Saccharomyces cerevisiae* cellular extract comprises an S60 extract.

4. The cell-free protein synthesis platform of claim 1, wherein the reaction buffer comprises NTPs, spermidine, putrescine, a glutamate salt, a magnesium salt and glycerol.

5. The cell-free protein synthesis platform of claim 1, wherein the reaction buffer comprises at least one component selected from the group consisting of NTPs, a polyamine, an organic anion, a divalent cation, an alcohol and combinations thereof.

6. The cell-free protein synthesis platform of claim 5, wherein the polyamine is selected from spermidine and putrescine; the organic anion is selected from glutamate and acetate; the divalent cation is selected from magnesium, calcium and manganese; and the alcohol comprises glycerol.

7. The cell-free protein synthesis platform of claim 1, wherein the *Saccharomyces cerevisiae* cellular extract is not pre-treated with a micrococcal nuclease.

8. The cell-free protein synthesis platform of claim 1, wherein the phage RNA polymerase is selected from SP6 RNA Polymerase, T3 RNA Polymerase and T7 RNA polymerase.

9. The cell-free protein synthesis platform of claim 1, wherein the phage RNA polymerase comprises T7 RNA polymerase.

10. The cell-free protein synthesis platform of claim 1, wherein the at least one DNA comprises a linear DNA or a circular DNA.

11. The cell-free protein synthesis platform of claim 1, wherein the at least one DNA comprises a linear DNA prepared from an amplification reaction.

12. The cell-free protein synthesis platform of claim 1, wherein the 5'-UTR comprises a cap-independent translation enhancing element selected from the group consisting of a TMV Ω sequence, a TEV 5'-UTR element, and a Tbm 5'-UTR element.

13. The cell-free protein synthesis platform of claim 1, wherein the 5'-UTR further comprises a yeast Kozak sequence or variant thereof.

14. The cell-free protein synthesis platform of claim 1, wherein the poly(A) 3'-terminus ranges from about 20 nucleotides to about 200 nucleotides in length.

15. A method of performing high-throughput protein synthesis in vitro, comprising:
   (a) providing a source nucleic acid;
   (b) preparing a transcription template from the source nucleic acid; and
   (c) synthesizing protein in vitro using a cell-free protein synthesis platform utilizing the transcription template, wherein the cell-free protein synthesis platform comprises a reaction mixture formed by combining:
      (i) a *Saccharomyces cerevisiae* cellular extract prepared from mid-exponential to late-exponential cultures in the range from about 6 $OD_{600}$ to about 18 $OD_{600}$;
      (ii) a reaction buffer;
      (iii) a phage RNA polymerase, and
      (iv) the transcription template,
   wherein the transcription template comprises: (i) at least one DNA encoding an open reading frame, (ii) a 5'-UTR comprising an internal ribosome entry site (IRES) or a cap-independent translation enhancer, and (iii) a 3'-UTR comprising a poly(A) 3'-terminus, and wherein the transcription template is operably linked to a promoter specific for the phage RNA polymerase; the phage RNA polymerase is capable of transcribing from the transcription template to form the translation template, and the reaction mixture formed by combining (a), (b), (c), and (d) can sustain cell-free protein synthesis through a combined transcription/translation reaction.

16. The method of claim 15, wherein the preparing a transcription template from the source nucleic acid comprises amplifying the source nucleic acid with a first primer and second primer in the presence of a DNA polymerase, wherein the first and second primers comprise gene-specific sequences capable of hybridizing the gene encoding an open reading frame in the source nucleic acid.

17. The method of claim 15, wherein the transcription template comprises a linear DNA.

18. The method of claim 15, wherein the phage RNA polymerase is selected from SP6 RNA Polymerase, T3 RNA Polymerase and T7 RNA polymerase.

* * * * *

SEQUENCE LISTING

```
<160> NUMBER OF SEQ ID NOS: 141

<210> SEQ ID NO 1
<211> LENGTH: 1804
<212> TYPE: DNA
<213> ORGANISM: Artificial Sequence
<220> FEATURE:
<223> OTHER INFORMATION: CappA90

<400> SEQUENCE: 1
gagaccacaa cggtttccct ctagaaataa ttttgtttaa ctttaagaag gagatataca      60
tatggaagac gccaaaaaca taaagaaagg cccggcgcca ttctatccgc tagaggatgg     120
aaccgctgga gagcaactgc ataaggctat gaagagatac gccctggttc ctggaacaat     180
tgcttttaca gatgcacata tcgaggtgaa catcacgtac gcggaatact tcgaaatgtc     240
cgttcggttg gcagaagcta tgaaacgata tgggctgaat acaaatcaca gaatcgtcgt     300
atgcagtgaa aactctcttc aattctttat gccggtgttg ggcgcgttat ttatcggagt     360
tgcagttgcg cccgcgaacg acatttataa tgaacgtgaa ttgctcaaca gtatgaacat     420
ttcgcagcct accgtagtgt ttgtttccaa aaagggggttg caaaaaattt tgaacgtgca     480
aaaaaaatta ccaataatcc agaaaattat tatcatggat tctaaaacgg attaccaggg     540
atttcagtcg atgtacacgt tcgtcacatc tcatctacct cccggtttta atgaatacga     600
ttttgtacca gagtcctttg atcgtgacaa aacaattgca ctgataatga actcctctgg     660
atctactggg ttacctaagg gtgtggccct tccgcataga actgcctgcg tcagattctc     720
gcatgccaga gatcctattt ttggcaatca aatcattccg gatactgcga ttttaagtgt     780
tgttccattc catcacggtt ttggaatgtt tactacactc ggatatttga tatgtggatt     840
tcgagtcgtc ttaatgtata gatttgaaga gagctgtttt ttacgatccc ttcaggatta     900
caaaattcaa agtgcgttgc tagtaccaac cctattttca ttcttcgcca aaagcactct     960
gattgacaaa tacgatttat ctaatttaca cgaaattgct tctgggggcg cacctctttc    1020
gaaagaagtc ggggaagcgg ttgcaaaacg cttccatctt ccagggatac gacaaggata    1080
tgggctcact gagactacat cagctattct gattacaccc gagggggatg ataaaccggg    1140
cgcggtcggt aaagttgttc catttttga agcgaaggtt gtggatctgg ataccgggaa    1200
aacgctgggc gttaatcaga gaggcgaatt atgtgtcaga ggacctatga ttatgtccgg    1260
ttatgtaaac aatccggaag cgaccaacgc cttgattgac aaggatggat ggctacattc    1320
tggagacata gcttactggg acgaagacga acacttcttc atagttgacc gcttgaagtc    1380
```

-continued

| | |
|---|---|
| tttaattaaa tacaaaggat accaggtggc ccccgctgaa ttggagtcga tattgttaca | 1440 |
| acaccccaac atcttcgacg cgggcgtggc aggtcttccc gacgatgacg ccggtgaact | 1500 |
| tcccgccgcc gttgttgttt tggagcacgg aaagacgatg acggaaaaag agatcgtgga | 1560 |
| ttacgtcgcc agtcaagtaa caaccgccaa aaagttgcgc ggaggagttg tgtttgtgga | 1620 |
| cgaagtaccg aaaggtctta ccggaaaact cgacgcaaga aaaatcagag agatcctcat | 1680 |
| aaaggccaag aagggcggaa agtccaaatt gtaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaa | 1804 |

<210> SEQ ID NO 2
<211> LENGTH: 2040
<212> TYPE: DNA
<213> ORGANISM: Artificial Sequence
<220> FEATURE:
<223> OTHER INFORMATION: HAPpA90

<400> SEQUENCE: 2

| | |
|---|---|
| gagaccacaa cggtttccct ctagataaac cccagtttta tatcgtatat gctatctaca | 60 |
| ggtccacttt acacttaata atataaaaat actactataa aggaaccaga aaataaaaa | 120 |
| agggtcatta tttatttgag cagatcatta tcaaacgcat aggaagagaa aaaacacagt | 180 |
| tttattttt ttccacacat atttattggt ctcctagtac atcaaagagc attttaatgg | 240 |
| gttgctgatt tgttttacct acattttcta gtacaaaaaa aaaacaaaaa aagacatatg | 300 |
| gaagacgcca aaaacataaa gaaaggcccg gtgccattct atccgctaga ggatggaacc | 360 |
| gctggagagc aactgcataa ggctatgaag agatacgccc tggttcctgg aacaattgct | 420 |
| tttacagatg cacatatcga ggtgaacatc acgtacgcgg aatacttcga atgtccgtt | 480 |
| cggttggcag aagctatgaa acgatatggg ctgaatacaa atcacagaat cgtcgtatgc | 540 |
| agtgaaaact ctcttcaatt ctttatgccg gtgttgggcg cgttatttat cggagttgca | 600 |
| gttgcgcccg cgaacgacat ttataatgaa cgtgaattgc tcaacagtat gaacatttcg | 660 |
| cagcctaccg tagtgtttgt ttccaaaaag gggttgcaaa aattttgaa cgtgcaaaaa | 720 |
| aaattaccaa taatccagaa aattattatc atggattcta aaacggatta ccagggattt | 780 |
| cagtcgatgt acacgttcgt cacatctcat ctacctcccg gttttaatga atacgatttt | 840 |
| gtaccagagt cctttgatcg tgacaaaaca attgcactga taatgaactc ctctggatct | 900 |
| actgggttac ctaagggtgt ggcccttccg catagaactg cctgcgtcag attctcgcat | 960 |
| gccagagatc ctatttttgg caatcaaatc attccggata ctgcgatttt aagtgttgtt | 1020 |
| ccattccatc acggttttgg aatgtttact acactcggat atttgatatg tggatttcga | 1080 |
| gtcgtcttaa tgtatagatt tgaagaagag ctgtttttac gatcccttca ggattacaaa | 1140 |
| attcaaagtg cgttgctagt accaacccta ttttcattct tcgccaaaag cactctgatt | 1200 |
| gacaaatacg atttatctaa tttacacgaa attgcttctg gggcgcacc tctttcgaaa | 1260 |
| gaagtcgggg aagcggttgc aaaacgcttc catcttccag ggatacgaca aggatatggg | 1320 |
| ctcactgaga ctacatcagc tattctgatt acacccgagg gggatgataa accgggcgcg | 1380 |
| gtcggtaaag ttgttccatt ttttgaagcg aaggttgtgg atctggatac cgggaaaacg | 1440 |
| ctgggcgtta atcagagagg cgaattatgt gtcagaggac ctatgattat gtccggttat | 1500 |
| gtaaacaatc cggaagcgac caacgccttg attgacaagg atggatggct acattctgga | 1560 |
| gacatagctt actgggacga agacgaacac ttcttcatag ttgaccgctt gaagtcttta | 1620 |

```
attaaataca aaggatacca ggtggccccc gctgaattgg agtcgatatt gttacaacac   1680
cccaacatct tcgacgcggg cgtggcaggt cttcccgacg atgacgccgg tgaacttccc   1740
gccgccgttg ttgttttgga gcacggaaag acgatgacgg aaaagagat cgtggattac    1800 gtcgccagtc aagtaacaac cgcgaaaaag ttgcgcggag gagttgtgtt tgtggacgaa    1860
gtaccgaaag gtcttaccgg aaaactcgac gcaagaaaaa tcagagagat cctcataaag    1920
gccaagaagg gcgaaaagtc caaattgtaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040

<210> SEQ ID NO 3
<211> LENGTH: 1992
<212> TYPE: DNA
<213> ORGANISM: Artificial Sequence
<220> FEATURE:
<223> OTHER INFORMATION: TFIIDpA90

<400> SEQUENCE: 3
gagaccacaa cggtttccct ctagatcgat gcggccgcga attcgggacg tgaaaattac     60
agtagttact gttttttttg gactataaga tcggggaaa gataacacat aagaaataaa    120
acgactacta gttagactgc tctgcggaag aagcaaggaa gtaaaggctg catttttattt   180 ttcttttcta gtccaacata aacaggtgta tcaagagaaa ctttttttaag agctcgtcga   240 cggatccata tggaagacgc caaaaacata agaaaggcc cggcgccatt ctatccgcta    300
gaggatggaa ccgctggaga gcaactgcat aaggctatga agagatacgc cctggttcct   360
ggaacaattg cttttacaga tgcacatatc gaggtgaaca tcacgtacgc ggaatacttc   420
gaaatgtccg ttcggttggc agaagctatg aaacgatatg gctgaatac aaatcacaga   480 atcgtcgtat gcagtgaaaa ctctcttcaa ttctttatgc cggtgttggg cgcgttattt    540
atcggagttg cagttgcgcc cgcgaacgac atttataatg aacgtgaatt gctcaacagt   600
atgaacattt cgcagcctac cgtagtgttt gtttccaaaa agggggttgca aaaattttg     660 aacgtgcaaa aaaattacc aataatccag aaaattatta tcatggattc taaaacggat    720
taccagggat ttcagtcgat gtacacgttc gtcacatctc atctacctcc cggttttaat   780
gaatacgatt ttgtaccaga gtcctttgat cgtgacaaaa caattgcact gataatgaac    840
tcctctggat ctactgggtt acctaagggt gtggcccttc cgcatagaac tgcctgcgtc   900
agattctcgc atgccagaga tcctattttt ggcaatcaaa tcattccgga tactgcgatt    960
ttaagtgttg ttccattcca tcacggtttt ggaatgttta ctacactcgg atatttgata   1020 tgtggattc gagtcgtctt aatgtataga tttgaagaag agctgttttt acgatcccctt   1080 caggattaca aaattcaaag tgcgttgcta gtaccaaccc tattttcatt cttcgccaaa   1140
agcactctga ttgacaaata cgatttatct aatttacacg aaattgcttc tgggggcgca   1200
cctctttcga agaagtcgg ggaagcggtt gcaaaacgct tccatcttcc agggatacga   1260
caaggatatg ggctcactga gactacatca gctattctga ttacacccga ggggatgat    1320 aaaccgggcg cggtcggtaa agttgttcca ttttttgaag cgaaggttgt ggatctggat    1380
accgggaaaa cgctgggcgt taatcagaga ggcgaattat gtgtcagagg acctatgatt   1440
atgtccggtt atgtaaacaa tccggaagcg accaacgcct tgattgacaa ggatggatgg   1500
ctacattctg gagacatagc ttactgggac gaagacgaac acttcttcat agttgaccgc   1560
ttgaagtctt taattaaata caaggatac caggtggccc ccgctgaatt ggagtcgata   1620
```

| | | |
|---|---|---|
| ttgttacaac accccaacat cttcgacgcg ggcgtggcag gtcttcccga cgatgacgcc | 1680 | |
| ggtgaacttc ccgccgccgt tgttgttttg gagcacggaa agacgatgac ggaaaaagag | 1740 | |
| atcgtggatt acgtcgccag tcaagtaaca accgccaaaa agttgcgcgg aggagttgtg | 1800 | |
| tttgtggacg aagtaccgaa aggtcttacc ggaaaactcg acgcaagaaa aatcagagag | 1860 | |
| atcctcataa aggccaagaa gggcggaaag tccaaattgt aaaaaaaaaa aaaaaaaaaa | 1920 | |
| aaaaaaaaaa aaaaaaaaaa aaaaaaaaaa aaaaaaaaaa aaaaaaaaaa aaaaaaaaaa | 1980 | |
| aaaaaaaaaa aa | 1992 | |

<210> SEQ ID NO 4
<211> LENGTH: 2303
<212> TYPE: DNA
<213> ORGANISM: Artificial Sequence
<220> FEATURE:
<223> OTHER INFORMATION: P150pA90

<400> SEQUENCE: 4

| | | |
|---|---|---|
| gagaccacaa cggtttccct ctagacccag ttcgatcctg ggcgaaatca tttttttgaa | 60 | |
| aattacatta ataaggcttt tttcaatatc tctggaacaa cgtttgtttc tacttactaa | 120 | |
| tagctttaag gaccctcttg gacatcatga tggcagactt ccatcgtagt gggatgatca | 180 | |
| tatgatgggc gctatcctca tcgcgactcg ataacgacgt gagaaacgat ttttttttt | 240 | |
| cttttttcacc gtattttgt gcgtcctttt tcaattatag cttttttta tttttttttt | 300 | |
| ttctcgtact gtttcactga caaaagtttt ttttcaagaa aaattttcga tgccgcgttc | 360 | |
| tctgtgtgca acgatggat ggtagatgga atttcaatat gttgcttgaa attttaccaa | 420 | |
| tcttgatatt gtgataattt acttaattat gattcttcct cttcccttca atttcttaaa | 480 | |
| gcttcttact ttactccttc ttgctcataa ataagcaagg taagaggaca actgtaatta | 540 | |
| cctattacaa taggatccat atggaagacg ccaaaaacat aaagaaaggc ccggcgccat | 600 | |
| tctatccgct agaggatgga accgctgag agcaactgca taaggctatg aagagatacg | 660 | |
| ccctggttcc tggaacaatt gcttttacag atgcacatat cgaggtgaac atcacgtacg | 720 | |
| cggaatactt cgaaatgtcc gttcggttgg cagaagctat gaaacgatat gggctgaata | 780 | |
| caaatcacag aatcgtcgta tgcagtgaaa actctcttca attctttatg ccggtgttgg | 840 | |
| gcgcgttatt tatcggagtt gcagttgcgc ccgcgaacga catttataat gaacgtgaat | 900 | |
| tgctcaacag tatgaacatt tcgcagccta ccgtagtgtt tgtttccaaa aagggggttgc | 960 | |
| aaaaaatttt gaacgtgcaa aaaaaattac caataatcca gaaaattatt atcatggatt | 1020 | |
| ctaaaacgga ttaccaggga tttcagtcga tgtacacgtt cgtcacatct catctacctc | 1080 | |
| ccggttttaa tgaatacgat tttgtaccag agtcctttga tcgtgacaaa acaattgcac | 1140 | |
| tgataatgaa ctcctctgga tctactgggt tacctaaggg tgtggcccct ccgcatagaa | 1200 | |
| ctgcctgcgt cagattctcg catgccagag atcctatttt tggcaatcaa atcattccgg | 1260 | |
| atactgcgat tttaagtgtt gttccattcc atcacggttt tggaatgttt actacactcg | 1320 | |
| gatatttgat atgtggattt cgagtcgtct taatgtatag atttgaagaa gagctgtttt | 1380 | |
| tacgatccct tcaggattac aaaattcaaa gtgcgttgct agtaccaacc ctattttcat | 1440 | |
| tcttcgccaa aagcactctg attgacaaat acgatttatc taatttacac gaaattgctt | 1500 | |
| ctgggggcgc acctctttcg aaagaagtcg ggaagcggt tgcaaaacgc ttccatcttc | 1560 | |
| cagggatacg acaaggatat gggctcactg agactacatc agctattctg attacacccg | 1620 | |
| aggggggatga taaaccgggc gcggtcggta agttgttcc attttttgaa gcgaaggttg | 1680 | |

| | |
|---|---|
| tggatctgga taccgggaaa acgctgggcg ttaatcagag aggcgaatta tgtgtcagag | 1740 |
| gacctatgat tatgtccggt tatgtaaaca atccggaagc gaccaacgcc ttgattgaca | 1800 |
| aggatggatg gctacattct ggagacatag cttactggga cgaagacgaa cacttcttca | 1860 |
| tagttgaccg cttgaagtct ttaattaaat acaaaggata ccaggtggcc cccgctgaat | 1920 |
| tggagtcgat attgttacaa caccccaaca tcttcgacgc gggcgtggca ggtcttcccg | 1980 |
| acgatgacgc cggtgaactt cccgccgccg ttgttgtttt ggagcacgga agacgatga | 2040 |
| cggaaaaaga gatcgtggat tacgtcgcca gtcaagtaac aaccgccaaa agttgcgcg | 2100 |
| gaggagttgt gtttgtggac gaagtaccga aaggtcttac cggaaaactc gacgcaagaa | 2160 |
| aaatcagaga gatcctcata aaggccaaga agggcggaaa gtccaaattg taaaaaaaaa | 2220 |
| aaaaaaaaaa aaaaaaaaaa aaaaaaaaaa aaaaaaaaaa aaaaaaaaaa aaaaaaaaaa | 2280 |
| aaaaaaaaaa aaaaaaaaaa aaa | 2303 |

<210> SEQ ID NO 5
<211> LENGTH: 2133
<212> TYPE: DNA
<213> ORGANISM: Artificial Sequence
<220> FEATURE:
<223> OTHER INFORMATION: YAP1pA90

<400> SEQUENCE: 5

| | |
|---|---|
| gagaccacaa cggtttccct ctagatagta accagcccta gctgtttggt tgatttgacc | 60 |
| taggttactc ttttctttt ctgggtgcgg gtaacaattt gggccccgca aagcgccgtc | 120 |
| tttgtcatgg gaaccggaaa ccctccgatg aagagtagga gggtggcaac tgatggatgc | 180 |
| gtaaggtctt aagagataca tttgcttaat agtcttccgt ttaccgatta agcacagtac | 240 |
| ctttacgtta tatataggat tggtgtttag cttttttcc tgagcccctg gttgacttgt | 300 |
| gcatgaacac gagccatttt tagtttgttt aagggaagtt ttttgccacc caaaacgttt | 360 |
| aaagaaggaa aagttgtttc ttaaacccat atggaagacg ccaaaaacat aaagaaaggc | 420 |
| ccggcgccat tctatccgct agaggatgga accgctggag agcaactgca taaggctatg | 480 |
| aagagatacg ccctggttcc tggaacaatt gcttttacag atgcacatat cgaggtgaac | 540 |
| atcacgtacg cggaatactt cgaaatgtcc gttcggttgg cagaagctat gaaacgatat | 600 |
| gggctgaata caaatcacag aatcgtcgta tgcagtgaaa actctcttca attctttatg | 660 |
| ccggtgttgg gcgcgttatt tatcggagtt gcagttgcgc ccgcgaacga catttataat | 720 |
| gaacgtgaat tgctcaacag tatgaacatt tcgcagccta ccgtagtgtt tgtttccaaa | 780 |
| aaggggttgc aaaaaatttt gaacgtgcaa aaaaaattac caataatcca gaaaattatt | 840 |
| atcatggatt ctaaaacgga ttaccaggga tttcagtcga tgtacacgtt cgtcacatct | 900 |
| catctacctc ccggttttaa tgaatacgat tttgtaccag agtcctttga tcgtgacaaa | 960 |
| acaattgcac tgataatgaa ctcctctgga tctactgggt tacctaaggg tgtggccctt | 1020 |
| ccgcatagaa ctgcctgcgt cagattctcg catgccagag atcctatttt tggcaatcaa | 1080 |
| atcattccgg atactgcgat tttaagtgtt gttccattcc atcacggttt tggaatgttt | 1140 |
| actacactcg gatatttgat atgtggattt cgagtcgtct taatgtatag atttgaagaa | 1200 |
| gagctgtttt tacgatccct tcaggattac aaaattcaaa gtgcgttgct agtaccaacc | 1260 |
| ctattttcat tcttcgccaa aagcactctg attgacaaat acgatttatc taatttacac | 1320 |
| gaaattgctt ctgggggcgc acctctttcg aaagaagtcg ggaagcggt tgcaaaacgc | 1380 |

```
ttccatcttc agggatacg acaaggatat gggctcactg agactacatc agctattctg    1440
attacacccg aggggatga taaaccgggc gcggtcggta agttgttcc attttttgaa      1500 gcgaaggttg tggatctgga taccgggaaa acgctgggcg ttaatcagag aggcgaatta   1560
tgtgtcagag gacctatgat tatgtccggt tatgtaaaca atccggaagc gaccaacgcc   1620
ttgattgaca aggatggatg gctacattct ggagacatag cttactggga cgaagacgaa   1680
cacttcttca tagttgaccg cttgaagtct ttaattaaat acaaaggata ccaggtggcc   1740
cccgctgaat tggagtcgat attgttacaa cacccccaaca tcttcgacgc gggcgtggca  1800
ggtcttcccg acgatgacgc cggtgaactt cccgccgccg ttgttgtttt ggagcacgga   1860
aagacgatga cggaaaaaga gatcgtggat tacgtcgcca gtcaagtaac aaccgccaaa   1920
aagttgcgcg gaggagttgt gtttgtggac gaagtaccga aaggtcttac cggaaaactc   1980
gacgcaagaa aaatcagaga gatcctcata aaggccaaga agggcggaaa gtccaaattg   2040
taaaaaaaaa aaaaaaaaa aaaaaaaaaa aaaaaaaaa aaaaaaaaaa aaaaaaaaa     2100 aaaaaaaaaa aaaaaaaaa aaaaaaaaaa aaa                                 2133
```

<210> SEQ ID NO 6  
<211> LENGTH: 1975  
<212> TYPE: DNA  
<213> ORGANISM: Artificial Sequence  
<220> FEATURE:  
<223> OTHER INFORMATION: IGRpA90

<400> SEQUENCE: 6

```
agaccacaac ggtttccctc tagagcaaaa atgtgatctt gcttgtaaat acaatttga      60 gaggttaata aattacaagt agtgctattt ttgtatttag gttagctatt tagctttacg    120
ttccaggatg cctagtggca gccccacaat atccaggaag ccctctctgc ggttttttcag  180 attaggtagt cgaaaaacct aagaaattta cctgctacat ttcaagattc atatggaaga   240
cgccaaaaac ataagaaag gcccggcgcc attctatccg ctagaggatg gaaccgctgg    300
agagcaactg cataaggcta tgaagagata cgccctggtt cctggaacaa ttgcttttac   360
agatgcacat atcgaggtga acatcacgta cgcggaatac ttcgaaatgt ccgttcggtt   420
ggcagaagct atgaaacgat atgggctgaa tacaaatcac agaatcgtcg tatgcagtga   480
aaactctctt caattcttta tgccggtgtt gggcgcgtta tttatcggag ttgcagttgc   540
gcccgcgaac gacatttata tgaacgtga attgctcaac agtatgaaca tttcgcagcc   600
taccgtagtg tttgtttcca aaagggggtt gcaaaaaatt ttgaacgtgc aaaaaaaatt   660
accaataatc cagaaaatta ttatcatgga ttctaaaacg gattaccagg gatttcagtc   720
gatgtacacg ttcgtcacat ctcatctacc tcccggtttt aatgaatacg attttgtacc  780
agagtccttt gatcgtgaca aaacaattgc actgataatg aactcctctg gatctactgg   840
gttacctaag ggtgtggccc ttccgcatag aactgcctgc gtcagattct cgcatgccag   900
agatcctatt tttggcaatc aaatcattcc ggatactgcg attttaagtg ttgttccatt   960
ccatcacggt tttggaatgt ttactacact cggatatttg atatgtggat ttcgagtcgt  1020
cttaatgtat agatttgaag aagagctgtt tttacgatcc cttcaggatt acaaaattca  1080
aagtgcgttg ctagtaccaa ccctattttc attcttcgcc aaaagcactc tgattgacaa  1140
atacgattta tctaatttac acgaaattgc ttctgggggc gcacctcttt cgaaagaagt  1200
cggggaagcg gttgcaaaac gcttccatct tccagggata cgacaaggat atgggctcac  1260
tgagactaca tcagctattc tgattacacc cgagggggat gataaaccgg gcgcggtcgg  1320
```

```
taaagttgtt ccattttttg aagcgaaggt tgtggatctg gataccggga aaacgctggg   1380
cgttaatcag agaggcgaat tatgtgtcag aggacctatg attatgtccg gttatgtaaa   1440
caatccggaa gcgaccaacg ccttgattga caaggatgga tggctacatt ctggagacat   1500
agcttactgg gacgaagacg aacacttctt catagttgac cgcttgaagt ctttaattaa   1560
atacaaagga taccaggtgg cccccgctga attggagtcg atattgttac aacaccccaa   1620
catcttcgac gcgggcgtgg caggtcttcc cgacgatgac gccggtgaac ttcccgccgc   1680
cgttgttgtt ttggagcacg gaaagacgat gacggaaaaa gagatcgtgg attacgtcgc   1740
cagtcaagta acaaccgcca aaagttgcg cggaggagtt gtgtttgtgg acgaagtacc   1800
gaaaggtctt accggaaaac tcgacgcaag aaaaatcaga gagatcctca taaaggccaa   1860
gaagggcgga aagtccaaat tgtaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaa        1975
```

<210> SEQ ID NO 7
<211> LENGTH: 1813
<212> TYPE: DNA
<213> ORGANISM: Artificial Sequence
<220> FEATURE:
<223> OTHER INFORMATION: A64pA90

<400> SEQUENCE: 7

```
gagaaaaaaa aaaaaaaaaa aaaaaaaaaa aaaaaaaaaa aaaaaaaaaa aaaaaaaaaa     60
aaaaaaacat atggaagacg ccaaaaacat aaagaaaggc ccggcgccat tctatccgct    120
agaggatgga accgctggag agcaactgca taaggctatg aagagatacg ccctggttcc    180
tggaacaatt gcttttacag atgcacatat cgaggtgaac atcacgtacg cggaatactt    240
cgaaatgtcc gttcggttgg cagaagctat gaaacgatat gggctgaata caaatcacag    300
aatcgtcgta tgcagtgaaa actctcttca attctttatg ccggtgttgg gcgcgttatt    360
tatcggagtt gcagttgcgc ccgcgaacga catttataat gaacgtgaat tgctcaacag    420
tatgaacatt tcgcagccta ccgtagtgtt tgtttccaaa aagggggttgc aaaaaatttt    480 gaacgtgcaa aaaaaattac caataatcca gaaaattatt atcatggatt ctaaaacgga    540
ttaccaggga tttcagtcga tgtacacgtt cgtcacatct catctacctc ccggttttaa    600
tgaatacgat tttgtaccag agtcctttga tcgtgacaaa acaattgcac tgataatgaa    660
ctcctctgga tctactgggt tacctaaggg tgtggccctt ccgcatagaa ctgcctgcgt    720
cagattctcg catgccagag atcctatttt tggcaatcaa atcattccgg atactgcgat    780
tttaagtgtt gttccattcc atcacggttt tggaatgttt actacactcg gatatttgat    840
atgtggattt cgagtcgtct taatgtatag atttgaagaa gagctgtttt tacgatccct    900
tcaggattac aaaattcaaa gtgcgttgct agtaccaacc ctattttcat tcttcgccaa    960
aagcactctg attgacaaat acgatttatc taatttacac gaaattgctt ctggggcgc   1020 acctctttcg aaagaagtcg ggaagcggt tgcaaaacgc ttccatcttc cagggatacg   1080
acaaggatat gggctcactg agactacatc agctattctg attacacccg agggggatga   1140
taaaccgggc gcggtcggta agttgttcc attttttgaa gcgaaggttg tggatctgga   1200
taccgggaaa acgctgggcg ttaatcagag aggcgaatta tgtgtcagag gacctatgat   1260
tatgtccggt tatgtaaaca atccggaagc gaccaacgcc ttgattgaca aggatggatg   1320
gctacattct ggagacatag cttactggga cgaagacgaa cacttcttca gttgaccg    1380
```

```
cttgaagtct ttaattaaat acaaaggata ccaggtggcc cccgctgaat tggagtcgat    1440
attgttacaa caccccaaca tcttcgacgc gggcgtggca ggtcttcccg acgatgacgc    1500
cggtgaactt cccgccgccg ttgttgtttt ggagcacgga aagacgatga cggaaaaaga    1560
gatcgtggat tacgtcgcca gtcaagtaac aaccgccaaa aagttgcgcg gaggagttgt    1620
gtttgtggac gaagtaccga aaggtcttac cggaaaactc gacgcaagaa aaatcagaga    1680
gatcctcata aaggccaaga agggcggaaa gtccaaattg taaaaaaaaa aaaaaaaaa     1740 aaaaaaaaaa aaaaaaaaaa aaaaaaaaaa aaaaaaaaaa aaaaaaaaaa aaaaaaaaaa    1800
aaaaaaaaaa aaa                                                      1813

<210> SEQ ID NO 8
<211> LENGTH: 1793
<212> TYPE: DNA
<213> ORGANISM: Artificial Sequence
<220> FEATURE:
<223> OTHER INFORMATION: HedrinpA90

<400> SEQUENCE: 8
gagtattttt attctttcgt aaaaaaatta gaaaaataaa atataaacat atggaagacg      60
ccaaaaacat aaagaaaggc ccggcgccat tctatccgct agaggatgga accgctggag     120
agcaactgca taaggctatg aagagatacg ccctggttcc tggaacaatt gcttttacag     180
atgcacatat cgaggtgaac atcacgtacg cggaatactt cgaaatgtcc gttcggttgg     240
cagaagctat gaaacgatat gggctgaata caaatcacag aatcgtcgta tgcagtgaaa     300
actctcttca attctttatg ccggtgttgg gcgcgttatt tatcggagtt gcagttgcgc     360
ccgcgaacga catttataat gaacgtgaat tgctcaacag tatgaacatt tcgcagccta     420
ccgtagtgtt tgtttccaaa aaggggttgc aaaaaatttt gaacgtgcaa aaaaaattac     480
caataatcca gaaaattatt atcatggatt ctaaaacgga ttaccaggga tttcagtcga     540
tgtacacgtt cgtcacatct catctacctc ccggttttaa tgaatacgat tttgtaccag     600
agtcctttga tcgtgacaaa acaattgcac tgataatgaa ctcctctgga tctactgggt     660
tacctaaggg tgtggccctt ccgcatagaa ctgcctgcgt cagattctcg catgccagag     720
atcctatttt tggcaatcaa atcattccgg atactgcgat tttaagtgtt gttccattcc     780
atcacggttt tggaatgttt actacactcg gatatttgat atgtggattt cgagtcgtct     840
taatgtatag atttgaagaa gagctgtttt tacgatccct tcaggattac aaaattcaaa     900
gtgcgttgct agtaccaacc ctattttcat tcttcgccaa agcactctg attgacaaat     960 acgatttatc taatttacac gaaattgctt ctggggcgc acctctttcg aaagaagtcg    1020
gggaagcggt tgcaaaacgc ttccatcttc caggatacg acaaggatat gggctcactg    1080
agactacatc agctattctg attacacccg agggggatga taaaccgggc gcggtcggta    1140
aagttgttcc attttttgaa gcgaaggttg tggatctgga taccgggaaa acgctgggcg    1200
ttaatcagag aggcgaatta tgtgtcagag gacctatgat tatgtccggt tatgtaaaca    1260
atccggaagc gaccaacgcc ttgattgaca aggatggatg gctacattct ggagacatag    1320
cttactggga cgaagacgaa cacttcttca tagttgaccg cttgaagtct ttaattaaat    1380
acaaaggata ccaggtggcc cccgctgaat tggagtcgat attgttacaa caccccaaca    1440
tcttcgacgc gggcgtggca ggtcttcccg acgatgacgc cggtgaactt cccgccgccg    1500
ttgttgtttt ggagcacgga aagacgatga cggaaaaaga gatcgtggat tacgtcgcca    1560
gtcaagtaac aaccgccaaa aagttgcgcg gaggagttgt gtttgtggac gaagtaccga    1620
```

| aaggtcttac cggaaaactc gacgcaagaa aaatcagaga gatcctcata aaggccaaga | 1680 |
| agggcggaaa gtccaaattg taaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaa | 1793 |

<210> SEQ ID NO 9
<211> LENGTH: 1814
<212> TYPE: DNA
<213> ORGANISM: Artificial Sequence
<220> FEATURE:
<223> OTHER INFORMATION: OMEGApA90

<400> SEQUENCE: 9

| gagtatttt acaacaatta ccaacaacaa caaacaacaa acaacattac aattactatt | 60 |
| tacaattaca tatggaagac gccaaaaaca taaagaaagg cccggcgcca ttctatccgc | 120 |
| tagaggatgg aaccgctgga gagcaactgc ataaggctat gaagagatac gccctggttc | 180 |
| ctggaacaat tgcttttaca gatgcacata tcgaggtgaa catcacgtac gcggaatact | 240 |
| tcgaaatgtc cgttcggttg cagaagcta tgaaacgata tgggctgaat acaaatcaca | 300 |
| gaatcgtcgt atgcagtgaa aactctcttc aattctttat gccggtgttg ggcgcgttat | 360 |
| ttatcggagt tgcagttgcg cccgcgaacg acatttataa tgaacgtgaa ttgctcaaca | 420 |
| gtatgaacat ttcgcagcct accgtagtgt ttgtttccaa aaaggggttg caaaaaattt | 480 |
| tgaacgtgca aaaaaaatta ccaataatcc agaaaattat tatcatggat tctaaaacgg | 540 |
| attaccaggg atttcagtcg atgtacacgt tcgtcacatc tcatctacct cccggtttta | 600 |
| atgaatacga ttttgtacca gagtcctttg atcgtgacaa aacaattgca ctgataatga | 660 |
| actcctctgg atctactggg ttacctaagg gtgtggccct tccgcataga actgcctgcg | 720 |
| tcagattctc gcatgccaga gatcctattt ttggcaatca aatcattccg gatactgcga | 780 |
| ttttaagtgt tgttccattc catcacggtt ttggaatgtt tactacactc ggatatttga | 840 |
| tatgtggatt tcgagtcgtc ttaatgtata gatttgaaga agagctgttt ttacgatccc | 900 |
| ttcaggatta caaaattcaa agtgcgttgc tagtaccaac cctatttca ttcttcgcca | 960 |
| aaagcactct gattgacaaa tacgatttat ctaatttaca cgaaattgct tctggggggcg | 1020 |
| cacctctttc gaaagaagtc ggggaagcgg ttgcaaaacg cttccatctt ccagggatac | 1080 |
| gacaaggata tgggctcact gagactacat cagctattct gattacaccc gagggggatg | 1140 |
| ataaaccggg cgcggtcggt aaagttgttc cattttttga agcgaaggtt gtggatctgg | 1200 |
| ataccgggaa aacgctgggc gttaatcaga gaggcgaatt atgtgtcaga ggacctatga | 1260 |
| ttatgtccgg ttatgtaaac aatccggaag cgaccaacgc cttgattgac aaggatggat | 1320 |
| ggctacattc tggagacata gcttactggg acgaagacga cacttcttc atagttgacc | 1380 |
| gcttgaagtc tttaattaaa tacaaaggat accaggtggc ccccgctgaa ttggagtcga | 1440 |
| tattgttaca acaccccaac atcttcgacg cgggcgtggc aggtcttccc gacgatgacg | 1500 |
| ccggtgaact tcccgccgcc gttgttgttt tggagcacgg aaagacgatg acggaaaaag | 1560 |
| agatcgtgga ttacgtcgcc agtcaagtaa caaccgccaa aaagttgcgc ggaggagttg | 1620 |
| tgtttgtgga cgaagtaccg aaaggtctta ccggaaaact cgacgcaaga aaatcagag | 1680 |
| agatcctcat aaaggccaag aagggcggaa agtccaaatt gtaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaa | 1814 |

<210> SEQ ID NO 10
<211> LENGTH: 1887
<212> TYPE: DNA
<213> ORGANISM: Artificial Sequence
<220> FEATURE:
<223> OTHER INFORMATION: TEVpA90

<400> SEQUENCE: 10

| | | | | | |
|---|---|---|---|---|---|
| gaaataacaa | atctcaacac | aacatataca | aaacaaacga | atctcaagca | atcaagcatt | 60 |
| ctacttctat | tgcagcaatt | taaatcattt | cttttaaagc | aaaagcaatt | ttctgaaaat | 120 |
| tttcaccatt | tacgaacgat | agcaatggaa | gacgccaaaa | acataaagaa | aggcccggcg | 180 |
| ccattctatc | cgctagagga | tggaaccgct | ggagagcaac | tgcataaggc | tatgaagaga | 240 |
| tacgccctgg | ttcctggaac | aattgctttt | acagatgcac | atatcgaggt | gaacatcacg | 300 |
| tacgcggaat | acttcgaaat | gtccgttcgg | ttggcagaag | ctatgaaacg | atatgggctg | 360 |
| aatacaaatc | acagaatcgt | cgtatgcagt | gaaaactctc | ttcaattctt | tatgccggtg | 420 |
| ttgggcgcgt | tatttatcgg | agttgcagtt | gcgcccgcga | acgacattta | taatgaacgt | 480 |
| gaattgctca | acagtatgaa | catttcgcag | cctaccgtag | tgtttgtttc | caaaaagggg | 540 |
| ttgcaaaaaa | ttttgaacgt | gcaaaaaaaa | ttaccaataa | tccagaaaat | tattatcatg | 600 |
| gattctaaaa | cggattacca | gggatttcag | tcgatgtaca | cgttcgtcac | atctcatcta | 660 |
| cctcccggtt | ttaatgaata | cgattttgta | ccagagtcct | ttgatcgtga | caaaacaatt | 720 |
| gcactgataa | tgaactcctc | tggatctact | gggttaccta | agggtgtggc | ccttccgcat | 780 |
| agaactgcct | gcgtcagatt | ctcgcatgcc | agagatccta | ttttttggcaa | tcaaatcatt | 840 |
| ccggatactg | cgattttaag | tgttgttcca | ttccatcacg | gttttggaat | gtttactaca | 900 |
| ctcggatatt | tgatatgtgg | atttcgagtc | gtcttaatgt | atagatttga | agaagagctg | 960 |
| tttttacgat | cccttcagga | ttacaaaatt | caaagtgcgt | tgctagtacc | aaccctattt | 1020 |
| tcattcttcg | ccaaaagcac | tctgattgac | aaatacgatt | tatctaattt | acacgaaatt | 1080 |
| gcttctgggg | gcgcacctct | ttcgaaagaa | gtcggggaag | cggttgcaaa | acgcttccat | 1140 |
| cttccaggga | tacgacaagg | atatgggctc | actgagacta | catcagctat | tctgattaca | 1200 |
| cccgaggggg | atgataaacc | gggcgcggtc | ggtaaagttg | ttccatttttt | tgaagcgaag | 1260 |
| gttgtggatc | tggataccgg | gaaaacgctg | ggcgttaatc | agagaggcga | attatgtgtc | 1320 |
| agaggaccta | tgattatgtc | cggttatgta | aacaatccgg | aagcgaccaa | cgccttgatt | 1380 |
| gacaaggatg | gatggctaca | ttctggagac | atagcttact | gggacgaaga | cgaacacttc | 1440 |
| ttcatagttg | accgcttgaa | gtctttaatt | aaatacaaag | gataccaggt | ggcccccgct | 1500 |
| gaattggagt | cgatattgtt | acaacacccc | aacatcttcg | acgcgggcgt | ggcaggtctt | 1560 |
| cccgacgatg | acgccggtga | acttcccgcc | gccgttgttg | ttttggagca | cggaaagacg | 1620 |
| atgacggaaa | aagagatcgt | ggattacgtc | gccagtcaag | taacaaccgc | gaaaaagttg | 1680 |
| cgcggaggag | ttgtgtttgt | ggacgaagta | ccgaaaggtc | ttaccggaaa | actcgacgca | 1740 |
| agaaaaatca | gagagatcct | cataaaggcc | aagaagggcg | gaaagtccaa | attgtaaaaa | 1800 |
| aaaaaaaaa | aaaaaaaaa | aaaaaaaaa | aaaaaaaaa | aaaaaaaaa | aaaaaaaaa | 1860 |
| aaaaaaaaa | aaaaaaaaa | aaaaaa | | | | 1887 |

<210> SEQ ID NO 11
<211> LENGTH: 1809
<212> TYPE: DNA
<213> ORGANISM: Artificial Sequence
<220> FEATURE:
<223> OTHER INFORMATION: TbmpA90

<400> SEQUENCE: 11

| | | | | | | |
|---|---|---|---|---|---|---|
| gatttaaatt | attgcaacaa | caacaacaat | tacaataata | acaaacaaaa | tacaaacaac | 60 |
| aacaacatgg | aagacgccaa | aaacataaag | aaaggcccgg | cgccattcta | tccgctagag | 120 |
| gatggaaccg | ctggagagca | actgcataag | gctatgaaga | gatacgccct | ggttcctgga | 180 |
| acaattgctt | ttacagatgc | acatatcgag | gtgaacatca | cgtacgcgga | atacttcgaa | 240 |
| atgtccgttc | ggttggcaga | agctatgaaa | cgatatgggc | tgaatacaaa | tcacagaatc | 300 |
| gtcgtatgca | gtgaaaactc | tcttcaattc | tttatgccgg | tgttgggcgc | gttatttatc | 360 |
| ggagttgcag | ttgcgcccgc | gaacgacatt | tataatgaac | gtgaattgct | caacagtatg | 420 |
| aacatttcgc | agcctaccgt | agtgtttgtt | tccaaaaagg | ggttgcaaaa | aattttgaac | 480 |
| gtgcaaaaaa | aattaccaat | aatccagaaa | attattatca | tggattctaa | aacggattac | 540 |
| cagggatttc | agtcgatgta | cacgttcgtc | acatctcatc | tacctcccgg | ttttaatgaa | 600 |
| tacgattttg | taccagagtc | ctttgatcgt | gacaaaacaa | ttgcactgat | aatgaactcc | 660 |
| tctggatcta | ctgggttacc | taaggggtgtg | gcccttccgc | atagaactgc | ctgcgtcaga | 720 |
| ttctcgcatg | ccagagatcc | tattttttggc | aatcaaatca | ttccggatac | tgcgatttta | 780 |
| agtgttgttc | cattccatca | cggttttgga | atgtttacta | cactcggata | tttgatatgt | 840 |
| ggatttcgag | tcgtcttaat | gtatagattt | gaagaagagc | tgttttttacg | atcccttcag | 900 |
| gattacaaaa | ttcaaagtgc | gttgctagta | ccaaccctat | tttcattctt | cgccaaaagc | 960 |
| actctgattg | acaaatacga | tttatctaat | ttacacgaaa | ttgcttctgg | gggcgcacct | 1020 |
| ctttcgaaag | aagtcgggga | agcggttgca | aaacgcttcc | atcttccagg | gatacgacaa | 1080 |
| ggatatgggc | tcactgagac | tacatcagct | attctgatta | cacccgaggg | ggatgataaa | 1140 |
| ccgggcgcgg | tcggtaaagt | tgttccattt | tttgaagcga | aggttgtgga | tctggatacc | 1200 |
| gggaaaacgc | tgggcgttaa | tcagagaggc | gaattatgtg | tcagaggacc | tatgattatg | 1260 |
| tccggttatg | taaacaatcc | ggaagcgacc | aacgccttga | ttgacaagga | tggatggcta | 1320 |
| cattctggag | acatagctta | ctgggacgaa | gacgaacact | tcttcatagt | tgaccgcttg | 1380 |
| aagtctttaa | ttaaatacaa | aggataccag | gtggcccccg | ctgaattgga | gtcgatattg | 1440 |
| ttacaacacc | ccaacatctt | cgacgcgggc | gtggcaggtc | ttcccgacga | tgacgccggt | 1500 |
| gaacttcccg | ccgccgttgt | tgtttttggag | cacggaaaga | cgatgacgga | aaaagagatc | 1560 |
| gtggattacg | tcgccagtca | agtaacaacc | gccaaaaagt | tgcgcggagg | agttgtgttt | 1620 |
| gtggacgaag | taccgaaagg | tcttaccgga | aaactcgacg | caagaaaaat | cagagagatc | 1680 |
| ctcataaagg | ccaagaaggg | cggaaagtcc | aaattgtaaa | aaaaaaaaa | aaaaaaaaa | 1740 |
| aaaaaaaaa | aaaaaaaaa | aaaaaaaaa | aaaaaaaaa | aaaaaaaaa | aaaaaaaaa | 1800 |
| aaaaaaaaa | | | | | | 1809 |

<210> SEQ ID NO 12
<211> LENGTH: 1817
<212> TYPE: DNA
<213> ORGANISM: Artificial Sequence
<220> FEATURE:
<223> OTHER INFORMATION: OMEGApA25

<400> SEQUENCE: 12

| | | | | | | |
|---|---|---|---|---|---|---|
| gagtattttt | acaacaatta | ccaacaacaa | caaacaacaa | acaacattac | aattactatt | 60 |

| | |
|---|---:|
| tacaattaca tatggaagac gccaaaaaca taaagaaagg cccggtgcca ttctatccgc | 120 |
| tagaggatgg aaccgctgga gagcaactgc ataaggctat gaagagatac gccctggttc | 180 |
| ctggaacaat tgcttttaca gatgcacata tcgaggtgaa catcacgtac gcggaatact | 240 |
| tcgaaatgtc cgttcggttg gcagaagcta tgaaacgata tgggctgaat acaaatcaca | 300 |
| gaatcgtcgt atgcagtgaa aactctcttc aattctttat gccggtgttg ggcgcgttat | 360 |
| ttatcggagt tgcagttgcg cccgcgaacg acatttataa tgaacgtgaa ttgctcaaca | 420 |
| gtatgaacat ttcgcagcct accgtagtgt ttgtttccaa aaaggggttg caaaaaattt | 480 |
| tgaacgtgca aaaaaaatta ccaataatcc agaaaattat tatcatggat tctaaaacgg | 540 |
| attaccaggg atttcagtcg atgtacacgt tcgtcacatc tcatctacct cccggtttta | 600 |
| atgaatacga ttttgtacca gagtcctttg atcgtgacaa acaattgca ctgataatga | 660 |
| actcctctgg atctactggg ttacctaagg gtgtggccct tccgcataga actgcctgcg | 720 |
| tcagattctc gcatgccaga gatcctattt ttggcaatca aatcattccg gatactgcga | 780 |
| ttttaagtgt tgttccattc catcacggtt ttggaatgtt tactacactc ggatatttga | 840 |
| tatgtggatt tcgagtcgtc ttaatgtata gatttgaaga agagctgttt ttacgatccc | 900 |
| ttcaggatta caaaattcaa agtgcgttgc tagtaccaac cctatttca ttcttcgcca | 960 |
| aaagcactct gattgacaaa tacgatttat ctaatttaca cgaaattgct tctggggcg | 1020 |
| cacctctttc gaaagaagtc ggggaagcgg ttgcaaaacg cttccatctt ccagggatac | 1080 |
| gacaaggata tgggctcact gagactacat cagctattct gattacaccc gagggggatg | 1140 |
| ataaaccggg cgcggtcgt aaagttgttc cattttttga agcgaaggtt gtggatctgg | 1200 |
| ataccgggaa aacgctgggc gttaatcaga gaggcgaatt atgtgtcaga ggacctatga | 1260 |
| ttatgtccgg ttatgtaaac aatccggaag cgaccaacgc cttgattgac aaggatggat | 1320 |
| ggctacattc tggagacata gcttactggg acgaagacga acacttcttc atagttgacc | 1380 |
| gcttgaagtc tttaattaaa tacaaaggat accaggtggc ccccgctgaa ttggagtcga | 1440 |
| tattgttaca cacccccaac atcttcgacg cgggcgtggc aggtcttccc gacgatgacg | 1500 |
| ccggtgaact tcccgccgcc gttgttgttt tggagcacgg aaagacgatg acggaaaaag | 1560 |
| agatcgtgga ttacgtcgcc agtcaagtaa caaccgcgaa aaagttgcgc ggaggagttg | 1620 |
| tgtttgtgga cgaagtaccg aaaggtctta ccggaaaact cgacgcaaga aaaatcagag | 1680 |
| agatcctcat aaaggccaag aagggcggaa agtccaaatt gtaaggatcc gtacgagctc | 1740 |
| atgcgaattc ctcgagcacc accaccacca ccactgagat ccggctgcta acaaaaaaaa | 1800 |
| aaaaaaaaaa aaaaaaa | 1817 |

```
<210> SEQ ID NO 13
<211> LENGTH: 1842
<212> TYPE: DNA
<213> ORGANISM: Artificial Sequence
<220> FEATURE:
<223> OTHER INFORMATION: OMEGApA50

<400> SEQUENCE: 13
```

| | |
|---|---:|
| gagtatttt acaacaatta ccaacaacaa caaacaacaa acaacattac aattactatt | 60 |
| tacaattaca tatggaagac gccaaaaaca taaagaaagg cccggtgcca ttctatccgc | 120 |
| tagaggatgg aaccgctgga gagcaactgc ataaggctat gaagagatac gccctggttc | 180 |
| ctggaacaat tgcttttaca gatgcacata tcgaggtgaa catcacgtac gcggaatact | 240 |
| tcgaaatgtc cgttcggttg gcagaagcta tgaaacgata tgggctgaat acaaatcaca | 300 |

```
gaatcgtcgt atgcagtgaa aactctcttc aattctttat gccggtgttg ggcgcgttat    360
ttatcggagt tgcagttgcg cccgcgaacg acatttataa tgaacgtgaa ttgctcaaca    420
gtatgaacat ttcgcagcct accgtagtgt ttgtttccaa aaagggggttg caaaaaattt   480 tgaacgtgca aaaaaaatta ccaataatcc agaaaattat tatcatggat tctaaaacgg    540
attaccaggg atttcagtcg atgtacacgt tcgtcacatc tcatctacct cccggtttta    600
atgaatacga ttttgtacca gagtcctttg atcgtgacaa aacaattgca ctgataatga    660
actcctctgg atctactggg ttacctaagg gtgtggccct tccgcataga actgcctgcg    720
tcagattctc gcatgccaga gatcctattt ttggcaatca aatcattccg gatactgcga    780
ttttaagtgt tgttccattc catcacggtt ttggaatgtt tactacactc ggatatttga    840
tatgtggatt tcgagtcgtc ttaatgtata gatttgaaga agagctgttt ttacgatccc    900
ttcaggatta caaaattcaa agtgcgttgc tagtaccaac cctattttca ttcttcgcca    960
aaagcactct gattgacaaa tacgatttat ctaatttaca cgaaattgct tctggggggcg  1020 caccctcttttc gaaagaagtc ggggaagcgg ttgcaaaacg cttccatctt ccagggatac  1080
gacaaggata tgggctcact gagactacat cagctattct gattacaccc gagggggatg   1140
ataaaccggg cgcggtcggt aaagttgttc cattttttga agcgaaggtt gtggatctgg   1200
ataccgggaa aacgctgggc gttaatcaga gaggcgaatt atgtgtcaga ggacctatga   1260
ttatgtccgg ttatgtaaac aatccggaag cgaccaacgc cttgattgac aaggatggat   1320
ggctacattc tggagacata gcttactggg acgaagacga acacttcttc atagttgacc   1380
gcttgaagtc tttaattaaa tacaaaggat accaggtggc ccccgctgaa ttggagtcga   1440
tattgttaca caccccaac atcttcgacg cgggcgtggc aggtcttccc gacgatgacg    1500
ccggtgaact tcccgccgcc gttgttgttt tggagcacgg aaagacgatg acggaaaaag   1560
agatcgtgga ttacgtcgcc agtcaagtaa caaccgcgaa aaagttgcgc ggaggagttg   1620
tgtttgtgga cgaagtaccg aaaggtctta ccggaaaact cgacgcaaga aaaatcagag   1680
agatcctcat aaaggccaag aagggcggaa agtccaaatt gtaaggatcc gtacgagctc   1740
atgcgaattc ctcgagcacc accaccacca ccactgagat ccggctgcta acaaaaaaaa   1800
aaaaaaaaaa aaaaaaaaaa aaaaaaaaaa aaaaaaaaaa aa                      1842
```

<210> SEQ ID NO 14
<211> LENGTH: 1962
<212> TYPE: DNA
<213> ORGANISM: Artificial Sequence
<220> FEATURE:
<223> OTHER INFORMATION: OMEGApA170

<400> SEQUENCE: 14

```
gagtattttt acaacaatta ccaacaacaa caaacaacaa acaacattac aattactatt     60
tacaattaca tatggaagac gccaaaaaca taaagaaagg cccggtgcca ttctatccgc    120
tagaggatgg aaccgctgga gagcaactgc ataaggctat gaagagatac gccctggttc    180
ctggaacaat tgcttttaca gatgcacata tcgaggtgaa catcacgtac gcggaatact    240
tcgaaatgtc cgttcggttg gcagaagcta tgaaacgata tgggctgaat acaaatcaca    300
gaatcgtcgt atgcagtgaa aactctcttc aattctttat gccggtgttg ggcgcgttat    360
ttatcggagt tgcagttgcg cccgcgaacg acatttataa tgaacgtgaa ttgctcaaca    420
gtatgaacat ttcgcagcct accgtagtgt ttgtttccaa aaagggggttg caaaaaattt   480
```

-continued

```
tgaacgtgca aaaaaatta ccaataatcc agaaaattat tatcatggat tctaaaacgg      540
attaccaggg atttcagtcg atgtacacgt tcgtcacatc tcatctacct cccggtttta    600
atgaatacga ttttgtacca gagtcctttg atcgtgacaa acaattgca ctgataatga     660
actcctctgg atctactggg ttacctaagg gtgtggccct tccgcataga actgcctgcg    720
tcagattctc gcatgccaga gatcctatttt ttggcaatca aatcattccg gatactgcga   780
ttttaagtgt tgttccattc catcacggtt ttggaatgtt tactacactc ggatatttga    840
tatgtggatt tcgagtcgtc ttaatgtata gatttgaaga gagctgtttt ttacgatccc    900
ttcaggatta caaaattcaa agtgcgttgc tagtaccaac cctattttca ttcttcgcca    960
aaagcactct gattgacaaa tacgatttat ctaatttaca cgaaattgct tctggggggcg  1020
cacctctttc gaaagaagtc ggggaagcgg ttgcaaaacg cttccatctt ccagggatac   1080
gacaaggata tgggctcact gagactacat cagctattct gattacaccc gagggggatg   1140
ataaaccggg cgcggtcggt aaagttgttc cattttttga agcgaaggtt gtggatctgg   1200
ataccgggaa aacgctgggc gttaatcaga gaggcgaatt atgtgtcaga ggacctatga   1260
ttatgtccgg ttatgtaaac aatccggaag cgaccaacgc cttgattgac aaggatggat   1320
ggctacattg tggagacata gcttactggg acgaagacga acacttcttc atagttgacc   1380
gcttgaagtc tttaattaaa tacaaaggat accaggtggc ccccgctgaa ttggagtcga   1440
tattgttaca cacccccaac atcttcgacg cgggcgtggc aggtcttccc gacgatgacg   1500
ccggtgaact tcccgccgcc gttgttgttt tggagcacgg aaagacgatg acggaaaaag   1560
agatcgtgga ttacgtcgcc agtcaagtaa caaccgcgaa aaagttgcgc ggaggagttg   1620
tgtttgtgga cgaagtaccg aaaggtctta ccggaaaaact cgacgcaaga aaaatcagag   1680
agatcctcat aaaggccaag aagggcgaa agtccaaatt gtaaggatcc gtacgagctc   1740
atgcgaattc ctcgagcacc accaccacca ccactgagat ccggctgcta acaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aa                     1962
```

<210> SEQ ID NO 15
<211> LENGTH: 3205
<212> TYPE: DNA
<213> ORGANISM: Artificial Sequence
<220> FEATURE:
<223> OTHER INFORMATION: OMEGAFBAL

<400> SEQUENCE: 15

```
gagtattttt acaacaatta ccaacaacaa caaacaacaa acaacattac aattactatt     60
tacaattaca tatggaagac gccaaaaaca taaagaaagg cccggtgcca ttctatccgc    120
tagaggatgg aaccgctgga gagcaactgc ataaggctat gaagagatac gccctggttc    180
ctggaacaat tgcttttaca gatgcacata tcgaggtgaa catcacgtac gcggaatact    240
tcgaaatgtc cgttcggttg gcagaagcta tgaaacgata tgggctgaat acaaatcaca    300
gaatcgtcgt atgcagtgaa aactctcttc aattctttat gccggtgttg ggcgcgttat    360
ttatcggagt tgcagttgcg cccgcgaacg acatttataa tgaacgtgaa ttgctcaaca    420
gtatgaacat ttcgcagcct accgtagtgt ttgtttccaa aaaggggttg caaaaaattt    480
tgaacgtgca aaaaaatta ccaataatcc agaaaattat tatcatggat tctaaaacgg    540
attaccaggg atttcagtcg atgtacacgt tcgtcacatc tcatctacct cccggtttta    600
```

```
atgaatacga ttttgtacca gagtcctttg atcgtgacaa aacaattgca ctgataatga    660
actcctctgg atctactggg ttacctaagg gtgtggccct tccgcataga actgcctgcg    720
tcagattctc gcatgccaga gatcctattt ttggcaatca aatcattccg gatactgcga    780
ttttaagtgt tgttccattc catcacggtt ttggaatgtt tactacactc ggatatttga    840
tatgtggatt tcgagtcgtc ttaatgtata gatttgaaga gagctgtttt tacgatccc    900 ttcaggatta caaaattcaa agtgcgttgc tagtaccaac cctattttca ttcttcgcca    960
aaagcactct gattgacaaa tacgatttat ctaatttaca cgaaattgct tctggggcg    1020 cacctctttc gaaagaagtc ggggaagcgg ttgcaaaacg cttccatctt ccagggatac    1080
gacaaggata tgggctcact gagactacat cagctattct gattacaccc gaggggatg    1140 ataaaccggg cgcggtcgt aaagttgttc cattttttga agcgaaggtt gtggatctgg    1200
ataccgggaa aacgctgggc gttaatcaga gaggcgaatt atgtgtcaga ggacctatga    1260
ttatgtccgg ttatgtaaac aatccggaag cgaccaacgc cttgattgac aaggatggat    1320
ggctacattc tggagacata gcttactggg acgaagacga acacttcttc atagttgacc    1380
gcttgaagtc tttaattaaa tacaaaggat accaggtggc ccccgctgaa ttggagtcga    1440
tattgttaca acccccaac atcttcgacg cgggcgtggc aggtcttccc gacgatgacg    1500
ccggtgaact tcccgccgcc gttgttgttt tggagcacgg aaagacgatg acggaaaaag    1560
agatcgtgga ttacgtcgcc agtcaagtaa caaccgcgaa aaagttgcgc ggaggagttg    1620
tgtttgtgga cgaagtaccg aaaggtctta ccggaaaaact cgacgcaaga aaaatcagag    1680
agatcctcat aaaggccaag aagggcggaa agtccaaatt gtaaggatcc gtacgagctc    1740
gagtattgaa tctgtttaga aataatggaa tattatttt atttatttat ttatattatt    1800
ggtcggctct tttcttctga aggtcaatga caaaatgata tgaaggaaat aatgatttct    1860
aaaattttac aacgtaagat attttacaa aagcctagct catcttttgt catgcactat    1920
tttactcacg cttgaaatta acggccagtc cactgcggag tcatttcaaa gtcatcctaa    1980
tcgatctatc gttttgata gctcattttg gagttcgcga ttgtcttctg ttattcacaa    2040 ctgtttaat ttttatttca ttctggaact cttcgagttc tttgtaaagt ctttcatagt    2100
agcttacttt atcctccaac atatttaact tcatgtcaat ttcggctctt aaattttcca    2160
catcatcaag ttcaacatca tcttttaact tgaatttatt ctctagctct tccaaccaag    2220
cctcattgct ccttgattta ctggtgaaaa gtgatacact ttgcgcgcaa tccaggtcaa    2280
aactttcctg caaagaattc accaatttct cgacatcata gtacaatttg ttttgttctc    2340
ccatcacaat ttaatatacc tgatggattc ttatgaagcg ctgggtaatg gacgtgtcac    2400
tctacttcgc cttttccct actccttta gtacggaaga caatgctaat aaataagagg    2460
gtaataataa tattattaat cggcaaaaaa gattaaacgc caagcgttta attatcagaa    2520
agcaaacgtc gtaccaatcc ttgaatgctt cccaattgta tattaagagt catcacagca    2580
acatattctt gttattaaat taattattat tgattttga tattgtataa aaaaaccaaa    2640
tatgtataaa aaagtgaat aaaaaatacc aagtatggag aaatatatta gaagtctata    2700
cgttaaaacc agaacgtgca caattttttt aatctgccaa atggaaaaaa cggaaatata    2760
cggaaaagaa gttgaagtaa tagttagaaa ggcaaaaaag gaagaaaca atttaaaata    2820 tcttaagatt atattagaaa caaacaccaa tgttcatttc attccttaga atatatccga    2880
atgaaatgac caacctactt gttttgtaaa ctgaggaaga aagaatatta tttctccgaa    2940
```

| aacttgtcat accgtagctt gtcttgcttt tatttgcttt tgaccttatt tttttcaaaa | 3000 |
| atcaccgtgc tttttgtgag ttttagatg ttgtgataaa ttgtcacttc tactgaattt | 3060 |
| tttctcacag aacatacaag caaaagggcg ttccgttgaa tgaacggatc ttatatgcct | 3120 |
| tttcaagtgc tcactgcgtc tgaatgcctt ctcacagtct ttacacttga aaggtttatt | 3180 |
| tttatcgtag ttgttggggt caatg | 3205 |

<210> SEQ ID NO 16
<211> LENGTH: 2399
<212> TYPE: DNA
<213> ORGANISM: Artificial Sequence
<220> FEATURE:
<223> OTHER INFORMATION: OMEGAFBAS

<400> SEQUENCE: 16

| gagtatttt acaacaatta ccaacaacaa caaacaacaa caacattac aattactatt | 60 |
| tacaattaca tatggaagac gccaaaaaca taaagaaagg cccggtgcca ttctatccgc | 120 |
| tagaggatgg aaccgctgga gagcaactgc ataaggctat gaagagatac gccctggttc | 180 |
| ctggaacaat tgcttttaca gatgcacata tcgaggtgaa catcacgtac gcggaatact | 240 |
| tcgaaatgtc cgttcggttg gcagaagcta tgaaacgata tgggctgaat acaaatcaca | 300 |
| gaatcgtcgt atgcagtgaa aactctcttc aattctttat gccggtgttg ggcgcgttat | 360 |
| ttatcggagt tgcagttgcg cccgcgaacg acatttataa tgaacgtgaa ttgctcaaca | 420 |
| gtatgaacat ttcgcagcct accgtagtgt ttgtttccaa aaaggggttg caaaaaattt | 480 |
| tgaacgtgca aaaaaaatta ccaataatcc agaaaattat tatcatggat ctaaaacgg | 540 |
| attaccaggg atttcagtcg atgtacacgt tcgtcacatc tcatctacct cccggtttta | 600 |
| atgaatacga ttttgtacca gagtcctttg atcgtgacaa acaattgca ctgataatga | 660 |
| actcctctgg atctactggg ttacctaagg gtgtggccct tccgcataga actgcctgcg | 720 |
| tcagattctc gcatgccaga gatcctattt ttggcaatca aatcattccg gatactgcga | 780 |
| ttttaagtgt tgttccattc catcacggtt ttggaatgtt tactacactc ggatatttga | 840 |
| tatgtggatt tcgagtcgtc ttaatgtata gatttgaaga agagctgttt ttacgatccc | 900 |
| ttcaggatta caaaattcaa agtgcgttgc tagtaccaac cctattttca ttcttcgcca | 960 |
| aaagcactct gattgacaaa tacgatttat ctaatttaca cgaaattgct tctgggggcg | 1020 |
| cacctctttc gaaagaagtc ggggaagcgg ttgcaaaacg cttccatctt ccagggatac | 1080 |
| gacaaggata tgggctcact gagactacat cagctattct gattacaccc gagggggatg | 1140 |
| ataaaccggg cgcggtcggt aaagttgttc cattttttga agcgaaggtt gtggatctgg | 1200 |
| ataccgggaa aacgctgggc gttaatcaga gaggcgaatt atgtgtcaga ggacctatga | 1260 |
| ttatgtccgg ttatgtaaac aatccggaag cgaccaacgc cttgattgac aaggatggat | 1320 |
| ggctacattc tggagacata gcttactggg acgaagacga acacttcttc atagttgacc | 1380 |
| gcttgaagtc tttaattaaa tacaaaggat accaggtggc ccccgctgaa ttggagtcga | 1440 |
| tattgttaca caccccaac atcttcgacg cgggcgtggc aggtcttccc gacgatgacg | 1500 |
| ccggtgaact tcccgccgcc gttgttgttt tggagcacgg aaagacgatg acggaaaaag | 1560 |
| agatcgtgga ttacgtcgcc agtcaagtaa caaccgcgaa aaagttgcgc ggaggagttg | 1620 |
| tgtttgtgga cgaagtaccg aaaggtctta ccggaaaact cgacgcaaga aaaatcagag | 1680 |
| agatcctcat aaaggccaag aagggcggaa agtccaaatt gtaaggatcc gtacgagctc | 1740 |
| gagtattgaa tctgtttaga aataatggaa tattattttt atttatttat ttatattatt | 1800 |

-continued

```
ggtcggctct tttcttctga aggtcaatga caaaatgata tgaaggaaat aatgatttct   1860
aaaattttac aacgtaagat attttttacaa aagcctagct catctttttgt catgcactat   1920 tttactcacg cttgaaatta acggccagtc cactgcggag tcatttcaaa gtcatcctaa   1980
tcgatctatc gttttttgata gctcattttg gagttcgcga ttgtcttctg ttattcacaa   2040
ctgttttaat ttttatttca ttctggaact cttcgagttc tttgtaaagt ctttcatagt   2100
agcttacttt atcctccaac atatttaact tcatgtcaat ttcggctctt aaattttcca   2160
catcatcaag ttcaacatca tcttttaact tgaatttatt ctctagctct tccaaccaag   2220
cctcattgct ccttgattta ctggtgaaaa gtgatacact ttgcgcgcaa tccaggtcaa   2280
aactttcctg caaagaattc accaatttct cgacatcata gtacaatttg ttttgttctc   2340
ccatcacaat ttaatatacc tgatggattc ttatgaagcg ctgggtaatg acgtgtca    2399
```

<210> SEQ ID NO 17
<211> LENGTH: 1940
<212> TYPE: DNA
<213> ORGANISM: Artificial Sequence
<220> FEATURE:
<223> OTHER INFORMATION: OMEGATMV13U200

<400> SEQUENCE: 17

```
gagtatttttt acaacaatta ccaacaacaa caaacaacaa acaacattac aattactatt    60
tacaattaca tatggaagac gccaaaaaca taaagaaagg cccggtgcca ttctatccgc   120
tagaggatgg aaccgctgga gagcaactgc ataaggctat gaagagatac gccctggttc   180
ctggaacaat tgcttttaca gatgcacata tcgaggtgaa catcacgtac gcggaatact   240
tcgaaatgtc cgttcggttg gcagaagcta tgaaacgata tgggctgaat acaaatcaca   300
gaatcgtcgt atgcagtgaa aactctcttc aattctttat gccggtgttg ggcgcgttat   360
ttatcggagt tgcagttgcg cccgcgaacg acatttataa tgaacgtgaa ttgctcaaca   420
gtatgaacat ttcgcagcct accgtagtgt ttgtttccaa aaagggggttg caaaaaattt   480 tgaacgtgca aaaaaaatta ccaataatcc agaaaattat tatcatggat tctaaaacgg   540
attaccaggg atttcagtcg atgtacacgt tcgtcacatc tcatctacct cccggttttaa   600 atgaatacga ttttgtacca gagtccttttg atcgtgacaa acaattgca ctgataatga   660 actcctctgg atctactggg ttacctaagg gtgtggccct tccgcataga actgcctgcg   720
tcagattctc gcatgccaga gatcctattt ttggcaatca aatcattccg gatactgcga   780
ttttaagtgt tgttccattc catcacggtt ttggaatgtt tactacactc ggatatttga   840
tatgtggatt tcgagtcgtc ttaatgtata gatttgaaga agagctgttt ttacgatccc   900
ttcaggatta caaaattcaa agtgcgttgc tagtaccaac ctatttttca ttcttcgcca   960
aaagcactct gattgacaaa tacgatttat ctaatttaca cgaaattgct tctggggcg   1020 cacctcttttc gaaagaagtc ggggaagcgg ttgcaaaacg cttccatctt ccagggatac   1080
gacaaggata tgggctcact gagactacat cagctattct gattacaccc gagggggatg   1140
ataaaccggg cgcggtcggt aaagttgttc catttttttga agcgaaggtt gtggatctgg   1200
ataccgggaa aacgctgggc gttaatcaga gaggcgaatt atgtgtcaga ggacctatga   1260
ttatgtccgg ttatgtaaac aatccggaag cgaccaacgc cttgattgac aaggatggat   1320
ggctacattc tggagacata gcttactggg acgaagacga acacttcttc atagttgacc   1380
gcttgaagtc ttttaattaaa tacaaaggat accaggtggc ccccgctgaa ttggagtcga   1440
```

```
tattgttaca acaccccaac atcttcgacg cgggcgtggc aggtcttccc gacgatgacg    1500
ccggtgaact tcccgccgcc gttgttgttt tggagcacgg aaagacgatg acggaaaaag    1560
agatcgtgga ttacgtcgcc agtcaagtaa caaccgcgaa aaagttgcgc ggaggagttg    1620
tgtttgtgga cgaagtaccg aaaggtctta ccggaaaact cgacgcaaga aaaatcagag    1680
agatcctcat aaaggccaag aagggcggaa agtccaaatt gtaaggatcc gtacgagctc    1740
aggaaaagtg aatatcaatg agtttatcga cctgacaaaa atggagaaga tcttaccgtc    1800
gatgtttacc cctgtaaaga gtgttatgtg ttccaaagtt gataaaataa tggttcatga    1860
gaatgagtca ttgtcagagg tgaaccttct taaaggagtt aagcttattg atagtggata    1920
cgtctgttta gccggtttgg                                                1940
```

<210> SEQ ID NO 18
<211> LENGTH: 2140
<212> TYPE: DNA
<213> ORGANISM: Artificial Sequence
<220> FEATURE:
<223> OTHER INFORMATION: OMEGATMV13U400

<400> SEQUENCE: 18

```
gagtattttt acaacaatta ccaacaacaa caaacaacaa acaacattac aattactatt      60
tacaattaca tatggaagac gccaaaaaca taaagaaagg cccggtgcca ttctatccgc     120
tagaggatgg aaccgctgga gagcaactgc ataaggctat gaagagatac gccctggttc     180
ctggaacaat tgcttttaca gatgcacata tcgaggtgaa catcacgtac gcggaatact     240
tcgaaatgtc cgttcggttg gcagaagcta tgaaacgata tgggctgaat acaaatcaca     300
gaatcgtcgt atgcagtgaa aactctcttc aattctttat gccggtgttg ggcgcgttat     360
ttatcggagt tgcagttgcg cccgcgaacg acatttataa tgaacgtgaa ttgctcaaca     420
gtatgaacat ttcgcagcct accgtagtgt ttgtttccaa aaagggggttg caaaaaattt     480 tgaacgtgca aaaaaaatta ccaataatcc agaaaattat tatcatggat tctaaaacgg     540
attaccaggg atttcagtcg atgtacacgt tcgtcacatc tcatctacct cccggtttta     600
atgaatacga ttttgtacca gagtccttg atcgtgacaa acaattgca ctgataatga     660 actcctctgg atctactggg ttacctaagg gtgtggccct tccgcataga actgcctgcg     720
tcagattctc gcatgccaga gatcctattt ttggcaatca aatcattccg gatactgcga     780
ttttaagtgt tgttccattc catcacggtt ttggaatgtt tactacactc ggatatttga     840
tatgtggatt tcgagtcgtc ttaatgtata gatttgaaga agagctgttt ttacgatccc     900
ttcaggatta caaaattcaa agtgcgttgc tagtaccaac cctattttca ttcttcgcca     960
aaagcactct gattgacaaa tacgatttat ctaatttaca cgaaattgct tctggggcg    1020 cacctctttc gaaagaagtc ggggaagcgg ttgcaaaacg cttccatctt ccagggatac    1080
gacaaggata tgggctcact gagactacat cagctattct gattacaccc gagggggatg    1140
ataaaccggg cgcggtcggt aaagttgttc cattttttga agcgaaggtt gtggatctgg    1200
ataccgggaa aacgctgggc gttaatcaga gaggcgaatt atgtgtcaga ggacctatga    1260
ttatgtccgg ttatgtaaac aatccggaag cgaccaacgc cttgattgac aaggatggat    1320
ggctacattc tggagacata gcttactggg acgaagacga acacttcttc atagttgacc    1380
gcttgaagtc tttaattaaa tacaaaggat accaggtggc cccgctgaa ttggagtcga    1440 tattgttaca acaccccaac atcttcgacg cgggcgtggc aggtcttccc gacgatgacg    1500
ccggtgaact tcccgccgcc gttgttgttt tggagcacgg aaagacgatg acggaaaaag    1560
```

```
agatcgtgga ttacgtcgcc agtcaagtaa caaccgcgaa aaagttgcgc ggaggagttg    1620
tgtttgtgga cgaagtaccg aaaggtctta ccggaaaact cgacgcaaga aaaatcagag    1680
agatcctcat aaaggccaag aagggcggaa agtccaaatt gtaaggatcc gtacgagctc    1740
aggaaaagtg aatatcaatg agtttatcga cctgacaaaa atggagaaga tcttaccgtc    1800
gatgtttacc cctgtaaaga gtgttatgtg ttccaaagtt gataaaataa tggttcatga    1860
gaatgagtca ttgtcagagg tgaaccttct taaaggagtt aagcttattg atagtggata    1920
cgtctgttta gccggtttgg tcgtcacggg cgaatggaac ttgcctgaca attgcagagg    1980
aggtgtgagc gtgtgtctgg tggacaaaag gatggaaaga gccgacgagg ccactctcgg    2040
atcttactac acagcagctg caaagaaaag atttcagttc aaggtcgttc ccaattatgc    2100
tataaccacc caggacgcga tgaaaaacgt ctggcaagtt                          2140
```

<210> SEQ ID NO 19
<211> LENGTH: 2440
<212> TYPE: DNA
<213> ORGANISM: Artificial Sequence
<220> FEATURE:
<223> OTHER INFORMATION: OMEGATMV13U700

<400> SEQUENCE: 19

```
gagtatttttt acaacaatta ccaacaacaa caaacaacaa acaacattac aattactatt      60
tacaattaca tatggaagac gccaaaaaca taaagaaagg cccggtgcca ttctatccgc     120
tagaggatgg aaccgctgga gagcaactgc ataaggctat gaagagatac gccctggttc     180
ctggaacaat tgcttttaca gatgcacata tcgaggtgaa catcacgtac gcggaatact     240
tcgaaatgtc cgttcggttg gcagaagcta tgaaacgata tgggctgaat acaaatcaca     300
gaatcgtcgt atgcagtgaa aactctcttc aattctttat gccggtgttg ggcgcgttat     360
ttatcggagt tgcagttgcg cccgcgaacg acatttataa tgaacgtgaa ttgctcaaca     420
gtatgaacat ttcgcagcct accgtagtgt ttgtttccaa aaaggggttg caaaaaattt     480
tgaacgtgca aaaaaaatta ccaataatcc agaaaattat tatcatggat tctaaaacgg     540
attaccaggg atttcagtcg atgtacacgt tcgtcacatc tcatctacct cccggtttta     600
atgaatacga ttttgtacca gagtcctttg atcgtgacaa acaattgcac tgataatga     660 actcctctgg atctactggg ttacctaagg gtgtggccct tccgcataga actgcctgcg     720
tcagattctc gcatgccaga gatcctattt ttggcaatca aatcattccg gatactgcga     780
ttttaagtgt tgttccattc catcacggtt ttggaatgtt tactacactc ggatatttga     840
tatgtggatt tcgagtcgtc ttaatgtata gatttgaaga agagctgttt ttacgatccc     900
ttcaggatta caaaattcaa agtgcgttgc tagtaccaac cctattttca ttcttcgcca     960
aaagcactct gattgacaaa tacgatttat ctaatttaca cgaaattgct tctggggcg    1020 cacctctttc gaaagaagtc ggggaagcgg ttgcaaaacg cttccatctt ccagggatac    1080
gacaaggata tgggctcact gagactacat cagctattct gattacaccc gagggggatg    1140
ataaaccggg cgcggtcggt aaagttgttc cattttttga agcgaaggtt gtggatctgg    1200
ataccgggaa aacgctgggc gttaatcaga gaggcgaatt atgtgtcaga ggacctatga    1260
ttatgtccgg ttatgtaaac aatccggaag cgaccaacgc cttgattgac aaggatggat    1320
ggctacattc tggagacata gcttactggg acgaagacga acacttcttc atagttgacc    1380
gcttgaagtc tttaattaaa tacaaaggat accaggtggc ccccgctgaa ttggagtcga    1440
```

```
tattgttaca acaccccaac atcttcgacg cgggcgtggc aggtcttccc gacgatgacg    1500
ccggtgaact tcccgccgcc gttgttgttt tggagcacgg aaagacgatg acggaaaaag    1560
agatcgtgga ttacgtcgcc agtcaagtaa caaccgcgaa aaagttgcgc ggaggagttg    1620
tgtttgtgga cgaagtaccg aaaggtctta ccggaaaact cgacgcaaga aaaatcagag    1680
agatcctcat aaaggccaag aagggcggaa agtccaaatt gtaaggatcc gtacgagctc    1740
aggaaaagtg aatatcaatg agtttatcga cctgacaaaa atggagaaga tcttaccgtc    1800
gatgtttacc cctgtaaaga gtgttatgtg ttccaaagtt gataaaataa tggttcatga    1860
gaatgagtca ttgtcagagg tgaaccttct taaaggagtt aagcttattg atagtggata    1920
cgtctgttta gccggtttgg tcgtcacggg cgaatggaac ttgcctgaca attgcagagg    1980
aggtgtgagc gtgtgtctgg tggacaaaag gatggaaaga gccgacgagg ccactctcgg    2040
atcttactac acagcagctg caaagaaaag atttcagttc aaggtcgttc ccaattatgc    2100
tataaccacc caggacgcga tgaaaaacgt ctggcaagtt ttagttaata ttagaaatgt    2160
aaagatgtca gcgggtttct gtccgctttc tctggagttt gtgtcggtgt gtattgttta    2220
tagaaataat ataaaattag gtttgagaga gaagattaca aacgtgagag acggagggcc    2280
catggaactt acagaagaag tcgttgatga gttcatggaa gatgtcccta tgtcaatcag    2340
gcttgcaaag tttcgatctc ggaccggaaa aaagagtgat gtccgtaaag ggaaaaatag    2400
tagtagtgac cggtcagtgc cgaacaagaa ctatagaaat                          2440

<210> SEQ ID NO 20
<211> LENGTH: 1944
<212> TYPE: DNA
<213> ORGANISM: Artificial Sequence
<220> FEATURE:
<223> OTHER INFORMATION: OMEGATMV23U

<400> SEQUENCE: 20
gagtattttt acaacaatta ccaacaacaa caaacaacaa acaacattac aattactatt      60
tacaattaca tatggaagac gccaaaaaca taaagaaagg cccggtgcca ttctatccgc     120
tagaggatgg aaccgctgga gagcaactgc ataaggctat gaagagatac gccctggttc     180
ctggaacaat tgcttttaca gatgcacata tcgaggtgaa catcacgtac gcggaatact     240
tcgaaatgtc cgttcggttg gcagaagcta tgaaacgata tgggctgaat acaaatcaca     300
gaatcgtcgt atgcagtgaa aactctcttc aattctttat gccggtgttg ggcgcgttat     360
ttatcggagt tgcagttgcg cccgcgaacg acatttataa tgaacgtgaa ttgctcaaca     420
gtatgaacat ttcgcagcct accgtagtgt ttgtttccaa aaaggggttg caaaaaattt     480
tgaacgtgca aaaaaaatta ccaataatcc agaaaattat tatcatggat tctaaaacgg     540
attaccaggg atttcagtcg atgtacacgt tcgtcacatc tcatctacct cccggtttta     600
atgaatacga ttttgtacca gagtcctttg atcgtgacaa acaattgca ctgataatga     660 actcctctgg atctactggg ttacctaagg gtgtggccct tccgcataga actgcctgcg     720
tcagattctc gcatgccaga gatcctattt ttggcaatca aatcattccg gatactgcga     780
ttttaagtgt tgttccattc catcacggtt tggaatgtt tactcactc ggatatttga     840 tatgtggatt tcgagtcgtc ttaatgtata gatttgaaga agagctgttt ttacgatccc     900
ttcaggatta caaaattcaa agtgcgttgc tagtaccaac cctatttca ttcttcgcca     960 aaagcactct gattgacaaa tacgatttat ctaatttaca cgaaattgct tctggggcg    1020 cacctctttc gaaagaagtc ggggaagcgg ttgcaaaacg cttccatctt ccagggatac    1080
```

```
gacaaggata tgggctcact gagactacat cagctattct gattacaccc gagggggatg   1140
ataaaccggg cgcggtcggt aaagttgttc cattttttga agcgaaggtt gtggatctgg   1200
ataccgggaa aacgctgggc gttaatcaga gaggcgaatt atgtgtcaga ggacctatga   1260
ttatgtccgg ttatgtaaac aatccggaag cgaccaacgc cttgattgac aaggatggat   1320
ggctacattc tggagacata gcttactggg acgaagacga acacttcttc atagttgacc   1380
gcttgaagtc tttaattaaa tacaaaggat accaggtggc ccccgctgaa ttggagtcga   1440
tattgttaca acaccccaac atcttcgacg cgggcgtggc aggtcttccc gacgatgacg   1500
ccggtgaact tcccgccgcc gttgttgttt tggagcacgg aaagacgatg acggaaaaag   1560
agatcgtgga ttacgtcgcc agtcaagtaa caaccgcgaa aaagttgcgc ggaggagttg   1620
tgtttgtgga cgaagtaccg aaaggtctta ccggaaaact cgacgcaaga aaaatcagag   1680
agatcctcat aaaggccaag aagggcggaa agtccaaatt gtaaggatcc gtacgagctc   1740
ggtagtcaag atgcataata aataacggat tgtgtccgta atcacacgtg gtgcgtacga   1800
taacgcatag tgttttttccc tccacttaga tcgaagggtt gtgtcttgga tcgcgcgggt   1860
caaatgtata tggttcatat acatccgcag gcacgtaata aagcgagggg ttcgaatccc   1920
cccgttaccc ccggtagggg ccca                                          1944
```

<210> SEQ ID NO 21
<211> LENGTH: 1724
<212> TYPE: DNA
<213> ORGANISM: Artificial Sequence
<220> FEATURE:
<223> OTHER INFORMATION: OMEGAN3U

<400> SEQUENCE: 21

```
gagtattttt acaacaatta ccaacaacaa caaacaacaa acaacattac aattactatt     60
tacaattaca tatggaagac gccaaaaaca taaagaaagg cccggcgcca ttctatccgc    120
tagaggatgg aaccgctgga gagcaactgc ataaggctat gaagagatac gccctggttc    180
ctggaacaat tgcttttaca gatgcacata tcgaggtgaa catcacgtac gcggaatact    240
tcgaaatgtc cgttcggttg gcagaagcta tgaaacgata tgggctgaat acaaatcaca    300
gaatcgtcgt atgcagtgaa aactctcttc aattctttat gccggtgttg ggcgcgttat    360
ttatcggagt tgcagttgcg cccgcgaacg acatttataa tgaacgtgaa ttgctcaaca    420
gtatgaacat ttcgcagcct accgtagtgt ttgtttccaa aaaggggttg caaaaaattt    480
tgaacgtgca aaaaaaatta ccaataatcc agaaaattat tatcatggat tctaaaacgg    540
attaccaggg atttcagtcg atgtacacgt tcgtcacatc tcatctacct cccggtttta    600
atgaatacga ttttgtacca gagtcctttg atcgtgacaa acaattgca ctgataatga    660 actcctctgg atctactggg ttacctaagg gtgtggccct tccgcataga actgcctgcg    720
tcagattctc gcatgccaga gatcctattt ttggcaatca aatcattccg gatactgcga    780
ttttaagtgt tgttccattc catcacggtt ttggaatgtt tactacactc ggatatttga    840
tatgtggatt tcgagtcgtc ttaatgtata gatttgaaga agagctgttt ttacgatccc    900
ttcaggatta caaaattcaa agtgcgttgc tagtaccaac cctatttttca ttcttcgcca    960 aaagcactct gattgacaaa tacgatttat ctaatttaca cgaaattgct tctggggcg   1020 cacctctttc gaaagaagtc ggggaagcgg ttgcaaaacg cttccatctt ccagggatac   1080
gacaaggata tgggctcact gagactacat cagctattct gattacaccc gagggggatg   1140
```

```
ataaaccggg cgcggtcggt aaagttgttc catttttga agcgaaggtt gtggatctgg      1200
ataccgggaa aacgctgggc gttaatcaga gaggcgaatt atgtgtcaga ggacctatga      1260
ttatgtccgg ttatgtaaac aatccggaag cgaccaacgc cttgattgac aaggatggat      1320
ggctacattc tggagacata gcttactggg acgaagacga acacttcttc atagttgacc      1380
gcttgaagtc tttaattaaa tacaaaggat accaggtggc ccccgctgaa ttggagtcga      1440
tattgttaca acaccccaac atcttcgacg cgggcgtggc aggtcttccc gacgatgacg      1500
ccggtgaact tcccgccgcc gttgttgttt tggagcacgg aaagacgatg acggaaaaag      1560
agatcgtgga ttacgtcgcc agtcaagtaa caaccgccaa aaagttgcgc ggaggagttg      1620
tgtttgtgga cgaagtaccg aaaggtctta ccggaaaaact cgacgcaaga aaaatcagag      1680
agatcctcat aaaggccaag aagggcggaa agtccaaatt gtaa                      1724
```

<210> SEQ ID NO 22
<211> LENGTH: 1804
<212> TYPE: DNA
<213> ORGANISM: Artificial Sequence
<220> FEATURE:
<223> OTHER INFORMATION: N5UpA90

<400> SEQUENCE: 22

```
gagaccacaa cggtttccct ctagaaataa ttttgtttaa ctttaagaag gagatataca        60 tatgaagac gccaaaaaca taagaaagg cccggcgcca ttctatccgc tagaggatgg       120
aaccgctgga gagcaactgc ataaggctat gaagagatac gccctggttc ctggaacaat       180
tgcttttaca gatgcacata tcgaggtgaa catcacgtac gcggaatact tcgaaatgtc       240
cgttcggttg gcagaagcta tgaaacgata tgggctgaat acaaatcaca gaatcgtcgt       300
atgcagtgaa aactctcttc aattctttat gccggtgttg ggcgcgttat ttatcggagt       360
tgcagttgcg cccgcgaacg acatttataa tgaacgtgaa ttgctcaaca gtatgaacat       420
ttcgcagcct accgtagtgt ttgtttccaa aaaggggttg caaaaaattt tgaacgtgca       480
aaaaaaatta ccaataatcc agaaaattat tatcatggat tctaaaacgg attaccaggg       540
atttcagtcg atgtacacgt tcgtcacatc tcatctacct cccggtttta atgaatacga       600
ttttgtacca gagtcctttg atcgtgacaa acaattgca ctgataatga actcctctgg       660
atctactggg ttacctaagg gtgtggccct tccgcataga actgcctgcg tcagattctc       720
gcatgccaga gatcctattt ttggcaatca aatcattccg gatactgcga ttttaagtgt       780
tgttccattc catcacggtt ttggaatgtt tactacactc ggatatttga tatgtggatt       840
tcgagtcgtc ttaatgtata gatttgaaga agagctgttt ttacgatccc ttcaggatta       900
caaaattcaa agtgcgttgc tagtaccaac cctattttca ttcttcgcca aaagcactct       960
gattgacaaa tacgatttat ctaatttaca cgaaattgct tctggggcg cacctctttc      1020 gaaagaagtc ggggaagcgg ttgcaaaacg cttccatctt ccaggatac gacaaggata      1080 tgggctcact gagactacat cagctattct gattacaccc gagggggatg ataaaccggg      1140
cgcggtcggt aaagttgttc catttttga agcgaaggtt gtggatctgg ataccgggaa      1200
aacgctgggc gttaatcaga gaggcgaatt atgtgtcaga ggacctatga ttatgtccgg      1260
ttatgtaaac aatccggaag cgaccaacgc cttgattgac aaggatggat ggctacattc      1320
tggagacata gcttactggg acgaagacga acacttcttc atagttgacc gcttgaagtc      1380
tttaattaaa tacaaaggat accaggtggc ccccgctgaa ttggagtcga tattgttaca      1440
acaccccaac atcttcgacg cgggcgtggc aggtcttccc gacgatgacg ccggtgaact      1500
```

```
tcccgccgcc gttgttgttt tggagcacgg aaagacgatg acggaaaaag agatcgtgga    1560
ttacgtcgcc agtcaagtaa caaccgccaa aaagttgcgc ggaggagttg tgtttgtgga    1620
cgaagtaccg aaaggtctta ccggaaaact cgacgcaaga aaaatcagag agatcctcat    1680
aaaggccaag aagggcggaa agtccaaatt gtaaaaaaaa aaaaaaaaa aaaaaaaaa      1740 aaaaaaaaaa aaaaaaaaaa aaaaaaaaaa aaaaaaaaaa aaaaaaaaaa aaaaaaaaaa    1800
aaaa                                                                 1804
```

<210> SEQ ID NO 23
<211> LENGTH: 1724
<212> TYPE: DNA
<213> ORGANISM: Artificial Sequence
<220> FEATURE:
<223> OTHER INFORMATION: OMEGANpA

<400> SEQUENCE: 23

```
gagtattttt acaacaatta ccaacaacaa caaacaacaa acaacattac aattactatt      60
tacaattaca tatggaagac gccaaaaaca taaagaaagg cccggcgcca ttctatccgc     120
tagaggatgg aaccgctgga gagcaactgc ataaggctat gaagagatac gccctggttc     180
ctggaacaat tgcttttaca gatgcacata tcgaggtgaa catcacgtac gcggaatact     240
tcgaaatgtc cgttcggttg gcagaagcta tgaaacgata tgggctgaat acaaatcaca     300
gaatcgtcgt atgcagtgaa aactctcttc aattctttat gccggtgttg ggcgcgttat     360
ttatcggagt tgcagttgcg cccgcgaacg acatttataa tgaacgtgaa ttgctcaaca     420
gtatgaacat ttcgcagcct accgtagtgt ttgtttccaa aaagggggttg caaaaaattt     480 tgaacgtgca aaaaaaatta ccaataatcc agaaaattat tatcatggat tctaaaacgg     540
attaccaggg atttcagtcg atgtacacgt tcgtcacatc tcatctacct cccggttttta    600 atgaatacga ttttgtacca gagtcctttg atcgtgacaa acaattgca ctgataatga     660 actcctctgg atctactggg ttacctaagg gtgtggccct tccgcataga actgcctgcg     720
tcagattctc gcatgccaga gatcctattt ttggcaatca aatcattccg gatactgcga     780
ttttaagtgt tgttccattc catcacggtt ttggaatgtt tactacactc ggatatttga     840
tatgtggatt tcgagtcgtc ttaatgtata gatttgaaga agagctgttt ttacgatccc     900
ttcaggatta caaaattcaa agtgcgttgc tagtaccaac cctatttttca ttcttcgcca     960 aaagcactct gattgacaaa tacgatttat ctaatttaca cgaaattgct tctgggggcg    1020
cacctctttc gaaagaagtc ggggaagcgg ttgcaaaacg cttccatctt ccagggatac    1080
gacaaggata tgggctcact gagactacat cagctattct gattacaccc gagggggatg    1140
ataaaccggg cgcggtcgt aaagttgttc cattttttga agcgaaggtt gtggatctgg     1200
ataccgggaa aacgctgggc gttaatcaga gaggcgaatt atgtgtcaga ggacctatga    1260
ttatgtccgg ttatgtaaac aatccggaag cgaccaacgc cttgattgac aaggatggat    1320
ggctacattc tggagacata gcttactggg acgaagacga acacttcttc atagttgacc    1380
gcttgaagtc tttaattaaa tacaaaggat accaggtggc ccccgctgaa ttggagtcga    1440
tattgttaca cacccccaac atcttcgacg cgggcgtggc aggtcttccc gacgatgacg    1500
ccggtgaact tcccgccgcc gttgttgttt tggagcacgg aaagacgatg acggaaaaag    1560
agatcgtgga ttacgtcgcc agtcaagtaa caaccgccaa aaagttgcgc ggaggagttg    1620
tgtttgtgga cgaagtaccg aaaggtctta ccggaaaact cgacgcaaga aaaatcagag    1680
```
agatcctcat aaaggccaag aagggcggaa agtccaaatt gtaa           1724

<210> SEQ ID NO 24
<211> LENGTH: 1642
<212> TYPE: DNA
<213> ORGANISM: Artificial Sequence
<220> FEATURE:
<223> OTHER INFORMATION: Luciferase ORF

<400> SEQUENCE: 24

| | |
|---|---|
| atggaagacg ccaaaaacat aaagaaaggc ccggaaccgc tggagagcaa ctgcataagg | 60 |
| ctatgaagag atacgccctg gttcctggaa caattgcttt tacagatgca catatcgagg | 120 |
| tgaacatcac gtacgcggaa tacttcgaaa tgtccgttcg gttggcagaa gctatgaaac | 180 |
| gatatgggct gaatacaaat cacagaatcg tcgtatgcag tgaaaactct cttcaattct | 240 |
| ttatgccggt gttgggcgcg ttatttatcg agttgcagt tgcgcccgcg aacgacattt | 300 |
| ataatgaacg tgaattgctc aacagtatga acatttcgca gcctaccgta gtgtttgttt | 360 |
| ccaaaaaggg gttgcaaaaa attttgaacg tgcaaaaaaa attaccaata atccagaaaa | 420 |
| ttattatcat ggattctaaa acggattacc agggatttca gtcgatgtac acgttcgtca | 480 |
| catctcatct acctcccggt tttaatgaat acgattttgt accagagtcc tttgatcgtg | 540 |
| acaaaacaat tgcactgata atgaactcct ctggatctac tgggttacct aagggtgtgg | 600 |
| cccttccgca tagaactgcc tgcgtcagat tctcgcatgc cagagatcct atttttggca | 660 |
| atcaaatcat tccggatact gcgattttaa gtgttgttcc attccatcac ggttttggaa | 720 |
| tgtttactac actcggatat ttgatatgtg gatttcgagt cgtcttaatg tatagatttg | 780 |
| aagaagagct gtttttacga tcccttcagg attacaaaat tcaaagtgcg ttgctagtac | 840 |
| caaccctatt ttcattcttc gccaaaagca ctctgattga caaatacgat ttatctaatt | 900 |
| tacacgaaat tgcttctggg ggcgcacctc tttcgaaaga agtcggggaa gcggttgcaa | 960 |
| aacgcttcca tcttccaggg atacgacaag gatatgggct cactgagact acatcagcta | 1020 |
| ttctgattac acccgagggg gatgataaac cgggcgcggt cggtaaagtt gttccatttt | 1080 |
| ttgaagcgaa ggttgtggat ctggataccg ggaaaacgct gggcgttaat cagagaggcg | 1140 |
| aattatgtgt cagaggacct atgattatgt ccggttatgt aaacaatccg gaagcgacca | 1200 |
| acgccttgat tgacaaggat ggatggctac attctggaga catagcttac tgggacgaag | 1260 |
| acgaacactt cttcatagtt gaccgcttga agtctttaat taaatacaaa ggataccagg | 1320 |
| tggcccccgc tgaattggag tcgatattgt tacaacaccc caacatcttc gacgcgggcg | 1380 |
| tggcaggtct tcccgacgat gacgccggtg aacttcccgc cgccgttgtt gttttggagc | 1440 |
| acggaaagac gatgacggaa aaagagatcg tggattacgt cgccagtcaa gtaacaaccg | 1500 |
| ccaaaaagtt gcgcggagga gttgtgtttg tggacgaagt accgaaaggt cttaccggaa | 1560 |
| aactcgacgc aagaaaaatc agagagatcc tcataaaggc caagaagggc ggaaagtcca | 1620 |
| aattgtgatc accaaattgt aa | 1642 |

<210> SEQ ID NO 25
<211> LENGTH: 37
<212> TYPE: DNA
<213> ORGANISM: Artificial Sequence
<220> FEATURE:
<223> OTHER INFORMATION: Forward Primer 1

<400> SEQUENCE: 25
ttactattta caattacata tggaagacgc caaaaac           37

<210> SEQ ID NO 26
<211> LENGTH: 37
<212> TYPE: DNA
<213> ORGANISM: Artificial Sequence
<220> FEATURE:
<223> OTHER INFORMATION: Reverse Primer 1

<400> SEQUENCE: 26
agcagccgga tctcagttta caatttggac tttccgc        37

<210> SEQ ID NO 27
<211> LENGTH: 120
<212> TYPE: DNA
<213> ORGANISM: Artificial Sequence
<220> FEATURE:
<223> OTHER INFORMATION: Forward Primer 2

<400> SEQUENCE: 27
acgctgcccg agatctcgat cccgcgaaat taatacgact cactataggg agtattttta        60
caacaattac caacaacaac aaacaacaaa caacattaca attactattt acaattacat       120

<210> SEQ ID NO 28
<211> LENGTH: 70
<212> TYPE: DNA
<213> ORGANISM: Artificial Sequence
<220> FEATURE:
<223> OTHER INFORMATION: Reverse Primer 2

<400> SEQUENCE: 28
tttttttttt tttttttttt tttttttttt tttttttttt tttttttttt gttagcagcc        60
ggatctcagt                                                                70

<210> SEQ ID NO 29
<211> LENGTH: 1843
<212> TYPE: DNA
<213> ORGANISM: Artificial Sequence
<220> FEATURE:
<223> OTHER INFORMATION: Luciferase Expression Construct

<400> SEQUENCE: 29
acgctgcccg agatctcgat cccgcgaaat taatacgact cactataggg agtattttta        60
caacaattac caacaacaac aaacaacaaa caacattaca attactattt acaattacat       120
atggaagacg ccaaaaacat aaagaaaggc ccggcgccat tctatccgct agaggatgga       180
accgctggag agcaactgca taaggctatg aagagatacg ccctggttcc tggaacaatt       240
gcttttacag atgcacatat cgaggtgaac atcacgtacg cggaatactt cgaaatgtcc       300
gttcggttgg cagaagctat gaaacgatat gggctgaata caaatcacag aatcgtcgta       360
tgcagtgaaa actctcttca attctttatg ccggtgttgg gcgcgttatt tatcggagtt       420
gcagttgcgc ccgcgaacga catttataat gaacgtgaat tgctcaacag tatgaacatt       480
tcgcagccta ccgtagtgtt tgtttccaaa aagggggttgc aaaaaatttt gaacgtgcaa       540
aaaaaattac caataatcca gaaaattatt atcatggatt ctaaaacgga ttaccaggga       600
tttcagtcga tgtacacgtt cgtcacatct catctacctc ccggttttaa tgaatacgat       660
tttgtaccag agtcctttga tcgtgacaaa acaattgcac tgataatgaa ctcctctgga       720
tctactgggt tacctaaggg tgtggccctt ccgcatagaa ctgcctgcgt cagattctcg       780
catgccagag atcctatttt tggcaatcaa atcattccgg atactgcgat tttaagtgtt       840

```
gttccattcc atcacggttt tggaatgttt actacactcg gatatttgat atgtggattt    900
cgagtcgtct taatgtatag atttgaagaa gagctgtttt tacgatccct tcaggattac    960
aaaattcaaa gtgcgttgct agtaccaacc ctattttcat tcttcgccaa aagcactctg   1020
attgacaaat acgatttatc taatttacac gaaattgctt ctgggggcgc acctctttcg   1080
aaagaagtcg gggaagcggt tgcaaaacgc ttccatcttc agggatacg acaaggatat    1140 gggctcactg agactacatc agctattctg attacacccg agggggatga taaaccgggc   1200
gcggtcggta agttgttcc attttttgaa gcgaaggttg tggatctgga taccgggaaa   1260
acgctgggcg ttaatcagag aggcgaatta tgtgtcagag gacctatgat tatgtccggt   1320
tatgtaaaca atccggaagc gaccaacgcc ttgattgaca aggatggatg gctacattct   1380
ggagacatag cttactggga cgaagacgaa cacttcttca tagttgaccg cttgaagtct   1440
ttaattaaat acaaaggata ccaggtggcc cccgctgaat tggagtcgat attgttacaa   1500 cacccccaaca tcttcgacgc gggcgtggca ggtcttcccg acgatgacgc cggtgaactt   1560
cccgccgccg ttgttgtttt ggagcacgga aagacgatga cggaaaaaga gatcgtggat   1620
tacgtcgcca gtcaagtaac aaccgccaaa aagttgcgcg gaggagttgt gtttgtggac   1680
gaagtaccga aaggtcttac cggaaaactc gacgcaagaa aaatcagaga gatcctcata   1740
aaggccaaga agggcggaaa gtccaaattg taaactgaga tccggctgct aacaaaaaaa   1800
aaaaaaaaaa aaaaaaaaaa aaaaaaaaaa aaaaaaaaaa aaa                    1843

<210> SEQ ID NO 30
<211> LENGTH: 550
<212> TYPE: PRT
<213> ORGANISM: Artificial Sequence
<220> FEATURE:
<223> OTHER INFORMATION: Luciferase

<400> SEQUENCE: 30

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190
```

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
        210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 31
<211> LENGTH: 954
<212> TYPE: DNA
<213> ORGANISM: Artificial Sequence
<220> FEATURE:
<223> OTHER INFORMATION: GFP (ORF)

<400> SEQUENCE: 31

```
atggagaaaa aaatcactac tccttccacc ccaccaccgc cgtattccag agggactaga      60
tatcttgcgc agcctagtgg caatactagt tctagtgccc taatgcaagg tcaaaaggcc     120
ccccaaaagc cttcacagaa cctagtccct gtcactccct caacaactaa gtcttttaaa     180
aatgcgccag cgccaggatc catggtgagc aagggcgagg agctgttcac cggggtggtg     240
cccatcctgg tcgagctgga cggcgacgta acggccaca  agttcagcgt gcgcggcgag     300
ggcgagggcg atgccaccaa cggcaagctg accctgaagt tcatctgcac caccggcaag     360
ctgcccgtgc cctggcccac cctcgtgacc accctgacct acggcgtgca gtgcttcagc     420
cgctaccccg accacatgaa gcagcacgac ttcttcaagt ccgccatgcc cgaaggctac     480
gtccaggagc gcaccatcac cttcaaggac gacggcacct acaagacccg cgccgaggtg     540
aagttcgagg gcgacaccct ggtgaaccgc atcgagctga agggcatcga cttcaaggag     600
gacggcaaca tcctggggca caagctggag tacaacttca acagccacaa cgtctatatc     660
accgccgaca gcagaagaa  cggcatcaag gccaacttca agatccgcca caacgtggag     720
gacggcagcg tgcagctcgc cgaccactac cagcagaaca cccccatcgg cgacggcccc     780
gtgctgctgc ccgacaacca ctacctgagc acccagtcca agctgagcaa agaccccaac     840
gagaagcgcg atcacatggt cctgctggag ttcgtgaccg ccgccgggat cactcacggc     900
atggacgagc tgtacaagga gctcggcatg gtcaccacc  atcatcatca ttaa           954
```

<210> SEQ ID NO 32
<211> LENGTH: 913
<212> TYPE: DNA
<213> ORGANISM: Artificial Sequence
<220> FEATURE:
<223> OTHER INFORMATION: GFP Expression Construct

<400> SEQUENCE: 32

```
acgctgcccg agatctcgat cccgcgaaat taatacgact cactataggg agtattttta      60
caacaattac caacaacaac aaacaacaaa caacattaca attactattt acaattacat     120
atgagcaaag gtgaagaact gtttaccggc gttgtgccga ttctggtgga actggatggc     180
gatgtgaacg gtcacaaatt cagcgtgcgt ggtgaaggtg aaggcgatgc cacgattggc     240
aaactgacgc tgaaatttat ctgcaccacc ggcaaactgc cggtgccgtg gccgacgctg     300
gtgaccaccc tgacctatgg cgttcagtgt tttagtcgct atccggatca catgaaacgt     360
cacgatttct ttaaatctgc aatgccggaa ggctatgtgc aggaacgtac gattagcttt     420
aaagatgatg gcaaatataa aacgcgcgcc gttgtgaaat ttgaaggcga tacc ctggtg    480
aaccgcattg aactgaaagg cacggatttt aaagaagatg gcaatatcct gggccataaa     540
ctggaataca actttaatag ccataatgtt tatattacgg cggataaaca gaaaaatggc     600
atcaaagcga attttaccgt tcgccataac gttgaagatg gcagtgtgca gctggcagat     660
cattatcagc agaatccccc gattggtgat ggtccggtgc tgctgccgga taatcattat     720
ctgagcacgc agaccgttct gtctaaagat ccgaacgaaa aaggcacgcg ggaccacatg     780
gttctgcacg aatatgtgaa tgcggcaggt attacgtgga gccatccgca gttcgaaaaa     840
taaactgaga tccggctgct aacaaaaaaa aaaaaaaaaa aaaaaaaaaa aaaaaaaaaa     900
aaaaaaaaaa aaa                                                         913
```

<210> SEQ ID NO 33
<211> LENGTH: 317
<212> TYPE: PRT

<213> ORGANISM: Artificial Sequence
<220> FEATURE:
<223> OTHER INFORMATION: GREEN FLUORESCENCE PROTEIN

<400> SEQUENCE: 33

Met Glu Lys Lys Ile Thr Thr Pro Ser Thr Pro Pro Pro Tyr Ser
1               5                   10                  15

Arg Gly Thr Arg Tyr Leu Ala Gln Pro Ser Gly Asn Thr Ser Ser
                20                  25                  30

Ala Leu Met Gln Gly Gln Lys Ala Pro Gln Lys Pro Ser Gln Asn Leu
            35                  40                  45

Val Pro Val Thr Pro Ser Thr Thr Lys Ser Phe Lys Asn Ala Pro Ala
50                      55                      60

Pro Gly Ser Met Val Ser Lys Gly Glu Glu Leu Phe Thr Gly Val Val
65                  70                      75                  80

Pro Ile Leu Val Glu Leu Asp Gly Asp Val Asn Gly His Lys Phe Ser
                85                      90                  95

Val Arg Gly Glu Gly Glu Gly Asp Ala Thr Asn Gly Lys Leu Thr Leu
                100                 105                 110

Lys Phe Ile Cys Thr Thr Gly Lys Leu Pro Val Pro Trp Pro Thr Leu
            115                 120                 125

Val Thr Thr Leu Thr Tyr Gly Val Gln Cys Phe Ser Arg Tyr Pro Asp
130                     135                     140

His Met Lys Gln His Asp Phe Phe Lys Ser Ala Met Pro Glu Gly Tyr
145                 150                 155                 160

Val Gln Glu Arg Thr Ile Thr Phe Lys Asp Asp Gly Thr Tyr Lys Thr
                165                 170                 175

Arg Ala Glu Val Lys Phe Glu Gly Asp Thr Leu Val Asn Arg Ile Glu
            180                 185                 190

Leu Lys Gly Ile Asp Phe Lys Glu Asp Gly Asn Ile Leu Gly His Lys
            195                 200                 205

Leu Glu Tyr Asn Phe Asn Ser His Asn Val Tyr Ile Thr Ala Asp Lys
        210                 215                 220

Gln Lys Asn Gly Ile Lys Ala Asn Phe Lys Ile Arg His Asn Val Glu
225                 230                 235                 240

Asp Gly Ser Val Gln Leu Ala Asp His Tyr Gln Gln Asn Thr Pro Ile
                245                 250                 255

Gly Asp Gly Pro Val Leu Leu Pro Asp Asn His Tyr Leu Ser Thr Gln
            260                 265                 270

Ser Lys Leu Ser Lys Asp Pro Asn Glu Lys Arg Asp His Met Val Leu
        275                 280                 285

Leu Glu Phe Val Thr Ala Ala Gly Ile Thr His Gly Met Asp Glu Leu
    290                 295                 300

Tyr Lys Glu Leu Gly Met Gly His His His His His
305                 310                 315

<210> SEQ ID NO 34
<211> LENGTH: 660
<212> TYPE: DNA
<213> ORGANISM: Artificial Sequence
<220> FEATURE:
<223> OTHER INFORMATION: CAT (ORF)

<400> SEQUENCE: 34
atggaaaaaa aaatcaccgg ctacaccacc gttgacatct ctcagtggca ccgtaaagaa      60
cactttgaag cgttccagtc tgtcgcgcag tgtacctaca accagaccgt tcagctagac     120

```
atcaccgcgt tcctgaaaac cgttaaaaaa aacaaacaca aattctaccc ggcgttcatt      180
cacatcctgg cgcgtctgat gaacgcgcac ccggaatttc gtatggcgat gaaagacggt      240
gaactggtta tctgggactc tgttcacccg tgctacaccg ttttccacga acagaccgaa      300
accttctctt ctctgtggtc tgaataccac gacgacttcc gtcagttcct gcacatctac      360
tctcaggacg ttgcgtgcta cggtgaaaac ctggcgtact cccgaaagg tttcatcgaa       420 aacatgttct tcgtttctgc gaacccgtgg gtttctttca cctctttcga cctgaacgtg      480
gcgaacatgg acaacttctt cgcgccggtt ttcactatgg gtaaatacta cacccagggt      540
gacaaagttc tgatgccgct ggcgatccag gttcaccacg cggtttgcga cggtttccac      600
gttggtcgta tgctgaacga actccagcag tattgcgacg aatggcaggg tggtgcgtaa      660
```

<210> SEQ ID NO 35
<211> LENGTH: 850
<212> TYPE: DNA
<213> ORGANISM: Artificial Sequence
<220> FEATURE:
<223> OTHER INFORMATION: CAT Expression Construct

<400> SEQUENCE: 35

```
acgctgcccg agatctcgat cccgcgaaat taatacgact cactataggg agtatttta       60 caacaattac caacaacaac aaacaacaaa caacattaca attactattt acaattacat      120
atggaaaaaa aaatcaccgg ctacaccacc gttgacatct ctcagtggca ccgtaaagaa      180
cactttgaag cgttccagtc tgtcgcgcag tgtacctaca accagaccgt tcagctagac      240
atcaccgcgt tcctgaaaac cgttaaaaaa aacaaacaca aattctaccc ggcgttcatt      300
cacatcctgg cgcgtctgat gaacgcgcac ccggaatttc gtatggcgat gaaagacggt      360
gaactggtta tctgggactc tgttcacccg tgctacaccg ttttccacga acagaccgaa      420
accttctctt ctctgtggtc tgaataccac gacgacttcc gtcagttcct gcacatctac      480
tctcaggacg ttgcgtgcta cggtgaaaac ctggcgtact cccgaaagg tttcatcgaa       540 aacatgttct tcgtttctgc gaacccgtgg gtttctttca cctctttcga cctgaacgtg      600
gcgaacatgg acaacttctt cgcgccggtt ttcactatgg gtaaatacta cacccagggt      660
gacaaagttc tgatgccgct ggcgatccag gttcaccacg cggtttgcga cggtttccac      720
gttggtcgta tgctgaacga actccagcag tattgcgacg aatggcaggg tggtgcgtaa      780
actgagatcc ggctgctaac aaaaaaaaaa aaaaaaaaaa aaaaaaaaaa aaaaaaaaaa      840
aaaaaaaaaa                                                             850
```

<210> SEQ ID NO 36
<211> LENGTH: 219
<212> TYPE: PRT
<213> ORGANISM: Artificial Sequence
<220> FEATURE:
<223> OTHER INFORMATION: CHLORAMPHENICAL ACETYLTRANSFERASE

<400> SEQUENCE: 36

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
```

```
                   50                  55                  60
Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
                115                 120                 125

Glu Asn Leu Ala Tyr Phe Pro Lys Gly Phe Ile Glu Asn Met Phe Phe
130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
                180                 185                 190

His Ala Val Cys Asp Gly Phe His Val Gly Arg Met Leu Asn Glu Leu
                195                 200                 205

Gln Gln Tyr Cys Asp Glu Trp Gln Gly Gly Ala
    210                 215

<210> SEQ ID NO 37
<211> LENGTH: 723
<212> TYPE: DNA
<213> ORGANISM: Artificial Sequence
<220> FEATURE:
<223> OTHER INFORMATION: Superfolder GFP (ORF)

<400> SEQUENCE: 37
atgagcaaag gtgaagaact gtttaccggc gttgtgccga ttctggtgga actggatggc    60
gatgtgaacg gtcacaaatt cagcgtgcgt ggtgaaggtg aaggcgatgc cacgattggc   120
aaactgacgc tgaaatttat ctgcaccacc ggcaaactgc cggtgccgtg gccgacgctg   180
gtgaccaccc tgacctatgg cgttcagtgt tttagtcgct atccggatca catgaaacgt   240
cacgatttct ttaaatctgc aatgccggaa ggctatgtgc aggaacgtac gattagcttt   300
aaagatgatg gcaaatataa acgcgcgcc gttgtgaaat ttgaaggcga tacccctggtg   360 aaccgcattg aactgaaagg cacggatttt aaagaagatg gcaatatcct gggccataaa   420
ctggaataca actttaatag ccataatgtt tatattacgg cggataaaca gaaaaatggc   480
atcaaagcga atttttaccgt tcgccataac gttgaagatg gcagtgtgca gctggcagat   540
cattatcagc agaatacccc gattggtgat ggtccggtgc tgctgccgga taatcattat   600
ctgagcacgc agaccgttct gtctaaagat ccgaacgaaa aaggcacgcg ggaccacatg   660
gttctgcacg aatatgtgaa tgcggcaggt attacgtgga ccatccgca gttcgaaaaa   720 taa                                                                 723

<210> SEQ ID NO 38
<211> LENGTH: 916
<212> TYPE: DNA
<213> ORGANISM: Artificial Sequence
<220> FEATURE:
<223> OTHER INFORMATION: Superfolder GFP Expression Construct

<400> SEQUENCE: 38
acgctgcccg agatctcgat cccgcgaaat taatacgact cactataggg agtattttta    60
```

```
caacaattac caacaacaac aaacaacaaa caacattaca attactattt acaattaaaa    120
aaaatgagca aaggtgaaga actgtttacc ggcgttgtgc cgattctggt ggaactggat    180
ggcgatgtga acggtcacaa attcagcgtg cgtggtgaag gtgaaggcga tgccacgatt    240
ggcaaactga cgctgaaatt tatctgcacc accggcaaac tgccggtgcc gtggccgacg    300
ctggtgacca ccctgaccta tggcgttcag tgttttagtc gctatccgga tcacatgaaa    360
cgtcacgatt tctttaaatc tgcaatgccg gaaggctatg tgcaggaacg tacgattagc    420
tttaaagatg atggcaaata taaaacgcgc gccgttgtga aatttgaagg cgatacccctg   480 gtgaaccgca ttgaactgaa aggcacggat tttaaagaag atggcaatat cctgggccat    540
aaactggaat acaactttaa tagccataat gtttatatta cggcggataa acagaaaaat    600
ggcatcaaag cgaattttac cgttcgccat aacgttgaag atggcagtgt gcagctggca    660
gatcattatc agcagaatac cccgattggt gatggtccgg tgctgctgcc ggataatcat    720
tatctgagca cgcagaccgt tctgtctaaa gatccgaacg aaaaaggcac gcgggaccac    780
atggttctgc acgaatatgt gaatgcggca ggtattacgt ggagccatcc gcagttcgaa    840
aaataaactg agatccggct gctaacaaaa aaaaaaaaa aaaaaaaaaa aaaaaaaaaa    900
aaaaaaaaaa aaaaaa                                                    916
```

<210> SEQ ID NO 39
<211> LENGTH: 240
<212> TYPE: PRT
<213> ORGANISM: Artificial Sequence
<220> FEATURE:
<223> OTHER INFORMATION: Superfolder GFP

<400> SEQUENCE: 39

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205
```

```
Lys Asp Pro Asn Glu Lys Gly Thr Arg Asp His Met Val Leu His Glu
    210                 215                 220

Tyr Val Asn Ala Ala Gly Ile Thr Trp Ser His Pro Gln Phe Glu Lys
    225                 230                 235                 240
```

```
<210> SEQ ID NO 40
<211> LENGTH: 771
<212> TYPE: DNA
<213> ORGANISM: Artificial Sequence
<220> FEATURE:
<223> OTHER INFORMATION: ANX scFv (ORF)

<400> SEQUENCE: 40
atggctcagg tacagttaca acaatcagga ttagaactcg taaaaccagg tgctagtgtt      60
aaaatctcct gcaaaacaag tggttatact tttacagaat atacgatgca ttgggtaaaa     120
caatctcatg gtaaaagttt agaatggatc ggaggcatca acccaaacaa tggcggcact     180
tcttataatc aaaaatttaa aggcaaagca atccttacag tcgacaaatc ttcatccacc     240
gcctatctcg aattacgtag tttaacatca gaagattcag ccgtttatta ttgcgcacgt     300
gacgatcgtt atccagcttg gtttgcttat tgggggcaag gtaccacagt tacagtatcc     360
tctggcggcg gcggatctgg cggcggcggc tccggtggag gtggttctac tgacatccaa     420
ctgactcaat ctccctcatc cctttctgca tcacttggcg aacgcgtctc gatcacctgt     480
cgcgcatctc aagacatcgg atcaaattta aattggcttc aacaaaaacc tgatggcacg     540
atcaaacgcc ttatttatgc cacctcctct ctcgatagcg gcgtcccgaa acgttttcct     600
ggttctcgta gcggttcaga ctattcattg acaatcagct cactcgaaag cgaagacttt     660
gtagattact attgccttca gtatgccagc agcccaccta catttggcgg aggtacaaaa     720
ttggaaatta acgcgcggc cgcatggagc catccgcagt tcgagaaata a               771
```

```
<210> SEQ ID NO 41
<211> LENGTH: 961
<212> TYPE: DNA
<213> ORGANISM: Artificial Sequence
<220> FEATURE:
<223> OTHER INFORMATION: ANX scFv Expression Construct

<400> SEQUENCE: 41
acgctgcccg agatctcgat cccgcgaaat taatacgact cactataggg agtatttta      60
caacaattac caacaacaac aaacaacaaa caacattaca attactattt acaattacat     120
atggctcagg tacagttaca acaatcagga ttagaactcg taaaaccagg tgctagtgtt     180
aaaatctcct gcaaaacaag tggttatact tttacagaat atacgatgca ttgggtaaaa     240
caatctcatg gtaaaagttt agaatggatc ggaggcatca acccaaacaa tggcggcact     300
tcttataatc aaaaatttaa aggcaaagca atccttacag tcgacaaatc ttcatccacc     360
gcctatctcg aattacgtag tttaacatca gaagattcag ccgtttatta ttgcgcacgt     420
gacgatcgtt atccagcttg gtttgcttat tgggggcaag gtaccacagt tacagtatcc     480
tctggcggcg gcggatctgg cggcggcggc tccggtggag gtggttctac tgacatccaa     540
ctgactcaat ctccctcatc cctttctgca tcacttggcg aacgcgtctc gatcacctgt     600
cgcgcatctc aagacatcgg atcaaattta aattggcttc aacaaaaacc tgatggcacg     660
atcaaacgcc ttatttatgc cacctcctct ctcgatagcg gcgtcccgaa acgttttcct     720
ggttctcgta gcggttcaga ctattcattg acaatcagct cactcgaaag cgaagacttt     780
```

```
gtagattact attgccttca gtatgccagc agcccaccta catttggcgg aggtacaaaa      840
ttggaaatta acgcgcggc cgcatggagc catccgcagt tcgagaaata aactgagatc       900
cggctgctaa caaaaaaaaa aaaaaaaaaa aaaaaaaaaa aaaaaaaaaa aaaaaaaaaa      960
a                                                                      961
```

<210> SEQ ID NO 42
<211> LENGTH: 256
<212> TYPE: PRT
<213> ORGANISM: Artificial Sequence
<220> FEATURE:
<223> OTHER INFORMATION: ANX scFv

<400> SEQUENCE: 42

```
Met Ala Gln Val Gln Leu Gln Gln Ser Gly Leu Glu Leu Val Lys Pro
 1               5                  10                  15

Gly Ala Ser Val Lys Ile Ser Cys Lys Thr Ser Gly Tyr Thr Phe Thr
                20                  25                  30

Glu Tyr Thr Met His Trp Val Lys Gln Ser His Gly Lys Ser Leu Glu
            35                  40                  45

Trp Ile Gly Gly Ile Asn Pro Asn Asn Gly Gly Thr Ser Tyr Asn Gln
 50                  55                  60

Lys Phe Lys Gly Lys Ala Ile Leu Thr Val Asp Lys Ser Ser Ser Thr
 65                  70                  75                  80

Ala Tyr Leu Glu Leu Arg Ser Leu Thr Ser Glu Asp Ser Ala Val Tyr
                85                  90                  95

Tyr Cys Ala Arg Asp Asp Arg Tyr Pro Ala Trp Phe Ala Tyr Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Thr Asp Ile Gln Leu Thr Gln Ser
    130                 135                 140

Pro Ser Ser Leu Ser Ala Ser Leu Gly Glu Arg Val Ser Ile Thr Cys
145                 150                 155                 160

Arg Ala Ser Gln Asp Ile Gly Ser Asn Leu Asn Trp Leu Gln Gln Lys
                165                 170                 175

Pro Asp Gly Thr Ile Lys Arg Leu Ile Tyr Ala Thr Ser Ser Leu Asp
            180                 185                 190

Ser Gly Val Pro Lys Arg Phe Ser Gly Ser Arg Ser Gly Ser Asp Tyr
        195                 200                 205

Ser Leu Thr Ile Ser Ser Leu Glu Ser Glu Asp Phe Val Asp Tyr Tyr
    210                 215                 220

Cys Leu Gln Tyr Ala Ser Ser Pro Pro Thr Phe Gly Gly Gly Thr Lys
225                 230                 235                 240

Leu Glu Ile Lys Arg Ala Ala Ala Trp Ser His Pro Gln Phe Glu Lys
                245                 250                 255
```

<210> SEQ ID NO 43
<211> LENGTH: 780
<212> TYPE: DNA
<213> ORGANISM: Artificial Sequence
<220> FEATURE:
<223> OTHER INFORMATION: BOT scFv (ORF)

<400> SEQUENCE: 43

```
atggctcaag ttcagttaca agaatctggt ggcggtttag ttcaaccagg tggctctctc       60
cgtctctcat gtgccgcatc gggcttcacc tttctgacc attatatgta ctgggtccgt      120
```

```
caagcgcccg gcaaaggact tgaatgggta gcaacaatct ctgatggtgg ctcttatacc    180
tattactctg actcagtcga aggtcgtttt acaacttctc gtgataactc aaaaaatact    240
ctctatttac aaatgaacag cttacgtgcc gaagatactg caatttatta ttgttcccgt    300
tatcgttatg acgacgctat ggattattgg ggccaaggca ctttagtaac agtttcatcc    360
ggtggtggcg gctccggcgg cggtggctct ggcggtggtg gaagtacaga aattgtttta    420
actcagagtc cggcgacatt atcactctcc cccggcgaac gtgctacaat ctcctgtcgt    480
gcctctgaaa gcgtagattc atacggacac tcctttatgc agtggtatca acaaaaaccg    540
ggacaagcac cacgtctctt aatttatcgt gcatcaaact tagaacctgg gattccagcc    600
cgtttcagtg gctctggatc aggtaccgat tttacattaa ccatctctag tttggaacca    660
gaagacttcg cagtttatta ttgccagcaa ggaaatgaag tcccatttac attcggtcaa    720
ggtacaaaag tggaaattaa acgcgcggcc gcatggagcc atccgcagtt cgagaaataa    780
```

<210> SEQ ID NO 44
<211> LENGTH: 970
<212> TYPE: DNA
<213> ORGANISM: Artificial Sequence
<220> FEATURE:
<223> OTHER INFORMATION: BOT scFv Expression Construct

<400> SEQUENCE: 44

```
acgctgcccg agatctcgat cccgcgaaat taatacgact cactataggg agtattttta     60
caacaattac caacaacaac aaacaacaaa caacattaca attactattt acaattacat    120
atggctcaag ttcagttaca agaatctggt ggcggtttag ttcaaccagg tggctctctc    180
cgtctctcat gtgccgcatc gggcttcacc ttttctgacc attatatgta ctgggtccgt    240
caagcgcccg gcaaaggact tgaatgggta gcaacaatct ctgatggtgg ctcttatacc    300
tattactctg actcagtcga aggtcgtttt acaacttctc gtgataactc aaaaaatact    360
ctctatttac aaatgaacag cttacgtgcc gaagatactg caatttatta ttgttcccgt    420
tatcgttatg acgacgctat ggattattgg ggccaaggca ctttagtaac agtttcatcc    480
ggtggtggcg gctccggcgg cggtggctct ggcggtggtg gaagtacaga aattgtttta    540
actcagagtc cggcgacatt atcactctcc cccggcgaac gtgctacaat ctcctgtcgt    600
gcctctgaaa gcgtagattc atacggacac tcctttatgc agtggtatca acaaaaaccg    660
ggacaagcac cacgtctctt aatttatcgt gcatcaaact tagaacctgg gattccagcc    720
cgtttcagtg gctctggatc aggtaccgat tttacattaa ccatctctag tttggaacca    780
gaagacttcg cagtttatta ttgccagcaa ggaaatgaag tcccatttac attcggtcaa    840
ggtacaaaag tggaaattaa acgcgcggcc gcatggagcc atccgcagtt cgagaaataa    900
actgagatcc ggctgctaac aaaaaaaaaa aaaaaaaaaa aaaaaaaaaa aaaaaaaaaa    960
aaaaaaaaaa                                                           970
```

<210> SEQ ID NO 45
<211> LENGTH: 259
<212> TYPE: PRT
<213> ORGANISM: Artificial Sequence
<220> FEATURE:
<223> OTHER INFORMATION: BOT scFv

<400> SEQUENCE: 45

```
Met Ala Gln Val Gln Leu Gln Glu Ser Gly Gly Gly Leu Val Gln Pro
1               5                   10                  15
```

Gly Gly Ser Leu Arg Leu Ser Cys Ala Ala Ser Gly Phe Thr Phe Ser
            20                  25                  30

Asp His Tyr Met Tyr Trp Val Arg Gln Ala Pro Gly Lys Gly Leu Glu
            35                  40                  45

Trp Val Ala Thr Ile Ser Asp Gly Gly Ser Tyr Thr Tyr Tyr Ser Asp
 50                  55                  60

Ser Val Glu Gly Arg Phe Thr Thr Ser Arg Asp Asn Ser Lys Asn Thr
 65                  70                  75                  80

Leu Tyr Leu Gln Met Asn Ser Leu Arg Ala Glu Asp Thr Ala Ile Tyr
                85                  90                  95

Tyr Cys Ser Arg Tyr Arg Tyr Asp Asp Ala Met Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Thr Glu Ile Val Leu Thr Gln Ser Pro
130                 135                 140

Ala Thr Leu Ser Leu Ser Pro Gly Glu Arg Ala Thr Ile Ser Cys Arg
145                 150                 155                 160

Ala Ser Glu Ser Val Asp Ser Tyr Gly His Ser Phe Met Gln Trp Tyr
            165                 170                 175

Gln Gln Lys Pro Gly Gln Ala Pro Arg Leu Leu Ile Tyr Arg Ala Ser
            180                 185                 190

Asn Leu Glu Pro Gly Ile Pro Ala Arg Phe Ser Gly Ser Gly Ser Gly
            195                 200                 205

Thr Asp Phe Thr Leu Thr Ile Ser Ser Leu Glu Pro Glu Asp Phe Ala
        210                 215                 220

Val Tyr Tyr Cys Gln Gln Gly Asn Glu Val Pro Phe Thr Phe Gly Gln
225                 230                 235                 240

Gly Thr Lys Val Glu Ile Lys Arg Ala Ala Ala Trp Ser His Pro Gln
                245                 250                 255

Phe Glu Lys

<210> SEQ ID NO 46
<211> LENGTH: 786
<212> TYPE: DNA
<213> ORGANISM: Artificial Sequence
<220> FEATURE:
<223> OTHER INFORMATION: MS2 scFv (ORF)

<400> SEQUENCE: 46
atggctgaag ttaaattagt agaaagtggt ggtggtttgg taaaacctgg tggatctctt      60
aaactctcgt gcaaagcaag cggctttact ttttcttctt atgctatgtc atgggtccgt     120
caaactcccg aaaaacgctt agaatgggta gcaacaattt caacaggcgg aggctataca     180
tatttcccag attctgttaa agggcgcttt acaatttccc gcgataatgc gaaaaatatc     240
ttatatttac aaatgaaatc cttacgttca gaagacacag ctacgtatta ttgtgctcgt     300
caaggcgact tggtgattg gtacttcgat gtatggggcg caggcacgac agttacagta     360
tcttcaggcg gcggcggttc tggtggcggt ggctccggtg gtggtggaag cacggatgtt     420
gtactgaccc aaactcccct tatctttacca gtctcattag gcgatcaagc aagcatttca     480
tgtcgctctt ctcaatctct tgttcactct aacggcaata cttacttaca ttggtatctt     540
caaaaaccag gccaatctcc taaactcctt atttataaag tttcaaatcg ttttcaggc     600 gtcccagatc gttttttccgg ctccggcagt ggcaccgatt ttaccttaaa aatttctcgt     660

```
gtagaagctg aagacttagg tgtatatttt tgccagcaat caactcacgt tccctggact    720
tttggtggtg gtacgaaatt agaaattaaa gcggccgcat ggagccatcc gcagttcgaa    780
aaataa                                                               786
```

<210> SEQ ID NO 47
<211> LENGTH: 976
<212> TYPE: DNA
<213> ORGANISM: Artificial Sequence
<220> FEATURE:
<223> OTHER INFORMATION: MS2 scFv Expression Construct

<400> SEQUENCE: 47

```
acgctgcccg agatctcgat cccgcgaaat taatacgact cactataggg agtatttta     60 caacaattac caacaacaac aaacaacaaa caacattaca attactattt acaattacat    120
atggctgaag ttaaattagt agaaagtggt ggtggtttgg taaaacctgg tggatctctt    180
aaactctcgt gcaaagcaag cggctttact ttttcttctt atgctatgtc atgggtccgt    240
caaactcccg aaaaacgctt agaatgggta gcaacaattt caacaggcgg aggctataca    300
tatttcccag attctgttaa agggcgcttt acaatttccc gcgataatgc gaaaaatatc    360
ttatatttac aaatgaaatc cttacgttca gaagacacag ctacgtatta ttgtgctcgt    420
caaggcgact ttggtgattg gtacttcgat gtatggggcg caggcacgac agttacagta    480
tcttcaggcg gcggcggttc tggtggcggt ggctccggtg tggtggaag cacggatgtt     540 gtactgaccc aaactccctt atctttacca gtctcattag cgatcaagc aagcatttca      600 tgtcgctctt ctcaatctct tgttcactct aacggcaata cttacttaca ttggtatctt    660
caaaaaccag gccaatctcc taaactcctt atttataaag tttcaaatcg ttttcaggc     720 gtcccagatc gttttttccgg ctccggcagt ggcaccgatt ttaccttaaa aatttctcgt   780
gtagaagctg aagacttagg tgtatatttt tgccagcaat caactcacgt tccctggact    840
tttggtggtg gtacgaaatt agaaattaaa gcggccgcat ggagccatcc gcagttcgaa    900
aaataaactg agatccggct gctaacaaaa aaaaaaaaa aaaaaaaaa aaaaaaaaa       960 aaaaaaaaaa aaaaaa                                                   976
```

<210> SEQ ID NO 48
<211> LENGTH: 261
<212> TYPE: PRT
<213> ORGANISM: Artificial Sequence
<220> FEATURE:
<223> OTHER INFORMATION: MS2 scFv

<400> SEQUENCE: 48

```
Met Ala Glu Val Lys Leu Val Glu Ser Gly Gly Gly Leu Val Lys Pro
1               5                   10                  15

Gly Gly Ser Leu Lys Leu Ser Cys Lys Ala Ser Gly Phe Thr Phe Ser
            20                  25                  30

Ser Tyr Ala Met Ser Trp Val Arg Gln Thr Pro Glu Lys Arg Leu Glu
        35                  40                  45

Trp Val Ala Thr Ile Ser Thr Gly Gly Gly Tyr Thr Tyr Phe Pro Asp
    50                  55                  60

Ser Val Lys Gly Arg Phe Thr Ile Ser Arg Asp Asn Ala Lys Asn Ile
65                  70                  75                  80

Leu Tyr Leu Gln Met Lys Ser Leu Arg Ser Glu Asp Thr Ala Thr Tyr
                85                  90                  95
```

```
Tyr Cys Ala Arg Gln Gly Asp Phe Gly Asp Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Ser Gly Gly Gly Ser Thr Asp Val Val Leu Thr Gln
            130                 135                 140

Thr Pro Leu Ser Leu Pro Val Ser Leu Gly Asp Gln Ala Ser Ile Ser
145                 150                 155                 160

Cys Arg Ser Ser Gln Ser Leu Val His Ser Asn Gly Asn Thr Tyr Leu
                165                 170                 175

His Trp Tyr Leu Gln Lys Pro Gly Gln Ser Pro Lys Leu Leu Ile Tyr
            180                 185                 190

Lys Val Ser Asn Arg Phe Ser Gly Val Pro Asp Arg Phe Ser Gly Ser
            195                 200                 205

Gly Ser Gly Thr Asp Phe Thr Leu Lys Ile Ser Arg Val Glu Ala Glu
        210                 215                 220

Asp Leu Gly Val Tyr Phe Cys Gln Gln Ser Thr His Val Pro Trp Thr
225                 230                 235                 240

Phe Gly Gly Gly Thr Lys Leu Glu Ile Lys Ala Ala Ala Trp Ser His
                245                 250                 255

Pro Gln Phe Glu Lys
        260

<210> SEQ ID NO 49
<211> LENGTH: 786
<212> TYPE: DNA
<213> ORGANISM: Artificial Sequence
<220> FEATURE:
<223> OTHER INFORMATION: MS2-A scFv (ORF)

<400> SEQUENCE: 49
atggctgaag ttaaattagt agaaagtggt ggtggtttgg taaaacctgg tggatctctt      60
aaactctcgt gcaaagcaag cggctttact ttttcttctt atgctatgtc atgggtccgt     120 caaactccg aaaaacgctt agaatgggta gcaacaattt caacaggcgg aggctataca     180
tatttcccag attctgttaa agggcgcttt acaatttccc gcgataatgc gaaaaatgct     240
ttatatttac aaatgaaatc cttacgttca gaagacacag ctacgtatta ttgtgctcgt     300
caaggcgact ttggtgattg gtacttcgat gtatggggcg caggcacgac agttacagta     360
tcttcaggcg gcggcggttc tggtggcggt ggctccggtg gtggtggaag cacggatgtt     420
gtactgaccc aaactccctt atctttacca gtctcattag gcgatcaagc aaccatttca     480
tgtcgctctt ctcaatctct tgttcactct aacggcaata cttacttaca ttggtatctt     540
caaaaaccag gccaatctcc taaactcctt atttataaag tttcaaatcg ttttcaggc     600 gtcccagatc gttttccgg ctccggcagt ggcaccgatt ttaccttaaa aatttctcgt      660
gtagaagctg aagacttagg tgtatatttt tgctttcaat caacttacgt tccctggact    720
tttggtggtg gtacgaaatt agaaattaaa gcggccgcat ggagccatcc gcagttcgaa   780
aaataa                                                                786

<210> SEQ ID NO 50
<211> LENGTH: 976
<212> TYPE: DNA
<213> ORGANISM: Artificial Sequence
<220> FEATURE:
<223> OTHER INFORMATION: MS2-A scFv Expression Construct
```

```
<400> SEQUENCE: 50
acgctgcccg agatctcgat cccgcgaaat taatacgact cactataggg agtattttta 60
caacaattac caacaacaac aaacaacaaa caacattaca attactattt acaattacat 120
atggctgaag ttaaattagt agaaagtggt ggtggtttgg taaaacctgg tggatctctt 180
aaactctcgt gcaaagcaag cggctttact ttttcttctt atgctatgtc atgggtccgt 240
```

```
caaactcccg aaaaacgctt agaatgggta gcaacaattt caacaggcgg aggctataca 300
tatttcccag attctgttaa agggcgcttt acaatttccc gcgataatgc gaaaaatgct 360
ttatatttac aaatgaaatc cttacgttca gaagacacag ctacgtatta ttgtgctcgt 420
caaggcgact ttggtgattg gtacttcgat gtatggggcg caggcacgac agttacagta 480
tcttcaggcg gcggcggttc tggtggcggt ggctccggtg gtggtggaag cacggatgtt 540
gtactgaccc aaactccctt atctttacca gtctcattag gcgatcaagc aaccatttca 600
tgtcgctctt ctcaatctct tgttcactct aacggcaata cttacttaca ttggtatctt 660
caaaaaccag gccaatctcc taaactcctt atttataaag tttcaaatcg tttttcaggc 720
gtcccagatc gtttttccgg ctccggcagt ggcaccgatt ttaccttaaa aatttctcgt 780
gtagaagctg aagacttagg tgtatatttt tgctttcaat caacttacgt tccctggact 840
tttggtggtg gtacgaaatt agaaattaaa gcggccgcat ggagccatcc gcagttcgaa 900
aaataaactg agatccggct gctaacaaaa aaaaaaaaaa aaaaaaaaaa aaaaaaaaaa 960
aaaaaaaaaa aaaaaa 976
```

<210> SEQ ID NO 51
<211> LENGTH: 261
<212> TYPE: PRT
<213> ORGANISM: Artificial Sequence
<220> FEATURE:
<223> OTHER INFORMATION: MS2-A scFv

<400> SEQUENCE: 51

Met Ala Glu Val Lys Leu Val Glu Ser Gly Gly Gly Leu Val Lys Pro
1               5                   10                  15

Gly Gly Ser Leu Lys Leu Ser Cys Lys Ala Ser Gly Phe Thr Phe Ser
            20                  25                  30

Ser Tyr Ala Met Ser Trp Val Arg Gln Thr Pro Glu Lys Arg Leu Glu
        35                  40                  45

Trp Val Ala Thr Ile Ser Thr Gly Gly Gly Tyr Thr Tyr Phe Pro Asp
    50                  55                  60

Ser Val Lys Gly Arg Phe Thr Ile Ser Arg Asp Asn Ala Lys Asn Ala
65                  70                  75                  80

Leu Tyr Leu Gln Met Lys Ser Leu Arg Ser Glu Asp Thr Ala Thr Tyr
                85                  90                  95

Tyr Cys Ala Arg Gln Gly Asp Phe Gly Asp Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Gly Ser Thr Asp Val Val Leu Thr Gln
    130                 135                 140

Thr Pro Leu Ser Leu Pro Val Ser Leu Gly Asp Gln Ala Thr Ile Ser
145                 150                 155                 160

Cys Arg Ser Ser Gln Ser Leu Val His Ser Asn Gly Asn Thr Tyr Leu
                165                 170                 175

-continued

```
His Trp Tyr Leu Gln Lys Pro Gly Gln Ser Pro Lys Leu Leu Ile Tyr
            180                 185                 190
Lys Val Ser Asn Arg Phe Ser Gly Val Pro Asp Arg Phe Ser Gly Ser
        195                 200                 205
Gly Ser Gly Thr Asp Phe Thr Leu Lys Ile Ser Arg Val Glu Ala Glu
    210                 215                 220
Asp Leu Gly Val Tyr Phe Cys Phe Gln Ser Tyr Val Pro Trp Thr
225                 230                 235                 240
Phe Gly Gly Gly Thr Lys Leu Glu Ile Lys Ala Ala Ala Trp Ser His
                245                 250                 255
Pro Gln Phe Glu Lys
            260

<210> SEQ ID NO 52
<211> LENGTH: 762
<212> TYPE: DNA
<213> ORGANISM: Artificial Sequence
<220> FEATURE:
<223> OTHER INFORMATION: 2E2 scFv (ORF)

<400> SEQUENCE: 52
atggctgaag tgcagttggt tgaatcaggt gggggtttag tacagccggg tggtagttta      60
cgtttgtcat gtgcggcatc aggttttatt tttagtagtg attggatgaa ttgggtacgt     120
caagcaccgg gaaaaggatt agaatgggtg gcgaatatta tcaagatggt tcagaaaaa     180 tattatgtgg attcagttaa aggtcgtttt acaatcagcc gtgacaacgc acaaaatagc     240
ttatacttac aaatgaacag tttacgggca gaagacacag cagtatatta ttgtgcaaag     300
gaattagggc cgtgggggca aggacatta gtgacggtga gtagcggggg aggggggcagc     360 ggcggtggtg gttcggagg gggaggttcg acacaggcag tagttattca ggaaagcgca     420
ctcacgacat ctccgggggg gacggttatt ctcacttgcc gcagcagtac aggaacgatt     480
acgacttcta actatgcaaa ttgggtccag aaaaaaccga tcatgtgtt tacgggttta     540 attggggcaa cgagcattcg cgcgccggga gtgccggtac gttttagcgg gtttcttatt     600
ggtggaaagg cagcattaac tattacagga gcgcaaaccg aagatgatgc tatgtattt     660 tgcgcgttat ggtataacac acactatgtt tttggaggtg gcacgaaggt tacagtattg     720
gggcaagcgg ccgcatggag ccatccgcag ttcgagaaat aa                       762

<210> SEQ ID NO 53
<211> LENGTH: 952
<212> TYPE: DNA
<213> ORGANISM: Artificial Sequence
<220> FEATURE:
<223> OTHER INFORMATION: 2E2 scFv Expression Construct

<400> SEQUENCE: 53
acgctgcccg agatctcgat cccgcgaaat taatacgact cactataggg agtattttta      60
caacaattac caacaacaac aaacaacaaa caacattaca attactattt acaattacat     120
atggctgaag tgcagttggt tgaatcaggt gggggtttag tacagccggg tggtagttta     180
cgtttgtcat gtgcggcatc aggttttatt tttagtagtg attggatgaa ttgggtacgt     240
caagcaccgg gaaaaggatt agaatgggtg gcgaatatta tcaagatggt tcagaaaaaa    300
tattatgtgg attcagttaa aggtcgtttt acaatcagcc gtgacaacgc acaaaatagc    360
ttatacttac aaatgaacag tttacgggca gaagacacag cagtatatta ttgtgcaaag    420
gaattagggc cgtgggggca aggacatta gtgacggtga gtagcggggg aggggggcagc    480
```

```
ggcggtggtg gttcgggagg gggaggttcg acacaggcag tagttattca ggaaagcgca      540
ctcacgacat ctccgggggg gacggttatt ctcacttgcc gcagcagtac aggaacgatt      600
acgacttcta actatgcaaa ttgggtccag aaaaaaccga atcatgtgtt tacgggttta      660
attggggcaa cgagcattcg cgcgccggga gtgccggtac gttttagcgg gtttcttatt      720
ggtggaaagg cagcattaac tattacagga gcgcaaaccg aagatgatgc tatgtatttt      780
tgcgcgttat ggtataacac acactatgtt tttggaggtg gcacgaaggt tacagtattg      840
gggcaagcgg ccgcatggag ccatccgcag ttcgagaaat aaactgagat ccggctgcta      900
acaaaaaaaa aaaaaaaaaa aaaaaaaaaa aaaaaaaaaa aaaaaaaaaa aa              952
```

<210> SEQ ID NO 54
<211> LENGTH: 253
<212> TYPE: PRT
<213> ORGANISM: Artificial Sequence
<220> FEATURE:
<223> OTHER INFORMATION: 2E2 scFv

<400> SEQUENCE: 54

```
Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Ile Phe Ser
            20                  25                  30

Ser Asp Trp Met Asn Trp Val Arg Gln Ala Pro Gly Lys Gly Leu Glu
        35                  40                  45

Trp Val Ala Asn Ile Asn Gln Asp Gly Ser Glu Lys Tyr Tyr Val Asp
    50                  55                  60

Ser Val Lys Gly Arg Phe Thr Ile Ser Arg Asp Asn Ala Gln Asn Ser
65                  70                  75                  80

Leu Tyr Leu Gln Met Asn Ser Leu Arg Ala Glu Asp Thr Ala Val Tyr
                85                  90                  95

Tyr Cys Ala Lys Glu Leu Gly Pro Trp Gly Gln Gly Thr Leu Val Thr
            100                 105                 110

Val Ser Ser Gly Gly Gly Gly Ser Gly Gly Gly Ser Gly Gly Gly
        115                 120                 125

Gly Ser Thr Gln Ala Val Val Ile Gln Glu Ser Ala Leu Thr Thr Ser
    130                 135                 140

Pro Gly Gly Thr Val Ile Leu Thr Cys Arg Ser Ser Thr Gly Thr Ile
145                 150                 155                 160

Thr Thr Ser Asn Tyr Ala Asn Trp Val Gln Lys Lys Pro Asn His Val
                165                 170                 175

Phe Thr Gly Leu Ile Gly Ala Thr Ser Ile Arg Ala Pro Gly Val Pro
            180                 185                 190

Val Arg Phe Ser Gly Phe Leu Ile Gly Gly Lys Ala Ala Leu Thr Ile
        195                 200                 205

Thr Gly Ala Gln Thr Glu Asp Asp Ala Met Tyr Phe Cys Ala Leu Trp
    210                 215                 220

Tyr Asn Thr His Tyr Val Phe Gly Gly Gly Thr Lys Val Thr Val Leu
225                 230                 235                 240

Gly Gln Ala Ala Ala Trp Ser His Pro Gln Phe Glu Lys
                245                 250
```

<210> SEQ ID NO 55
<211> LENGTH: 762
<212> TYPE: DNA

<213> ORGANISM: Artificial Sequence
<220> FEATURE:
<223> OTHER INFORMATION: 2E2-3d scFv (ORF)

<400> SEQUENCE: 55

```
atggctgaag tgcagttggt tgaatcaggt gggggtttag tacagccggg tggtagttta      60
cgtttgtcat gtaaggcatc aggttttatt tttagtagtg attggatgaa ttggttccgt     120
caagcaccgg gaaaaggatt agaatgggtg gcgaatatta atcaagatgg ttcagaaaaa     180
tattatgtgg attcagttaa aggtcgtttt acaatcagcc gtgacaacgc acaaaatacc     240
ttatacttac aaatgaacag tttacgggca gaagacacag gagtatatta ttgtgcaaag     300
gaattagggc cgtgggggca aggacatta gtgacggtga gtagcggggg aggggggcagc    360
ggcggtggtg gttcgggagg gggaggttcg acacaggcag tagttactca ggaaagcgca     420
ctcacgacat ctccgggggg gacggttact ctcacttgcc gcagcagtac aggaacgatt     480
acgacttcta actatgcaaa ttgggtccag aaaaaaccga atcatgtgtt tacgggttta     540
attgggggcaa cgagcattcg cgcgccggga gtgccggtac gttttagcgg gtctcttatt    600
ggtggaaagg cagcattaac tattacagga gcgcaaaccg aagatgatgc tatgtatttt     660
tgcgcgttat ggtataacac acactatgtt tttggaggtg gcacgaaggt tacagtattg     720
gggcaagcgg ccgcatggag ccatccgcag ttcgaaaaat aa                         762
```

<210> SEQ ID NO 56
<211> LENGTH: 952
<212> TYPE: DNA
<213> ORGANISM: Artificial Sequence
<220> FEATURE:
<223> OTHER INFORMATION: 2E2-3d scFv Expression Construct

<400> SEQUENCE: 56

```
acgctgcccg agatctcgat cccgcgaaat taatacgact cactataggg agtatttta      60
caacaattac caacaacaac aaacaacaaa caacattaca attactattt acaattacat    120
atggctgaag tgcagttggt tgaatcaggt gggggtttag tacagccggg tggtagttta    180
cgtttgtcat gtaaggcatc aggttttatt tttagtagtg attggatgaa ttggttccgt    240
caagcaccgg gaaaaggatt agaatgggtg gcgaatatta atcaagatgg ttcagaaaaa    300
tattatgtgg attcagttaa aggtcgtttt acaatcagcc gtgacaacgc acaaaatacc    360
ttatacttac aaatgaacag tttacgggca gaagacacag gagtatatta ttgtgcaaag    420
gaattagggc cgtgggggca aggacatta gtgacggtga gtagcggggg aggggggcagc   480
ggcggtggtg gttcgggagg gggaggttcg acacaggcag tagttactca ggaaagcgca    540
ctcacgacat ctccgggggg gacggttact ctcacttgcc gcagcagtac aggaacgatt    600
acgacttcta actatgcaaa ttgggtccag aaaaaaccga atcatgtgtt tacgggttta    660
attgggggcaa cgagcattcg cgcgccggga gtgccggtac gttttagcgg gtctcttatt   720
ggtggaaagg cagcattaac tattacagga gcgcaaaccg aagatgatgc tatgtatttt    780
tgcgcgttat ggtataacac acactatgtt tttggaggtg gcacgaaggt tacagtattg    840
gggcaagcgg ccgcatggag ccatccgcag ttcgaaaaat aaactgagat ccggctgcta    900
acaaaaaaaa aaaaaaaaaa aaaaaaaaaa aaaaaaaaaa aaaaaaaaaa aa             952
```

<210> SEQ ID NO 57
<211> LENGTH: 253
<212> TYPE: PRT
<213> ORGANISM: Artificial Sequence
<220> FEATURE:
<223> OTHER INFORMATION: 2E2-3d scFv

<400> SEQUENCE: 57

Met Ala Glu Val Gln Leu Val Glu Ser Gly Gly Gly Leu Val Gln Pro
1               5                   10                  15

Gly Gly Ser Leu Arg Leu Ser Cys Lys Ala Ser Gly Phe Ile Phe Ser
            20                  25                  30

Ser Asp Trp Met Asn Trp Phe Arg Gln Ala Pro Gly Lys Gly Leu Glu
        35                  40                  45

Trp Val Ala Asn Ile Asn Gln Asp Gly Ser Glu Lys Tyr Tyr Val Asp
    50                  55                  60

Ser Val Lys Gly Arg Phe Thr Ile Ser Arg Asp Asn Ala Gln Asn Thr
65                  70                  75                  80

Leu Tyr Leu Gln Met Asn Ser Leu Arg Ala Glu Asp Thr Gly Val Tyr
                85                  90                  95

Tyr Cys Ala Lys Glu Leu Gly Pro Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Thr Gln Ala Val Val Thr Gln Glu Ser Ala Leu Thr Thr Ser
    130                 135                 140

Pro Gly Gly Thr Val Thr Leu Thr Cys Arg Ser Ser Thr Gly Thr Ile
145                 150                 155                 160

Thr Thr Ser Asn Tyr Ala Asn Trp Val Gln Lys Lys Pro Asn His Val
                165                 170                 175

Phe Thr Gly Leu Ile Gly Ala Thr Ser Ile Arg Ala Pro Gly Val Pro
            180                 185                 190

Val Arg Phe Ser Gly Ser Leu Ile Gly Gly Lys Ala Ala Leu Thr Ile
        195                 200                 205

Thr Gly Ala Gln Thr Glu Asp Asp Ala Met Tyr Phe Cys Ala Leu Trp
    210                 215                 220

Tyr Asn Thr His Tyr Val Phe Gly Gly Gly Thr Lys Val Thr Val Leu
225                 230                 235                 240

Gly Gln Ala Ala Ala Trp Ser His Pro Gln Phe Glu Lys
                245                 250

<210> SEQ ID NO 58
<211> LENGTH: 1518
<212> TYPE: DNA
<213> ORGANISM: Artificial Sequence
<220> FEATURE:
<223> OTHER INFORMATION: HPV16L1 scFv

<400> SEQUENCE: 58
atgagcctgt ggctgcccag cgaggccacc gtgtacctgc ccccgtgcc cgtgagcaag     60 gtggtgagca ccgacgagta cgtggccagg accaacatct actaccacgc cggcaccagc    120
aggctgctgg ccgtgggcca ccctacttc cccatcaaga agcccaacaa caacaagatc     180
ctggtgccca aggtgagcgg cctgcagtac agggtgttca ggatccacct gcccgacccc    240
aacaagttcg gcttccccga caccagcttc tacaaccccg acacccagag gctggtgtgg    300
gcctgcgtgg gcgtggaggt gggcaggggc cagcccctgg gcgtgggcat cagcggccac    360
cccctgctga acaagctgga cgacaccgag aacgccagcg cctacgccgc caacgccggc    420
gtggacaaca gggagtgcat cagcatggac tacaagcaga cccagctgtg cctgatcggc    480

| | |
|---|---|
| tgcaagcccc ccatcggcga gcactggggc aagggcagcc cctgcaccaa cgtggccgtg | 540 |
| aaccccggcg actgccccc cctggagctg atcaacaccg tgatccagga cggcgacatg | 600 |
| gtggacaccg gcttcggcgc catggacttc accaccctgc aggccaacaa gagcgaggtg | 660 |
| cccctggaca tctgcaccag catctgcaag taccccgact acatcaagat ggtgagcgag | 720 |
| ccctacggcg acagcctgtt cttctacctg aggagggagc agatgttcgt gaggcacctg | 780 |
| ttcaacaggg ccggcgccgt gggcgagaac gtgcccgacg acctgtacat caagggcagc | 840 |
| ggcagcaccg ccaacctggc cagcagcaac tacttcccca cccccagcgg cagcatggtg | 900 |
| accagcgacg cccagatctt caacaagccc tactggctgc agagggccca gggccacaac | 960 |
| aacggcatct gctggggcaa ccagctgttc gtgaccgtgg tggacaccac caggagcacc | 1020 |
| aacatgagcc tgtgcgccgc catcagcacc agcgagacca cctacaagaa caccaacttc | 1080 |
| aaggagtacc tgaggcacgg cgaggagtac gacctgcagt tcatcttcca gctgtgcaag | 1140 |
| atcaccctga ccgccgacgt gatgacctac atccacagca tgaacagcac catcctggag | 1200 |
| gactggaact tcggcctgca gccccccccc ggcggcaccc tggaggacac ctacaggttc | 1260 |
| gtgaccagcc aggccatcgc ctgccagaag cacaccccc cgccccaa ggaggacccc | 1320 |
| ctgaagaagt acaccttctg ggaggtgaac ctgaaggaga agttcagcgc cgacctggac | 1380 |
| cagttccccc tgggcaggaa gttcctgctg caggccggcc tgaaggccaa gcccaagttc | 1440 |
| accctgggca gaggaaggc caccccccacc ccagcagca ccagcaccac cgccaagagg | 1500 |
| aagaagagga agctgtga | 1518 |

<210> SEQ ID NO 59
<211> LENGTH: 1708
<212> TYPE: DNA
<213> ORGANISM: Artificial Sequence
<220> FEATURE:
<223> OTHER INFORMATION: HPV16L1 scFv Expression Construct

<400> SEQUENCE: 59

| | |
|---|---|
| acgctgcccg agatctcgat cccgcgaaat taatacgact cactataggg agtatttta | 60 |
| caacaattac caacaacaac aaacaacaaa caacattaca attactattt acaattacat | 120 |
| atgagcctgt ggctgcccag cgaggccacc gtgtacctgc cccccgtgcc cgtgagcaag | 180 |
| gtggtgagca ccgacgagta cgtggccagg accaacatct actaccacgc cggcaccagc | 240 |
| aggctgctgg ccgtgggcca ccctacttc cccatcaaga agcccaacaa caacaagatc | 300 |
| ctggtgccca aggtgagcgg cctgcagtac agggtgttca ggatccacct gccccgacccc | 360 |
| aacaagttcg gcttccccga caccagcttc tacaaccccg acacccagag gctggtgtgg | 420 |
| gcctgcgtgg gcgtggaggt gggcaggggc cagcccctgg gcgtgggcat cagcggccac | 480 |
| cccctgctga caagctgga cgacaccgag aacgccagcg cctacgccgc caacgccggc | 540 |
| gtggacaaca gggagtgcat cagcatggac tacaagcaga cccagctgtg cctgatcggc | 600 |
| tgcaagcccc ccatcggcga gcactggggc aagggcagcc cctgcaccaa cgtggccgtg | 660 |
| aaccccggcg actgccccc cctggagctg atcaacaccg tgatccagga cggcgacatg | 720 |
| gtggacaccg gcttcggcgc catggacttc accaccctgc aggccaacaa gagcgaggtg | 780 |
| cccctggaca tctgcaccag catctgcaag taccccgact acatcaagat ggtgagcgag | 840 |
| ccctacggcg acagcctgtt cttctacctg aggagggagc agatgttcgt gaggcacctg | 900 |
| ttcaacaggg ccggcgccgt gggcgagaac gtgcccgacg acctgtacat caagggcagc | 960 |
| ggcagcaccg ccaacctggc cagcagcaac tacttcccca cccccagcgg cagcatggtg | 1020 |

```
accagcgacg cccagatctt caacaagccc tactggctgc agagggccca gggccacaac    1080
aacggcatct gctggggcaa ccagctgttc gtgaccgtgg tggacaccac caggagcacc    1140
aacatgagcc tgtgcgccgc catcagcacc agcgagacca cctacaagaa caccaacttc    1200
aaggagtacc tgaggcacgg cgaggagtac gacctgcagt tcatcttcca gctgtgcaag    1260
atcaccctga ccgccgacgt gatgacctac atccacagca tgaacagcac catcctggag    1320
gactggaact tcggcctgca gccccccccc ggcggcaccc tggaggacac ctacaggttc    1380
gtgaccagcc aggccatcgc ctgccagaag cacacccccc ccgcccccaa ggaggacccc    1440
ctgaagaagt acaccttctg ggaggtgaac ctgaaggaga gttcagcgc cgacctggac    1500 cagttccccc tgggcaggaa gttcctgctg caggccggcc tgaaggccaa gcccaagttc    1560
accctgggca agaggaaggc caccccccacc accagcagca ccagcaccac cgccaagagg    1620
aagaagagga agctgtgaac tgagatccgg ctgctaacaa aaaaaaaaaa aaaaaaaaaa    1680
aaaaaaaaaa aaaaaaaaaa aaaaaaaa                                       1708
```

<210> SEQ ID NO 60
<211> LENGTH: 505
<212> TYPE: PRT
<213> ORGANISM: Artificial Sequence
<220> FEATURE:
<223> OTHER INFORMATION: HPV16L1 scFv

<400> SEQUENCE: 60

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240
```

```
Pro Tyr Gly Asp Ser Leu Phe Phe Tyr Leu Arg Arg Glu Gln Met Phe
            245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
            290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
            325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
            370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
            405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
            450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505

<210> SEQ ID NO 61
<211> LENGTH: 4366
<212> TYPE: DNA
<213> ORGANISM: Artificial Sequence
<220> FEATURE:
<223> OTHER INFORMATION: pK7LUC

<400> SEQUENCE: 61
tcgacggatc gttccactga gcgtcagacc ccgtagaaaa gatcaaagga tcttcttgag     60
atcctttttt tctgcgcgta atctgctgct tgcaaacaaa aaaaccaccg ctaccagcgg    120
tggtttgttt gccggatcaa gagctaccaa ctcttttttcc gaaggtaact ggcttcagca    180
gagcgcagat accaaatact gtccttctag tgtagccgta gttaggccac cacttcaaga    240
actctgtagc accgcctaca tacctcgctc tgctaatcct gttaccagtg gctgctgcca    300
gtggcgataa gtcgtgtctt accgggttgg actcaagacg atagttaccg gataaggcgc    360
agcggtcggg ctgaacgggg ggttcgtgca cacagcccag cttggagcga acgacctaca    420
ccgaactgag atacctacag cgtgagcatt gagaaagcgc cacgcttccc gaagggagaa    480
aggcggacag gtatccggta agcggcaggg tcggaacagg agagcgcacg agggagcttc    540
```

```
caggggaaa cgcctggtat ctttatagtc ctgtcgggtt tcgccacctc tgacttgagc    600
gtcgatttt gtgatgctcg tcagggggc ggagcctatg gaaaaacgcc agcaacgcgg    660
ccttttacg gttcctggcc ttttgctggc cttttgctca catgttcttt cctgcgttat    720
cccctgattc tgtggataac cgtattaccg cctttgagtg agctgatacc gctcgccgca    780
gccgaacgac cgagcgcagc gagtcagtga gcgaggaagc ggaagaagct cgcacgccaa    840
tacgcaaacc gcctctcccc gcgcgttggc cgattcatta atgcagctgg cacgacaggt    900
ttcccgactg gaaagcgggc agtgagcgca acgcaattaa tgtgagttag ctcactcatt    960
aggcacccca ggctttacac tttatgcttc cggctcgtat gttgtgtgga attgtgagcg   1020
gataacaatt tcacacagga aacagctatg accatgatta cgaattcaga tctcgatccc   1080
gcgaaattaa tacgactcac tatagggaga ccacaacggt ttccctctag aaataatttt   1140
gtttaacttt aagaaggaga tatacatatg gaagacgcca aaaacataaa gaaaggcccg   1200
gcgccattct atccgctaga ggatggaacc gctggagagc aactgcataa ggctatgaag   1260
agatacgccc tggttcctgg aacaattgct tttacagatg cacatatcga ggtgaacatc   1320
acgtacgcgg aatacttcga atgtccgtt cggttggcag aagctatgaa cgatatgggg   1380
ctgaatacaa atcacagaat cgtcgtatgc agtgaaaact ctcttcaatt ctttatgccg   1440
gtgttgggcg cgttatttat cggagttgca gttgcgcccg cgaacgacat ttataatgaa   1500
cgtgaattgc tcaacagtat gaacatttcg cagcctaccg tagtgtttgt ttccaaaaag   1560
gggttgcaaa aaattttgaa cgtgcaaaaa aaattaccaa taatccagaa aattattatc   1620
atggattcta aaacggatta ccagggattt cagtcgatgt acacgttcgt cacatctcat   1680
ctacctcccg gttttaatga atacgatttt gtaccagagt cctttgatcg tgacaaaaca   1740
attgcactga taatgaactc ctctggatct actgggttac ctaagggtgt ggcccttccg   1800
catagaactg cctgcgtcag attctcgcat gccagagatc ctatttttgg caatcaaatc   1860
attccggata ctgcgatttt aagtgttgtt ccattccatc acggttttgg aatgtttact   1920
acactcggat atttgatatg tggatttcga gtcgtcttaa tgtatagatt tgaagaagag   1980
ctgtttttac gatcccttca ggattacaaa attcaaagtg cgttgctagt accaacccta   2040
ttttcattct tcgccaaaag cactctgatt gacaaatacg atttatctaa tttacacgaa   2100
attgcttctg ggggcgcacc tctttcgaaa gaagtcgggg aagcggttgc aaaacgcttc   2160
catcttccag ggatacgaca aggatatggg ctcactgaga ctacatcagc tattctgatt   2220
acacccgagg gggatgataa accgggcgcg gtcggtaaag ttgttccatt ttttgaagcg   2280
aaggttgtgg atctggatac cgggaaaacg ctgggcgtta atcagagagg cgaattatgt   2340
gtcagaggac ctatgattat gtccggttat gtaaacaatc cggaagcgac caacgccttg   2400
attgacaagg atggatggct acattctgga gacatagctt actgggacga agacgaacac   2460
ttcttcatag ttgaccgctt gaagtcttta attaaataca aaggatacca ggtggccccc   2520
gctgaattgg agtcgatatt gttacaacac cccaacatct tcgacgcggg cgtggcaggt   2580
cttcccgacg atgacgccgg tgaacttccc gccgccgttg ttgttttgga gcacggaaag   2640
acgatgacgg aaaagagat cgtggattac gtcgccagtc aagtaacaac cgccaaaaag   2700
ttgcgcggag gagttgtgtt tgtggacgaa gtaccgaaag gtcttaccgg aaaactcgac   2760
gcaagaaaaa tcagagagat cctcataaag gccaagaagg gcggaaagtc caaattgtaa   2820
gtcgaccggc tgctaacaaa gcccgaaagg aagctgagtt ggctgctgcc accgctgagc   2880
```

| | |
|---|---|
| aataactagc ataaccccctt ggggcctcta aacgggtctt gagggggtttt ttgctgaaag | 2940 |
| gaggaactat atccggataa cctcgagctg cagggcatgc aagcttggca ctggccgtcg | 3000 |
| ttttacaacg tcgtgactgg gaaaaccctg gcgttaccca acttaatcgc cttgcagcac | 3060 |
| atccccctttt cgccagctgg cgtaatagcg aagaggcccg caccgatcgc ccttcccaac | 3120 |
| agttgcgcag cctgaatggc gaatgcgatt tattcaacaa agccgccgtc ccgtcaagtc | 3180 |
| agcgtaatgc tctgccagtg ttacaaccaa ttaaccaatt ctgattagaa aaactcatcg | 3240 |
| agcatcaaat gaaactgcaa tttattcata tcaggattat caataccata ttttttgaaaa | 3300 |
| agccgtttct gtaatgaagg agaaaactca ccgaggcagt tccataggat ggcaagatcc | 3360 |
| tggtatcggt ctgcgattcc gactcgtcca acatcaatac aacctattaa tttcccctcg | 3420 |
| tcaaaaataa ggttatcaag tgagaaatca ccatgagtga cgactgaatc cggtgagaat | 3480 |
| ggcaaaagct tatgcatttc tttccagact tgttcaacag gccagccatt acgctcgtca | 3540 |
| tcaaaatcac tcgcatcaac caaaccgtta ttcattcgtg attgcgcctg agcgagacga | 3600 |
| aatacgcgat cgctgttaaa aggacaatta caaacaggaa tcgaatgcaa ccggcgcagg | 3660 |
| aacactgcca gcgcatcaac aatatttttca cctgaatcag gatattcttc taatacctgg | 3720 |
| aatgctgttt tcccggggat cgcagtggtg agtaaccatg catcatcagg agtacggata | 3780 |
| aaatgcttga tggtcggaag aggcataaat tccgtcagcc agtttagtct gaccatctca | 3840 |
| tctgtaacat cattggcaac gctacctttg ccatgtttca gaaacaactc tggcgcatcg | 3900 |
| ggcttcccat acaatcgata gattgtcgca cctgattgcc cgacattatc gcgagcccat | 3960 |
| ttatacccat ataaatcagc atccatgttg gaatttaatc gcggcttcga gcaagacgtt | 4020 |
| tcccgttgaa tatggctcat aacaccccctt gtattactgt ttatgtaagc agacagtttt | 4080 |
| attgttcatg atgatatatt tttatcttgt gcaatgtaac atcagagatt ttgagacaca | 4140 |
| acgtggcttt gttgaataaa tcgaactttt gctgagttga aggatcagat cacgcatctt | 4200 |
| cccgacaacg cagaccgttc cgtggcaaag caaaagttca aaatcaccaa ctggcccacc | 4260 |
| tacaacaaag ctctcatcaa ccgtggctcc ctcactttct ggctggatga tggggcgatt | 4320 |
| caggcctggt atgagtcagc aacaccttct tcacgaggca gacctc | 4366 |

<210> SEQ ID NO 62
<211> LENGTH: 29
<212> TYPE: DNA
<213> ORGANISM: Artificial Sequence
<220> FEATURE:
<223> OTHER INFORMATION: pET23LucA-f

<400> SEQUENCE: 62

| | |
|---|---|
| ggtggtcata tggaagacgc caaaaacat | 29 |

<210> SEQ ID NO 63
<211> LENGTH: 122
<212> TYPE: DNA
<213> ORGANISM: Artificial Sequence
<220> FEATURE:
<223> OTHER INFORMATION: pET23LucA-r

<400> SEQUENCE: 63

| | |
|---|---|
| ggtggtctcg agtttttttt tttttttttt tttttttttt tttttttttt tttttttttt | 60 |
| tttttttttt tttttttttt tttttttttt tttttttttt ttttacaatt tggactttcc | 120 |
| gc | 122 |

<210> SEQ ID NO 64
<211> LENGTH: 3666
<212> TYPE: DNA
<213> ORGANISM: Artificial Sequence
<220> FEATURE:
<223> OTHER INFORMATION: pET23c

<400> SEQUENCE: 64

```
gaatgacttg gttgagtact caccagtcac agaaaagcat cttacggatg gcatgacagt      60
aagagaatta tgcagtgctg ccataaccat gagtgataac actgcggcca acttacttct     120
gacaacgatc ggaggaccga aggagctaac cgcttttttg cacaacatgg gggatcatgt     180
aactcgcctt gatcgttggg aaccggagct gaatgaagcc ataccaaacg acgagcgtga     240
caccacgatg cctgcagcaa tggcaacaac gttgcgcaaa ctattaactg gcgaactact     300
tactctagct tcccggcaac aattaataga ctggatggag gcggataaag ttgcaggacc     360
acttctgcgc tcggcccttc cggctggctg gtttattgct gataaatctg gagccggtga     420
gcgtgggtct cgcggtatca ttgcagcact ggggccagat ggtaagccct cccgtatcgt     480
agttatctac acgacgggga gtcaggcaac tatggatgaa cgaaatagac agatcgctga     540
gataggtgcc tcactgatta agcattggta actgtcagac caagtttact catatatact     600
ttagattgat ttaaaacttc atttttaatt taaaaggatc taggtgaaga tcctttttga     660
taatctcatg accaaaatcc cttaacgtga gttttcgttc cactgagcgt cagaccccgt     720
agaaaagatc aaaggatctt cttgagatcc ttttttttctg cgcgtaatct gctgcttgca     780
aacaaaaaaa ccaccgctac cagcggtggt ttgtttgccg gatcaagagc taccaactct     840
ttttccgaag gtaactggct tcagcagagc gcagatacca atactgtcc ttctagtgta     900 gccgtagtta ggccaccact tcaagaactc tgtagcaccg cctacatacc tcgctctgct     960
aatcctgtta ccagtggctg ctgccagtgg cgataagtcg tgtcttaccg ggttggactc    1020
aagacgatag ttaccggata aggcgcagcg gtcgggctga acggggggtt cgtgcacaca    1080
gcccagcttg gagcgaacga cctacaccga actgagatac ctacagcgtg agctatgaga    1140
aagcgccacg cttcccgaag ggagaaaggc ggacaggtat ccggtaagcg cagggtcgg    1200 aacaggagag cgcacgaggg agcttccagg gggaaacgcc tggtatcttt atagtcctgt    1260
cgggtttcgc cacctctgac ttgagcgtcg atttttgtga tgctcgtcag gggggcggag    1320
cctatggaaa aacgccagca acgcggcctt tttacggttc ctggccttttt gctggccttt    1380 tgctcacatg ttctttcctg cgttatcccc tgattctgtg ataaccgta ttaccgcctt    1440 tgagtgagct gataccgctc gccgcagccg aacgaccgag cgcagcgagt cagtgagcga    1500
ggaagcggaa gagcgcctga tgcggtattt tctccttacg catctgtgcg gtatttcaca    1560
ccgcatatat ggtgcactct cagtacaatc tgctctgatg ccgcatagtt aagccagtat    1620
acactccgct atcgctacgt gactgggtca tggctgcgcc ccgacacccg ccaacacccg    1680
ctgacgcgcc ctgacgggct tgtctgctcc cggcatccgc ttacagacaa gctgtgaccg    1740
tctccgggag ctgcatgtgt cagaggtttt caccgtcatc accgaaacgc gcgaggcagc    1800
tgcggtaaag ctcatcagcg tggtcgtgaa gcgattcaca gatgtctgcc tgttcatccg    1860
cgtccagctc gttgagtttc tccagaagcg ttaatgtctg gcttctgata aagcgggcca    1920
tgttaagggc ggttttttcc tgtttggtca ctgatgcctc cgtgtaaggg ggatttctgt    1980
tcatgggggt aatgataccg atgaaacgag agaggatgct cacgatacgg gttactgatg    2040
atgaacatgc ccggttactg gaacgttgtg agggtaaaca ctggcggta tggatgcggc    2100
```

| | |
|---|---|
| gggaccagag aaaaatcact cagggtcaat gccagcgctt cgttaataca gatgtaggtg | 2160 |
| ttccacaggg tagccagcag catcctgcga tgcagatccg aacataatg gtgcagggcg | 2220 |
| ctgacttccg cgtttccaga ctttacgaaa cacggaaacc gaagaccatt catgttgttg | 2280 |
| ctcaggtcgc agacgttttg cagcagcagt cgcttcacgt tcgctcgcgt atcggtgatt | 2340 |
| cattctgcta accagtaagg caaccccgcc agcctagccg ggtcctcaac gacaggagca | 2400 |
| cgatcatgcg cacccgtggc caggacccaa cgctgcccga gatctcgatc ccgcgaaatt | 2460 |
| aatacgactc actataggga gaccacaacg gtttccctct agaaataatt ttgtttaact | 2520 |
| ttaagaagga gatatacata tggctagcat gactggtgga cagcaaatgg gtcgcggatc | 2580 |
| cgaattcgag ctccgtcgac aagcttgcgg ccgcactcga gcaccaccac caccaccact | 2640 |
| gagatccggc tgctaacaaa gcccgaaagg aagctgagtt ggctgctgcc accgctgagc | 2700 |
| aataactagc ataacccctt ggggcctcta aacgggtctt gaggggtttt tgctgaaag | 2760 |
| gaggaactat atccggattg gcgaatggga cgcgccctgt agcggcgcat taagcgcggc | 2820 |
| gggtgtggtg gttacgcgca gcgtgaccgc tacacttgcc agcgccctag cgcccgctcc | 2880 |
| tttcgctttc ttcccttcct ttctcgccac gttcgccggc tttccccgtc aagctctaaa | 2940 |
| tcgggggctc cctttagggt tccgatttag tgctttacgg cacctcgacc ccaaaaaact | 3000 |
| tgattagggt gatggttcac gtagtgggcc atcgccctga tagacggttt ttcgcccttt | 3060 |
| gacgttggag tccacgttct ttaatagtgg actcttgttc caaactggaa caacactcaa | 3120 |
| ccctatctcg gtctattctt ttgatttata agggattttg ccgatttcgg cctattggtt | 3180 |
| aaaaaatgag ctgatttaac aaaaatttaa cgcgaatttt aacaaaatat taacgtttac | 3240 |
| aatttcaggt ggcacttttc ggggaaatgt gcgcggaacc cctatttgtt tatttttcta | 3300 |
| aatacattca aatatgtatc cgctcatgag acaataaccc tgataaatgc ttcaataata | 3360 |
| ttgaaaaagg aagagtatga gtattcaaca tttccgtgtc gcccttattc ccttttttgc | 3420 |
| ggcattttgc cttcctgttt ttgctcaccc agaaacgctg gtgaaagtaa aagatgctga | 3480 |
| agatcagttg ggtgcacgag tgggttacat cgaactggat ctcaacagcg gtaagatcct | 3540 |
| tgagagtttt cgccccgaag aacgttttcc aatgatgagc acttttaaag ttctgctatg | 3600 |
| tggcgcggta ttatcccgta ttgacgccgg gcaagagcaa ctcggtcgcc gcatacacta | 3660 |
| ttctca | 3666 |

<210> SEQ ID NO 65
<211> LENGTH: 5333
<212> TYPE: DNA
<213> ORGANISM: Artificial Sequence
<220> FEATURE:
<223> OTHER INFORMATION: pET23LucA

<400> SEQUENCE: 65

| | |
|---|---|
| gccagcgccc tagcgcccgc tcctttcgct ttcttccctt cctttctcgc cacgttcgcc | 60 |
| ggctttcccc gtcaagctct aaatcggggg ctccctttag ggttccgatt tagtgcttta | 120 |
| cggcacctcg accccaaaaa acttgattag ggtgatggtt cacgtagtgg gccatcgccc | 180 |
| tgatagacgt tttttcgccc tttgacgttg gagtccacgt tctttaatag tggactcttg | 240 |
| ttccaaactg gaacaacact caaccctatc tcggtctatt cttttgattt ataagggatt | 300 |
| ttgccgattt cggcctattg gttaaaaaat gagctgattt aacaaaaatt taacgcgaat | 360 |
| tttaacaaaa tattaacgtt tacaatttca ggtggcactt tcggggaaa tgtgcgcgga | 420 |
| acccctattt gtttattttt ctaaatacat tcaaatatgt atccgctcat gagacaataa | 480 |

```
ccctgataaa tgcttcaata atattgaaaa aggaagagta tgagtattca acatttccgt    540 gtcgcccttα ttcccttttt tgcggcattt tgccttcctg ttttttgctca cccagaaacg   600 ctggtgaaag taaaagatgc tgaagatcag ttgggtgcac gagtgggtta catcgaactg   660
gatctcaaca gcggtaagat ccttgagagt tttcgcccc gaagaacgttt tccaatgatg    720 agcacttttα aagttctgct atgtggcgcg gtattatccc gtattgacgc cgggcaagag    780
caactcggtc gccgcataca ctattctcag aatgacttgg ttgagtactc accagtcaca   840
gaaaagcatc ttacggatgg catgacagta agagaattat gcagtgctgc cataaccatg   900
agtgataaca ctgcggccaa cttacttctg acaacgatcg gaggaccgaa ggagctaacc   960
gcttttttgc acaacatggg ggatcatgta actcgccttg atcgttggga accggagctg   1020
aatgaagcca taccaaacga cgagcgtgac accacgatgc ctgcagcaat ggcaacaacg   1080
ttgcgcaaac tattaactgg cgaactactt actctagctt cccggcaaca attaatagac   1140
tggatggagg cggataaagt tgcaggacca cttctgcgct cggcccttcc ggctggctgg   1200
tttattgctg ataaatctgg agccggtgag cgtgggtctc gcggtatcat tgcagcactg   1260
gggccagatg gtaagccctc ccgtatcgta gttatctaca cgacggggag tcaggcaact   1320
atggatgaac gaaatagaca gatcgctgag ataggtgcct cactgattaa gcattggtaa   1380
ctgtcagacc aagtttactc atatatactt tagattgatt taaaacttca tttttaattt   1440
aaaaggatct aggtgaagat cctttttgat aatctcatga ccaaaatccc ttaacgtgag   1500
ttttcgttcc actgagcgtc agaccccgta gaaaagatca aaggatcttc ttgagatcct   1560
ttttttctgc gcgtaatctg ctgcttgcaa acaaaaaaac caccgctacc agcggtggtt   1620
tgtttgccgg atcaagagct accaactctt tttccgaagg taactggctt cagcagagcg   1680
cagataccaa atactgtcct tctagtgtag ccgtagttag gccaccactt caagaactct   1740
gtagcaccgc ctacatacct cgctctgcta atcctgttac cagtggctgc tgccagtggc   1800
gataagtcgt gtcttaccgg gttggactca agacgatagt taccggataa ggcgcagcgg   1860
tcgggctgaa cggggggttc gtgcacacag cccagcttgg agcgaacgac ctacaccgaa   1920
ctgagatacc tacagcgtga gctatgagaa agcgccacgc ttcccgaagg gagaaaggcg   1980
gacaggtatc cggtaagcgg cagggtcgga acaggagagc gcacgaggga gcttccaggg   2040
ggaaacgcct ggtatcttta tagtcctgtc gggtttcgcc acctctgact tgagcgtcga   2100
tttttgtgat gctcgtcagg gggcggagc ctatggaaaa acgccagcaa cgcggccttt   2160
ttacggttcc tggccttttg ctggccttttt gctcacatgt tctttcctgc gttatcccct   2220
gattctgtgg ataaccgtat taccgccttt gagtgagctg ataccgctcg ccgcagccga   2280
acgaccgagc gcagcgagtc agtgagcgag gaagcggaag agcgcctgat gcggtatttt   2340
ctccttacgc atctgtgcgg tatttcacac cgcatatatg gtgcactctc agtacaatct   2400
gctctgatgc cgcatagtta agccagtata cactccgcta tcgctacgtg actgggtcat   2460
ggctgcgccc cgacacccgc caacacccgc tgacgcgccc tgacgggctt gtctgctccc   2520
ggcatccgct tacagacaag ctgtgaccgt ctccgggagc tgcatgtgtc agaggttttc   2580
accgtcatca ccgaaacgcg cgaggcagct gcggtaaagc tcatcagcgt ggtcgtgaag   2640
cgattcacag atgtctgcct gttcatccgc gtccagctcg ttgagtttct ccagaagcgt   2700
taatgtctgg cttctgataa agcgggccat gttaagggcg ttttttcct gtttggtcac   2760 tgatgcctcc gtgtaagggg gatttctgtt catgggggta atgataccga tgaaacgaga   2820
```

```
gaggatgctc acgatacggg ttactgatga tgaacatgcc cggttactgg aacgttgtga   2880
gggtaaacaa ctggcggtat ggatgcggcg ggaccagaga aaaatcactc agggtcaatg   2940
ccagcgcttc gttaatacag atgtaggtgt tccacagggt agccagcagc atcctgcgat   3000
gcagatccgg aacataatgg tgcagggcgc tgacttccgc gtttccagac tttacgaaac   3060
acggaaaccg aagaccattc atgttgttgc tcaggtcgca gacgttttgc agcagcagtc   3120
gcttcacgtt cgctcgcgta tcggtgattc attctgctaa ccagtaaggc aaccccgcca   3180
gcctagccgg gtcctcaacg acaggagcac gatcatgcgc acccgtggcc aggacccaac   3240
gctgcccgag atctcgatcc cgcgaaatta atacgactca ctatagggag accacaacgg   3300
tttccctcta gaaataattt tgtttaactt taagaaggag atatacatat ggaagacgcc   3360
aaaaacataa agaaaggccc ggcgccattc tatccgctag aggatggaac cgctggagag   3420
caactgcata aggctatgaa gagatacgcc ctggttcctg aacaattgc ttttacagat    3480
gcacatatcg aggtgaacat cacgtacgcg aatacttcg aaatgtccgt tcggttggca    3540
gaagctatga acgatatgg gctgaataca aatcacagaa tcgtcgtatg cagtgaaaac   3600
tctcttcaat tctttatgcc ggtgttgggc gcgttattta tcggagttgc agttgcgccc   3660
gcgaacgaca tttataatga acgtgaattg ctcaacagta tgaacatttc gcagcctacc   3720
gtagtgtttg tttccaaaaa ggggttgcaa aaaattttga acgtgcaaaa aaaattacca   3780
ataatccaga aaattattat catggattct aaaacggatt accagggatt tcagtcgatg   3840
tacacgttcg tcacatctca tctacctccc ggttttaatg aatacgattt tgtaccagag   3900
tcctttgatc gtgacaaaac aattgcactg ataatgaact cctctggatc tactgggtta   3960
cctaagggtg tggcccttcc gcatagaact gcctgcgtca gattctcgca tgccagagat   4020
cctatttttg gcaatcaaat cattccggat actgcgattt taagtgttgt tccattccat   4080
cacggttttg gaatgtttac tacactcgga tatttgatat gtggatttcg agtcgtctta   4140
atgtatagat ttgaagaaga gctgttttta cgatcccttc aggattacaa aattcaaagt   4200
gcgttgctag taccaaccct attttcattc ttcgccaaaa gcactctgat tgacaaatac   4260
gatttatcta atttcacga aattgcttct ggggcgcac ctctttcgaa agaagtcggg   4320
gaagcggttg caaaacgctt ccatcttcca gggatacgac aaggatatgg gctcactgag   4380
actacatcag ctattctgat tacacccgag gggatgata aaccgggcgc ggtcggtaaa   4440
gttgttccat ttttttgaagc gaaggttgtg gatctggata ccgggaaaac gctgggcgtt   4500
aatcagagag gcgaattatg tgtcagagga cctatgatta tgtccggtta tgtaaacaat   4560
ccggaagcga ccaacgcctt gattgacaag gatggatggc tacattctgg agacatagct   4620
tactgggacg aagacgaaca cttcttcata gttgaccgct tgaagtcttt aattaaatac   4680
aaaggatacc aggtggcccc cgctgaattg gagtcgatat tgttacaaca ccccaacatc   4740
ttcgacgcgg gcgtggcagg tcttcccgac gatgacgccg gtgaacttcc cgccgccgtt   4800
gttgttttgg agcacggaaa gacgatgacg gaaaaagaga tcgtggatta cgtcgccagt   4860
caagtaacaa ccgccaaaaa gttgcgcgga ggagttgtgt ttgtggacga agtaccgaaa   4920
ggtcttaccg gaaaactcga cgcaagaaaa atcagagaga tcctcataaa ggccaagaag   4980
ggcggaaagt ccaaattgta aaaaaaaaa aaaaaaaaaa aaaaaaaaa aaaaaaaaa    5040
aaaaaaaaaa aaaaaaaaa aaaaaaaaa aaaaaaaaaa aaaaaaaaa actcgagcac   5100
caccaccacc accactgaga tccggctgct aacaaagccc gaaaggaagc tgagttggct   5160
gctgccaccg ctgagcaata actagcataa ccccttgggg cctctaaacg ggtcttgagg   5220
```

```
ggtttttttgc tgaaaggagg aactatatcc ggattggcga atgggacgcg ccctgtagcg    5280
gcgcattaag cgcggcgggt gtggtggtta cgcgcagcgt gaccgctaca ctt            5333
```

<210> SEQ ID NO 66
<211> LENGTH: 20
<212> TYPE: DNA
<213> ORGANISM: Artificial Sequence
<220> FEATURE:
<223> OTHER INFORMATION: PolyA-f

<400> SEQUENCE: 66

```
gcccgaaagg aagctgagtt                                                   20
```

<210> SEQ ID NO 67
<211> LENGTH: 45
<212> TYPE: DNA
<213> ORGANISM: Artificial Sequence
<220> FEATURE:
<223> OTHER INFORMATION: PolyA25-r

<400> SEQUENCE: 67

```
tttttttttt tttttttttt tttttgttag cagccggatc tcagt                       45
```

<210> SEQ ID NO 68
<211> LENGTH: 70
<212> TYPE: DNA
<213> ORGANISM: Artificial Sequence
<220> FEATURE:
<223> OTHER INFORMATION: PolyA50-r

<400> SEQUENCE: 68

```
tttttttttt tttttttttt tttttttttt tttttttttt tttttttttt gttagcagcc       60
ggatctcagt                                                              70
```

<210> SEQ ID NO 69
<211> LENGTH: 190
<212> TYPE: DNA
<213> ORGANISM: Artificial Sequence
<220> FEATURE:
<223> OTHER INFORMATION: PolyA170-r

<400> SEQUENCE: 69

```
tttttttttt tttttttttt tttttttttt tttttttttt tttttttttt tttttttttt       60
tttttttttt tttttttttt tttttttttt tttttttttt tttttttttt tttttttttt      120
tttttttttt tttttttttt tttttttttt tttttttttt tttttttttt gttagcagcc      180
ggatctcagt                                                             190
```

<210> SEQ ID NO 70
<211> LENGTH: 39
<212> TYPE: DNA
<213> ORGANISM: Artificial Sequence
<220> FEATURE:
<223> OTHER INFORMATION: TF5UTR-f

<400> SEQUENCE: 70

```
ggtggttcta gagggacgtg aaaattacag tagttactg                              39
```

<210> SEQ ID NO 71
<211> LENGTH: 42
<212> TYPE: DNA
<213> ORGANISM: Artificial Sequence
<220> FEATURE:

<223> OTHER INFORMATION: TF5UTR-r

<400> SEQUENCE: 71
ggtggtcata tgttaaaaaa gtttctcttg atacacctgt tt                              42

<210> SEQ ID NO 72
<211> LENGTH: 26
<212> TYPE: DNA
<213> ORGANISM: Artificial Sequence
<220> FEATURE:
<223> OTHER INFORMATION: HAP270-f

<400> SEQUENCE: 72
taaaccccag ttttatatcg tatatg                                               26

<210> SEQ ID NO 73
<211> LENGTH: 22
<212> TYPE: DNA
<213> ORGANISM: Artificial Sequence
<220> FEATURE:
<223> OTHER INFORMATION: HAP270-r

<400> SEQUENCE: 73
tctagaggga aaccgttgtg gt                                                   22

<210> SEQ ID NO 74
<211> LENGTH: 33
<212> TYPE: DNA
<213> ORGANISM: Artificial Sequence
<220> FEATURE:
<223> OTHER INFORMATION: YAP1-f

<400> SEQUENCE: 74
ggtggttcta gatagtaacc agccctagct gtt                                       33

<210> SEQ ID NO 75
<211> LENGTH: 36
<212> TYPE: DNA
<213> ORGANISM: Artificial Sequence
<220> FEATURE:
<223> OTHER INFORMATION: YAP1-r

<400> SEQUENCE: 75
ggtggtcata tgggtttaag aaacaacttt tccttc                                    36

<210> SEQ ID NO 76
<211> LENGTH: 5521
<212> TYPE: DNA
<213> ORGANISM: Artificial Sequence
<220> FEATURE:
<223> OTHER INFORMATION: pET23TFIIDLucA

<400> SEQUENCE: 76
ttccgattta gtgctttacg gcacctcgac cccaaaaaac ttgattaggg tgatggttca          60
cgtagtgggc catcgccctg atagacggtt tttcgccctt tgacgttgga gtccacgttc         120
tttaatagtg gactcttgtt ccaaactgga acaacactca accctatctc ggtctattct         180
tttgatttat aagggatttt gccgatttcg gcctattggt taaaaaatga gctgatttaa         240
caaaaattta acgcgaattt taacaaaata ttaacgttta caatttcagg tggcactttt         300
cggggaaatg tgcgcggaac ccctatttgt ttatttttct aaatacattc aaatatgtat         360
ccgctcatga gacaataacc ctgataaatg cttcaataat attgaaaaag gaagagtatg         420
agtattcaac atttccgtgt cgcccttatt ccctttttg cggcattttg ccttcctgtt          480

```
tttgctcacc cagaaacgct ggtgaaagta aaagatgctg aagatcagtt gggtgcacga    540
gtgggttaca tcgaactgga tctcaacagc ggtaagatcc ttgagagttt tcgccccgaa    600
gaacgttttc caatgatgag cacttttaaa gttctgctat gtggcgcggt attatcccgt    660
attgacgccg ggcaagagca actcggtcgc cgcatacact attctcagaa tgacttggtt    720
gagtactcac cagtcacaga aaagcatctt acggatggca tgacagtaag agaattatgc    780
agtgctgcca taaccatgag tgataacact gcggccaact tacttctgac aacgatcgga    840
ggaccgaagg agctaaccgc ttttttgcac aacatggggg atcatgtaac tcgccttgat    900
cgttgggaac cggagctgaa tgaagccata ccaaacgacg agcgtgacac cacgatgcct    960
gcagcaatgg caacaacgtt gcgcaaacta ttaactggcg aactacttac tctagcttcc   1020
cggcaacaat taatagactg gatggaggcg gataaagttg caggaccact tctgcgctcg   1080
gcccttccgg ctggctggtt tattgctgat aaatctggag ccggtgagcg tgggtctcgc   1140
ggtatcattg cagcactggg gccagatggt aagccctccc gtatcgtagt tatctacacg   1200
acggggagtc aggcaactat ggatgaacga atagacaga tcgctgagat aggtgcctca   1260
ctgattaagc attggtaact gtcagaccaa gtttactcat atatacttta gattgattta   1320
aaacttcatt tttaatttaa aaggatctag gtgaagatcc ttttttgataa tctcatgacc   1380 aaaatccctt aacgtgagtt ttcgttccac tgagcgtcag accccgtaga aaagatcaaa   1440
ggatcttctt gagatccttt ttttctgcgc gtaatctgct gcttgcaaac aaaaaaacca   1500
ccgctaccag cggtggtttg tttgccggat caagagctac caactctttt tccgaaggta   1560
actggcttca gcagagcgca gataccaaat actgtccttc tagtgtagcc gtagttaggc   1620
caccacttca agaactctgt agcaccgcct acatacctcg ctctgctaat cctgttacca   1680
gtggctgctg ccagtggcga taagtcgtgt cttaccgggt tggactcaag acgatagtta   1740
ccggataagg cgcagcggtc gggctgaacg gggggttcgt gcacacagcc cagcttggag   1800
cgaacgacct acaccgaact gagatacccta cagcgtgagc tatgagaaag cgccacgctt   1860
cccgaaggga aaaggcgga caggtatccg gtaagcggca gggtcggaac aggagagcgc   1920
acgagggagc ttccaggggg aaacgcctgg tatctttata gtcctgtcgg gtttcgccac   1980
ctctgacttg agcgtcgatt tttgtgatgc tcgtcagggg ggcggagcct atggaaaaac   2040
gccagcaacg cggccttttt acggttcctg gccttttgct ggccttttgc tcacatgttc   2100
tttcctgcgt tatcccctga ttctgtggat aaccgtatta ccgcctttga gtgagctgat   2160
accgctcgcc gcagccgaac gaccgagcgc agcgagtcag tgagcgagga gcggaagag   2220 cgcctgatgc ggtattttct ccttacgcat ctgtgcggta tttcacaccg catatatggt   2280
gcactctcag tacaatctgc tctgatgccg catagttaag ccagtataca ctccgctatc   2340
gctacgtgac tgggtcatgg ctgcgccccg acacccgcca acacccgctg acgcgccctg   2400
acgggcttgt ctgctcccgg catccgctta cagacaagct gtgaccgtct ccgggagctg   2460
catgtgtcag aggttttcac cgtcatcacc gaaacgcgcg aggcagctgc ggtaaagctc   2520
atcagcgtgg tcgtgaagcg attcacagat gtctgcctgt tcatccgcgt ccagctcgtt   2580
gagtttctcc agaagcgtta atgtctggct tctgataaag cgggccatgt taagggcggt   2640 ttttcctgt ttggtcactg atgcctccgt gtaaggggga tttctgttca tgggggtaat   2700
gataccgatg aaacgagaga ggatgctcac gatacgggtt actgatgatg aacatgcccg   2760
gttactggaa cgttgtgagg gtaaacaact ggcggtatgg atgcggcggg accagagaaa   2820
```

```
aatcactcag ggtcaatgcc agcgcttcgt taatacagat gtaggtgttc cacagggtag    2880
ccagcagcat cctgcgatgc agatccggaa cataatggtg cagggcgctg acttccgcgt    2940
ttccagactt tacgaaacac ggaaaccgaa gaccattcat gttgttgctc aggtcgcaga    3000
cgttttgcag cagcagtcgc ttcacgttcg ctcgcgtatc ggtgattcat tctgctaacc    3060
agtaaggcaa ccccgccagc ctagccgggt cctcaacgac aggagcacga tcatgcgcac    3120
ccgtggccag gacccaacgc tgcccgagat ctcgatcccg cgaaattaat acgactcact    3180
atagggagac cacaacggtt tccctctaga tcgatgcggc cgcgaattcg ggacgtgaaa    3240
attacagtag ttactgtttt ttttggacta taagatcggg ggaagataaa cacataagaa    3300
ataaaacgac tactagttag actgctctgc ggaagaagca aggaagtaaa ggctgcattt    3360
tattttcttt ttctagtcca acataaacag gtgtatcaag agaaactttt ttaagagctc    3420
gtcgacggat ccatatggaa gacgccaaaa acataaagaa aggcccggcg ccattctatc    3480
cgctagagga tggaaccgct ggagagcaac tgcataaggc tatgaagaga tacgccctgg    3540
ttcctggaac aattgctttt acagatgcac atatcgaggt gaacatcacg tacgcggaat    3600
acttcgaaat gtccgttcgg ttggcagaag ctatgaaacg atatgggctg aatacaaatc    3660
acagaatcgt cgtatgcagt gaaaactctc ttcaattctt tatgccggtg ttgggcgcgt    3720
tatttatcgg agttgcagtt gcgcccgcga acgacattta taatgaacgt gaattgctca    3780
acagtatgaa catttcgcag cctaccgtag tgtttgtttc caaaaggggg ttgcaaaaaa    3840
ttttgaacgt gcaaaaaaaa ttaccaataa tccagaaaat tattatcatg gattctaaaa    3900
cggattacca gggatttcag tcgatgtaca cgttcgtcac atctcatcta cctcccggtt    3960
ttaatgaata cgattttgta ccagagtcct ttgatcgtga caaaacaatt gcactgataa    4020
tgaactcctc tggatctact gggttaccta agggtgtggc ccttccgcat agaactgcct    4080
gcgtcagatt ctcgcatgcc agagatccta ttttggcaa tcaaatcatt ccggatactg    4140
cgattttaag tgttgttcca ttccatcacg gttttggaat gtttactaca ctcggatatt    4200
tgatatgtgg atttcgagtc gtcttaatgt atagatttga agaagagctg ttttttacgat    4260
cccttcagga ttacaaaatt caaagtgcgt tgctagtacc aaccctattt tcattcttcg    4320
ccaaaagcac tctgattgac aaatacgatt tatctaattt acacgaaatt gcttctgggg    4380
gcgcacctct ttcgaaagaa gtcggggaag cggttgcaaa acgcttccat cttccaggga    4440
tacgacaagg atatgggctc actgagacta catcagctat tctgattaca cccgaggggg    4500
atgataaacc gggcgcggtc ggtaaagttg ttccattttt tgaagcgaag gttgtggatc    4560
tggataccgg gaaaacgctg ggcgttaatc agagaggcga attatgtgtc agaggaccta    4620
tgattatgtc cggttatgta aacaatccgg aagcgaccaa cgccttgatt gacaaggatg    4680
gatggctaca ttctggagac atagcttact gggacgaaga cgaacacttc ttcatagttg    4740
accgcttgaa gtctttaatt aaatacaaag gataccaggt ggccccccgct gaattggagt    4800
cgatattgtt acaacacccc aacatcttcg acgcgggcgt ggcaggtctt cccgacgatg    4860
acgccggtga acttcccgcc gccgttgttg ttttggagca cggaaagacg atgacggaaa    4920
aagagatcgt ggattacgtc gccagtcaag taacaaccgc caaaaagttg gcggaggag    4980
ttgtgtttgt ggacgaagta ccgaaaggtc ttaccggaaa actcgacgca agaaaaatca    5040
gagagatcct cataaaggcc aagaagggcg gaaagtccaa attgtaaaaa aaaaaaaaaa    5100
aaaaaaaaaa aaaaaaaaaa aaaaaaaaaa aaaaaaaaaa aaaaaaaaaa aaaaaaaaaa    5160
aaaaaaaaaa aaaaaactc gagcaccacc accaccacca ctgagatccg gctgctaaca    5220
```

```
aagcccgaaa ggaagctgag ttggctgctg ccaccgctga gcaataacta gcataacccc      5280
ttggggcctc taaacgggtc ttgaggggtt ttttgctgaa aggaggaact atatccggat      5340
tggcgaatgg gacgcgccct gtagcggcgc attaagcgcg gcgggtgtgg tggttacgcg      5400
cagcgtgacc gctacacttg ccagcgccct agcgcccgct cctttcgctt tcttcccttc      5460
ctttctcgcc acgttcgccg gctttccccg tcaagctcta atcggggc tcccctttagg      5520 g                                                                     5521

<210> SEQ ID NO 77
<211> LENGTH: 5560
<212> TYPE: DNA
<213> ORGANISM: Artificial Sequence
<220> FEATURE:
<223> OTHER INFORMATION: pET23HAP270LucA

<400> SEQUENCE: 77
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
ctttctcgcc acgttcgccg gctttccccg tcaagctcta atcggggc tcccctttagg       180 gttccgattt agtgctttac ggcacctcga ccccaaaaaa cttgattagg gtgatggttc       240
acgtagtggg ccatcgccct gatagacggt ttttcgccct tgacgttgg agtccacgtt       300 ctttaatagt ggactcttgt tccaaactgg aacaacactc aaccctatct cggtctattc       360
ttttgattta tagggatttt gccgatttc ggcctattgg ttaaaaaatg agctgattta       420
acaaaaattt aacgcgaatt ttaacaaaat attaacgttt acaatttcag gtggcacttt       480
tcggggaaat gtgcgcggaa cccctatttg tttatttttc taaatacatt caaatatgta       540
tccgctcatg agacaataac cctgataaat gcttcaataa tattgaaaaa ggaagagtat       600
gagtattcaa catttccgtg tcgcccttat tcccttttt gcggcatttt gccttcctgt       660
ttttgctcac ccagaaacgc tggtgaaagt aaaagatgct gaagatcagt tgggtgcacg       720
agtgggttac atcgaactgg atctcaacag cggtaagatc cttgagagtt ttcgccccga       780
agaacgtttt ccaatgatga gcacttttaa agttctgcta tgtggcgcgg tattatcccg       840
tattgacgcc gggcaagagc aactcggtcg ccgcatacac tattctcaga atgacttggt       900
tgagtactca ccagtcacag aaaagcatct tacggatggc atgacagtaa gagaattatg       960
cagtgctgcc ataaccatga gtgataacac tgcggccaac ttacttctga caacgatcgg      1020
aggaccgaag gagctaaccg cttttttgca acatggggg atcatgtaa ctcgccttga      1080 tcgttgggaa ccggagctga atgaagccat accaaacgac gagcgtgaca ccacgatgcc      1140
tgcagcaatg gcaacaacgt tgcgcaaact attaactggc gaactactta ctctagcttc      1200
ccggcaacaa ttaatagact ggatggaggc ggataaagtt gcaggaccac ttctgcgctc      1260
ggcccttccg gctggctggt ttattgctga taaatctgga gccggtgagc gtgggtctcg      1320
cggtatcatt gcagcactgg ggccagatgg taagccctcc cgtatcgtag ttatctacac      1380
gacggggagt caggcaacta tggatgaacg aaatagacag atcgctgaga taggtgcctc      1440
actgattaag cattggtaac tgtcagacca agtttactca tatatacttt agattgattt      1500
aaaacttcat ttttaattta aaaggatcta ggtgaagatc ctttttgata atctcatgac      1560
caaaatccct taacgtgagt tttcgttcca ctgagcgtca gacccccgtag aaaagatcaa      1620 aggatcttct tgagatcctt ttttttctgcg cgtaatctgc tgcttgcaaa caaaaaaacc      1680
```

-continued

```
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag ataaacccca gttttatatc gtatatgcta    3420
tctacaggtc cactttacac ttaataatat aaaaatacta ctataaagga accagaaaaa    3480
taaaaagggg tcattattta tttgagcaga tcattatcaa acgcatagga agagaaaaaa    3540
cacagtttta ttttttttcc acacatattt attggtctcc tagtacatca aagagcattt    3600
taatgggttg ctgatttgtt ttacctacat tttctagtac aaaaaaaaaa caaaaaaaga    3660
catatggaag acgccaaaaa cataaagaaa ggcccggtgc cattctatcc gctagaggat    3720
ggaaccgctg gagagcaact gcataaggct atgaagagat acgccctggt tcctggaaca    3780
attgctttta cagatgcaca tatcgaggtg aacatcacgt acgcggaata cttcgaaatg    3840
tccgttcggt tggcagaagc tatgaaacga tatgggctga atacaaatca cagaatcgtc    3900
gtatgcagtg aaaactctct tcaattcttt atgccggtgt tgggcgcgtt atttatcgga    3960
gttgcagttg cgcccgcgaa cgacatttat aatgaacgtg aattgctcaa cagtatgaac    4020
atttcgcagc ctaccgtagt gtttgtttcc aaaaagggt tgcaaaaaat tttgaacgtg    4080
```

```
caaaaaaaat taccaataat ccagaaaatt attatcatgg attctaaaac ggattaccag    4140
ggatttcagt cgatgtacac gttcgtcaca tctcatctac ctcccggttt taatgaatac    4200
gattttgtac cagagtcctt tgatcgtgac aaaacaattg cactgataat gaactcctct    4260
ggatctactg ggttacctaa gggtgtggcc cttccgcata gaactgcctg cgtcagattc    4320
tcgcatgcca gagatcctat ttttggcaat caaatcattc cggatactgc gattttaagt    4380
gttgttccat tccatcacgg ttttggaatg tttactacac tcggatattt gatatgtgga    4440
tttcgagtcg tcttaatgta tagatttgaa gaagagctgt ttttacgatc ccttcaggat    4500
tacaaaattc aaagtgcgtt gctagtacca accctatttt cattcttcgc caaaagcact    4560
ctgattgaca aatacgattt atctaattta cacgaaattg cttctggggg cgcacctctt    4620
tcgaaagaag tcggggaagc ggttgcaaaa cgcttccatc ttccaggat acgacaagga    4680 tatgggctca ctgagactac atcagctatt ctgattacac ccgaggggga tgataaaccg    4740
ggcgcggtcg gtaaagttgt tccatttttt gaagcgaagg ttgtggatct ggataccggg    4800
aaaacgctgg gcgttaatca gagaggcgaa ttatgtgtca gaggacctat gattatgtcc    4860
ggttatgtaa acaatccgga agcgaccaac gccttgattg acaaggatgg atggctacat    4920
tctggagaca tagcttactg ggacgaagac gaacacttct tcatagttga ccgcttgaag    4980
tctttaatta aatacaaagg ataccaggtg gcccccgctg aattggagtc gatattgtta    5040
caacacccca acatcttcga cgcgggcgtg gcaggtcttc ccgacgatga cgccggtgaa    5100
cttcccgccg ccgttgttgt tttggagcac ggaaagacga tgacgaaaaa agagatcgtg    5160
gattacgtcg ccagtcaagt aacaaccgcg aaaaagttgc gcggaggagt tgtgtttgtg    5220
gacgaagtac cgaaaggtct taccggaaaa ctcgacgcaa gaaaaatcag agagatcctc    5280
ataaaggcca agaagggcgg aaagtccaaa ttgtaaaaaa aaaaaaaaaa aaaaaaaaaa    5340
aaaaaaaaaa aaaaaaaaaa aaaaaaaaaa aaaaaaaaaa aaaaaaaaaa aaaaaaaaaa    5400
aactcgagca ccaccaccac caccactgag atccggctgc taacaaagcc cgaaaggaag    5460
ctgagttggc tgctgccacc gctgagcaat aactagcata accccttggg gcctctaaac    5520
gggtcttgag gggttttgct aaaggagaaa actaacctat                         5560
```

<210> SEQ ID NO 78
<211> LENGTH: 5662
<212> TYPE: DNA
<213> ORGANISM: Artificial Sequence
<220> FEATURE:
<223> OTHER INFORMATION: pET23YAP1LucA

<400> SEQUENCE: 78

```
ttccgattta gtgctttacg gcacctcgac cccaaaaaac ttgattaggg tgatggttca      60
cgtagtgggc catcgccctg atagacggtt tttcgccctt tgacgttgga gtccacgttc     120
tttaatagtg gactcttgtt ccaaactgga acaacactca accctatctc ggtctattct     180
tttgatttat aagggatttt gccgatttcg gcctattggt taaaaaatga gctgatttaa     240
caaaaattta acgcgaattt taacaaaata ttaacgttta caatttcagg tggcactttt     300
cggggaaatg tgcgcggaac ccctatttgt ttatttttct aaatacattc aaatatgtat     360
ccgctcatga gacaataacc ctgataaatg cttcaataat attgaaaaag gaagagtatg     420
agtattcaac atttccgtgt cgcccttatt cccttttttg cggcattttg ccttcctgtt     480
tttgctcacc cagaaacgct ggtgaaagta aaagatgctg aagatcagtt gggtgcacga     540
```

```
gtgggttaca tcgaactgga tctcaacagc ggtaagatcc ttgagagttt tcgccccgaa     600
gaacgttttc caatgatgag cacttttaaa gttctgctat gtggcgcggt attatcccgt     660
attgacgccg ggcaagagca actcggtcgc cgcatacact attctcagaa tgacttggtt     720
gagtactcac cagtcacaga aaagcatctt acggatggca tgacagtaag agaattatgc     780
agtgctgcca taaccatgag tgataacact gcggccaact tacttctgac aacgatcgga     840
ggaccgaagg agctaaccgc ttttttgcac aacatggggg atcatgtaac tcgccttgat     900
cgttgggaac cggagctgaa tgaagccata ccaaacgacg agcgtgacac cacgatgcct     960
gcagcaatgg caacaacgtt gcgcaaacta ttaactggcg aactacttac tctagcttcc    1020
cggcaacaat taatagactg gatggaggcg gataaagttg caggaccact tctgcgctcg    1080
gcccttccgg ctggctggtt tattgctgat aaatctggag ccggtgagcg tgggtctcgc    1140
ggtatcattg cagcactggg gccagatggt aagccctccc gtatcgtagt tatctacacg    1200
acggggagtc aggcaactat ggatgaacga aatagacaga tcgctgagat aggtgcctca    1260
ctgattaagc attggtaact gtcagaccaa gtttactcat atatacttta gattgattta    1320
aaacttcatt tttaatttaa aaggatctag gtgaagatcc tttttgataa tctcatgacc    1380
aaaatccctt aacgtgagtt ttcgttccac tgagcgtcag accccgtaga aaagatcaaa    1440
ggatcttctt gagatccttt ttttctgcgc gtaatctgct gcttgcaaac aaaaaaacca    1500
ccgctaccag cggtggtttg tttgccggat caagagctac caactctttt tccgaaggta    1560
actggcttca gcagagcgca gataccaaat actgtccttc tagtgtagcc gtagttaggc    1620
caccacttca agaactctgt agcaccgcct acatacctcg ctctgctaat cctgttacca    1680
gtggctgctg ccagtggcga taagtcgtgt cttaccgggt tggactcaag acgatagtta    1740
ccggataagg cgcagcggtc gggctgaacg gggggttcgt gcacacagcc cagcttggag    1800
cgaacgacct acaccgaact gagatacccta cagcgtgagc tatgagaaag cgccacgctt    1860
cccgaaggga gaaaggcgga caggtatccg gtaagcggca gggtcggaac aggagagcgc    1920
acgagggagc ttccaggggg aaacgcctgg tatctttata gtcctgtcgg gtttcgccac    1980
ctctgacttg agcgtcgatt tttgtgatgc tcgtcagggg ggcggagcct atggaaaaac    2040
gccagcaacg cggccttttt acggttcctg gccttttgct ggccttttgc tcacatgttc    2100
tttcctgcgt tatcccctga ttctgtggat aaccgtatta ccgcctttga gtgagctgat    2160
accgctcgcc gcagccgaac gaccgagcgc agcgagtcag tgagcgagga agcggaagag    2220
cgcctgatgc ggtattttct ccttacgcat ctgtgcggta tttcacaccg catatatggt    2280
gcactctcag tacaatctgc tctgatgccg catagttaag ccagtataca ctccgctatc    2340
gctacgtgac tgggtcatgg ctgcgccccg acacccgcca cacccgctg acgcgccctg    2400 acgggcttgt ctgctcccgg catccgctta cagacaagct gtgaccgtct ccgggagctg    2460
catgtgtcag aggttttcac cgtcatcacc gaaacgcgcg aggcagctgc ggtaaagctc    2520
atcagcgtgg tcgtgaagcg attcacagat gtctgcctgt tcatccgcgt ccagctcgtt    2580
gagtttctcc agaagcgtta atgtctggct tctgataaag cgggccatgt taagggcggt    2640
tttttcctgt ttggtcactg atgcctccgt gtaaggggga tttctgttca tgggggtaat    2700
gataccgatg aaacgagaga ggatgctcac gatacgggtt actgatgatg aacatgcccg    2760
gttactggaa cgttgtgagg gtaaacaact ggcggtatgg atgcggcggg accagagaaa    2820
aatcactcag ggtcaatgcc agcgcttcgt taatacagat gtaggtgttc cacagggtag    2880
ccagcagcat cctgcgatgc agatccggaa cataatggtg cagggcgctg acttccgcgt    2940
```

```
ttccagactt tacgaaacac ggaaaccgaa gaccattcat gttgttgctc aggtcgcaga    3000
cgttttgcag cagcagtcgc ttcacgttcg ctcgcgtatc ggtgattcat tctgctaacc    3060
agtaaggcaa ccccgccagc ctagccgggt cctcaacgac aggagcacga tcatgcgcac    3120
ccgtggccag gacccaacgc tgcccgagat ctcgatcccg cgaaattaat acgactcact    3180
atagggagac cacaacggtt ccctctaga tagtaaccag ccctagctgt ttggttgatt     3240
tgacctaggt tactcttttc tttttctggg tgcgggtaac aatttgggcc ccgcaaagcg    3300
ccgtctttgt catgggaacc ggaaaccctc cgatgaagag taggagggtg gcaactgatg    3360
gatgcgtaag gtcttaagag atacatttgc ttaatagtct tccgtttacc gattaagcac    3420
agtacccttta cgttatatat aggattggtg tttagctttt tttcctgagc ccctggttga   3480
cttgtgcatg aacacgagcc attttagtt tgtttaaggg aagttttttg ccacccaaaa     3540
cgtttaaaga aggaaaagtt gtttcttaaa cccatatgga agacgccaaa aacataaaga    3600
aaggcccggc gccattctat ccgctagagg atggaaccgc tggagagcaa ctgcataagg    3660
ctatgaagag atacgccctg gttcctggaa caattgcttt tacagatgca catatcgagg    3720
tgaacatcac gtacgcggaa tacttcgaaa tgtccgttcg gttggcagaa gctatgaaac    3780
gatatgggct gaatacaaat cacagaatcg tcgtatgcag tgaaaactct cttcaattct    3840
ttatgccggt gttgggcgcg ttatttatcg gagttgcagt tgcgcccgcg aacgacattt    3900
ataatgaacg tgaattgctc aacagtatga acatttcgca gcctaccgta gtgtttgttt    3960
ccaaaaaggg gttgcaaaaa attttgaacg tgcaaaaaaa attaccaata atccagaaaa    4020
ttattatcat ggattctaaa acggattacc agggatttca gtcgatgtac acgttcgtca    4080
catctcatct acctcccggt tttaatgaat acgattttgt accagagtcc tttgatcgtg    4140
acaaaacaat tgcactgata atgaactcct ctggatctac tgggttacct aagggtgtgg    4200
cccttccgca tagaactgcc tgcgtcagat tctcgcatgc cagagatcct atttttggca    4260
atcaaatcat tccggatact gcgattttaa gtgttgttcc attccatcac ggttttggaa    4320
tgtttactac actcggatat ttgatatgtg gatttcgagt cgtcttaatg tatagatttg    4380
aagaagagct gtttttacga tcccttcagg attacaaaat tcaaagtgcg ttgctagtac    4440
caaccctatt ttcattcttc gccaaaagca ctctgattga caaatacgat ttatctaatt    4500
tacacgaaat gcttctgggg gcgcacctc tttcgaaaga agtcgggaa gcggttgcaa      4560
aacgcttcca tcttccaggg atacgacaag gatatgggct cactgagact acatcagcta    4620
ttctgattac acccgagggg gatgataaac cgggcgcggt cggtaaagtt gttccatttt    4680
ttgaagcgaa ggttgtggat ctggataccg ggaaaacgct gggcgttaat cagagaggcg    4740
aattatgtgt cagaggacct atgattatgt ccggttatgt aaacaatccg gaagcgacca    4800
acgccttgat tgacaaggat ggatggctac attctggaga catagcttac tgggacgaag    4860
acgaacactt cttcatagtt gaccgcttga agtctttaat taaatacaaa ggataccagg    4920
tggcccccgc tgaattggag tcgatattgt tacaacaccc caacatcttc gacgcgggcg    4980
tggcaggtct tcccgacgat gacgccggtg aacttcccgc cgccgttgtt gttttggagc    5040
acggaaagac gatgacggaa aaagagatcg tggattacgt cgccagtcaa gtaacaaccg    5100
ccaaaaagtt gcgcggagga gttgtgtttg tggacgaagt accgaaaggt cttaccggaa    5160
aactcgacga agaaaaatc agagagatcc tcataaaggc caagaagggc ggaaagtcca    5220
aattgtaaaa aaaaaaaaaa aaaaaaaaaa aaaaaaaaaa aaaaaaaaaa aaaaaaaaaa    5280
```

```
aaaaaaaaaa aaaaaaaaaa aaaaaaaaaa aaaaaaaact cgagcaccac caccaccacc    5340
actgagatcc ggctgctaac aaagcccgaa aggaagctga gttggctgct gccaccgctg    5400
agcaataact agcataaccc cttggggcct ctaaacgggt cttgaggggt ttttgctga     5460 aaggaggaac tatatccgga ttggcgaatg ggacgcgccc tgtagcggcg cattaagcgc    5520
ggcgggtgtg gtggttacgc gcagcgtgac cgctacactt gccagcgccc tagcgcccgc    5580
tcctttcgct ttcttccctt cctttctcgc cacgttcgcc ggctttcccc gtcaagctct    5640
aaatcggggg ctccctttag gg                                             5662
```

<210> SEQ ID NO 79
<211> LENGTH: 527
<212> TYPE: DNA
<213> ORGANISM: Artificial Sequence
<220> FEATURE:
<223> OTHER INFORMATION: 5' UTR of p150 gene

<400> SEQUENCE: 79

```
cccagttcga tcctgggcga atcattttt ttgaaaatta cattaataag gcttttttca      60
atatctctgg aacaacgttt gtttctactt actaatagct ttaaggaccc tcttggacat    120
catgatggca gacttccatc gtagtgggat gatcatatga tgggcgctat cctcatcgcg    180
actcgataac gacgtgagaa acgattttt tttttcttt tcaccgtatt tttgtgcgtc     240 cttttcaat tatagctttt ttttatttt tttttttctc gtactgtttc actgacaaaa     300
gttttttttc aagaaaaatt ttcgatgccg cgttctctgt gtgcaacgga tggatggtag    360
atggaatttc aatatgttgc ttgaaatttt accaatcttg atattgtgat aatttactta    420
attatgattc ttcctcttcc cttcaatttc ttaaagcttc ttactttact ccttcttgct    480
cataaataag caaggtaaga ggacaactgt aattacctat tacaata                  527
```

<210> SEQ ID NO 80
<211> LENGTH: 32
<212> TYPE: DNA
<213> ORGANISM: Artificial Sequence
<220> FEATURE:
<223> OTHER INFORMATION: P150-f

<400> SEQUENCE: 80

```
ggtggttcta gacccagttc gatcctgggc ga                                   32
```

<210> SEQ ID NO 81
<211> LENGTH: 42
<212> TYPE: DNA
<213> ORGANISM: Artificial Sequence
<220> FEATURE:
<223> OTHER INFORMATION: P150-r

<400> SEQUENCE: 81

```
ggtggtggat cctattgtaa taggtaatta cagttgtcct ct                        42
```

<210> SEQ ID NO 82
<211> LENGTH: 65
<212> TYPE: DNA
<213> ORGANISM: Artificial Sequence
<220> FEATURE:
<223> OTHER INFORMATION: OMEGA sequence (65nt) from TMV

<400> SEQUENCE: 82

```
tattttaca acaattacca acaacaacaa acaacaaaca acattacaat tactatttac     60
aatta                                                                 65
```

<210> SEQ ID NO 83
<211> LENGTH: 25
<212> TYPE: DNA
<213> ORGANISM: Artificial Sequence
<220> FEATURE:
<223> OTHER INFORMATION: Primer Sf-f

<400> SEQUENCE: 83
catatggaag acgccaaaaa cataa                                              25

<210> SEQ ID NO 84
<211> LENGTH: 87
<212> TYPE: DNA
<213> ORGANISM: Artificial Sequence
<220> FEATURE:
<223> OTHER INFORMATION: OMEGA-R

<400> SEQUENCE: 84
taattgtaaa tagtaattgt aatgttgttt gttgtttgtt gttgttggta attgttgtaa        60
aaatactccc tatagtgagt cgtatta                                            87

<210> SEQ ID NO 85
<211> LENGTH: 44
<212> TYPE: DNA
<213> ORGANISM: Artificial Sequence
<220> FEATURE:
<223> OTHER INFORMATION: 5'-UTR of polyhedrin gene

<400> SEQUENCE: 85 tattttatt ctttcgtaaa aaattagaa aataaaata taaa                            44

<210> SEQ ID NO 86
<211> LENGTH: 66
<212> TYPE: DNA
<213> ORGANISM: Artificial Sequence
<220> FEATURE:
<223> OTHER INFORMATION: Polyhedrin-r

<400> SEQUENCE: 86
tttatatttt attttctaa ttttttacg aaagaataaa aatactccct atagtgagtc          60
gtatta                                                                   66

<210> SEQ ID NO 87
<211> LENGTH: 64
<212> TYPE: DNA
<213> ORGANISM: Artificial Sequence
<220> FEATURE:
<223> OTHER INFORMATION: 5'-end poly(A)64

<400> SEQUENCE: 87
aaaaaaaaaa aaaaaaaaaa aaaaaaaaaa aaaaaaaaaa aaaaaaaaaa aaaaaaaaaa        60
aaaa                                                                     64

<210> SEQ ID NO 88
<211> LENGTH: 86
<212> TYPE: DNA
<213> ORGANISM: Artificial Sequence
<220> FEATURE:
<223> OTHER INFORMATION: PolyA64-r

<400> SEQUENCE: 88
tttttttttt tttttttttt tttttttttt tttttttttt tttttttttt tttttttttt        60

```
ttttctccct atagtgagtc gtatta                                      86
```

<210> SEQ ID NO 89
<211> LENGTH: 143
<212> TYPE: DNA
<213> ORGANISM: Artificial Sequence
<220> FEATURE:
<223> OTHER INFORMATION: 5'-UTR fragment from tobacco etch virus (TEV)
      (Accession number: NC_001555)

<400> SEQUENCE: 89

```
aaataacaaa tctcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gca                                          143
```

<210> SEQ ID NO 90
<211> LENGTH: 163
<212> TYPE: DNA
<213> ORGANISM: Artificial Sequence
<220> FEATURE:
<223> OTHER INFORMATION: oligo TEV-r

<400> SEQUENCE: 90

```
tgctatcgtt cgtaaatggt gaaattttc agaaaattgc ttttgcttta aagaaatga     60 tttaaattgc tgcaatagaa gtagaatgct tgattgcttg agattcgttt gttttgtata  120
tgttgtgttg agatttgtta tttccctata gtgagtcgta tta                    163
```

<210> SEQ ID NO 91
<211> LENGTH: 65
<212> TYPE: DNA
<213> ORGANISM: Artificial Sequence
<220> FEATURE:
<223> OTHER INFORMATION: 5'-UTR fragment from Crucifer tobamovirus
      (CfTbm) genome (Accession number: NC_003355.1)

<400> SEQUENCE: 91

```
atttaaatta ttgcaacaac aacaacaatt acaataataa caaacaaaat acaaacaaca    60
acaac                                                               65
```

<210> SEQ ID NO 92
<211> LENGTH: 86
<212> TYPE: DNA
<213> ORGANISM: Artificial Sequence
<220> FEATURE:
<223> OTHER INFORMATION: CfTbm-r

<400> SEQUENCE: 92

```
gttgttgttg tttgtatttt gtttgttatt attgtaattg ttgttgttgt tgcasataat    60
ttaaatccct atagtgagtc gtatta                                         86
```

<210> SEQ ID NO 93
<211> LENGTH: 192
<212> TYPE: DNA
<213> ORGANISM: Artificial Sequence
<220> FEATURE:
<223> OTHER INFORMATION: IRES sequence of the cricket paralysis virus
      (CrPV) intergenic region (IGR)

<400> SEQUENCE: 93

```
aaagcaaaaa tgtgatcttg cttgtaaata caatttgag aggttaataa attacaagta     60
gtgctatttt tgtatttagg ttagctattt agctttacgt tccaggatgc ctagtggcag   120
```

-continued

```
cccccacaata tccaggaagc cctctctgcg gttttttcaga ttaggtagtc gaaaaaccta    180
agaaatttac ct                                                         192

<210> SEQ ID NO 94
<211> LENGTH: 5505
<212> TYPE: DNA
<213> ORGANISM: Artificial Sequence
<220> FEATURE:
<223> OTHER INFORMATION: plasmid pSalI-IGR

<400> SEQUENCE: 94
gccagcgccc tagcgcccgc tcctttcgct ttcttccctt cctttctcgc cacgttcgcc    60
ggctttcccc gtcaagctct aaatcggggg ctccctttag ggttccgatt tagtgcttta   120
cggcacctcg accccaaaaa acttgattag ggtgatggtt cacgtagtgg gccatcgccc   180
tgatagacgg ttttttcgccc tttgacgttg gagtccacgt tctttaatag tggactcttg   240
ttccaaactg gaacaacact caaccctatc tcggtctatt cttttgattt ataagggatt   300
ttgccgattt cggcctattg gttaaaaaat gagctgattt aacaaaaatt taacgcgaat   360
tttaacaaaa tattaacgtt tacaatttca ggtggcactt ttcggggaaa tgtgcgcgga   420 accccctattt gtttattttt ctaaatacat tcaaatatgt atccgctcat gagacaataa   480
ccctgataaa tgcttcaata atattgaaaa aggaagagta tgagtattca acatttccgt   540
gtcgccctta ttcccttttt tgcggcattt tgccttcctg ttttttgctca cccagaaacg   600 ctggtgaaag taaaagatgc tgaagatcag ttgggtgcac gagtgggtta catcgaactg   660
gatctcaaca gcggtaagat ccttgagagt tttcgccccg aagaacgttt tccaatgatg   720
agcactttta aagttctgct atgtggcgcg gtattatccc gtattgacgc cgggcaagag   780
caactcggtc gccgcataca ctattctcag aatgacttgg ttgagtactc accagtcaca   840
gaaaagcatc ttacggatgg catgacagta agagaattat gcagtgctgc cataaccatg   900
agtgataaca ctgcggccaa cttacttctg acaacgatcg gaggaccgaa ggagctaacc   960
gcttttttgc acaacatggg ggatcatgta actcgccttg atcgttggga accggagctg  1020
aatgaagcca taccaaacga cgagcgtgac accacgatgc ctgcagcaat ggcaacaacg  1080
ttgcgcaaac tattaactgg cgaactactt actctagctt cccggcaaca attaatagac  1140
tggatggagg cggataaagt tgcaggacca cttctgcgct cggcccttcc ggctggctgg  1200
tttattgctg ataaatctgg agccggtgag cgtgggtctc gcggtatcat tgcagcactg  1260
gggccagatg gtaagccctc ccgtatcgta gttatctaca cgacggggag tcaggcaact  1320
atggatgaac gaaatagaca gatcgctgag ataggtgcct cactgattaa gcattggtaa  1380
ctgtcagacc aagtttactc atatatactt tagattgatt taaaacttca ttttttaattt  1440 aaaaggatct aggtgaagat cctttttgat aatctcatga ccaaaatccc ttaacgtgag  1500
ttttcgttcc actgagcgtc agaccccgta gaaaagatca aaggatcttc ttgagatcct  1560
ttttttctgc gcgtaatctg ctgcttgcaa acaaaaaaac caccgctacc agcggtggtt  1620
tgtttgccgg atcaagagct accaactctt tttccgaagg taactggctt cagcagagcg  1680
cagataccaa atactgtcct tctagtgtag ccgtagttag gccaccactt caagaactct  1740
gtagcaccgc ctacatacct cgctctgcta atcctgttac cagtggctgc tgccagtggc  1800
gataagtcgt gtcttaccgg gttggactca agacgatagt taccggataa ggcgcagcgg  1860
tcgggctgaa cggggggttc gtgcacacag cccagcttgg agcgaacgac ctacaccgaa  1920
ctgagatacc tacagcgtga gctatgagaa agcgccacgc ttcccgaagg gagaaaggcg  1980
```

```
gacaggtatc cggtaagcgg cagggtcgga acaggagagc gcacgaggga gcttccaggg    2040
ggaaacgcct ggtatcttta tagtcctgtc gggtttcgcc acctctgact tgagcgtcga    2100
tttttgtgat gctcgtcagg ggggcggagc ctatggaaaa acgccagcaa cgcggccttt    2160
ttacggttcc tggccttttg ctggcctttt gctcacatgt tctttcctgc gttatcccct    2220
gattctgtgg ataaccgtat taccgccttt gagtgagctg ataccgctcg ccgcagccga    2280
acgaccgagc gcagcgagtc agtgagcgag gaagcggaag agcgcctgat gcggtatttt    2340
ctccttacgc atctgtgcgg tatttcacac cgcatatatg gtgcactctc agtacaatct    2400
gctctgatgc cgcatagtta agccagtata cactccgcta tcgctacgtg actgggtcat    2460
ggctgcgccc cgacacccgc caacacccgc tgacgcgccc tgacgggctt gtctgctccc    2520
ggcatccgct tacagacaag ctgtgaccgt ctccggagc tgcatgtgtc agaggttttc    2580
accgtcatca ccgaaacgcg cgaggcagct gcggtaaagc tcatcagcgt ggtcgtgaag    2640
cgattcacag atgtctgcct gttcatccgc gtccagctcg ttgagtttct ccagaagcgt    2700
taatgtctgg cttctgataa agcgggccat gttaagggcg gttttttcct gtttggtcac    2760
tgatgcctcc gtgtaagggg gatttctgtt catgggggta atgataccga tgaaacgaga    2820
gaggatgctc acgatacggg ttactgatga tgaacatgcc cggttactgg aacgttgtga    2880
gggtaaacaa ctggcggtat ggatgcggcg ggaccagaga aaaatcactc agggtcaatg    2940
ccagcgcttc gttaatacag atgtaggtgt tccacagggt agccagcagc atcctgcgat    3000
gcagatccgg aacataatgg tgcagggcgc tgacttccgc gtttccagac tttacgaaac    3060
acggaaaccg aagaccattc atgttgttgc tcaggtcgca gacgttttgc agcagcagtc    3120
gcttcacgtt cgctcgcgta tcggtgattc attctgctaa ccagtaaggc aaccccgcca    3180
gcctagccgg gtcctcaacg acaggagcac gatcatgcgc acccgtggcc aggacccaac    3240
gctgcccgag atctcgatcc cgcgaaatta atacgactca ctatagggag accacaacgg    3300
tttccctcta gagcaaaaat gtgatcttgc ttgtaaatac aattttgaga ggttaataaa    3360
ttacaagtag tgctattttt gtatttaggt tagctattta gctttacgtt ccaggatgcc    3420
tagtggcagc cccacaatat ccaggaagcc ctctctgcgg ttttcagat taggtagtcg    3480
aaaaacctaa gaaatttacc tgctacattt caagattcat atggaagacg ccaaaaacat    3540
aaagaaaggc ccggcgccat tctatccgct agaggatgga accgctggag agcaactgca    3600
taaggctatg aagagatacg ccctggttcc tggaacaatt gcttttacag atgcacatat    3660
cgaggtgaac atcacgtacg cggaatactt cgaaatgtcc gttcggttgg cagaagctat    3720
gaaacgatat gggctgaata caaatcacag aatcgtcgta tgcagtgaaa actctcttca    3780
attctttatg ccggtgttgg gcgcgttatt tatcggagtt gcagttgcgc ccgcgaacga    3840
catttataat gaacgtgaat tgctcaacag tatgaacatt tcgcagccta ccgtagtgtt    3900
tgtttccaaa aaggggttgc aaaaaatttt gaacgtgcaa aaaaaattac caataatcca    3960
gaaaattatt atcatggatt ctaaaacgga ttaccaggga tttcagtcga tgtacacgtt    4020
cgtcacatct catctacctc ccggttttaa tgaatacgat tttgtaccag agtcctttga    4080
tcgtgacaaa acaattgcac tgataatgaa ctcctctgga tctactgggt tacctaaggg    4140
tgtggccctt ccgcatagaa ctgcctgcgt cagattctcg catgccagag atcctatttt    4200
tggcaatcaa atcattccgg atactgcgat tttaagtgtt gttccattcc atcacggttt    4260
tggaatgttt actacactcg gatatttgat atgtggattt cgagtcgtct taatgtatag    4320
```

```
atttgaagaa gagctgtttt tacgatccct tcaggattac aaaattcaaa gtgcgttgct    4380
agtaccaacc ctattttcat tcttcgccaa aagcactctg attgacaaat acgatttatc    4440
taatttacac gaaattgctt ctgggggcgc acctctttcg aaagaagtcg gggaagcggt    4500
tgcaaaacgc ttccatcttc cagggatacg acaaggatat gggctcactg agactacatc    4560
agctattctg attacacccg aggggatga taaaccgggc gcggtcggta agttgttcc     4620 attttttgaa gcgaaggttg tggatctgga taccgggaaa acgctgggcg ttaatcagag    4680
aggcgaatta tgtgtcagag gacctatgat tatgtccggt tatgtaaaca atccggaagc    4740
gaccaacgcc ttgattgaca aggatggatg gctacattct ggagacatag cttactggga    4800
cgaagacgaa cacttcttca tagttgaccg cttgaagtct ttaattaaat acaaaggata    4860
ccaggtggcc cccgctgaat tggagtcgat attgttacaa cacccaacaa tcttcgacgc    4920
gggcgtggca ggtcttcccg acgatgacgc cggtgaactt cccgccgccg ttgttgtttt    4980
ggagcacgga aagacgatga cggaaaaaga gatcgtggat tacgtcgcca gtcaagtaac    5040
aaccgccaaa aagttgcgcg gaggagttgt gtttgtggac gaagtaccga aaggtcttac    5100
cggaaaactc gacgcaagaa aaatcagaga gatcctcata aaggccaaga agggcggaaa    5160
gtccaaattg taaaaaaaaa aaaaaaaaa aaaaaaaaaa aaaaaaaaa aaaaaaaaa     5220 aaaaaaaaaa aaaaaaaaaa aaaaaaaaa aaaaaaaaaa aaactcgagc accaccaca    5280 ccaccactga gatccggctg ctaacaaagc ccgaaaggaa gctgagttgg ctgctgccac    5340
cgctgagcaa taactagcat aaccccttgg ggcctctaaa cgggtcttga ggggttttt     5400 gctgaaagga ggaactatat ccggattggc gaatgggacg cgccctgtag cggcgcatta    5460
agcgcggcgg gtgtggtggt tacgcgcagc gtgaccgcta cactt                   5505

<210> SEQ ID NO 95
<211> LENGTH: 35
<212> TYPE: DNA
<213> ORGANISM: Artificial Sequence
<220> FEATURE:
<223> OTHER INFORMATION: Primer IGR-f

<400> SEQUENCE: 95
ggtggttcta gagcaaaaat gtgatcttgc ttgta                                 35

<210> SEQ ID NO 96
<211> LENGTH: 36
<212> TYPE: DNA
<213> ORGANISM: Artificial Sequence
<220> FEATURE:
<223> OTHER INFORMATION: Primer IGR-r

<400> SEQUENCE: 96
ggtggtcata tgaatcttga aatgtagcag gtaaat                                36

<210> SEQ ID NO 97
<211> LENGTH: 662
<212> TYPE: DNA
<213> ORGANISM: Artificial Sequence
<220> FEATURE:
<223> OTHER INFORMATION: 3'-UTR of yeast FBA1 gene (Accession number:
      NM_001179626) (short fragment)

<400> SEQUENCE: 97
gagtattgaa tctgtttaga aataatggaa tattattttt atttatttat ttatattatt      60
ggtcggctct tttcttctga aggtcaatga caaaatgata tgaaggaaat aatgatttct    120
```

```
aaaattttac aacgtaagat attttacaa aagcctagct catcttttgt catgcactat    180
tttactcacg cttgaaatta acggccagtc cactgcggag tcatttcaaa gtcatcctaa    240
tcgatctatc gttttgata gctcattttg gagttcgcga ttgtcttctg ttattcacaa     300
ctgttttaat ttttatttca ttctggaact cttcgagttc tttgtaaagt ctttcatagt    360
agcttacttt atcctccaac atatttaact tcatgtcaat ttcggctctt aaattttcca    420
catcatcaag ttcaacatca tcttttaact tgaatttatt ctctagctct tccaaccaag    480
cctcattgct ccttgattta ctggtgaaaa gtgatacact ttgcgcgcaa tccaggtcaa    540
aactttcctg caaagaattc accaatttct cgacatcata gtacaaattg ttttgttctc    600
ccatcacaat ttaatatacc tgatggattc ttatgaagcg ctgggtaatg gacgtgtcac    660
tc    662
```

<210> SEQ ID NO 98
<211> LENGTH: 1465
<212> TYPE: DNA
<213> ORGANISM: Artificial Sequence
<220> FEATURE:
<223> OTHER INFORMATION: 3'-UTR of yeast FBA1 gene (Accession number:
      NM_001179626) (long fragment)

<400> SEQUENCE: 98

```
gagtattgaa tctgtttaga aataatggaa tattattttt atttatttat ttatattatt     60
ggtcggctct tttcttctga aggtcaatga caaaatgata tgaaggaaat aatgatttct    120
aaaattttac aacgtaagat attttacaa aagcctagct catcttttgt catgcactat    180
tttactcacg cttgaaatta acggccagtc cactgcggag tcatttcaaa gtcatcctaa    240
tcgatctatc gttttgata gctcattttg gagttcgcga ttgtcttctg ttattcacaa     300
ctgttttaat ttttatttca ttctggaact cttcgagttc tttgtaaagt ctttcatagt    360
agcttacttt atcctccaac atatttaact tcatgtcaat ttcggctctt aaattttcca    420
catcatcaag ttcaacatca tcttttaact tgaatttatt ctctagctct tccaaccaag    480
cctcattgct ccttgattta ctggtgaaaa gtgatacact ttgcgcgcaa tccaggtcaa    540
aactttcctg caaagaattc accaatttct cgacatcata gtacaaattg ttttgttctc    600
ccatcacaat ttaatatacc tgatggattc ttatgaagcg ctgggtaatg gacgtgtcac    660
tctacttcgc cttttccct actccttta gtacggaaga caatgctaat aaataagagg    720
gtaataataa tattattaat cggcaaaaaa gattaaacgc caagcgttta attatcagaa    780
agcaaacgtc gtaccaatcc ttgaatgctt cccaattgta tattaagagt catcacagca    840
acatattctt gttattaaat taattattat tgattttga tattgtataa aaaaccaaa     900 tatgtataaa aaagtgaat aaaaaatacc aagtatggag aaatatatta gaagtctata    960
cgttaaaacc agaacgtgca caatttttt aatctgccaa atggaaaaaa cggaaatata   1020
cggaaaagaa gttgaagtaa tagttagaaa ggcaaaaaag gaaagaaaca atttaaaata   1080
tcttaagatt atattagaaa caaacaccaa tgttcatttc attccttaga atatatccga   1140
atgaaatgac caacctactt gttttgtaaa ctgaggaaga aagaatatta tttctccgaa   1200
aacttgtcat accgtagctt gtcttgcttt tatttgcttt tgaccttatt ttttttcaaaa   1260 atcaccgtgc ttttgtgag ttttagatg ttgtgataaa ttgtcacttc tactgaattt    1320
tttctcacag aacatacaag caaagggcg ttccgttgaa tgaacggatc ttatatgcct   1380
tttcaagtgc tcactgcgtc tgaatgcctt ctcacagtct ttacacttga aaggtttatt   1440
```
tttatcgtag ttgttggggt caatg                                          1465

<210> SEQ ID NO 99
<211> LENGTH: 40
<212> TYPE: DNA
<213> ORGANISM: Artificial Sequence
<220> FEATURE:
<223> OTHER INFORMATION: FBA3UTR-f

<400> SEQUENCE: 99
ggtggtgagc tcgagtattg aatctgttta gaaataatgg                            40

<210> SEQ ID NO 100
<211> LENGTH: 32
<212> TYPE: DNA
<213> ORGANISM: Artificial Sequence
<220> FEATURE:
<223> OTHER INFORMATION: FBA3UTR1-r

<400> SEQUENCE: 100
ggtggtctcg agtgacacgt ccattaccca gc                                    32

<210> SEQ ID NO 101
<211> LENGTH: 32
<212> TYPE: DNA
<213> ORGANISM: Artificial Sequence
<220> FEATURE:
<223> OTHER INFORMATION: FBA3UTR2-r

<400> SEQUENCE: 101
ggtggtctcg agcattgacc ccaacaacta cg                                    32

<210> SEQ ID NO 102
<211> LENGTH: 792
<212> TYPE: DNA
<213> ORGANISM: Artificial Sequence
<220> FEATURE:
<223> OTHER INFORMATION: TMV1, ranges from 4920 to 5711 of genome

<400> SEQUENCE: 102
aggaaaagtg aatatcaatg agtttatcga cctgacaaaa atggagaaga tcttaccgtc      60
gatgtttacc cctgtaaaga gtgttatgtg ttccaaagtt gataaaataa tggttcatga     120
gaatgagtca ttgtcagagg tgaaccttct taaaggagtt aagcttattg atagtggata     180
cgtctgttta gccggtttgg tcgtcacggg cgaatggaac ttgcctgaca attgcagagg     240
aggtgtgagc gtgtgtctgg tggacaaaag gatggaaaga ccgacgagg ccactctcgg      300
atcttactac acagcagctg caaagaaaag atttcagttc aaggtcgttc ccaattatgc     360
tataaccacc caggacgcga tgaaaaacgt ctggcaagtt ttagttaata ttagaaatgt     420
aaagatgtca gcgggtttct gtccgctttc tctggagttt gtgtcggtgt gtattgttta     480
tagaaataat ataaaattag gtttgagaga gaagattaca aacgtgagag acggagggcc     540
catggaactt acagaagaag tcgttgatga gttcatggaa gatgtcccta tgtcaatcag     600
gcttgcaaag tttcgatctc ggaccggaaa aaagagtgat gtccgtaaag gaaaaatag     660
tagtagtgac cggtcagtgc cgaacaagaa ctatagaaat gttaaggatt ttggaggaat     720
gagtttaaaa aagaataatt taatcgatga tgattcggag gctactgtcg ccgaatcgga     780
ttcgttttaa at                                                         792

<210> SEQ ID NO 103
<211> LENGTH: 204

```
<212> TYPE: DNA
<213> ORGANISM: Artificial Sequence
<220> FEATURE:
<223> OTHER INFORMATION: TMV2 ranges from 6192 to 6395 genome

<400> SEQUENCE: 103
ggtagtcaag atgcataata aataacggat tgtgtccgta atcacacgtg gtgcgtacga    60
taacgcatag tgttttctcc tccacttaga tcgaagggtt gtgtcttgga tcgcgcgggt   120
caaatgtata tggttcatat acatccgcag gcacgtaata aagcgagggg ttcgaatccc   180
cccgttaccc ccggtagggg ccca                                          204

<210> SEQ ID NO 104
<211> LENGTH: 30
<212> TYPE: DNA
<213> ORGANISM: Artificial Sequence
<220> FEATURE:
<223> OTHER INFORMATION: TMV13U200

<400> SEQUENCE: 104
ggtggtctcg agccaaaccg gctaaacaga                                     30

<210> SEQ ID NO 105
<211> LENGTH: 33
<212> TYPE: DNA
<213> ORGANISM: Artificial Sequence
<220> FEATURE:
<223> OTHER INFORMATION: TMV13U400

<400> SEQUENCE: 105
ggtggtctcg agaacttgcc agacgttttt cat                                 33

<210> SEQ ID NO 106
<211> LENGTH: 35
<212> TYPE: DNA
<213> ORGANISM: Artificial Sequence
<220> FEATURE:
<223> OTHER INFORMATION: TMV13U700

<400> SEQUENCE: 106
ggtggtctcg agatttctat agttcttgtt cggca                               35

<210> SEQ ID NO 107
<211> LENGTH: 40
<212> TYPE: DNA
<213> ORGANISM: Artificial Sequence
<220> FEATURE:
<223> OTHER INFORMATION: TMV13U-f

<400> SEQUENCE: 107
ggtggtgagc tcaggaaaag tgaatatcaa tgagtttatc                          40

<210> SEQ ID NO 108
<211> LENGTH: 30
<212> TYPE: DNA
<213> ORGANISM: Artificial Sequence
<220> FEATURE:
<223> OTHER INFORMATION: TMV13U200-r

<400> SEQUENCE: 108
ggtggtctcg agccaaaccg gctaaacaga                                     30

<210> SEQ ID NO 109
<211> LENGTH: 33
<212> TYPE: DNA
```

```
<213> ORGANISM: Artificial Sequence
<220> FEATURE:
<223> OTHER INFORMATION: TMV13U400-r

<400> SEQUENCE: 109
ggtggtctcg agaacttgcc agacgttttt cat                                    33

<210> SEQ ID NO 110
<211> LENGTH: 35
<212> TYPE: DNA
<213> ORGANISM: Artificial Sequence
<220> FEATURE:
<223> OTHER INFORMATION: TMV13U700-r

<400> SEQUENCE: 110
ggtggtctcg agatttctat agttcttgtt cggca                                  35

<210> SEQ ID NO 111
<211> LENGTH: 204
<212> TYPE: DNA
<213> ORGANISM: Artificial Sequence
<220> FEATURE:
<223> OTHER INFORMATION: TMV2 FRAGMENT

<400> SEQUENCE: 111
ggtagtcaag atgcataata ataacggat tgtgtccgta atcacacgtg gtgcgtacga        60
taacgcatag tgttttttccc tccacttaga tcgaagggtt gtgtcttgga tcgcgcgggt     120
caaatgtata tggttcatat acatccgcag gcacgtaata aagcgagggg ttcgaatccc      180
cccgttaccc ccggtagggg ccca                                             204

<210> SEQ ID NO 112
<211> LENGTH: 32
<212> TYPE: DNA
<213> ORGANISM: Artificial Sequence
<220> FEATURE:
<223> OTHER INFORMATION: TMV23U-f

<400> SEQUENCE: 112
ggtggtgagc tcggtagtca agatgcataa ta                                     32

<210> SEQ ID NO 113
<211> LENGTH: 29
<212> TYPE: DNA
<213> ORGANISM: Artificial Sequence
<220> FEATURE:
<223> OTHER INFORMATION: tmv23u-r

<400> SEQUENCE: 113
ggtggtctcg agtgggcccc taccggggg                                         29

<210> SEQ ID NO 114
<211> LENGTH: 37
<212> TYPE: DNA
<213> ORGANISM: Artificial Sequence
<220> FEATURE:
<223> OTHER INFORMATION: QEluc-f

<400> SEQUENCE: 114 ttactatttta caattacata tggaagacgc caaaaac                               37

<210> SEQ ID NO 115
<211> LENGTH: 37
<212> TYPE: DNA
<213> ORGANISM: Artificial Sequence
```

```
<220> FEATURE:
<223> OTHER INFORMATION: QEluc-r

<400> SEQUENCE: 115
agcagccgga tctcagttta caatttggac tttccgc                            37

<210> SEQ ID NO 116
<211> LENGTH: 38
<212> TYPE: DNA
<213> ORGANISM: Artificial Sequence
<220> FEATURE:
<223> OTHER INFORMATION: QEGFP-f

<400> SEQUENCE: 116
ttactattta caattacata tgagcaaagg tgaagaac                           38

<210> SEQ ID NO 117
<211> LENGTH: 36
<212> TYPE: DNA
<213> ORGANISM: Artificial Sequence
<220> FEATURE:
<223> OTHER INFORMATION: QEGFP-r

<400> SEQUENCE: 117
agcagccgga tctcagttta tttttcgaac tgcgga                             36

<210> SEQ ID NO 118
<211> LENGTH: 39
<212> TYPE: DNA
<213> ORGANISM: Artificial Sequence
<220> FEATURE:
<223> OTHER INFORMATION: QECAT-f

<400> SEQUENCE: 118
ttactattta caattacata tggaaaaaaa aatcaccgg                          39

<210> SEQ ID NO 119
<211> LENGTH: 34
<212> TYPE: DNA
<213> ORGANISM: Artificial Sequence
<220> FEATURE:
<223> OTHER INFORMATION: QECAT-r

<400> SEQUENCE: 119
agcagccgga tctcagttta cgcaccaccc tgcc                               34

<210> SEQ ID NO 120
<211> LENGTH: 22
<212> TYPE: DNA
<213> ORGANISM: Artificial Sequence
<220> FEATURE:
<223> OTHER INFORMATION: T7 promoter

<400> SEQUENCE: 120
taatacgact cactataggg ag                                            22

<210> SEQ ID NO 121
<211> LENGTH: 65
<212> TYPE: DNA
<213> ORGANISM: Artificial Sequence
<220> FEATURE:
<223> OTHER INFORMATION: OMEGA sequence

<400> SEQUENCE: 121 tattttaca acaattacca acaacaacaa acaacaaaca acattacaat tactatttac    60
``` aatta 65

<210> SEQ ID NO 122
<211> LENGTH: 50
<212> TYPE: DNA
<213> ORGANISM: Artificial Sequence
<220> FEATURE:
<223> OTHER INFORMATION: poly(A)50 tail

<400> SEQUENCE: 122
aaaaaaaaaa aaaaaaaaaa aaaaaaaaaa aaaaaaaaaa aaaaaaaaaa 50

<210> SEQ ID NO 123
<211> LENGTH: 120
<212> TYPE: DNA
<213> ORGANISM: Artificial Sequence
<220> FEATURE:
<223> OTHER INFORMATION: QET70me-f

<400> SEQUENCE: 123
acgctgcccg agatctcgat cccgcgaaat taatacgact cactataggg agtattttta 60
caacaattac caacaacaac aaacaacaaa caacattaca attactattt acaattacat 120

<210> SEQ ID NO 124
<211> LENGTH: 4341
<212> TYPE: DNA
<213> ORGANISM: Artificial Sequence
<220> FEATURE:
<223> OTHER INFORMATION: pET23c-GFP-cyc3

<400> SEQUENCE: 124
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta agggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg agacaataac cctgataaat gcttcaataa tattgaaaaa ggaagagtat 600
gagtattcaa catttccgtg tcgcccttat tcccttttt gcggcatttt gccttcctgt 660
ttttgctcac ccagaaacgc tggtgaaagt aaaagatgct gaagatcagt tgggtgcacg 720
agtgggttac atcgaactgg atctcaacag cggtaagatc cttgagagtt ttcgccccga 780
agaacgtttt ccaatgatga gcacttttaa agttctgcta tgtggcgcgg tattatcccg 840
tattgacgcc gggcaagagc aactcggtcg ccgcatacac tattctcaga atgacttggt 900
tgagtactca ccagtcacag aaaagcatct tacggatggc atgacagtaa gagaattatg 960
cagtgctgcc ataaccatga gtgataacac tgcggccaac ttacttctga caacgatcgg 1020
aggaccgaag gagctaaccg cttttttgca caacatgggg gatcatgtaa ctcgccttga 1080
tcgttgggaa ccggagctga atgaagccat accaaacgac gagcgtgaca ccacgatgcc 1140
tgcagcaatg gcaacaacgt tgcgcaaact attaactggc gaactactta ctctagcttc 1200
ccggcaacaa ttaatagact ggatggaggc ggataaagtt gcaggaccac ttctgcgctc 1260

```
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc cttttgata atctcatgac     1560 caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatgaaaaaa   2220
cgccagcaac gcggcctttt tacggttcct ggccttttgc tggccttttg ctcacatgtt    2280
ctttcctgcg ttatccctg attctgtgga taaccgtatt accgcctttg agtgagctga     2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atggggtaa     2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag aaataatttt gtttaacttt aagaaggaga    3420
tatacatatg gctagcatga ctagcaaagg agaagaactt ttcactggag ttgtcccaat    3480
tcttgttgaa ttagatggtg atgttaatgg gcacaaattt tctgtcagtg agagggtgaa    3540
aggtgatgct acatacggaa agcttaccct taaatttatt tgcactactg gaaaactacc    3600
```

-continued

| | |
|---|---|
| tgttccatgg ccaacacttg tcactacttt ctcttatggt gttcaatgct tttcccgtta | 3660 |
| tccggatcat atgaaacggc atgactttt caagagtgcc atgcccgaag gttatgtaca | 3720 |
| ggaacgcact atatctttca aagatgacgg gaactacaag acgcgtgctg aagtcaagtt | 3780 |
| tgaaggtgat acccttgtta atcgtatcga gttaaaaggt attgatttta agaagatgg | 3840 |
| aaacattctc ggacacaaac tcgagtacaa ctataactca cacaatgtat acatcacggc | 3900 |
| agacaaacaa aagaatggaa tcaaagctaa cttcaaaatt cgccacaaca ttgaagatgg | 3960 |
| atccgttcaa ctagcagacc attatcaaca aaatactcca attggcgatg ccctgtcct | 4020 |
| tttaccagac aaccattacc tgtcgacaca atctgccctt atcgaaagat cccaacgaaa | 4080 |
| agagagacca catggtcctt cttgagtttg taacagctgc tgggattaca catggcatgg | 4140 |
| atgaactata caaaccggg atccggcggg cggccgcact cgagcaccac caccaccac | 4200 |
| actgagatcc ggctgctaac aaagcccgaa aggaagctga gttggctgct gccaccgctg | 4260 |
| agcaataact agcataaccc cttggggcct ctaaacgggt cttgagggt tttttgctga | 4320 |
| aaggaggaac tatatccgga t | 4341 |

<210> SEQ ID NO 125
<211> LENGTH: 19
<212> TYPE: DNA
<213> ORGANISM: Artificial Sequence
<220> FEATURE:
<223> OTHER INFORMATION: T7 terminator

<400> SEQUENCE: 125

| | |
|---|---|
| ctgagcaata actagcata | 19 |

<210> SEQ ID NO 126
<211> LENGTH: 29
<212> TYPE: DNA
<213> ORGANISM: Artificial Sequence
<220> FEATURE:
<223> OTHER INFORMATION: luciferase sense primer

<400> SEQUENCE: 126

| | |
|---|---|
| ggtggtcata tggaagacgc caaaaacat | 29 |

<210> SEQ ID NO 127
<211> LENGTH: 122
<212> TYPE: DNA
<213> ORGANISM: Artificial Sequence
<220> FEATURE:
<223> OTHER INFORMATION: luciferase anti-sense primer

<400> SEQUENCE: 127

| | |
|---|---|
| ggtggtctcg agtttttttt tttttttttt tttttttttt tttttttttt | 60 |
| tttttttttt tttttttttt tttttttttt tttttttttt ttttacaatt tggactttcc | 120 |
| gc | 122 |

<210> SEQ ID NO 128
<211> LENGTH: 5343
<212> TYPE: DNA
<213> ORGANISM: Artificial Sequence
<220> FEATURE:
<223> OTHER INFORMATION: pET23OMEGALucA

<400> SEQUENCE: 128

| | |
|---|---|
| gccagcgccc tagcgcccgc tcctttcgct ttcttccctt cctttctcgc cacgttcgcc | 60 |
| ggctttcccc gtcaagctct aaatcggggg ctcccttag ggttccgatt tagtgcttta | 120 |

```
cggcacctcg accccaaaaa acttgattag ggtgatggtt cacgtagtgg gccatcgccc    180
tgatagacgg ttttttcgccc tttgacgttg gagtccacgt tctttaatag tggactcttg    240
ttccaaactg gaacaacact caaccctatc tcggtctatt cttttgattt ataagggatt    300
ttgccgattt cggcctattg gttaaaaaat gagctgattt aacaaaaatt taacgcgaat    360
tttaacaaaa tattaacgtt tacaatttca ggtggcactt ttcggggaaa tgtgcgcgga    420
acccctattt gtttattttt ctaaatacat tcaaatatgt atccgctcat gagacaataa    480
ccctgataaa tgcttcaata atattgaaaa aggaagagta tgagtattca acatttccgt    540
gtcgccctta ttcccttttt tgcggcattt tgccttcctg tttttgctca cccagaaacg    600
ctggtgaaag taaaagatgc tgaagatcag ttgggtgcac gagtgggtta catcgaactg    660
gatctcaaca gcggtaagat ccttgagagt tttcgccccg aagaacgttt tccaatgatg    720
agcactttta aagttctgct atgtggcgcg gtattatccc gtattgacgc cgggcaagag    780
caactcggtc gccgcataca ctattctcag aatgacttgg ttgagtactc accagtcaca    840
gaaaagcatc ttacggatgg catgacagta agagaattat gcagtgctgc cataaccatg    900
agtgataaca ctgcggccaa cttacttctg acaacgatcg gaggaccgaa ggagctaacc    960
gcttttttgc acaacatggg ggatcatgta actcgccttg atcgttggga accggagctg   1020
aatgaagcca taccaaacga cgagcgtgac accacgatgc ctgcagcaat ggcaacaacg   1080
ttgcgcaaac tattaactgg cgaactactt actctagctt cccggcaaca attaatagac   1140
tggatggagg cggataaagt tgcaggacca cttctgcgct cggcccttcc ggctggctgg   1200
tttattgctg ataaatctgg agccggtgag cgtgggtctc gcggtatcat tgcagcactg   1260
gggccagatg gtaagccctc ccgtatcgta gttatctaca cgacggggag tcaggcaact   1320
atggatgaac gaaatagaca gatcgctgag ataggtgcct cactgattaa gcattggtaa   1380
ctgtcagacc aagtttactc atatatactt tagattgatt taaaacttca ttttttaattt   1440 aaaaggatct aggtgaagat cctttttgat aatctcatga ccaaaatccc ttaacgtgag   1500
ttttcgttcc actgagcgtc agaccccgta gaaaagatca aaggatcttc ttgagatcct   1560 tttttttctgc gcgtaatctg ctgcttgcaa acaaaaaaac caccgctacc agcggtggtt   1620
tgtttgccgg atcaagagct accaactctt tttccgaagg taactggctt cagcagagcg   1680
cagataccaa atactgtcct tctagtgtag ccgtagttag gccaccactt caagaactct   1740
gtagcaccgc ctacatacct cgctctgcta atcctgttac cagtggctgc tgccagtggc   1800
gataagtcgt gtcttaccgg gttggactca agacgatagt taccggataa ggcgcagcgg   1860
tcgggctgaa cggggggttc gtgcacacag cccagcttgg agcgaacgac ctacaccgaa   1920
ctgagatacc tacagcgtga gctatgagaa agcgccacgc ttcccgaagg gagaaaggcg   1980
gacaggtatc cggtaagcgg cagggtcgga acaggagagc gcacgaggga gcttccaggg   2040
ggaaacgcct ggtatcttta tagtcctgtc gggtttcgcc acctctgact tgagcgtcga   2100
tttttgtgat gctcgtcagg gggcggagc ctatggaaaa acgccagcaa cgcggccttt   2160
ttacggttcc tggccttttg ctggcctttt gctcacatgt tctttcctgc gttatcccct   2220
gattctgtgg ataaccgtat taccgccttt gagtgagctg ataccgctcg ccgcagccga   2280
acgaccgagc gcagcgagtc agtgagcgag gaagcggaag agcgcctgat gcggtatttt   2340
ctccttacgc atctgtgcgg tatttcacac cgcatatatg gtgcactctc agtacaatct   2400
gctctgatgc cgcatagtta agccagtata cactccgcta tcgctacgtg actgggtcat   2460
```

| | |
|---|---|
| ggctgcgccc cgacacccgc caacacccgc tgacgcgccc tgacgggctt gtctgctccc | 2520 |
| ggcatccgct tacagacaag ctgtgaccgt ctccgggagc tgcatgtgtc agaggttttc | 2580 |
| accgtcatca ccgaaacgcg cgaggcagct gcggtaaagc tcatcagcgt ggtcgtgaag | 2640 |
| cgattcacag atgtctgcct gttcatccgc gtccagctcg ttgagtttct ccagaagcgt | 2700 |
| taatgtctgg cttctgataa agcgggccat gttaagggcg ttttttcct gtttggtcac | 2760 |
| tgatgcctcc gtgtaagggg gatttctgtt catgggggta atgataccga tgaaacgaga | 2820 |
| gaggatgctc acgatacggg ttactgatga tgaacatgcc cggttactgg aacgttgtga | 2880 |
| gggtaaacaa ctggcggtat ggatgcggcg ggaccagaga aaaatcactc agggtcaatg | 2940 |
| ccagcgcttc gttaatacag atgtaggtgt tccacagggt agccagcagc atcctgcgat | 3000 |
| gcagatccgg aacataatgg tgcagggcgc tgacttccgc gtttccagac tttacgaaac | 3060 |
| acggaaaccg aagaccattc atgttgttgc tcaggtcgca gacgttttgc agcagcagtc | 3120 |
| gcttcacgtt cgctcgcgta tcggtgattc attctgctaa ccagtaaggc aaccccgcca | 3180 |
| gcctagccgg gtcctcaacg acaggagcac gatcatgcgc acccgtggcc aggacccaac | 3240 |
| gctgcccgag atctcgatcc cgcgaaatta atacgactca ctatagggag tattttaca | 3300 |
| acaattacca acaacaacaa acaacaaaca acattacaat tactatttac aattacatat | 3360 |
| ggaagacgcc aaaaacataa agaaaggccc ggcgccattc tatccgctag aggatggaac | 3420 |
| cgctggagag caactgcata aggctatgaa gagatacgcc ctggttcctg gaacaattgc | 3480 |
| ttttacagat gcacatatcg aggtgaacat cacgtacgcg gaatacttcg aaatgtccgt | 3540 |
| tcggttggca gaagctatga acgatatgg gctgaataca atcacagaa tcgtcgtatg | 3600 |
| cagtgaaaac tctcttcaat tctttatgcc ggtgttgggc gcgttattta tcggagttgc | 3660 |
| agttgcgccc gcgaacgaca tttataatga acgtgaattg ctcaacagta tgaacatttc | 3720 |
| gcagcctacc gtagtgtttg tttccaaaaa ggggttgcaa aaattttga acgtgcaaaa | 3780 |
| aaaattacca ataatccaga aaattattat catggattct aaaacggatt accagggatt | 3840 |
| tcagtcgatg tacacgttcg tcacatctca tctacctccc ggttttaatg aatacgattt | 3900 |
| tgtaccagag tccttttgatc gtgacaaaac aattgcactg ataatgaact cctctggatc | 3960 |
| tactgggtta cctaagggtg tggcccttcc gcatagaact gcctgcgtca gattctcgca | 4020 |
| tgccagagat cctatttttg gcaatcaaat cattccggat actgcgattt taagtgttgt | 4080 |
| tccattccat cacggttttg gaatgtttac tacactcgga tatttgatat gtggatttcg | 4140 |
| agtcgtctta atgtatagat ttgaagaaga gctgttttta cgatcccttc aggattacaa | 4200 |
| aattcaaagt gcgttgctag taccaaccct attttcattc ttcgccaaaa gcactctgat | 4260 |
| tgacaaatac gatttatcta atttacacga aattgcttct gggggcgcac ctcttttcgaa | 4320 |
| agaagtcggg gaagcggttg caaaacgctt ccatcttcca gggatacgac aaggatatgg | 4380 |
| gctcactgag actacatcag ctattctgat tacacccgag ggggatgata aaccgggcgc | 4440 |
| ggtcggtaaa gttgttccat tttttgaagc gaaggttgtg gatctggata ccgggaaaac | 4500 |
| gctgggcgtt aatcagagag gcgaattatg tgtcagagga cctatgatta tgtccggtta | 4560 |
| tgtaaacaat ccggaagcga ccaacgcctt gattgacaag gatggatggc tacattctgg | 4620 |
| agacatagct tactgggacg aagacgaaca cttcttcata gttgaccgct tgaagtcttt | 4680 |
| aattaaatac aaaggatacc aggtggcccc cgctgaattg gagtcgatat tgttacaaca | 4740 |
| ccccaacatc ttcgacgcgg gcgtggcagg tcttcccgac gatgacgccg gtgaacttcc | 4800 |
| cgccgccgtt gttgttttgg agcacggaaa gacgatgacg gaaaaagaga tcgtggatta | 4860 |

```
cgtcgccagt caagtaacaa ccgccaaaaa gttgcgcgga ggagttgtgt ttgtggacga    4920
agtaccgaaa ggtcttaccg gaaaactcga cgcaagaaaa atcagagaga tcctcataaa    4980
ggccaagaag ggcggaaagt ccaaattgta aaaaaaaaa aaaaaaaaaa aaaaaaaaaa      5040
aaaaaaaaaa aaaaaaaaaa aaaaaaaaaa aaaaaaaaaa aaaaaaaaaa aaaaaaaaaa    5100
actcgagcac caccaccacc accactgaga tccggctgct aacaaagccc gaaaggaagc    5160
tgagttggct gctgccaccg ctgagcaata actagcataa ccccttgggg cctctaaacg    5220
ggtcttgagg ggttttttgc tgaaaggagg aactatatcc ggattggcga atgggacgcg    5280
ccctgtagcg gcgcattaag cgcggcgggt gtggtggtta cgcgcagcgt gaccgctaca    5340
ctt                                                                 5343
```

<210> SEQ ID NO 129
<211> LENGTH: 21
<212> TYPE: DNA
<213> ORGANISM: Artificial Sequence
<220> FEATURE:
<223> OTHER INFORMATION: backbone sense primer

<400> SEQUENCE: 129
gtgattcatt ctgctaacca g                                             21

<210> SEQ ID NO 130
<211> LENGTH: 20
<212> TYPE: DNA
<213> ORGANISM: Artificial Sequence
<220> FEATURE:
<223> OTHER INFORMATION: backbone anti-sense primer

<400> SEQUENCE: 130
ccccaagggg ttatgctagt                                               20

<210> SEQ ID NO 131
<211> LENGTH: 60
<212> TYPE: DNA
<213> ORGANISM: Artificial Sequence
<220> FEATURE:
<223> OTHER INFORMATION: T7-OMEGA-f

<400> SEQUENCE: 131
ccgcgaaatt aatacgactc actataggga gatatttta caacaattac caacaacaac    60

<210> SEQ ID NO 132
<211> LENGTH: 60
<212> TYPE: DNA
<213> ORGANISM: Artificial Sequence
<220> FEATURE:
<223> OTHER INFORMATION: SP6-OMEGA-f

<400> SEQUENCE: 132
ccgcgaaata tttaggtgac actatagaag agtattttta caacaattac caacaacaac    60

<210> SEQ ID NO 133
<211> LENGTH: 59
<212> TYPE: DNA
<213> ORGANISM: Artificial Sequence
<220> FEATURE:
<223> OTHER INFORMATION: T3-OMEGA-f

<400> SEQUENCE: 133
ccgcgaaata attaccctc actaaaggga atatttttac aacaattacc aacaacaac     59

<210> SEQ ID NO 134
<211> LENGTH: 57
<212> TYPE: DNA
<213> ORGANISM: Artificial Sequence
<220> FEATURE:
<223> OTHER INFORMATION: P1.1-OMEGA-Kozak(No Kozak)-sfGFP-f

<400> SEQUENCE: 134
acaaacaaca ttacaattac tatttacaat tacatatgag caaaggtgaa gaactgt        57

<210> SEQ ID NO 135
<211> LENGTH: 61
<212> TYPE: DNA
<213> ORGANISM: Artificial Sequence
<220> FEATURE:
<223> OTHER INFORMATION: P1.1-OMEGA-Kozak(Consensus Full)-sfGFP-f

<400> SEQUENCE: 135
acaaacaaca ttacaattac tatttacaat tacccaccat ggagcaaagg tgaagaactg    60
t                                                                    61

<210> SEQ ID NO 136
<211> LENGTH: 60
<212> TYPE: DNA
<213> ORGANISM: Artificial Sequence
<220> FEATURE:
<223> OTHER INFORMATION: P1.1-OMEGA-Kozak(S. cer partial)-sfGFP-f

<400> SEQUENCE: 136
acaaacaaca ttacaattac tatttacaat taaaaaaaat gagcaaaggt gaagaactgt    60

<210> SEQ ID NO 137
<211> LENGTH: 63
<212> TYPE: DNA
<213> ORGANISM: Artificial Sequence
<220> FEATURE:
<223> OTHER INFORMATION: P1.1-OMEGA-Kozak(S. cer full)-sfGFP-f

<400> SEQUENCE: 137
acaaacaaca ttacaattac tatttacaat taaaaaaaat gtctagcaaa ggtgaagaac    60
tgt                                                                  63

<210> SEQ ID NO 138
<211> LENGTH: 916
<212> TYPE: DNA
<213> ORGANISM: Artificial Sequence
<220> FEATURE:
<223> OTHER INFORMATION: OMEGA-(No Kozak)-sfGFP

<400> SEQUENCE: 138
acgctgcccg agatctcgat cccgcgaaat taatacgact cactataggg agtattttta    60
caacaattac caacaacaac aaacaacaaa caacattaca attactattt acaattacat   120
atgtctagca aaggtgaaga actgtttacc ggcgttgtgc cgattctggt ggaactggat   180
ggcgatgtga acggtcacaa attcagcgtg cgtggtgaag gtgaaggcga tgccacgatt   240
ggcaaactga cgctgaaatt tatctgcacc accggcaaac tgccggtgcc gtggccgacg   300
ctggtgacca ccctgaccta tggcgttcag tgttttagtc gctatccgga tcacatgaaa   360
cgtcacgatt tctttaaatc tgcaatgccg gaaggctatg tgcaggaacg tacgattagc   420
tttaaagatg atggcaaata taaaacgcgc gccgttgtga atttgaagg cgataccctg   480 gtgaaccgca ttgaactgaa aggcacggat tttaaagaag atggcaatat cctgggccat   540

```
aaactggaat acaactttaa tagccataat gtttatatta cggcggataa acagaaaaat    600
ggcatcaaag cgaattttac cgttcgccat aacgttgaag atggcagtgt gcagctggca    660
gatcattatc agcagaatac cccgattggt gatggtccgg tgctgctgcc ggataatcat    720
tatctgagca cgcagaccgt tctgtctaaa gatccgaacg aaaaaggcac gcgggaccac    780
atggttctgc acgaatatgt gaatgcggca ggtattacgt ggagccatcc gcagttcgaa    840
aaataaactg agatccggct gctaacaaaa aaaaaaaaaa aaaaaaaaaa aaaaaaaaaa    900
aaaaaaaaaa aaaaaa                                                    916

<210> SEQ ID NO 139
<211> LENGTH: 917
<212> TYPE: DNA
<213> ORGANISM: Artificial Sequence
<220> FEATURE:
<223> OTHER INFORMATION: OMEGA-Kozak (Consensus)-sfGFP

<400> SEQUENCE: 139
acgctgcccg agatctcgat cccgcgaaat taatacgact cactataggg agtatttta     60 caacaattac caacaacaac aaacaacaaa caacattaca attactattt acaattaccc    120
accatggagc aaaggtgaag aactgtttac cggcgttgtg ccgattctgg tggaactgga    180
tggcgatgtg aacggtcaca aattcagcgt gcgtggtgaa ggtgaaggcg atgccacgat    240
tggcaaactg acgctgaaat ttatctgcac caccggcaaa ctgccggtgc cgtggccgac    300
gctggtgacc accctgacct atggcgttca gtgttttagt cgctatccgg atcacatgaa    360
acgtcacgat ttctttaaat ctgcaatgcc ggaaggctat gtgcaggaac gtacgattag    420
ctttaaagat gatggcaaat ataaaacgcg cgccgttgtg aaatttgaag gcgataccct    480
ggtgaaccgc attgaactga aaggcacgga ttttaaagaa gatggcaata tcctgggcca    540
taaactggaa tacaacttta atagccataa tgtttatatt acggcggata acagaaaaa     600 tggcatcaaa gcgaatttta ccgttcgcca taacgttgaa gatggcagtg tgcagctggc    660
agatcattat cagcagaata ccccgattgg tgatggtccg gtgctgctgc cggataatca    720
ttatctgagc acgcagaccg ttctgtctaa agatccgaac gaaaaaggca cgcgggacca    780
catggttctg cacgaatatg tgaatgcggc aggtattacg tggagccatc cgcagttcga    840
aaaataaact gagatccggc tgctaacaaa aaaaaaaaaa aaaaaaaaaa aaaaaaaaaa    900
aaaaaaaaaa aaaaaaa                                                   917

<210> SEQ ID NO 140
<211> LENGTH: 916
<212> TYPE: DNA
<213> ORGANISM: Artificial Sequence
<220> FEATURE:
<223> OTHER INFORMATION: OMEGA-Kozak (S. cer partial)-sfGFP

<400> SEQUENCE: 140
acgctgcccg agatctcgat cccgcgaaat taatacgact cactataggg agtatttta     60 caacaattac caacaacaac aaacaacaaa caacattaca attactattt acaattaaaa    120
aaaatgagca aaggtgaaga actgtttacc ggcgttgtgc cgattctggt ggaactggat    180
ggcgatgtga acggtcacaa attcagcgtg cgtggtgaag gtgaaggcga tgccacgatt    240
ggcaaactga cgctgaaatt tatctgcacc accggcaaac tgccggtgcc gtggccgacg    300
ctggtgacca ccctgaccta tggcgttcag tgttttagtc gctatccgga tcacatgaaa    360
```

```
cgtcacgatt tctttaaatc tgcaatgccg gaaggctatg tgcaggaacg tacgattagc    420
tttaaagatg atggcaaata taaaacgcgc gccgttgtga aatttgaagg cgataccctg    480
gtgaaccgca ttgaactgaa aggcacggat tttaaagaag atggcaatat cctgggccat    540
aaactggaat acaactttaa tagccataat gtttatatta cggcggataa acagaaaaat    600
ggcatcaaag cgaattttac cgttcgccat aacgttgaag atggcagtgt gcagctggca    660
gatcattatc agcagaatac cccgattggt gatggtccgg tgctgctgcc ggataatcat    720
tatctgagca cgcagaccgt tctgtctaaa gatccgaacg aaaaaggcac gcgggaccac    780
atggttctgc acgaatatgt gaatgcggca ggtattacgt ggagccatcc gcagttcgaa    840
aaataaactg agatccggct gctaacaaaa aaaaaaaaa aaaaaaaaa aaaaaaaaa    900 aaaaaaaaaa aaaaaa    916

<210> SEQ ID NO 141
<211> LENGTH: 919
<212> TYPE: DNA
<213> ORGANISM: Artificial Sequence
<220> FEATURE:
<223> OTHER INFORMATION: OMEGA-Kozak(S. cer full)-sfGFP

<400> SEQUENCE: 141
acgctgcccg agatctcgat cccgcgaaat taatacgact cactataggg agtattttta    60
caacaattac caacaacaac aaacaacaaa caacattaca attactattt acaattaaaa    120
aaaatgtcta gcaaaggtga agaactgttt accggcgttg tgccgattct ggtggaactg    180
gatggcgatg tgaacggtca caaattcagc gtgcgtggtg aaggtgaagg cgatgccacg    240
attggcaaac tgacgctgaa atttatctgc accaccggca aactgccggt gccgtggccg    300
acgctggtga ccaccctgac ctatggcgtt cagtgtttta gtcgctatcc ggatcacatg    360
aaacgtcacg atttctttaa atctgcaatg ccggaaggct atgtgcagga acgtacgatt    420
agctttaaag atgatggcaa atataaaacg cgcgccgttg tgaaatttga aggcgatacc    480
ctggtgaacc gcattgaact gaaaggcacg gattttaaag aagatggcaa tatcctgggc    540
cataaactgg aatacaactt taatagccat aatgttttata ttacggcgga taaacagaaa    600
aatggcatca aagcgaattt taccgttcgc cataacgttg aagatggcag tgtgcagctg    660
gcagatcatt atcagcagaa tacccccgatt ggtgatggtc cggtgctgct gccggataat    720
cattatctga gcacgcagac cgttctgtct aaagatccga cgaaaaagg cacgcgggac    780 cacatggttc tgcacgaata tgtgaatgcg gcaggtatta cgtggagcca tccgcagttc    840
gaaaaataaa ctgagatccg gctgctaaca aaaaaaaaaa aaaaaaaaaa aaaaaaaaaa    900 aaaaaaaaa aaaaaaaa    919
```